United States Patent
Fox et al.

(10) Patent No.: US 7,244,727 B2
(45) Date of Patent: Jul. 17, 2007

(54) FUSED BICYCLIC NITROGEN-CONTAINING HETEROCYCLES

(75) Inventors: Brian M. Fox, San Mateo, CA (US); Noboru Furukawa, Takatsuki (JP); Xiaolin Hao, Millbrae, CA (US); Kiyosei Iio, Takatsuki (JP); Takashi Inaba, Takatsuki (JP); Simon M. Jackson, San Carlos, CA (US); Frank Kayser, San Francisco, CA (US); Marc Labelle, Burlingame, CA (US); Kexue Li, Mountain View, CA (US); Takuya Matsui, Takatsuki (JP); Dustin L. McMinn, Pacifica, CA (US); Nobuya Ogawa, Takatsuki (JP); Steven M. Rubenstein, Pacifica, CA (US); Shoichi Sagawa, Takatsuki (JP); Kazuyuki Sugimoto, Takatsuki (JP); Masahiro Suzuki, Takatsuki (JP); Masahiro Tanaka, Takatsuki (JP); Guosen Ye, Phoenixville, PA (US); Atsuhito Yoshida, Takatsuki (JP); Jian Zhang, Foster City, CA (US)

(73) Assignee: Japan Tobacco Inc., Tokyo (JP)

( * ) Notice: Subject to any disclaimer, the term of this patent is extended or adjusted under 35 U.S.C. 154(b) by 286 days.

(21) Appl. No.: 10/720,844

(22) Filed: Nov. 21, 2003

(65) Prior Publication Data

US 2004/0209871 A1 Oct. 21, 2004

Related U.S. Application Data

(60) Provisional application No. 60/428,600, filed on Nov. 22, 2002.

(51) Int. Cl.
*C07D 498/04* (2006.01)
*A61K 31/542* (2006.01)
*A61P 3/04* (2006.01)
*A61P 3/08* (2006.01)
*C07D 491/04* (2006.01)
*C07D 495/04* (2006.01)
*A61K 31/538* (2006.01)
*A61K 31/519* (2006.01)

(52) U.S. Cl. ............ 514/230.5; 544/105; 544/48; 544/255; 514/224.2; 514/260.1

(58) Field of Classification Search ............. 544/105; 514/230.5
See application file for complete search history.

(56) References Cited

U.S. PATENT DOCUMENTS

| 4,166,452 A | 9/1979 | Generales, Jr. |
| 4,256,108 A | 3/1981 | Theeuwes |
| 4,265,874 A | 5/1981 | Bonsen et al. |
| 6,069,143 A | 5/2000 | Ali et al. |
| 6,512,099 B2 | 1/2003 | Omura et al. |

FOREIGN PATENT DOCUMENTS

| EP | 1 431 267 A1 | 6/2004 |
| JP | 05-213985 A | 8/1993 |
| JP | 2002-284741 A | 10/2002 |
| JP | 2004-067635 A | 3/2004 |
| KR | 2003-045230 A | 6/2003 |
| WO | WO 01/32632 A2 | 5/2001 |
| WO | WO 01/32632 A3 | 5/2001 |
| WO | WO 03/016254 A1 | 2/2003 |
| WO | WO 03/018536 A1 | 3/2003 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Lin et al., Journal of Medicinal Chmeistry 22(6): 741-743, 1979.*
Mirza et al., Journal of Chemical Societ Section C, Organic 3: 437-444, 1970. CA 72: 78966, 1970.*
Chen et al., Trends in Cardiovascular Medicine 10: 188-192, 2000.*
Chen et al. Arterioscler. Vasc. Biol. 25 (3): 482-486, 2005.*
Cecil Textbook of Medicine, edited by Bennet, J.C., and Plym F., 20th edition vol. 1, 1004-1010, 1996.*
Bagdade, *Diabetes Reviews*, 5(4): 392-409 (1997).
Barone, *Journal of Medicinal Chemistry*, 6: 39-42 (Jan. 1963).
Bast et al., "Imunostimulants", Chapter 60, Section 16, pp. 790-799, in *Cancer Medicine*, 5th ed: (Hamilton, Ontario, CA: B.C. Decker, 2000).
Berge et al., *Journal of Pharmaceutical Sciences*, 66(1): 1-19 (Jan. 1977).
Buhman et al., *Journal of Biological Chemistry*, 277(28): 25474-25479 (Jul. 12, 2002).
Cases et al., *Journal of Biological Chemistry*, 276(42): 38870-38876 (Oct. 19, 2001).
Cases et al., *Proc. Natl. Acad. Sci. USA*, 95: 13018-13023 (Oct. 1998).
Chen et al., *Diabetes*, 51: 3189-3195 (2002).
Chen et al., *Diabetes Reviews*, 5(4): 331-342 (1997).
Chen et al., *Journal of Clinical Investigation*, 109(8): 1049-1055 (Apr. 2002).
Chen et al., *Journal of Clinical Investigation*, 111: 1715-1722 (2003).
Chen et al., *Trends Cardiovasc. Med.*, 10(5): 188-192 (2000).
Chiasson et al., *Annals of Internal Medicine*, 121(12): 928-935 (Dec. 15, 1994).
Chung et al., *Planta Med.*, 70: 256-258 (2004).
Clemmons, *Diabetes Reviews*, 5(4): 353-364 (1997).
Coniff et al., *American Journal of Medicine*, 98: 443-451 (May 1995).
Coniff et al., *Clinical Therapeutics* 19(1): 16-26 (1997).

(Continued)

*Primary Examiner*—Venkataraman Balasubramanian
(74) *Attorney, Agent, or Firm*—Leydig, Voit & Mayer, Ltd.

(57) ABSTRACT

Compounds, pharmaceutical compositions and methods that are useful in the treatment or prevention of metabolic and cell proliferative diseases or conditions are provided herein. In particular, the invention provides compounds which modulate the activity of proteins involved in lipid metabolism and cell proliferation.

57 Claims, No Drawings

OTHER PUBLICATIONS

Farese et al., *Curr. Opin. Lipidol.*, 11: 229-234 (2000).
Garg et al., *Diabetes Reviews*, 5(4): 425-433 (1997).
Haffner, *Diabetes Care*, 21(1): 160-178 (Jan. 1998).
Hsueh et al., *Diabetes Reviews*, 5(4): 343-352 (1997).
Iwamoto et al., *Diabetic Medicine*, 13(4); 365-370 (Apr. 1996).
Jokl et al., *Diabetes Reviews*, 5(4): 316-330 (1997).
Ko et al., *Archives of Pharmacal Research*, 25(4): 446-448 (2002).
Kwiterovich, *The American Journal of Cardiology*, 82(12A): 3U-17U (Dec. 17, 1998).
Laakso et al., *Diabetes Reviews*, 5(4): 294-315 (1997).
Landauer et al., *Journal of Chemical Society:* 3721-3722 (1953).
Lee et al., *Planta Med*, 70: 197-200 (2004).
Lewis et al., *Endocrine Reviews*, 23(2): 201-229 (Apr. 2002).
Lopes-Virella et al., *Diabetes Reviews*, 5(4): 410-424 (1997).
Lyons et al., *Diabetes Reviews*, 5(4):365-391 (1997).
Mahler et al., *Journal of Clinical Endocrinology & Metabolism*, 84(4): 1165-1171 (Apr. 1999).
Malloy et al., "Chapter 4: A Risk Factor for Atherosclerosis: Triglyceride-rich Lipoproteins," *Advances in Internal Medicine*, 47: 111-136 (Mosby, Inc., 2001).
Nahm et al., *Tetrahedron Letters*, 22(39): 3815-3818 (1981).
Oelkers et al., *Journal of Biological Chemistry*, 273(41): 26765-26771 (Oct. 9, 1998).
Purnell et al., *Diabetes Reviews*, 5(4): 434-444 (1997).
Rustan et al., *Journal of Lipid Research*, 29: 1417-1426 (1988).
Smith et al., *Nature Genetics*, 25: 87-90 (May 2000).
Tomoda et al., *The Journal of Antibiotics*, 48(9): 937-941 (Sep. 1995).
Tomoda et al., *The Journal of Antibiotics*, 52(8): 689-694 (Aug. 1999).
Turner et al., "Insulin resistance, impaired glucose tolerance and non-insulin-dependent diabetes, pathologic mechanisms and treatment: Current status and therapeutic possibilities," *Progress in Drug Research*, 51: 33-94 (Basel, Switzerland: Birkhäuser Verlag, 1998).
United Kingdom Prospective Diabetes Study (UKPDS) Group, *Diabetes Care*, 21(1): 87-92 (Jan. 1998).
Wermuth (ed.), "Molecular Variations Based on Isosteric Replacements," *The Practice of Medicinal Chemistry*, 13: 203-237 (London: Academic Press Limited, 1996).
Chen et al., *Diabetes*, 54(12): 3379-3386 (2005).
Gaziano et al., *Circulation*, 96: 2520-2525 (1997).
Kim et al., *J. Medicinal Chemistry*, 17(3): 369-371 (1974).
Robbins et al., "Blood Vessels" in *Pathologic Basis of Disease*, 6th ed., W. B. Saunders Company: Philadelphia, 498-510 (1999).
Subauste et al., *Curr. Drug Targets Immune Endocr. Metabol. Disord.*, 3(4): 263-270 (2003).
Turkish et al., *J. Biol. Chem.*, 280(15): 14755-14764 (2005).
Vaziri et al., *Kidney Int.*, 66(1): 262-267 (2004).
Yu et al., *Hepatology*, 42(2): 362-371 (2005).

* cited by examiner

FUSED BICYCLIC NITROGEN-CONTAINING HETEROCYCLES

CROSS-REFERENCES TO RELATED APPLICATIONS

This application claims the benefit of U.S. Provisional Application Ser. No. 60/428,600, filed Nov. 22, 2002, the content of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

Triglycerides represent the major form of energy stored in eukaryotes. Disorders or imbalances in triglyceride metabolism are implicated in the pathogenesis of and increased risk for obesity, insulin resistance syndrome and type II diabetes, nonalcoholic fatty liver disease and coronary heart disease (see, Lewis, et al, *Endocrine Reviews* (2002) 23:201 and Malloy and Kane, *Adv Intern Med* (2001) 47:111). Additionally, hypertriglyceridemia is often an adverse consequence of cancer therapy (see, Bast, et al. *Cancer Medicine*, 5th Ed., (2000) B. C. Decker, Hamilton, Ontario, Calif.).

A key enzyme in the synthesis of triglycerides is acyl CoA:diacylglycerol acyltransferase, or DGAT. DGAT is a microsomal enzyme that is widely expressed in mammalian tissues and that catalyzes the joining of 1,2-diacylglycerol and fatty acyl CoA to form triglycerides at the endoplasmic reticulum (reviewed in Chen and Farese, *Trends Cardiovasc Med* (2000) 10:188 and Farese, et al, *Curr Opin Lipidol* (2000) 11:229). It was originally thought that DGAT uniquely controlled the catalysis of the final step of acylation of diacylglycerol to triglyceride in the two major pathways for triglyceride synthesis, the glycerol phosphate and monoacylglycerol pathways. Because triglycerides are considered essential for survival, and their synthesis was thought to occur through a single mechanism, inhibition of triglyceride synthesis through inhibiting the activity of DGAT has been largely unexplored.

Genes encoding mouse DGAT1 and the related human homologs ARGP1 and ARGP2 now have been cloned and characterized (Cases, et al, *Proc Natl Acad Sci* (1998) 95:13018; Oelkers, et al, *J Biol Chem* (1998) 273:26765). The gene for mouse DGAT1 has been used to create DGAT knock-out mice to better elucidate the function of the DGAT gene. Unexpectedly, mice unable to express a functional DGAT enzyme (Dgat–/–mice) are viable and still able to synthesize triglycerides, indicating that multiple catalytic mechanisms contribute to triglyceride synthesis (Smith, et al, *Nature Genetics* (2000) 25:87). Other enzymes that catalyze triglyceride synthesis, for example, DGAT2 and diacylglycerol transacylase, also have been identified (Buhman, *J Biol Chem*, supra and Cases, et al, *J Biol Chem* (2001) 276:38870).

Significantly, Dgat–/–mice are resistant to diet-induced obesity and remain lean. Even when fed a high fat diet (21% fat) Dgat–/–mice maintain weights comparable to mice fed a regular diet (4% fat) and have lower total body triglyceride levels. The obesity resistance in Dgat–/–mice is not due to deceased caloric intake, but the result of increased energy expenditure and decreased resistance to insulin and leptin (Smith, et al, *Nature Genetics*, supra; Chen and Farese, *Trends Cardiovasc Med*, supra; and Chen, et al, *J Clin Invest* (2002) 109:1049). Additionally, Dgat–/–mice have reduced rates of triglyceride absorption (Buhman, et al, *J Biol Chem* (2002) 277:25474). In addition to improved triglyceride metabolism, Dgat–/–mice also have improved glucose metabolism, with lower glucose and insulin levels following a glucose load, in comparison to wild-type mice (Chen and Farese, *Trends Cardiovasc Med*, supra).

The finding that multiple enzymes contribute to catalyzing the synthesis of triglyceride from diacylglycerol is significant, because it presents the opportunity to modulate one catalytic mechanism of this biochemical reaction to achieve therapeutic results in an individual with minimal adverse side effects. Compounds that inhibit the conversion of diacylglycerol to triglyceride, for instance by specifically inhibiting the activity of the human homolog of DGAT1, will find use in lowering corporeal concentrations and absorption of triglycerides to therapeutically counteract the pathogenic effects caused by abnormal metabolism of triglycerides in obesity, insulin resistance syndrome and overt type II diabetes, congestive heart failure and atherosclerosis, and as a consequence of cancer therapy.

Because of the ever increasing prevalence of obesity, type II diabetes, heart disease and cancer in societies throughout the world, there is a pressing need in developing new therapies to effectively treat and prevent these diseases. Therefore there is an interest in developing compounds that can potently and specifically modulate a single catalytic mechanism of the enzymatic conversion of diacylglycerol to triglyceride. Of particular promise are compounds that specifically inhibit the catalytic activity of DGAT1 and its other mammalian homologs.

BRIEF SUMMARY OF THE INVENTION

The present invention provides fused bicyclic nitrogen-containing heterocyclic compounds that are useful for treating or preventing conditions and disorders associated with DGAT in animals, particularly humans.

In general, the compounds of the present invention are represented by the formula (I):

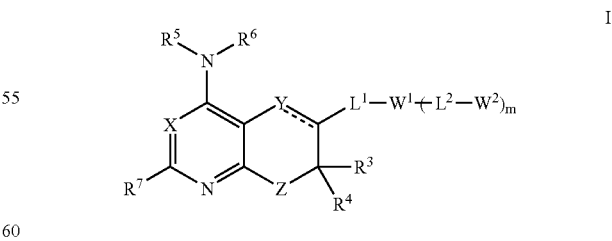

I or a pharmaceutically acceptable salt, prodrug or stereoisomer thereof, in which the letter X represents $C(R^1)$ or N; the letter Y represents $C(R^1)$, $C(R^2)(R^2)$, N or N(2); and the letter Z represents O or S. The symbol $L^1$ represents a bond, $(C_1-C_4)$alkylene, $(C_2-C_4)$alkenylene, O or $N(R^a)C(O)$; and $W^1$ represents a substituted or unsubstituted member selected from cyclo($C_3$-$C_8$)alkyl, heterocyclo($C_3$-$C_8$)alkyl, aryl and heteroaryl. The subscript m is 0 or 1, indicating the presence (m is 1) or absence (m is 0) of the additional moiety, $L^2$-$W^2$. For those embodiments in which m is 1, the symbol $L^2$ represents a bond, O, ($C_1$-$C_4$)alkylene, ($C_2$-$C_4$)alkenylene, ($C_1$-$C_4$)heteroalkylene or N($R^a$)C(O); and the symbol $W^2$ represents a substituted or unsubstituted member selected from cyclo($C_3$-$C_8$)alkyl, heterocyclo($C_3$-$C_8$)alkyl, aryl and heteroaryl.

The remaining substituents, $R^1$ through $R^7$ and $R^a$ and $R^b$ have the following meanings: each $R^1$ is independently selected from H, ($C_1$-$C_8$)alkyl, ($C_2$-$C_8$)alkenyl, ($C_2$-$C_8$)alkynyl, fluoro($C_1$-$C_8$)alkyl, aryl, aryl($C_1$-$C_4$)alkyl, C(O)$R^a$, $CO_2R^a$ and C(O)NR$^a$R$^b$; each $R^2$ is independently selected from H, ($C_1$-$C_8$)alkyl, ($C_2$-$C_8$)alkenyl, ($C_2$-$C_8$)alkynyl, fluoro($C_1$-$C_8$)alkyl, C(O)$R^a$, $CO_2R^a$, C(O)NR$^a$R$^b$, aryl and aryl($C_1$-$C_4$)alkyl; $R^3$ and $R^4$ are independently selected from H, ($C_1$-$C_8$)alkyl, ($C_2$-$C_8$)alkenyl, ($C_2$-$C_8$)alkynyl, C(O)$R^a$, $CO_2R^a$, C(O)NR$^a$R$^b$ and ($C_1$-$C_4$)alkylene-O$R^a$; $R^5$ and $R^6$ are independently selected from H, ($C_1$-$C_8$)alkyl, ($C_2$-$C_8$)alkenyl, ($C_2$-$C_8$)alkynyl, C(O)$R^a$ and $CO_2R^a$; $R^7$ is selected from H, ($C_1$-$C_8$)alkyl, halo($C_1$-$C_4$)alkyl, ($C_2$-$C_8$)alkenyl, ($C_2$-$C_8$)alkynyl, C(O)$R^a$, O$R^a$ and NR$^a$R$^b$; and each $R^a$ and $R^b$ is independently selected from H, ($C_1$-$C_8$)alkyl, ($C_2$-$C_8$)alkenyl, ($C_2$-$C_8$)alkynyl, fluoro($C_1$-$C_8$)alkyl, aryl and aryl($C_1$-$C_4$)alkyl.

The dotted line indicates an optional bond. In other optional embodiments, $R^3$ and $R^4$ may be combined to form a 3-, 4-, 5- or 6-membered spiro ring; $R^2$, $R^3$ or $R^4$ may be combined with $W^1$ to form a 5-, 6- or 7-membered fused ring having from 0 to 3 heteroatoms selected from the group consisting of N, O and S; $R^5$ and $R^6$ may be combined with the nitrogen atom to which each is attached to form a 5-, 6- or 7-membered ring; when X is C($R^1$), $R^5$ or $R^6$ may be combined with $R^1$ to form a 5-, 6- or 7-membered fused ring containing the nitrogen atom to which $R^5$ or $R^6$ is attached; when X is C($R^1$), $R^7$ may be combined with $R^1$ to form a 5-, 6- or 7-membered fused ring; $R^2$ or $R^1$, when provided as a part of Y, can be combined with $R^5$ to form a 5- or 6-membered ring with the nitrogen to which $R^5$ is attached, optionally bearing an oxo moiety; and when m is 1 and $L^2$ is a bond, a substituent on $W^2$ may be combined with a substituent on $W^1$ to form a 5-, 6- or 7-membered ring fused to $W^1$ and spiro or fused to $W^2$, wherein the ring is saturated or unsaturated and has 0, 1 or 2 heteroatoms selected from N, O and S as ring members.

Within the above compounds of formula I, the compound is other than

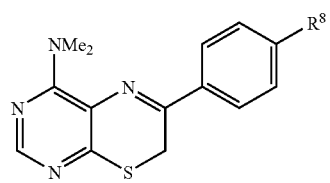

wherein $R^8$ is H, $NO_2$, Cl, methoxy, methyl or phenyl.

Unless otherwise indicated, the compounds provided in the above formula are meant to include all pharmaceutically acceptable salts, prodrugs or stereoisomers thereof.

The present invention also provides pharmaceutical compositions comprising a compound of the invention and a pharmaceutically acceptable carrier or excipient.

The present invention also provides methods for treating or preventing a condition or disorder selected from the group consisting of obesity, diabetes, anorexia nervosa, bulimia, cachexia, syndrome X, metabolic syndrome, insulin resistance, hyperglycemia, hyperuricemia, hyperinsulinemia, hypercholesterolemia, hyperlipidemia, dyslipidemia, mixed dyslipidemia, hypertriglyceridemia, nonalcoholic fatty liver disease, atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, vascular stenosis, solid tumors, skin cancer, melanoma, lymphoma, breast cancer, lung cancer, colorectal cancer, stomach cancer, esophageal cancer, pancreatic cancer, prostate cancer, kidney cancer, liver cancer, bladder cancer, cervical cancer, uterine cancer, testicular cancer and ovarian cancer, comprising administering to a subject in need thereof a therapeutically effective amount of a compound of the invention. For this method and the methods provided below, the compound of the invention will, in some embodiments, be administered in combination with a second therapeutic agent.

The present invention also provides methods for treating or preventing conditions and disorders associated with DGAT, comprising administering to a subject in need thereof a therapeutically effective amount of a compound of the invention.

The present invention further provides methods for treating or preventing conditions and disorders mediated by DGAT, comprising administering to a subject in need thereof a therapeutically effective amount of a compound of the invention.

The present invention further provides methods for modulating DGAT comprising contacting a cell with a compound of the invention.

BRIEF DESCRIPTION OF THE DRAWINGS

Not Applicable

DETAILED DESCRIPTION OF THE INVENTION

Abbreviations and Definitions

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

As used herein, "diabetes" refers to type I diabetes mellitus juvenile onset diabetes, insulin dependent-diabetes mellitus or IDDM) or type II diabetes mellitus (non-insulin-dependent diabetes mellitus or NIDDM), preferably, type II diabetes.

As used herein, "syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

As used herein, the term "obesity" refers to the excessive accumulation of body fat. Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Metabolic disorders, such as hyperlidemia and diabetes, and cardiovascular disorders, such as hypertension and coronary artery disease, are commonly associated with obesity.

The term "modulate" refers to the ability of a compound to increase or decrease the function, or activity, of DGAT. "Modulation", as used herein in its various forms, is intended to encompass antagonism, agonism, partial antagonism and/or partial agonism of the activity associated with DGAT. DGAT inhibitors are compounds that, e.g., bind to, partially or totally block stimulation, decrease, prevent, delay activation, inactivate, desensitize, or down regulate signal transduction. DGAT activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "DGAT" refers to the acyl CoA:diacylglycerol acyltransferase or a variant thereof, unless otherwise stated. DGAT variants include proteins substantially homologous to native DGAT, i.e., proteins having one or more naturally or non-naturally occurring amino acid deletions, insertions or substitutions (e.g., DGAT derivatives, homologs and fragments). The amino acid sequence of a DGAT variant preferably is at least about 80% identical to a native DGAT, more preferably at least about 90% identical, and most preferably at least about 95% identical.

As used herein, the term "DGAT-associated condition or disorder" refers to a condition or disorder associated with inappropriate, e.g., less than or greater than normal, DGAT activity and at least partially responsive to or affected by DGAT modulation (e.g., a DGAT inhibitor or antagonist results in some improvement in patient well-being in at least some patients). Inappropriate DGAT functional activity might arise as the result of DGAT expression in cells which normally do not express DGAT decreased DGAT expression or increased DGAT expression. A DGAT-associated condition or disorder may include a DGAT-mediated condition or disorder.

As used herein, the term "DGAT-mediated condition or disorder" and the like refers to a condition or disorder characterized by inappropriate, e.g., less than or greater than normal, DGAT activity. A DGAT-mediated condition or disorder may be completely or partially mediated by inappropriate DGAT activity. However, a DGAT-mediated condition or disorder is one in which modulation of DGAT results in some effect on the underlying condition or disease (e.g., a DGAT inhibitor or antagonist results in some improvement in patient well-being in at least some patients).

The term "alkyl," by itself or as part of another substituent, means, unless otherwise stated, a straight or branched chain, or cyclic hydrocarbon radical, or combination thereof, which is fully saturated, having the number of carbon atoms designated (i.e. $C_1$-$C_8$ means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. $C_2$-$C_8$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. Similarly, "alkenylene" and "alkynylene" refer to unsaturated versions of alkylene, having at least one double bond or a triple bond, respectively. For example, "alkenylene" is meant to include —$CH_2CH$=$CHCH_2$—, while "alkynylene" is meant to include —$CH_2C$≡$CCH_2$—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C$_3$-C$_8$ means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C$_1$-C$_4$)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C$_1$-C$_4$)alkyl" is meant to include trifluoromethyl, pentachloroethyl, 1,1,1-trifluoro-2-bromo-2-chloroethyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term "heteroaryl" refers to aryl groups (or rings) that contain from one to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R', —CN and —NO$_2$, in a number ranging from zero to three, with those groups having zero, one or two substituents being particularly preferred. R', R" and R'" each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Additionally, the above substituents can be attached to the alkyl group (or alkylene, cycloalkyl and the like) via a spacer of from one to four carbon atoms, generally present as methylene or branched unsubstituted alkylene (e.g. —CH$_2$CH$_2$— and —CH(CH$_3$)CH$_2$—), alkenylene or alkynylene group. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R', —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$. Additionally, each of the preferred and further preferred substituents can be attached to the alkyl group (or alkylene, cycloalkyl and the like) via a spacer of from one to four carbon atoms, generally present as methylene or branched unsubstituted alkylene groups.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO$_2$R', —NR'—C(O)NR"R''', —NR'—SO$_2$NR"R''', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R', —N$_3$, —CH(Ph)$_2$, perfluoro(C$_1$-C$_4$)alkoxy and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl and heteroaryl, (unsubstituted aryl)-(C$_1$-C$_4$)alkyl and (unsubstituted aryl)oxy-(C$_1$-C$_4$)alkyl. When the aryl group is 1,2,3,4-tetrahydronaphthalene, it may be substituted with a substituted or unsubstituted (C$_3$-C$_7$)spirocycloalkyl group. The (C$_3$-C$_7$)spirocycloalkyl group may be substituted in the same manner as defined herein for "cycloalkyl". Typically, an aryl or heteroaryl group will have from zero to three substituents, with those groups having two or fewer substituents being preferred in the present invention. In one embodiment of the invention, an aryl or heteroaryl group will be unsubstituted or monosubstituted. In another embodiment, an aryl or heteroaryl group will be unsubstituted. When substituted, the above substituents can be attached to the aryl or heteroaryl group via a spacer of from one to four carbon atoms, generally present as methylene or branched unsubstituted alkylene groups (e.g. —CH$_2$CH$_2$— and —CH(CH$_3$)CH$_2$—).

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R', —N$_3$, —CH(Ph)$_2$, perfluoro(C$_1$-C$_4$)alkoxy and perfluoro(C$_1$-C$_4$)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR'SO$_2$R', perfluoro(C$_1$-C$_4$)alkoxy and perfluoro(C$_1$-C$_4$)alkyl. As above, these substituents are optionally attached to the aryl or heteroaryl moiety via a spacer of from one to four methylene groups.

It is to be understood that the substituent —CO$_2$H, as used herein, includes bioisosteric replacements therefor, such as:

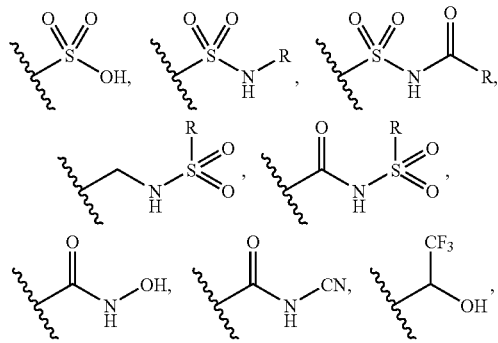

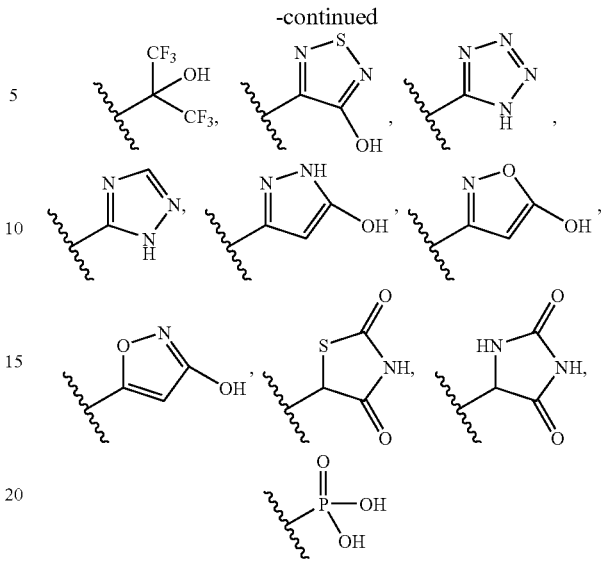

and the like. See, e.g., *The Practice of Medicinal Chemistry*; Wermuth, C. G., Ed.; Academic Press: New York, 1996; p. 203.

Two of the substituents on adjacent atoms of the aryl or heteroaryl ring may optionally be replaced with a substituent of the formula —T—C(O)—(CH$_2$)q—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)r—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)t—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the free acid form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the free base form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

It is to be understood that when a compound of the invention contains one or more asymmetric carbon atoms (optical centers) or double bonds, the present invention includes individual stereoisomers and geometric isomers as well as mixtures thereof. For example, when m is 1 and $W^2$ is substituted cyclo($C_3$-$C_8$)alkyl (e.g., A.4 below), the 1,4-cis and trans isomers and racemates thereof are intended to be within the scope of the invention.

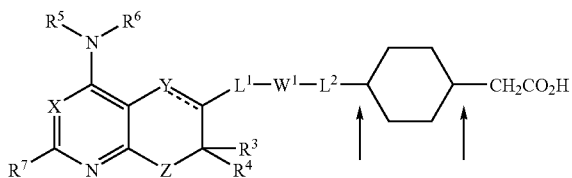

A.4

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

EMBODIMENT OF THE INVENTION

Compounds

In one aspect, the present invention provides compounds of formula (I):

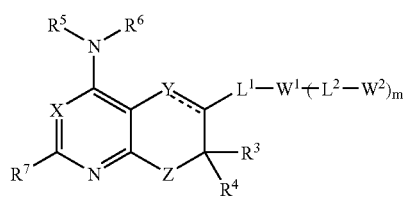

or a pharmaceutically acceptable salt, prodrug or stereoisomer thereof. In this formula, the letter X represents $C(R^1)$ or N; the letter Y represents $C(R^1)$, $C(R^2)(R^2)$, N or $N(R^2)$; and the letter Z represents O or S.

Turning next to the substituents on the bicyclic heteroaromatic nucleus, the symbol $L^1$ represents a bond, ($C_1$-$C_4$) alkylene, ($C_2$-$C_4$)alkenylene, O or $N(R^a)C(O)$; and $W^1$ represents a substituted or unsubstituted member selected from cyclo($C_3$-$C_8$)alkyl, heterocyclo($C_3$-$C_8$)alkyl, aryl and heteroaryl. The subscript m is 0 or 1, indicating the presence (m is 1) or absence (m is 0) of the additional moiety, $L^2$-$W^2$. For those embodiments in which m is 1, the symbol L2 represents a bond, O, ($C_1$-$C_4$)alkylene, ($C_2$-$C_4$)alkenylene, ($C_1$-$C_4$)heteroalkylene or $N(R^a)C(O)$; and the symbol $W^2$ represents a substituted or unsubstituted member selected from cyclo($C_3$-$C_8$)alkyl, heterocyclo($C_3$-$C_8$)alkyl, aryl and heteroaryl. When m is 1 and $L^2$ is a bond, a substituent on $W^2$ may be combined with a substituent on $W^1$ to form a 5-, 6- or 7-membered ring fused to $W^1$ and spiro or fused to $W^2$, wherein the ring is saturated or unsaturated and has 0, 1 or 2 heteroatoms selected from N, O and S as ring members. Substituents for each of $W^1$ and $W^2$ can be selected from the substituents provided in the definitions above as well as the recited substituents for various specific embodiments below.

The remaining substituents, $R^1$ through $R^7$ and $R^a$ and $R^b$ have the following meanings: each $R^1$ is independently selected from H, ($C_1$-$C_8$)alkyl, ($C_2$-$C_8$)alkenyl, ($C_2$-$C_8$)alkynyl, fluoro($C_1$-$C_8$)alkyl, aryl, aryl($C_1$-$C_4$)alkyl, $C(O)R^a$, $CO_2R^a$ and $C(O)NR^aR^b$; each $R2$ is independently selected from H, ($C_1$-$C_8$)alkyl, ($C_2$-$C_8$)alkenyl, ($C_2$-$C_8$)alkynyl, fluoro($C_1$-$C_8$)alkyl, $C(O)R^a$, $CO_2R^a$, $C(O)NR^aR^b$, aryl and aryl($C_1$-$C_4$)alkyl; $R^3$ and $R^4$ are independently selected from H, ($C_1$-$C_8$)alkyl, ($C_2$-$C_8$)alkenyl, ($C_2$-$C_8$)alkynyl, $C(O)R^a$, $CO_2R^a$, $C(O)NR^aR^b$ and ($C_1$-$C_4$)alkylene-$OR^a$; $R^5$ and $R^6$ are independently selected from H, ($C_1$-$C_8$)alkyl, ($C_2$-$C_8$) alkenyl, ($C_2$-$C_8$)alkynyl, $C(O)R^a$ and $CO_2R^a$; $R^7$ is selected from H, ($C_1$-$C_8$)alkyl, halo($C_1$-$C_4$)alkyl, ($C_2$-$C_8$)alkenyl, ($C_2$-$C_8$)alkynyl, $C(O)R^a$, $OR^a$ and $NR^aR^b$; and each $R^a$ and $R^b$ is independently selected from H, ($C_1$-$C_8$)alkyl, ($C_2$-$C_8$) alkenyl, ($C_2$-$C_8$)alkynyl, fluoro($C_1$-$C_8$)alkyl, aryl and aryl ($C_1$-$C_4$)alkyl.

The dotted line indicates an optional bond. In other optional embodiments, $R^3$ and $R^4$ may be combined to form a 3-, 4-, 5- or 6-membered spiro ring; $R^2$, $R^3$ or $R^4$ may be combined with $W^1$ to form a 5-, 6- or 7-membered fused ring having from 0 to 3 heteroatoms selected from the group consisting of N, O and S; $R^5$ and $R^6$ may be combined with the nitrogen atom to which each is attached to form a 5-, 6- or 7-membered ring; $R^2$ or $R^1$, when provided as a part of Y, can be combined with $R^5$ to form a 5- or 6-membered ring with the nitrogen to which $R^5$ is attached, optionally bearing an oxo moiety; when X is $C(R^1)$, $R^5$ or $R^6$ may be combined with $R^1$ to form a 5-, 6- or 7-membered fused ring containing the nitrogen atom to which $R^5$ or $R^6$ is attached; and when X is $C(R^1)$, $R^7$ may be combined with $R^1$ to form a 5-, 6- or 7-membered fused ring.

In preferred embodiments, $R^1$ and $R^2$ are each independently H or $(C_1-C_8)$alkyl; $R^3$ and $R^4$ are each independently H or $(C_1-C_4)$alkyl; $R^5$ and $R^6$ are each H, $(C_1-C_4)$alkyl or are combined with the nitrogen to which each is attached to form a 5- or 6-membered ring (e.g. a pyrollidine or piperidine ring); and $R^7$ is H, $(C_1-C_8)$alkyl or halo$(C_1-C_4)$alkyl.

Within the above compounds of formula (I), the compound is other than

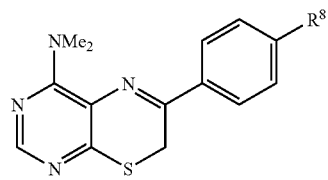

wherein $R^8$ is H, $NO_2$, Cl, methoxy, methyl or phenyl.

Within formula (I) above, a number of groups of embodiments are preferred.

In one group of preferred embodiments, X is N. Still more preferably, X is N and Z is O. Within this group of embodiments, $L^1$ is preferably a bond and $W^1$ is a substituted or unsubstituted member selected from benzene, pyridine, thiophene, oxazole, thiazole, benzoxazole, benzthiazole, benzofuran, benzothiophene, $(C_4-C_7)$cycloalkane, $(C_5-C_7)$ cycloalkene, 1,2,3,4-tetrahydronaphthalene and indane. Still more preferably, $W^1$ is a substituted or unsubstituted member selected from benzene, pyridine, thiophene, $(C_4-C_7)$ cycloalkane, 1,2,3,4-tetrahydronaphthalene and indane. For those embodiments in which $W^1$ is a substituted benzene, the substituents ($R^c$ below), other than $L^2-W^2$, are preferably selected from halogen (including F, Cl, Br and I), $R^{c1}$, $OR^{c1}$, $N(R^{c1})_2$, $SR^{c1}$, $NO_2$, CN, $(C_1-C_8)$haloalkyl and $(C_1-C_8)$ haloalkoxy, wherein each $R^{c1}$ group is independently H, $(C_1-C_8)$alkyl, $(C_2-C_8)$alkenyl or $(C_2-C_8)$alkynyl, and optionally, two $R^{c1}$ groups attached to a common nitrogen atom are combined to form a five- or six membered ring. Additionally, the substituted benzene will preferably have from one to four substituents, more preferably one or two substitutents and most preferably one substituent. Substituents for each of $W^1$ and $W^2$ can be selected from the substituents provided in the definitions above as well as the recited substituents for various specific embodiments below.

In one group of specific embodiments, the subscript m is 0 and $L^1$ is a bond. Still more preferably, $W^1$ is selected from a substituted or unsubstituted benzene, pyridine, thiophene, oxazole, thiazole, benzoxazole, benzthiazole, benzofuran, benzothiophene, $(C_4-C_7)$cycloalkane, $(C_5-C_7)$cycloalkene, 1,2,3,4-tetrahydronaphthalene and indane. Still more preferably, $W^1$ is a substituted or unsubstituted member selected from benzene, pyridine, thiophene, $(C_4-C_7)$cycloalkane, 1,2, 3,4-tetrahydronaphthalene and indane. Even further preferred are those embodiments depicted as formulae Ia, Ib, Ic, Id, Ie, If and Ig below:

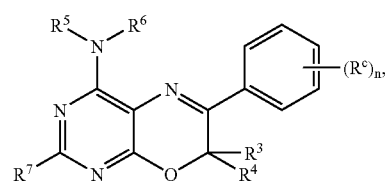

Ia

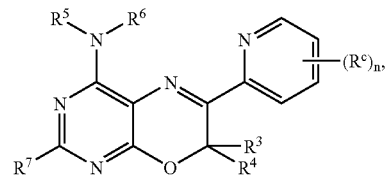

Ib

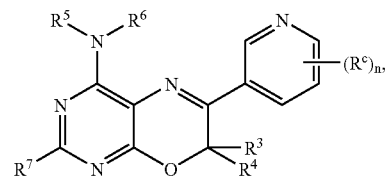

Ic

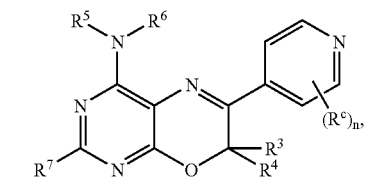

Id

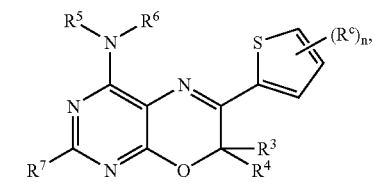

Ie

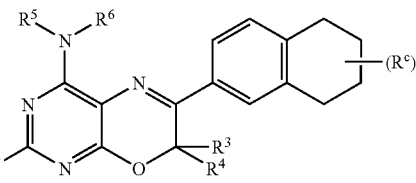

If

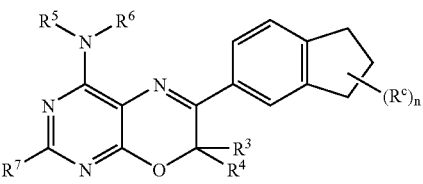

Ig wherein the subscript n is an integer of from 0 to 4 and each $R^c$ represents a substituent independently selected from halogen (including F, Cl, Br and I), $R^{c1}$, $OR^{c1}$, $N(R^{c1})_2$, $SR^{c1}$, $NO_2$, CN, $(C_1-C_8)$haloalkyl and $(C_1-C_8)$haloalkoxy, wherein each $R^{c1}$ group is independently H, $(C_1-C_8)$alkyl, $(C_2-C_8)$alkenyl or $(C_2-C_8)$alkynyl and when $R^c$ is $N(R^{c1})_2$, the two $R^{c1}$ groups may be combined to form a five- or six-membered ring. Optionally, for If and Ig, two $R^{c1}$ groups may be combined to form a 3-, 4-, 5-, 6- or 7-membered optionally substituted spirocyclic ring. The remaining substitutents have the meanings provided above with respect to the general formula I.

In a related group of specific embodiments, X is N, Z is O, $L^1$ is preferably a bond, $W^1$ is a substituted or unsubstituted member selected from benzene, pyridine, thiophene, oxazole, thiazole, benzoxazole, benzthiazole, benzofuran, benzothiophene, $(C_4-C_7)$cycloalkane, $(C_5-C_7)$cycloalkene, 1,2,3,4-tetrahydronaphthalene and indane, and m is 1. In this group of embodiments, $L^2$ is preferably a bond, O, or a $(C_1-C_4)$heteroalkylene (e.g., —OCH$_2$—, —OCH$_2$CH$_2$—, —NHCH$_2$—) and $W^2$ is a substituted or unsubstituted member selected from benzene, pyridine and $(C_4-C_7)$cycloalkane.

In one group of particularly preferred embodiments, the compound is selected from the group:

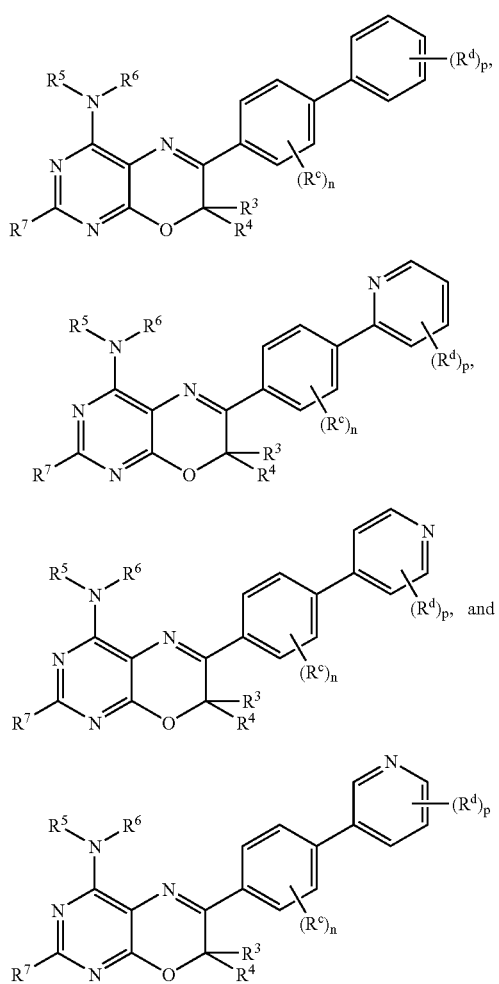

wherein the subscript n is an integer of from 0 to 4 and each $R^c$ represents a substituent independently selected from halogen (including F, Cl, Br and I), $R^{c1}$, $OR^{c1}$, $N(R^{c1})_2$, $SR^{c1}$, $NO_2$, CN, $(C_1-C_8)$haloalkyl and $(C_1-C_8)$haloalkoxy, wherein each $R^{c1}$ group is independently H, $(C_1-C_8)$alkyl, $(C_2-C_8)$alkenyl or $(C_2-C_8)$alkynyl, and optionally, two $R^{c1}$ groups attached to a common nitrogen atom are combined to form a five- or six membered ring. Additionally, the subscript p is an integer of from 0 to 4, more preferably 0, 1 or 2, and each $R^d$ is a substituent independently selected from halogen (including F, Cl, Br and I), $R^{d1}$, $OR^{d1}$, $N(R^{d1})_2$, —(CH$_2$)$_t$—S(O)$_u$R$^e$, NO$_2$, CN, $(C_1-C_8)$haloalkyl, $(C_1-C_8)$ haloalkoxy, aryl$(C_1-C_4)$alkyl, heteroaryl$(C_1-C_4)$alkyl, —CH(R$^f$)—CO$_2$R$^e$, —C(R$^f$)$_2$—CO$_2$R$^e$, —C(O)CO$_2$R$^e$, —(CH$_2$)$_t$—CO$_2$R$^e$, —(CH$_2$)$_t$—C(O)R$^e$, —(CH$_2$)$_t$—C(O)NR$^e$R$^f$, —(CH$_2$)$_t$—NHSO$_2$R$^e$, —(CH$_2$)$_t$—SO$_2$NR$^e$R$^f$, —(CH$_2$)$_t$—NR$^e$R$^f$, —(CH$_2$)$_t$—OR$^e$, —(CH$_2$)$_t$—NHSO$_2$NHCO$_2$R$^e$, —(CH$_2$)$_t$—NHSO$_2$NR$^e$R$^f$, —(CH$_2$)$_t$—CONHSO$_2$R$^e$, —(CH$_2$)$_t$—W$^3$, —(CH$_2$)$_t$—NHCO$_2$R$^e$, —(CH$_2$)$_t$—NR$^f$COR$^e$, —(CH$_2$)$_t$—NHCONR$^e$R$^f$ and —(CH$_2$)$_t$—NHCO—(CH$_2$)$_t$—OCOR$^e$, wherein the subscript t in each instance is an integer of from 0 to 8, the subscript u is an integer of from 0 to 2, $R^{d1}$ is selected from H, $(C_1-C_8)$alkyl, $(C_2-C_8)$alkenyl, $(C_2-C_8)$alkynyl and $(C_3-C_8)$cycloalkyl, wherein the aliphatic portion is optionally substituted with OH, CO$_2$H, NH$_2$, CONH$_2$, phenyl, halogen, halo$(C_1-C_4)$alkyl and CO$_2$R$^g$, and optionally two $R^{d1}$ groups attached to a common nitrogen are combined to form a five or six-membered ring; and wherein each $R^e$ and $R^f$ is independently H or $(C_1-C_8)$alkyl or when attached to a common nitrogen atom are combined to form a 5- or 6-membered ring, or are optionally selected from

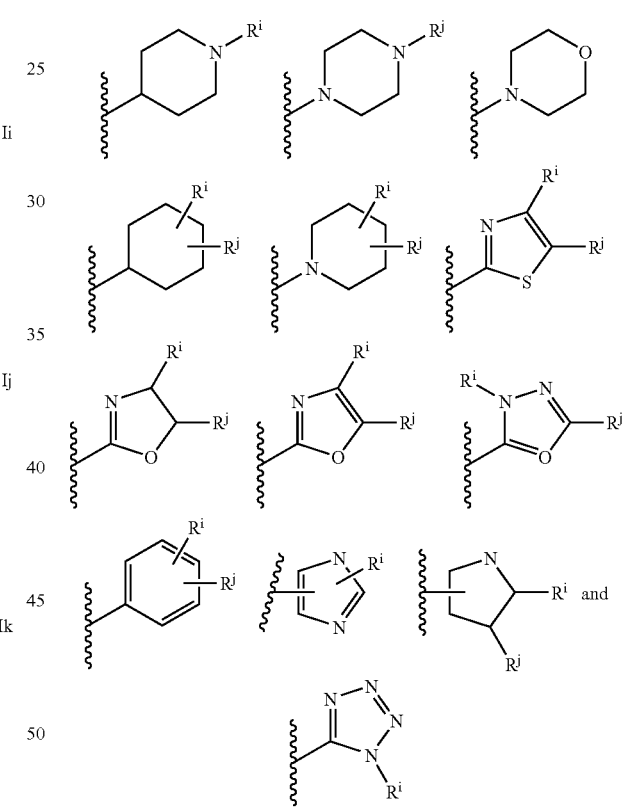

and wherein any alkyl portion of $R^e$ and $R^f$ is optionally substituted with a member selected from OH, COOH, NH$_2$, CONH$_2$, phenyl, dialkylamino and COOR$^g$ wherein $R^g$ is a $(C_1-C_4)$alkyl; and $W^3$ is selected from

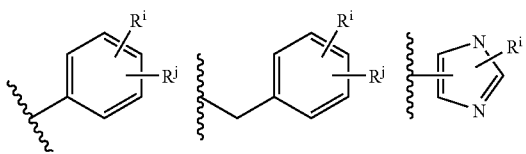

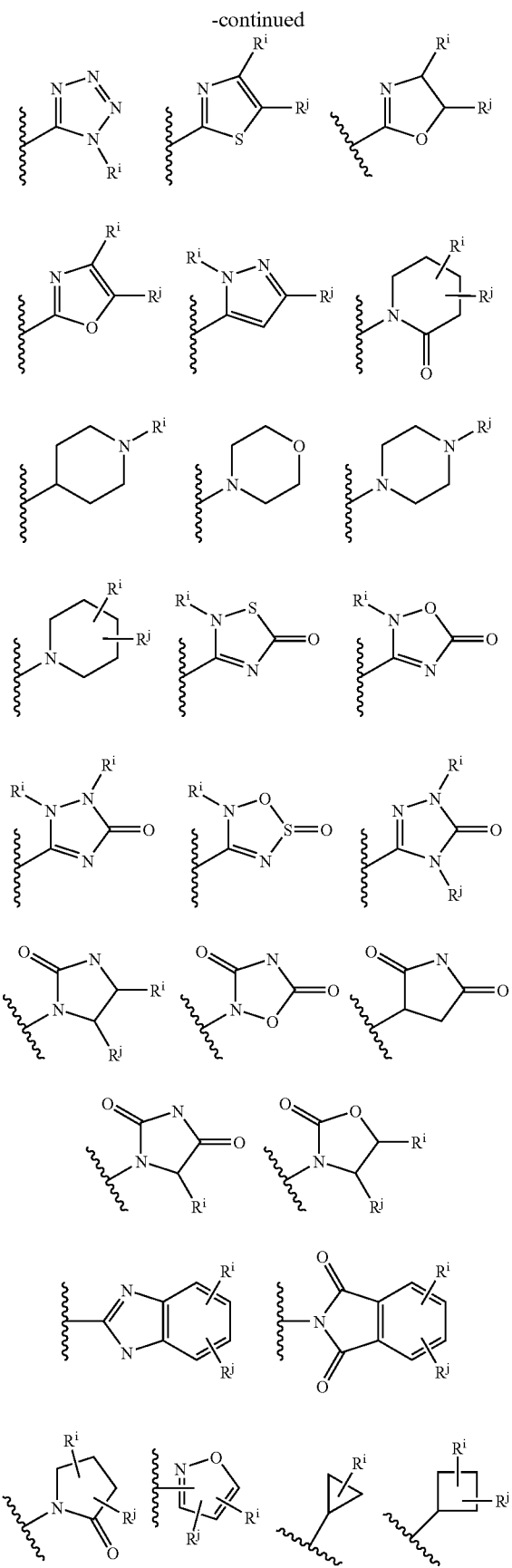

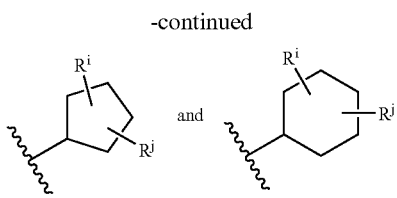

wherein each $R^i$ and each $R^j$ is independently selected from H, OH, COOH, halogen, halo($C_1$-$C_4$)alkyl, hydroxy($C_1$-$C_4$)alkyl, ($C_1$-$C_6$)alkyl, ($C_1$-$C_6$)alkoxy, ($C_1$-$C_6$)alkoxy($C_4$)alkyl and COO($C_1$-$C_4$)alkyl, wherein the aliphatic portions are unsubstituted or optionally substituted with halogen.

In some embodiments, the $R^d$ substituents are selected from halogen (including F, Cl, Br and I), $R^{d1}$, $OR^{d1}$, N($R^{d1}$)$_2$, $SR^{d1}$, $NO_2$, CN, ($C_1$-$C_8$)haloalkyl, ($C_1$-$C_8$)haloalkoxy, aryl($C_1$-$C_4$)alkyl, heteroaryl($C_1$-$C_4$)alkyl, ($C_1$-$C_8$)alkylene-$CO_2R^e$, $C(O)R^e$, $CO_2R^e$, —$CH_2$—$CO_2R^e$, —CH($R^f$)—$CO_2R^e$, —$C(R^f)_2$—$CO_2R^e$, —$CH_2CH_2CO_2$, —C(O)NR$^e$R$^f$, —$CH_2$C(O)NR$^e$R$^f$, —$CH_2CH_2$CONR$^e$R$^f$, —$NHSO_2R^e$, —$CH_2NHSO_2R^e$, —$CH_2CH_2NHSO_2R^e$, —$CH_2SO_2$NR$^e$R$^f$, —$CH_2CH_2SO_2$NR$^e$R$^f$, —$CH_2OH$, —$CH_2$NR$^e$R$^f$, $CH_2CH_2OH$, —$CH_2C(CH_3)_2OH$, —$CH_2$—$W^3$, —$CH_2CH_2$—$W^3$ and —$C(O)CO_2R^e$, wherein each $R^{d1}$, $R^e$, $R^f$ and $W^3$ have the meanings provided above, with respect to formulae Ih, Ii, Ij and Ik, and the remaining substitutents have the meanings provided above with respect to the general formula I.

In still other preferred embodiments, the compound has a formula selected from:

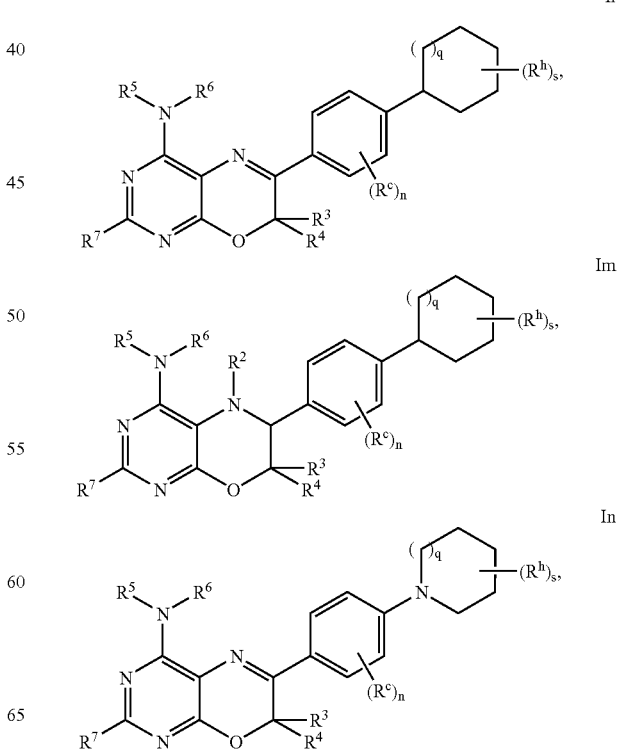

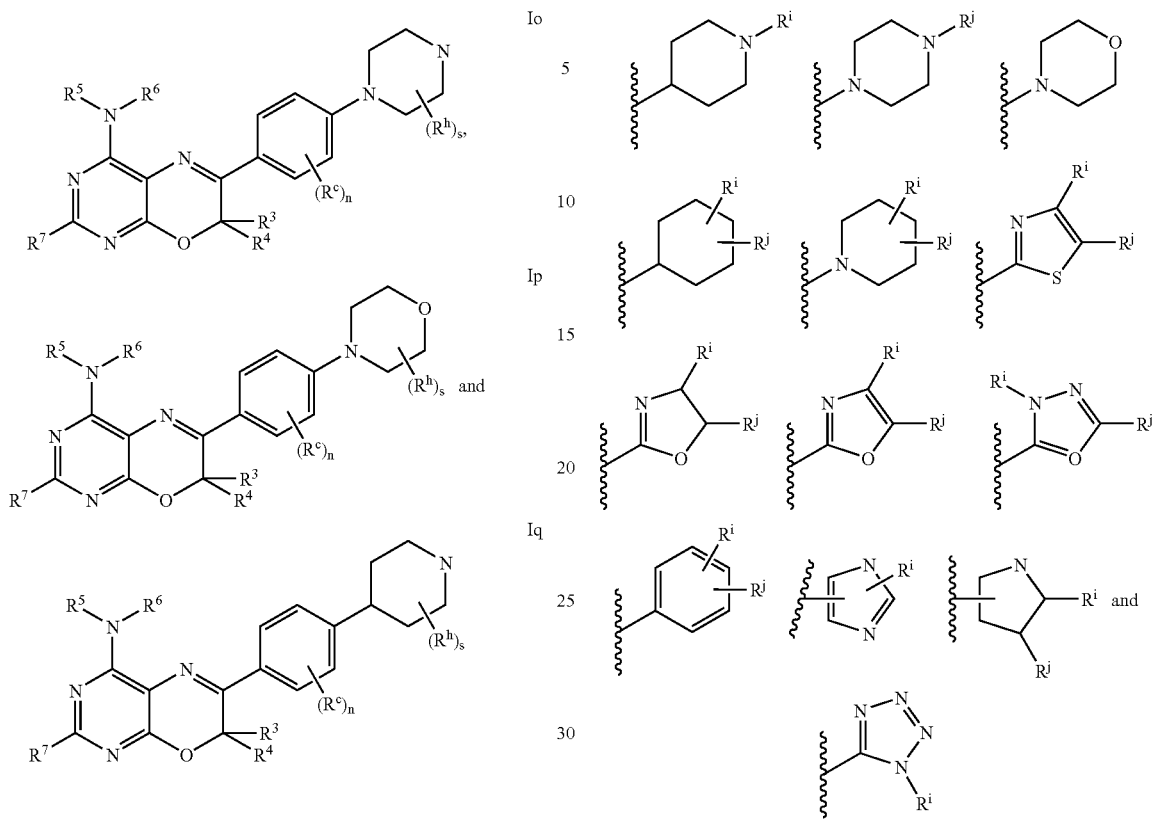

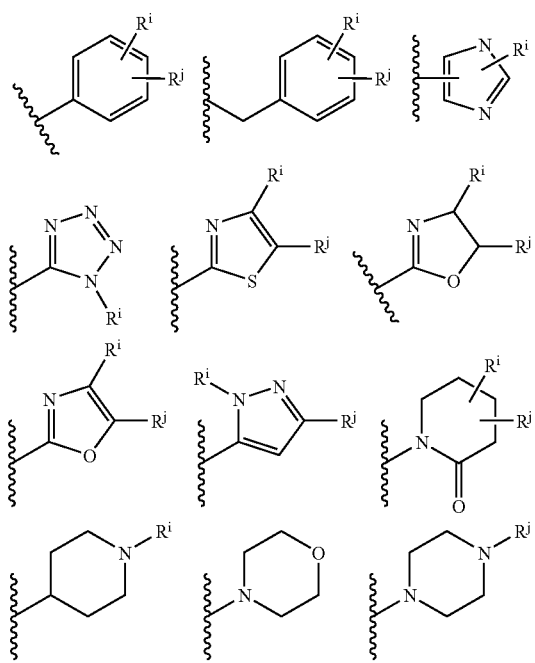

wherein each of $R^2$, $R^3$, $R^4$, $R^5$, $R^6$, $R^7$ and $R^c$, as well as the subscript n have the meanings provided above with respect to formulae Ia-Ik. The subscript q is an integer of from 0 to 3, more preferably, 0 or 1. The subscript s is an integer of from 0 to 4, more preferably 0, 1 or 2, and each $R^h$ is a substituent independently selected from oxo, halogen (including F, Cl, Br and I), $R^{h1}$, $OR^{h1}$, $N(R^{h1})_2$, $-(CH_2)_t-S(O)_uR^e$, $NO_2$, CN, $(C_1-C_8)$haloalkyl, $(C_1-C_8)$haloalkoxy, aryl$(C_1-C_4)$alkyl, heteroaryl$(C_1-C_4)$alkyl, $-CH(R^f)-CO_2R^e$, $-C(R^f)_2-CO_2R^e$, $-C(O)CO_2R^e$, $=CH-CONR^eR^f$, $=CH-CO_2R^e$, $-(CH_2)_t-CO_2R^e$, $-(CH_2)_t-C(O)R^e$, $-(CH_2)_t-C(O)NR^eR^f$, $-(CH_2)_t-NHSO_2R^e$, $-(CH_2)_t-SO_2NR^eR^f$, $-(CH_2)_t-NR^eR^f$, $-(CH_2)_t-OR^e$, $-(CH_2)_t-NHSO_2NHCO_2R^e$, $-(CH_2)_t-NHSO_2NR^eR^f$, $-(CH_2)_t-CONHSO_2R^e$, $-(CH_2)_t-W^3$, $-(CH_2)_t-NHCO_2R^e$, $-(CH_2)_t-NR^fCOR^e$, $-(CH_2)_t-NHCONR^eR^f$ and $-(CH_2)_t-NHCO-(CH_2)_t-OCOR^e$, wherein the subscript t in each instance is an integer of from 0 to 8, the subscript u is an integer of from 0 to 2, $R^{h1}$ is selected from H, $(C_1-C_8)$alkyl, $(C_2-C_8)$alkenyl, $(C_2-C_8)$alkynyl and $(C_3-C_8)$cycloalkyl, wherein the aliphatic portion is optionally substituted with OH, $CO_2H$, $NH_2$, $CONH_2$, phenyl, halogen, halo$(C_1-C_4)$alkyl and $CO_2R^g$, and optionally two $R^{h1}$ groups attached to a common nitrogen are combined to form a five or six-membered ring, or a $R^h$ and an $R^{h1}$ group may be combined to form a 3-, 4-, 5- or 6-membered spiro or fused ring having from zero to two heteroatoms selected from N, O and S; and wherein each $R^e$ and $R^f$ is independently H or $(C_1-C_8)$alkyl or when attached to a common nitrogen atom are combined to form a 5- or 6-membered ring, or are optionally selected from and wherein any alkyl portion of $R^e$ and $R^f$ is optionally substituted with a member selected from OH, COOH, $NH_2$, $CONH_2$, phenyl, dialkylamino and $COOR^g$ wherein Rg is a $(C_1-C_4)$alkyl; and $W^3$ is selected from -continued

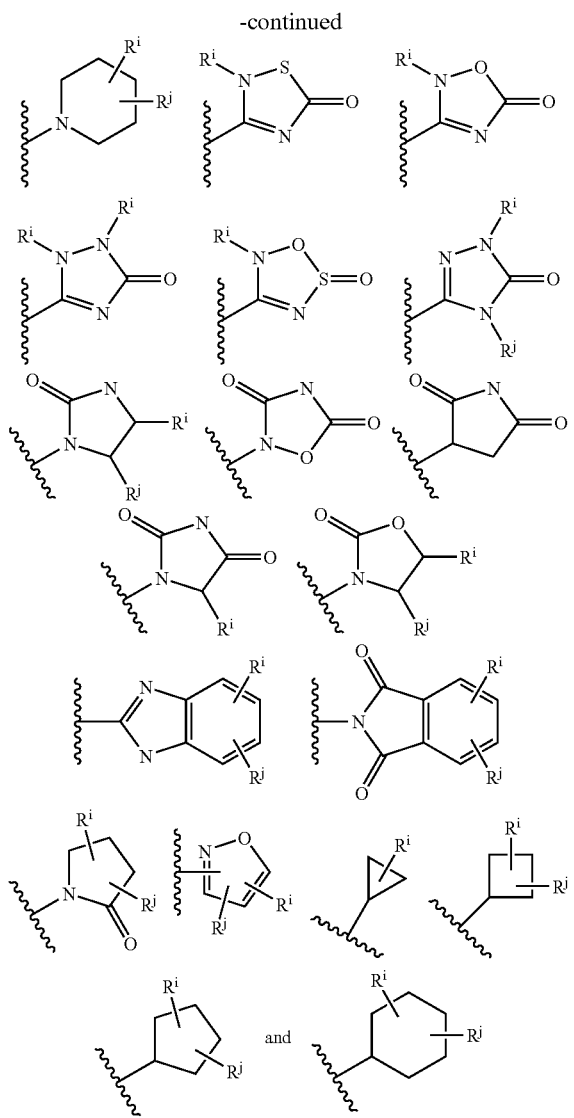

wherein each $R^i$ and each $R^j$ is independently selected from H, OH, COOH, halogen, halo($C_1$-$C_4$)alkyl, hydroxy($C_1$-$C_4$)alkyl, ($C_1$-$C_6$)alkyl, ($C_1$-$C_6$)alkoxy, ($C_1$-$C_6$)alkoxy($C_1$-$C_4$)alkyl and COO($C_1$-$C_4$)alkyl, wherein the aliphatic portions are unsubstituted or optionally substituted with halogen.

In some embodiments, the $R^h$ substituents are selected from oxo, halogen (including F, Cl, Br and I), $R^{h1}$, $OR^{h1}$, $N(R^{h1})_2$, $SR^{h1}$, $NO_2$, CN, ($C_1$-$C_8$)haloalkyl, ($C_1$-$C_8$)haloalkoxy, aryl($C_1$-$C_4$)alkyl, heteroaryl($C_1$-$C_4$)alkyl, ($C_1$-$C_8$)alkylene-$CO_2R^e$, $C(O)R^e$, $CO_2R^e$, =CH—$CONR^eR^f$, =CH—$CO_2R^e$, —$CH_2$-$CO_2R^e$, —CH($R^f$)—$CO_2R^e$, —C($R^f$)$_2$—$CO_2R^e$, —$CH_2CH_2CO_2R^e$, —$C(O)NR^eR^f$, —$CH_2C(O)NR^eR^f$, —$CH_2CH_2CONR^eR^f$, —$NHSO_2R^e$, —$CH_2NHSO_2R^e$, —$CH_2CH_2NHSO_2R^e$, —$CH_2SO_2NR^eR^f$, —$CH_2CH_2SO_2NR^eR^f$, —$CH_2OH$, —$CH_2NR^eR^f$, $CH_2CH_2OH$, —$CH_2C(CH_3)_2OH$, —$CH_2$—$W^3$, —$CH_2CH_2$—$W^3$ and —$C(O)CO_2R^e$, wherein $R^{h1}$, $R^e$, $R^f$ and $W^3$ have the meanings provided above, with respect to formulae Il, Im, In, Io, Ip and Iq, and the remaining substitutents have the meanings provided above with respect to the general formula I.

In some embodiments of each of formulae Ia through Iq, $R^2$ (when present) is H or a ($C_1$-$C_8$)alkyl; $R^3$ and $R^4$ are each independently H. ($C_1$-$C_4$)alkyl or are combined to form a 3-, 4-, 5- or 6-membered spirocyclic ring; $R^5$ and $R^6$ are each H, ($C_1$-$C_4$)alkyl or are combined with the nitrogen to which each is attached to form a 5- or 6-membered ring (e.g. a pyrollidine or piperidine ring); and $R^7$ is H, ($C_1$-$C_8$)alkyl or halo($C_1$-$C_4$)alkyl. Still further preferred are those embodiments in which the subscript n is 0, q is 1 and s is 1. In a particularly preferred group of embodiments, the compound has the formula Il, Im or In, and $R^h$ represents a substituent having the formula $C(O)R^e$, $CO_2R^e$, =CH—$CO_2R^e$, —$CH_2$—$CO_2R^e$, —$CH_2NHCOR^e$, —CH($R^f$)—$CO_2R^e$, —C($R^f$)$_2$—$CO_2R^e$, —$CH_2CH_2CO_2R^e$, —$C(O)NR^eR^f$, =CH—$CONR^eR^f$, —$CH_2C(O)NR^eR^f$, —$CH_2CH_2C(O)NR^eR^f$, —$CH_2CH_2NHCO_2R^e$, —$CH_2NHCO_2R^e$, —$NHSO_2R^e$, —$CH_2NHSO_2R^e$, —$CH_2CH_2NHSO_2R^e$, —$CH_2SO_2NR^eR^f$, —$CH_2CH_2SO_2NR^eR^f$, —$CH_2OH$, —$CH_2NR^eR^f$, —$CH_2CH_2OH$, —$CH_2C(CH_3)_2OH$, —$CH_2W^3$, —$CH_2CH_2$—$W^3$, —$C(O)CO_2CO_2R^e$ or —$CH_2$—$C(CF_3)_2$—OH. In an additional group of preferred embodiments, the compounds have the formula Il in which $R^3$ and $R^4$ are independently H or unsubstituted ($C_1$-$C_4$)alkyl; $R^5$ and $R^6$ are independently H or unsubstituted ($C_1$-$C_4$)alkyl; $R^7$ is selected from H, unsubstituted ($C_1$-$C_4$)alkyl or halo($C_1$-$C_4$)alkyl; the subscript n is 0, 1 or 2 and $R^c$ is selected from fluoro, chloro, bromo, cyano, methyl, trifluoromethyl and nitro; $R^h$ is selected from $CO_2R^e$, =CH—$CO_2R^e$, —$CH_2$—$CO_2R^e$, —$CH_2NHCOR^e$, —CH($R^f$)—$CO_2R^e$, —C($R^f$)$_2$—$CO_2R^e$, —$CH_2CH_2CO_2R^e$, —$C(O)NR^eR^f$, =CH—$CONR^eR^f$, —$CH_2C(O)NR^eR^f$, —$CH_2CH_2C(O)NR^eR^f$, —$CH_2CH_2NHCO_2R^e$, —$CH_2NHCO_2R^e$, —$CH_2NR^eR^f$, —$CH_2$—$W^3$ and —$CH_2CH_2$—$W^3$; wherein each $R^e$ and $R^f$ is H or ($C_1$-$C_4$)alkyl optionally substituted with a member selected from OH, COOH, $NH_2$, $CONH_2$, phenyl, dialkylamino and $COOR^g$ wherein $R^g$ is a ($C_1$-$C_4$)alkyl; and wherein $W^3$ is selected from

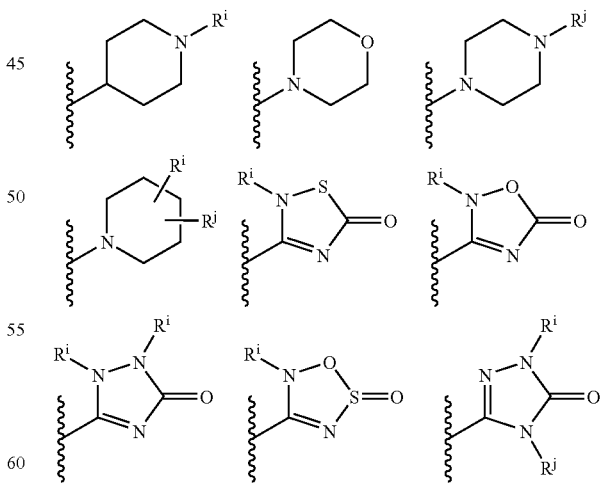

wherein $R^i$ and $R^j$ are each independently selected from H and ($C_1$-$C_4$)alkyl.

In still other groups of preferred embodiments, the compounds are represented by formulae Ir through Iy.

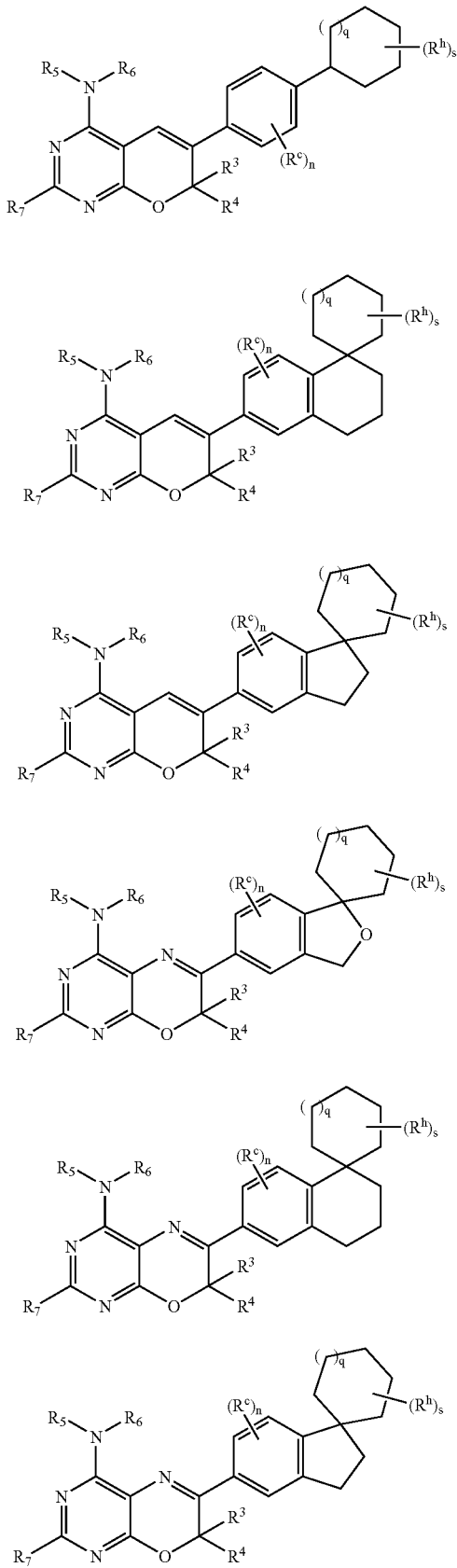

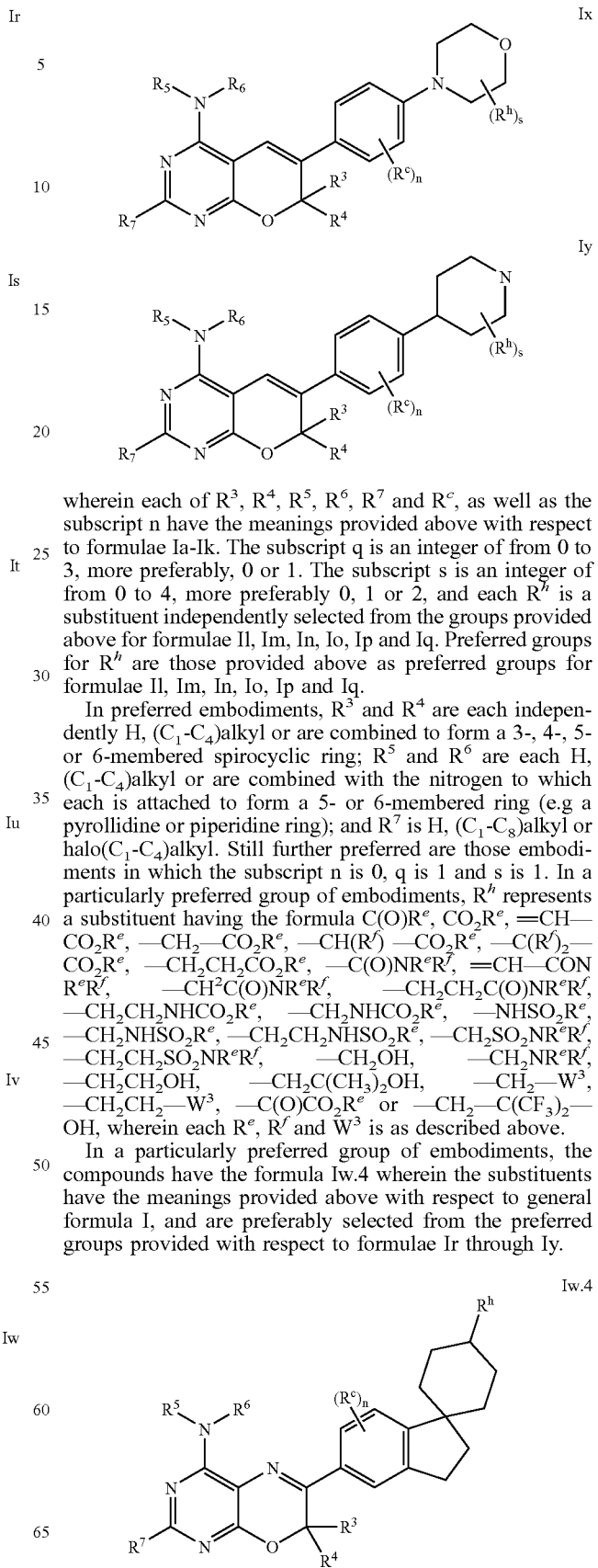

wherein each of $R^3$, $R^4$, $R^5$, $R^6$, $R^7$ and $R^c$, as well as the subscript n have the meanings provided above with respect to formulae Ia-Ik. The subscript q is an integer of from 0 to 3, more preferably, 0 or 1. The subscript s is an integer of from 0 to 4, more preferably 0, 1 or 2, and each $R^h$ is a substituent independently selected from the groups provided above for formulae Il, Im, In, Io, Ip and Iq. Preferred groups for $R^h$ are those provided above as preferred groups for formulae Il, Im, In, Io, Ip and Iq.

In preferred embodiments, $R^3$ and $R^4$ are each independently H, $(C_1$-$C_4)$alkyl or are combined to form a 3-, 4-, 5- or 6-membered spirocyclic ring; $R^5$ and $R^6$ are each H, $(C_1$-$C_4)$alkyl or are combined with the nitrogen to which each is attached to form a 5- or 6-membered ring (e.g a pyrollidine or piperidine ring); and $R^7$ is H, $(C_1$-$C_8)$alkyl or halo$(C_1$-$C_4)$alkyl. Still further preferred are those embodiments in which the subscript n is 0, q is 1 and s is 1. In a particularly preferred group of embodiments, $R^h$ represents a substituent having the formula $C(O)R^e$, $CO_2R^e$, =CH—$CO_2R^e$, —$CH_2$—$CO_2R^e$, —$CH(R^f)$—$CO_2R^e$, —$C(R^f)_2$—$CO_2R^e$, —$CH_2CH_2CO_2R^e$, —$C(O)NR^eR^f$, =CH—$CONR^eR^f$, —$CH_2C(O)NR^eR^f$, —$CH_2CH_2C(O)NR^eR^f$, —$CH_2CH_2NHCO_2R^e$, —$CH_2NHCO_2R^e$, —$NHSO_2R^e$, —$CH_2NHSO_2R^e$, —$CH_2CH_2NHSO_2R^e$, —$CH_2SO_2NR^eR^f$, —$CH_2CH_2SO_2NR^eR^f$, —$CH_2OH$, —$CH_2NR^eR^f$, —$CH_2CH_2OH$, —$CH_2C(CH_3)_2OH$, —$CH_2$—$W^3$, —$CH_2CH_2$—$W^3$, —$C(O)CO_2R^e$ or —$CH_2$—$C(CF_3)_2$—OH, wherein each $R^e$, $R^f$ and $W^3$ is as described above.

In a particularly preferred group of embodiments, the compounds have the formula Iw.4 wherein the substituents have the meanings provided above with respect to general formula I, and are preferably selected from the preferred groups provided with respect to formulae Ir through Iy.

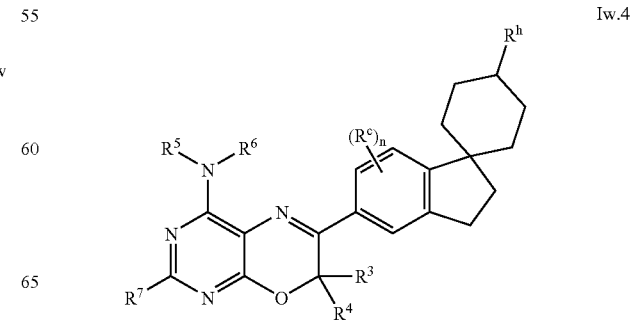

More preferably, the compounds of formula Iw.4 are those in which $R^3$ and $R^4$ are independently H or unsubstituted $(C_1-C_4)$alkyl; $R^5$ and $R^6$ are independently H or unsubstituted $(C_1-C_4)$alkyl; $R^7$ is selected from H, unsubstituted $(C_1-C_4)$alkyl or halo$(C_1-C_4)$alkyl; the subscript n is 0, 1 or 2 and $R^c$ is selected from fluoro, chloro, bromo, cyano, methyl, trifluoromethyl and nitro; $R^h$ is selected from $CO_2R^e$, $=CH-CO_2R^e$, $-CH_2-CO_2R^e$, $-CH_2NHCOR^e$, $-CH(R^f)-CO_2R^e$, $-C(R^f)_2-CO_2R^e$, $-CH_2CH_2CO_2R^e$, $-C(O)NR^eR^f$, $=CH-CONR^eR^f$, $-CH_2C(O)NR^eR^f$, $-CH_2CH_2C(O)NR^eR^f$, $-CH_2CH_2NHCO_2R^e$, $-CH_2NHCO_2R^e$, $-CH_2NR^eR^f$, $-CH_2-W^3$ and $-CH_2CH_2-W^3$; wherein each $R^e$ and $R^f$ is H or $(C_1-C_4)$ alkyl optionally substituted with a member selected from OH, COOH, $NH_2$, $CONH_2$, phenyl, dialkylamino and $COOR^g$ wherein $R^g$ is a $(C_1-C_4)$alkyl; and wherein $W^3$ is selected from

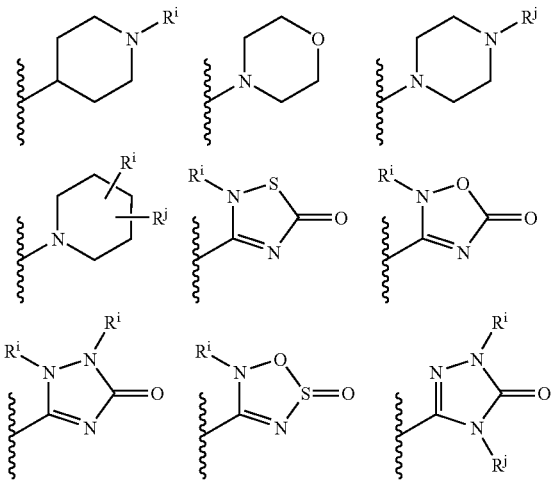

wherein $R^1$ and $R^1$ are each independently selected from H and unsubstituted $(C_1-C_4)$alkyl.

In other particularly preferred groups of embodiments, the compounds are represented by the formulae Il.4 and Ig.4:

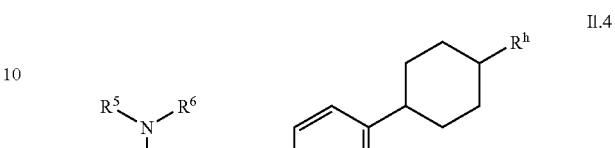

Il.4 and

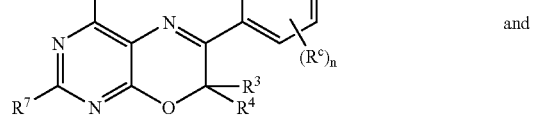

Ig.4

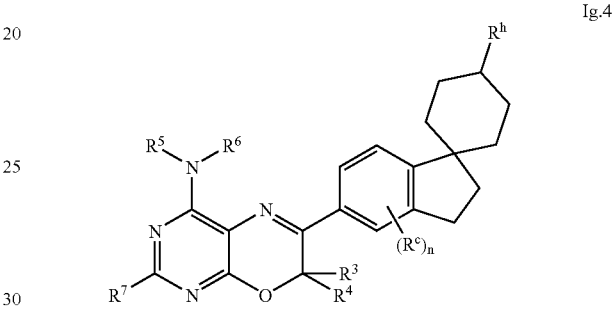

wherein each of the substituents have the meanings and preferred groups as provided above for formulae Ir through Iy.

The more preferred compounds of the present invention are those that are provided in the examples below and further exemplified in Tables 1-10.

In one particularly preferred group of embodiments, the compounds are selected from:

Preparation of compounds

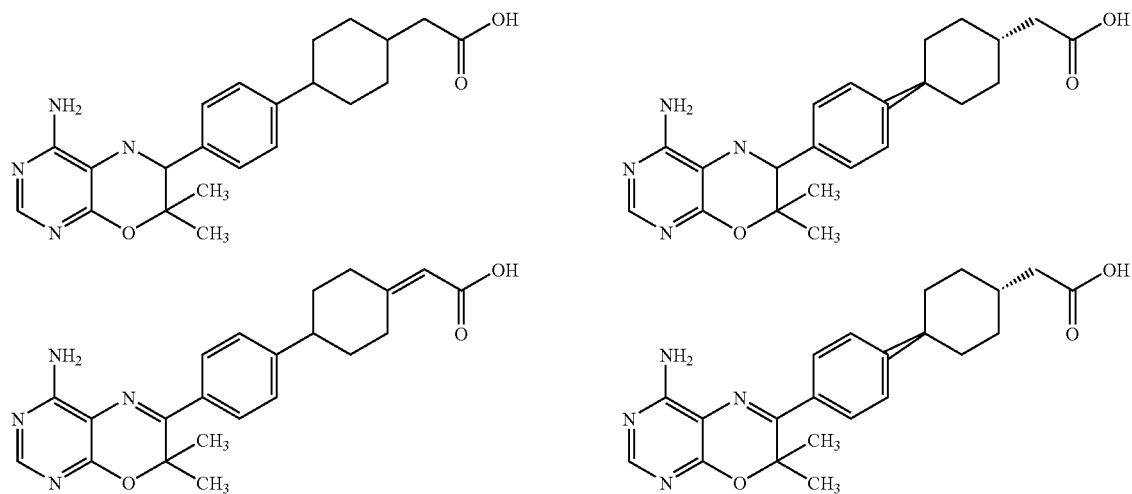

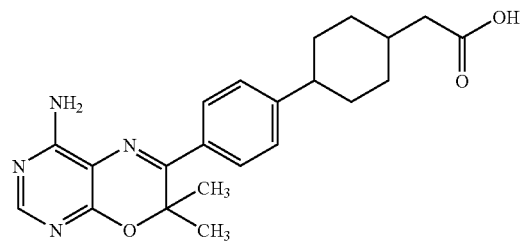
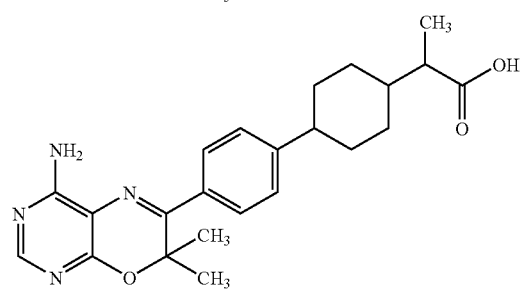
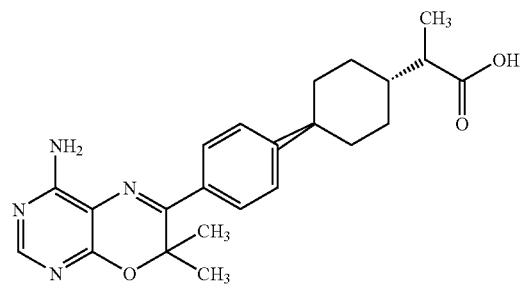
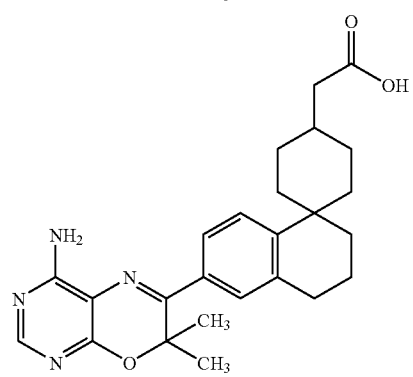
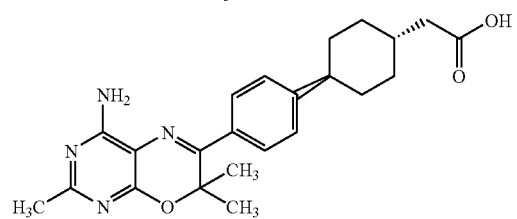
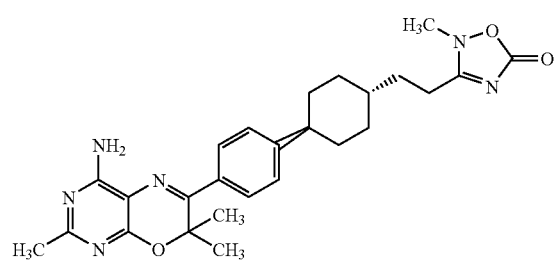
-continued
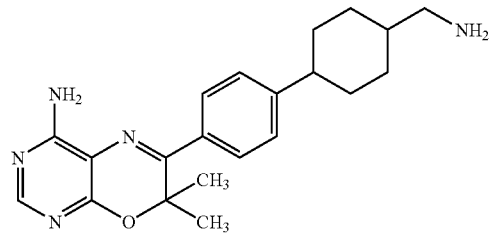
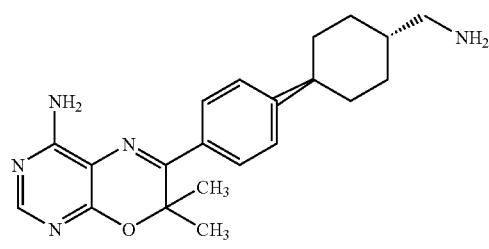
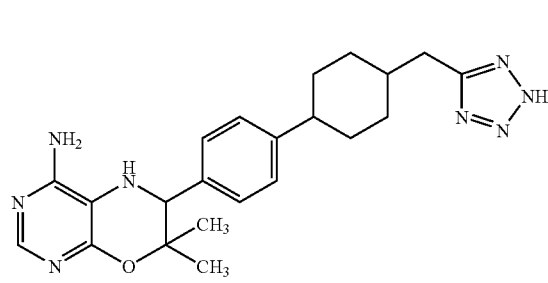
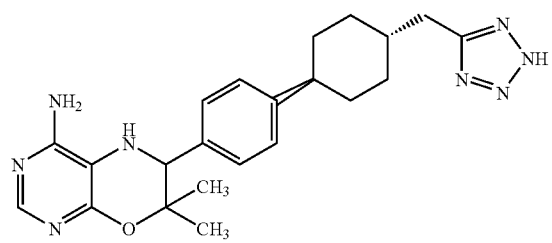
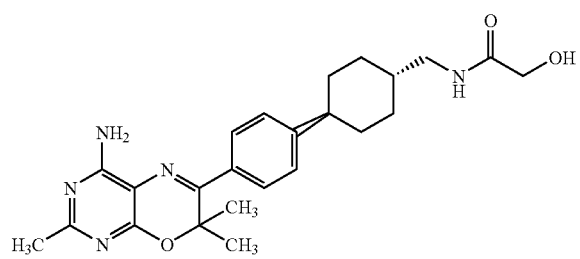
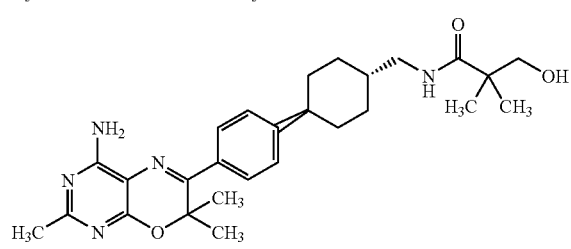

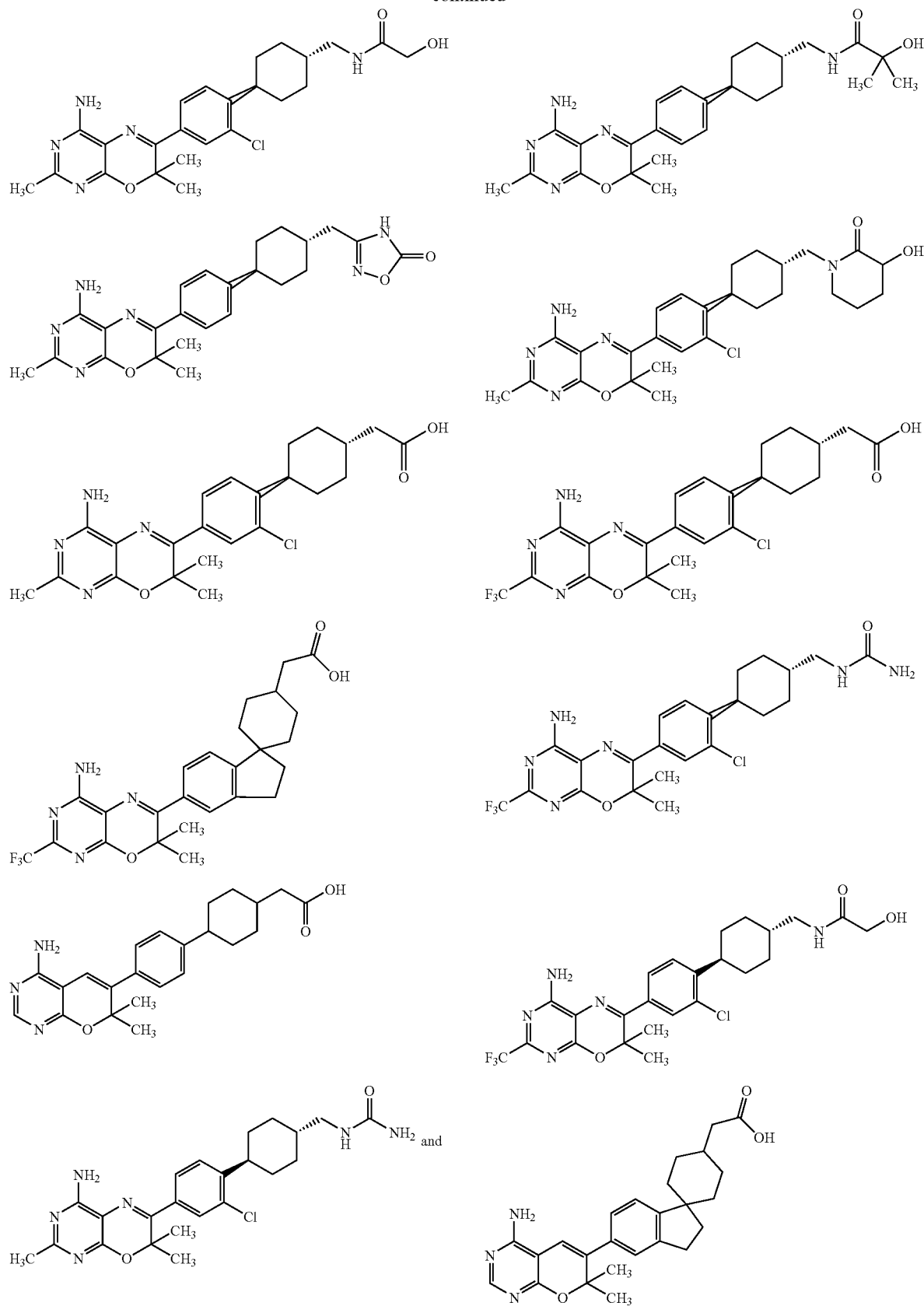

Compounds of the present invention can be prepared beginning with commercially available starting materials and using general synthetic techniques known to those of skill in the art. Outlined below are reaction schemes suitable for preparing such compounds. Further exemplification is found in the specific Examples provided.

Scheme 1

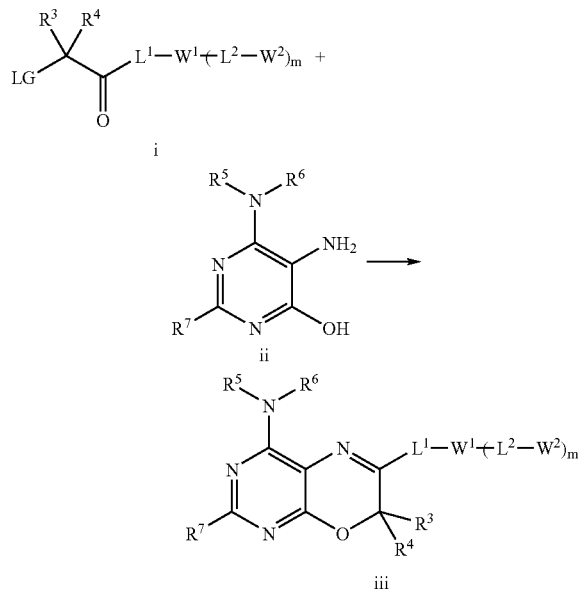

As shown in Scheme 1, compounds of the present invention wherein X is N, Y is N and Z is O, can be prepared from a suitably substituted pyrimidine (ii) and a substituted ketone (i) wherein LG indicates a leaving group such as a halogen atom, toluenesulfonate, methanesulfonate or trifluoromethanesulfonate. Condensation of i and ii in an organic solvent or mixture of solvents (including aqueous mixtures) in the presence or absence of an acid (e.g., HCl) or base (e.g., NaHCO$_3$) provides, after workup, a compound of formula iii. Reduction of iii with a reducing agent such as, for example, sodium borohydride, lithium borohydride or sodium triacetoxyborohydride, provides still other compounds of the present invention, illustrated as iv in Scheme 2.

Scheme 2

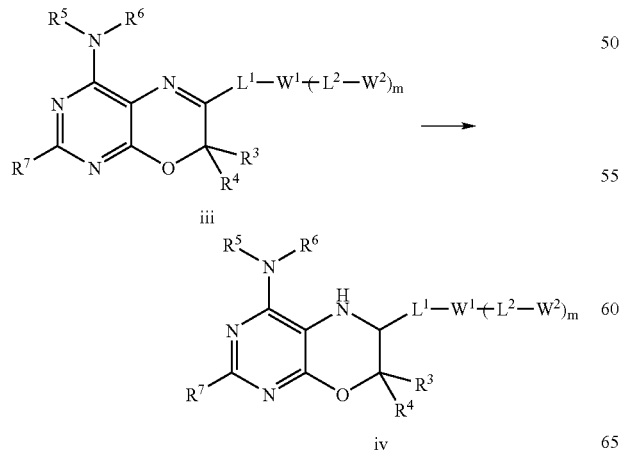

Schemes 3a-3i illustrate a number of methods for the preparation of intermediate compounds of general structure i. In Scheme 3a, a benzene derivative, such as 4-phenylcyclohexanone (v), is functionalized to introduce a desired substituent on the cyclohexane ring. In the example shown, a Horner-Emmons or similar Wittig reaction is used to introduce an α,β-unsaturated ester group, producing vi (e.g., reaction with a suitable phosphonate in the presence of a base such as sodium hydride in a solvent such as DMF or THF). Catalytic hydrogenation of vi using, for example, a palladium or platinum catalyst in a relatively polar solvent such as THF, methanol, or an aqueous mixture containing an alcohol or THF as a co-solvent, for example, is used to reduce the double bond, producing compound vii. A Friedel-Crafts acylation reaction is then used to attach a haloacetyl group on the phenyl ring of vii, forming the functionalized acetophenone (ix). Preferably, the leaving group in this sequence is Cl or Br. Suitable Lewis acids for the acylation include, for example, AlCl$_3$, AlBr$_3$, BCl$_3$, TiCl$_4$, and the like; suitable solvents are well known in the art, and include CS$_2$, nitrobenzene, dichloromethane, and similar solvents that are unreactive toward the reagents and Lewis acids employed. Those of skill in the art will appreciate that other synthesis methods are also known for making such intermediates, such as, for example, acylation of a metalated aromatic species, such as an aryllithium or aryl Grignard reagent, with, for example, an acylating agent such as an N-methyl-N-methoxy amide (commonly referred to as a Weinreb amide) of a chloroacetic acid derivative (see, e.g., Nahm and Weinreb (1981) *Tetrahedron Lett.* 22:3815-3818) or a suitable acylester. Such methods provide access to other isomers of these functionalized acetophenone derivatives.

Scheme 3a

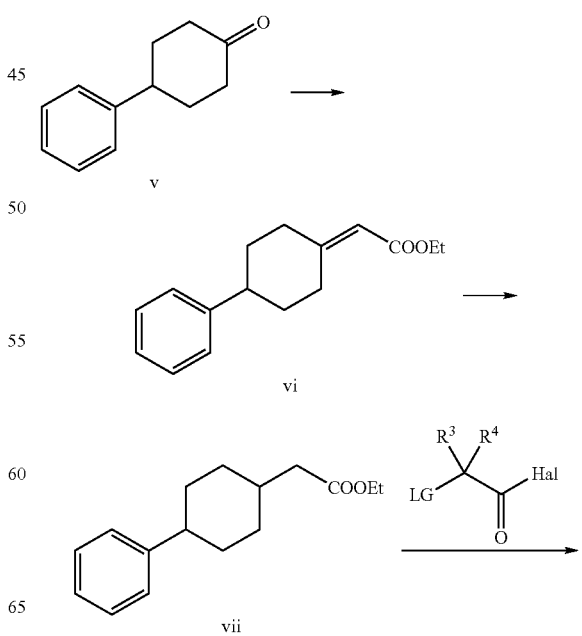

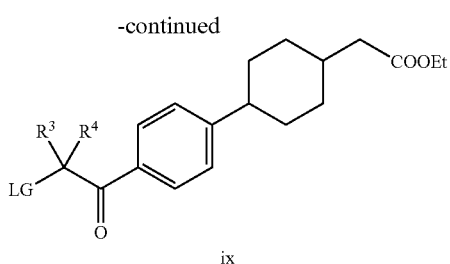

Alternatively, vii may be alkylated by treatment with a base such as lithium diisopropylamide or lithium hexamethyldisilazide in a suitable solvent such as THF, followed by reaction with an alkylating agent, such as an alkyl halide, alkyl methanesulfonate, alkyl trifluoromethanesulfonate or alkyl toluenesulfonate, to give intermediate x (Scheme 3b). If desired, the sequence may be repeated to give intermediates of the general formula xi. Acylation of xi can be accomplished as described above to give xii.

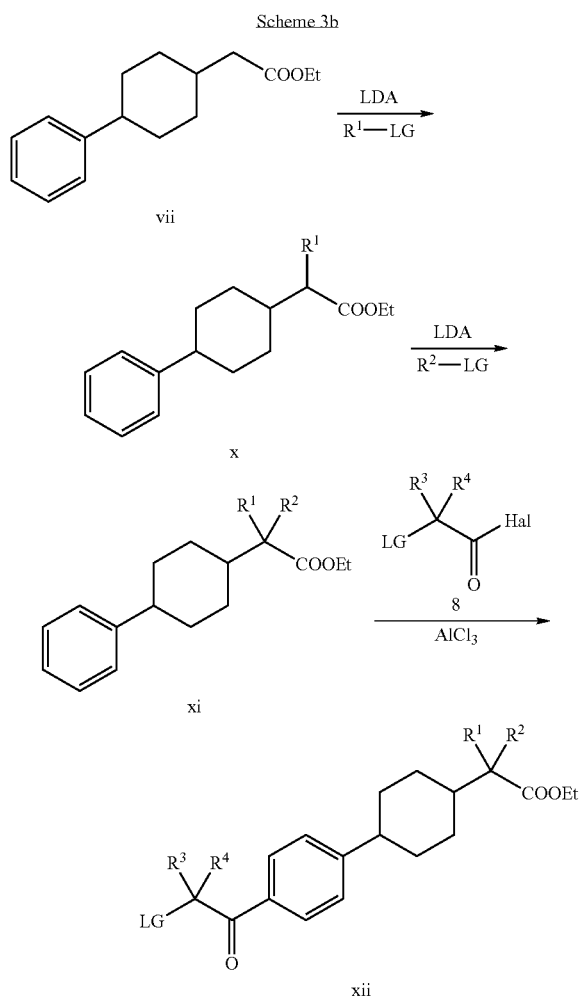

Similar approaches can be used to produce other functionalized acetophenone derivatives (see Scheme 3c). For example, 4-phenylcyclohexanone (v) can be converted into an aldehyde in two steps, using a Wittig reaction with methoxymethyltriphenylphosphorane in a suitable solvent such as THF, DME or dioxane to produce xiv, for example, followed by mildly acidic hydrolysis. This aldehyde can be homologated into an α,β-unsaturated ester by a Wittig reaction with (carbomethoxy)methylenetriphenylphosphorane in a suitable solvent. If desired, the double bond can be reduced via catalytic hydrogenation using palladium on carbon, for example, to produce xv. Suitable solvents for such hydrogenation reactions include ethanol or ethyl acetate. Acylation of xv to produce a functionalized acetophenone derivative (xvi) can be accomplished as described above for acylation of vii.

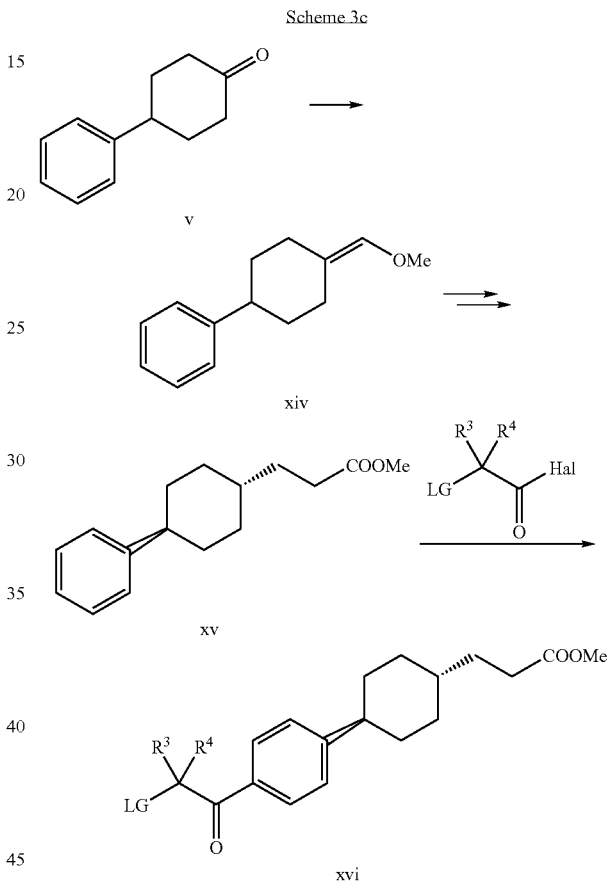

Scheme 3d illustrates the synthesis of another functionalized acetophenone derivatives of general formula i, suitable for synthesizing compounds of the present invention.

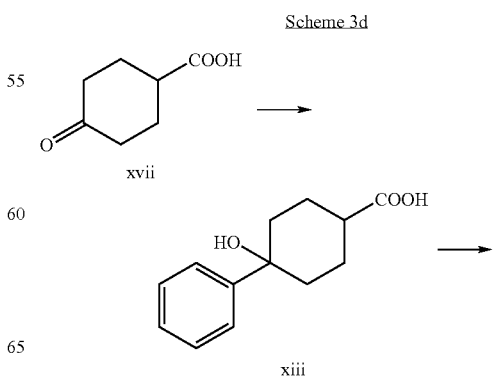

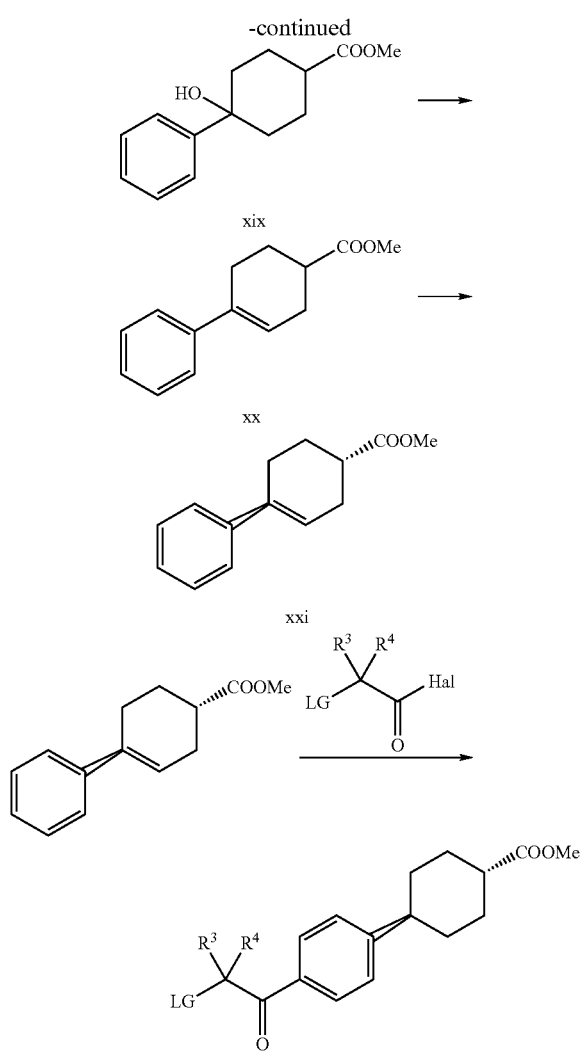

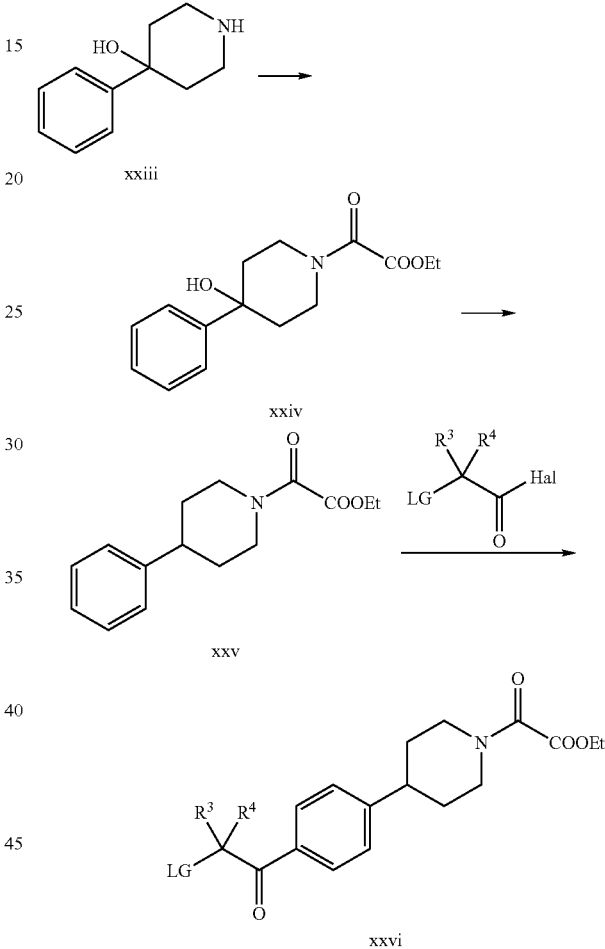

reagents and conditions known to the skilled artisan (e.g., acylation with diethyl oxalate or ethyl oxalyl chloride in the presence of a mild base such as triethylamine or pyridine) to produce xxiv. The N-functionalized (e.g., N-acylated) compound is then dehydrated and reduced catalytically as described above in Scheme 3d to produce a 4-phenylpiperidine oxalate amide (xxv). This compound is then acylated as described above to produce the corresponding functionalized acetophenone derivatives (xxvi).

In Scheme 3d, a phenyl group is introduced using, for example, phenyl Grignard reagent or phenyllithium to provide xiii. The carboxylic acid functional group can be esterified under standard conditions to produce xix, and dehydration can be accomplished using an acid catalyst such as acetic acid, hydrochloric acid or trifluoroacetic acid in a suitable solvent such as chloroform or toluene to produce xx. Reduction of the cyclohexene double bond can be performed under catalytic hydrogenation conditions using palladium, typically, as the catalyst, to provide xxi. This reduction produces a mixture of isomers (both cis and trans-disubstituted cyclohexanes are produced); if desired, these can be separated or equilibrated using a base such as alkoxide or DBU in methanol or toluene to produce primarily the more thermodynamically stable trans-disubstituted isomer. Acylation of xxi to produce the functionalized acetophenone xxii is performed as described above.

Compounds of the present invention that contain a heterocyclic ring for $W^2$ can be synthesized by a similar sequence, provided the heterocyclic ring is stable to the acylation reaction conditions. For example, a compound where $W^2$ is an acylated piperidine can be synthesized in this manner, using a functionalized acetophenone derivative such as that produced by the sequence shown in Scheme 3e. In this sequence, 4-hydroxy-4-phenylpiperidine (xxiii) is alkylated, sulfonylated or acylated on nitrogen using Similarly, the phenylpiperazine xxvii can be alkylated, sulfonylated, or acylated on nitrogen to give the N-functionalized compound xxviii, which can in turn be acylated as described previously to produce the functionalized acetophenone derivative xxix.

Scheme 3f

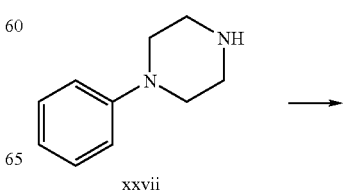

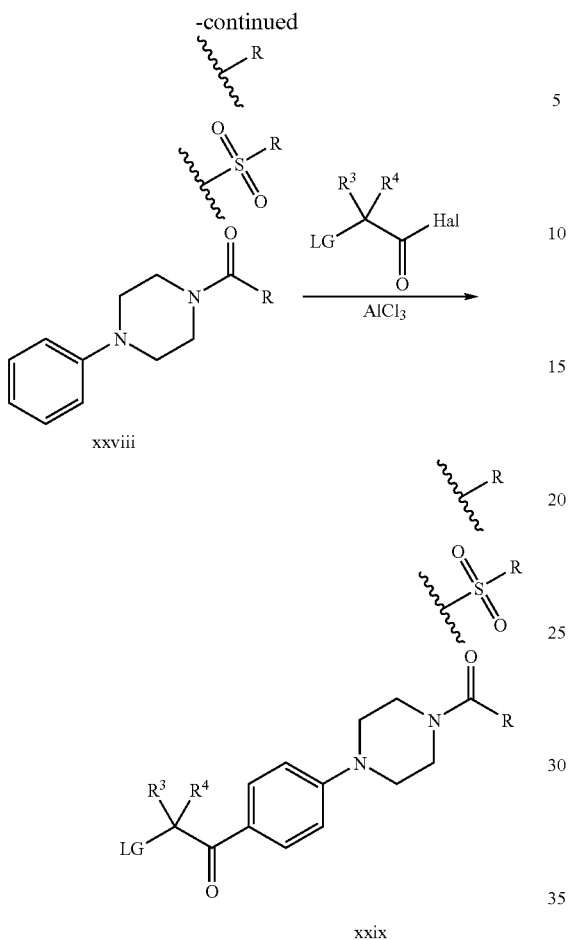

Other compounds of the present invention having a heterocycle as $W^2$ can be produced by attaching the heterocyclic group on an acetophenone, then halogenating the acetophenone at the α carbon to produce a compound of general formula i, as shown in Scheme 3g. In this sequence, a 4-fluoroacetophenone compound (xxiv) is synthesized by acylation of fluorobenzene under typical Friedel-Crafts conditions as described above. The 4-fluoro group is then subject to aromatic nucleophilic displacement reactions; in the scheme, it is displaced by a substituted piperidine group by reaction with the nucleophilic piperidine in a polar aprotic solvent such as DMSO or DMF. Functionalization of the carbon atom bearing $R^3$ and $R^4$ to produce xxvi can be accomplished using for example, bromine ($Br_2$) or chlorine ($Cl_2$) in a polar solvent such as DME or ethyl acetate, in the presence of an acid catalyst such as acetic acid or hydrobromic acid.

Scheme 3g

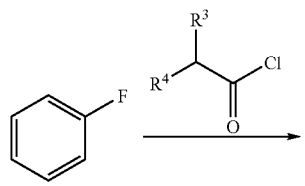

Certain functionalized acetophenone derivatives suitable for the preparation of compounds of the present invention where $L^1$ is a bond can be prepared from substituted acetophenone, especially when $R^3$ and $R^4$ are identical groups, as shown in Scheme 3h. For example, an acetophenone substituted with —$L^2$—$W^2$ (xxxiii) can be alkylated with an alkylating agent such as methyl iodide, ethyl bromide, or other similar alkylating agent in the presence of a base such as lithium diisopropylamide, lithium hexamethyldisilazide or sodium hydride, and using a solvent such as DMF, DME, THF or toluene. This produces an acetophenone where $R^3$ and $R^4$ are the same. This acetophenone can then be halogenated as described above in Scheme 3g to produce a functionalized acetophenone of general formula i, which will condense with substituted pyrimidines as shown in Scheme 1 to prepare compounds of the present invention.

Scheme 3h

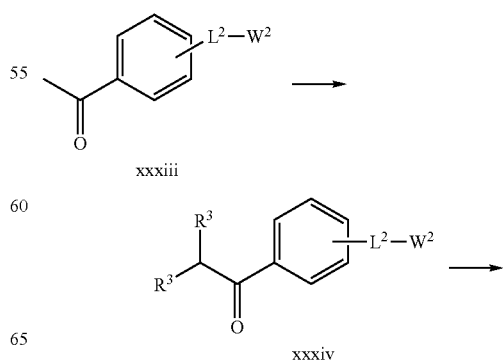

-continued

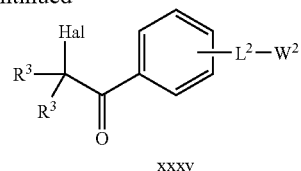

xxxv

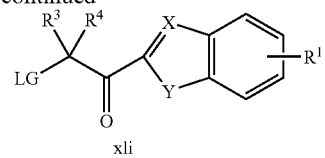

xli

The preparation of compounds of the invention that contain a heterocyclic ring for W¹ can be synthesized using similar procedures, as outlined in Scheme 3g. For example, a substituted or unsubstituted heterocycle xxxvi such as a furan, thiophene, pyrrole, oxazole, thiazole, imidazole or thiadiazole can be lithiated with, for example butyllithium or lithium diisopropyamide in a suitable solvent such as THF, DME or dioxane. The metalated species may be reacted with, for example, an amide, such as an dimethylamide or an N-methyl-N-methoxyamide to produce the acylated heterocycle xxxvii, which in turn can be halogenated as described above to produce a functionalized acetophenone derivative of general formula xxxviii. In a similar sequence, a substituted or unsubstituted benzofuran, benzothiophene, benzopyrrole, benzoxazole, benzothiazole, benzimidazole or benzothiadiazole (xxxix) can be lithiated and acylated to give xl, which in turn can be halogenated as previously described. One of skill in the art will appreciate that other heterocycles can also be used in these transformations.

As shown in Scheme 4, compounds of general formula iv having a substituted phenyl ring as W1 and a substituted cyclohexane ring as L2-W2 (e.g., xlii) can be prepared from these substituted acetophenone derivatives like ix.

Scheme 4

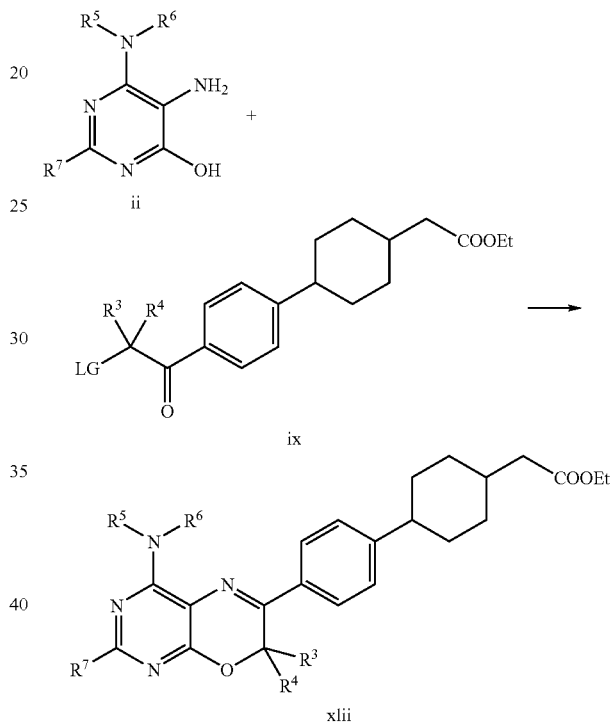

Scheme 3i

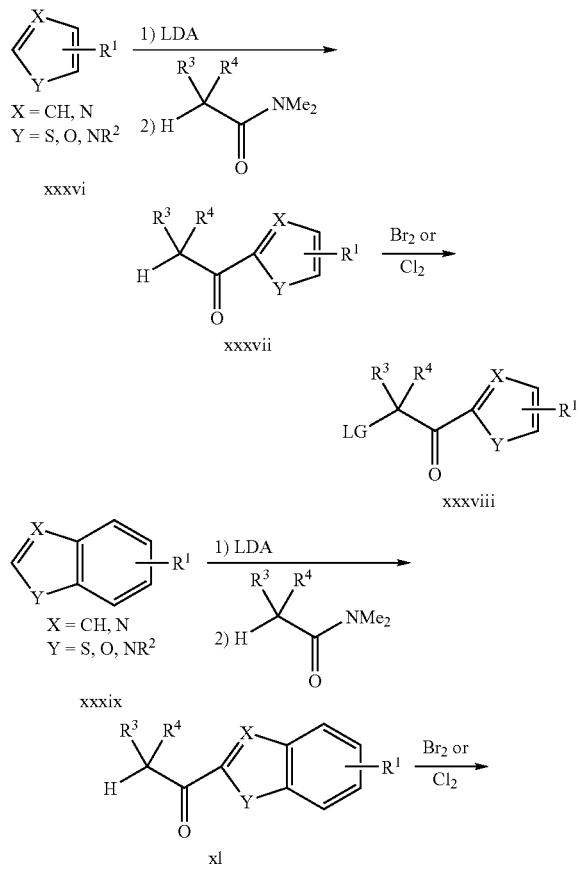

Compounds such as xlii can be used to make other compounds of the present invention by, for example, hydrolysis of the ethyl ester to provide a carboxylic acid compound xliii. (Scheme 5) Ester hydrolysis can be accomplished in most solvents that will dissolve xlii and are at least partially miscible with water, by treating a solution of xlii with aqueous base such as sodium hydroxide or potassium hydroxide, for example. The carboxylic acid can, in turn, be converted into other groups such as an amide by methods well known to those of ordinary skill in the art. For example, the carboxylic acid can be activated by condensation with a variety of coupling reagents, including hydroxybenzotriazole (HOBt) and N-hydroxysuccinimide (HOSu), for example, using dicyclohexylcarbodiimide (DCC) or a similar carbodiimide reagent or a wide variety of reagents such as those developed for formation of peptide bonds. Conditions for such reactions are well known to those or ordinary skill in the art. The activated intermediate, an ester of HOBt or HOSu, for example, can then be condensed with a wide variety of nucleophiles such as, for example, amines, alcohols, and thiols. Scheme 5 shows the conversion of a compound of formula xlii into an amide (xliv) by this sequence, using ammonia as the nucleophile.

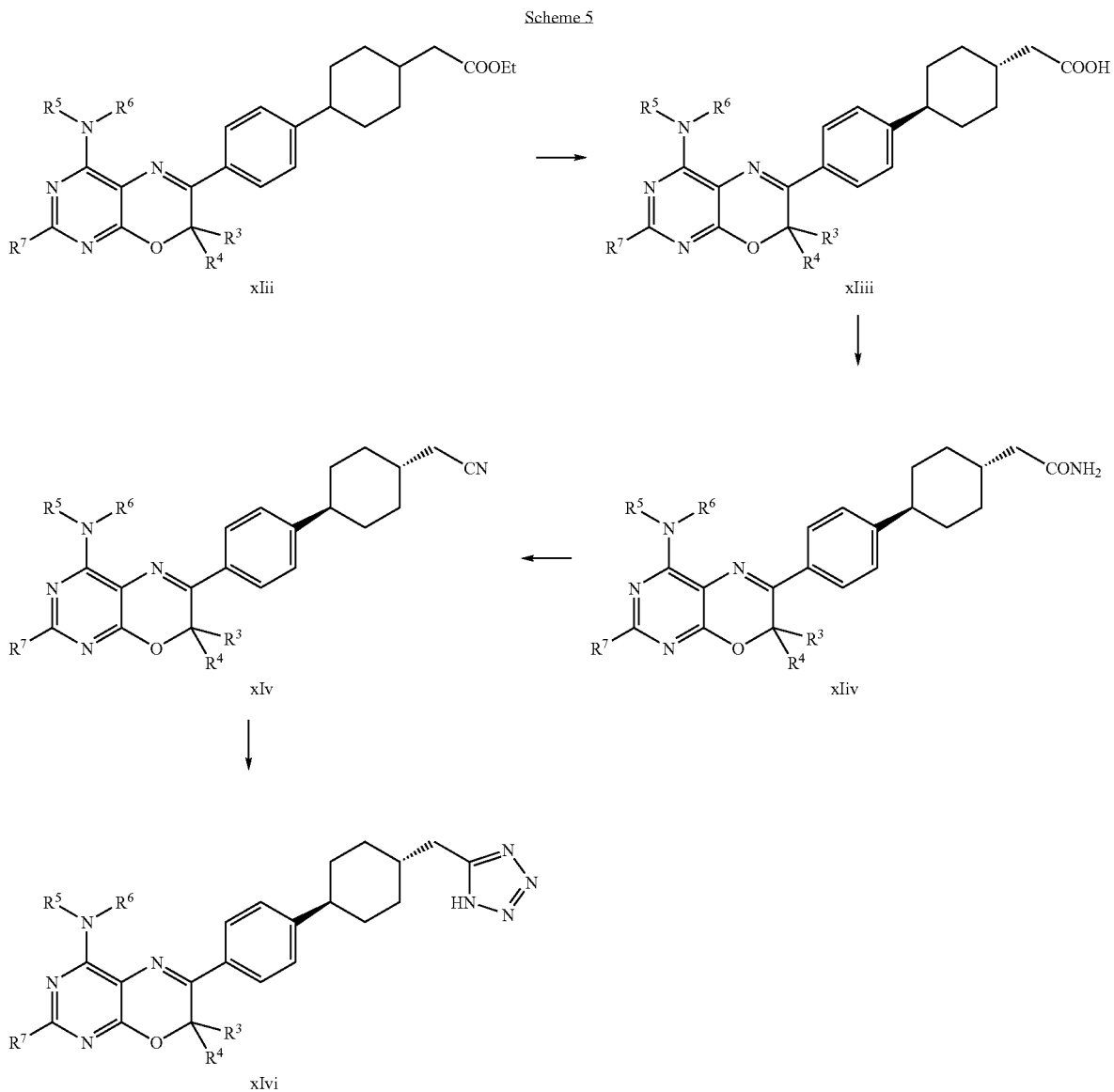

Dehydration of the amide xliv to a nitrite (xlv) can be accomplished by a variety of methods. See Scheme 5 above. Phosphorous pentoxide is the most common dehydrating reagent for this reaction, but many others are known to those skilled in the art. The nitrite can, in turn, be converted into other groups such as a tetrazole (xlvi) by methods well known to those of ordinary skill in the art. For example, reacting the nitrite with an azide, such as sodium azide, lithium azide or hydrazoic acid in a solvent such as DMF or water will accomplish this transformation.

Schemes 6a and 6b illustrate one approach to the preparation of compounds of formula I in which $W^1$ is a phenylene moiety having an additional substituents other than the $L^2$-$W^2$ component. As seen in Scheme 6a, intermediate bromoacetophenones xlvii can be nitrated under standard conditions (nitric acid, sulfuric acid in solvents such as chloroform, methylene chloride, acetic acid, or neat) to provide xlviii. Reduction of the nitro group is accompanied by debromination to provide xlix using catalytic hydrogenation or $SnCl_2$ (generally in alcoholic solvents). Chloride replacement of the amino group is accomplished using copper chloride in the presence of a suitable nitrite (e.g., t-butyl nitrite, sodium nitrite) and solvent, to provide intermediates such as l. Bromine can be reintroduced, providing li using standard brominating conditions (e.g., HBr/HOAc, $Br_2$/N-bromosuccinimide or $CuBr_2$). Alternatively, xlvii can be chlorinated directly to provide li using standard reagents (e.g., sulfuryl chloride, $Cl_2$ or N-chlorosuccinimide) and conditions known to one of skill in the art.

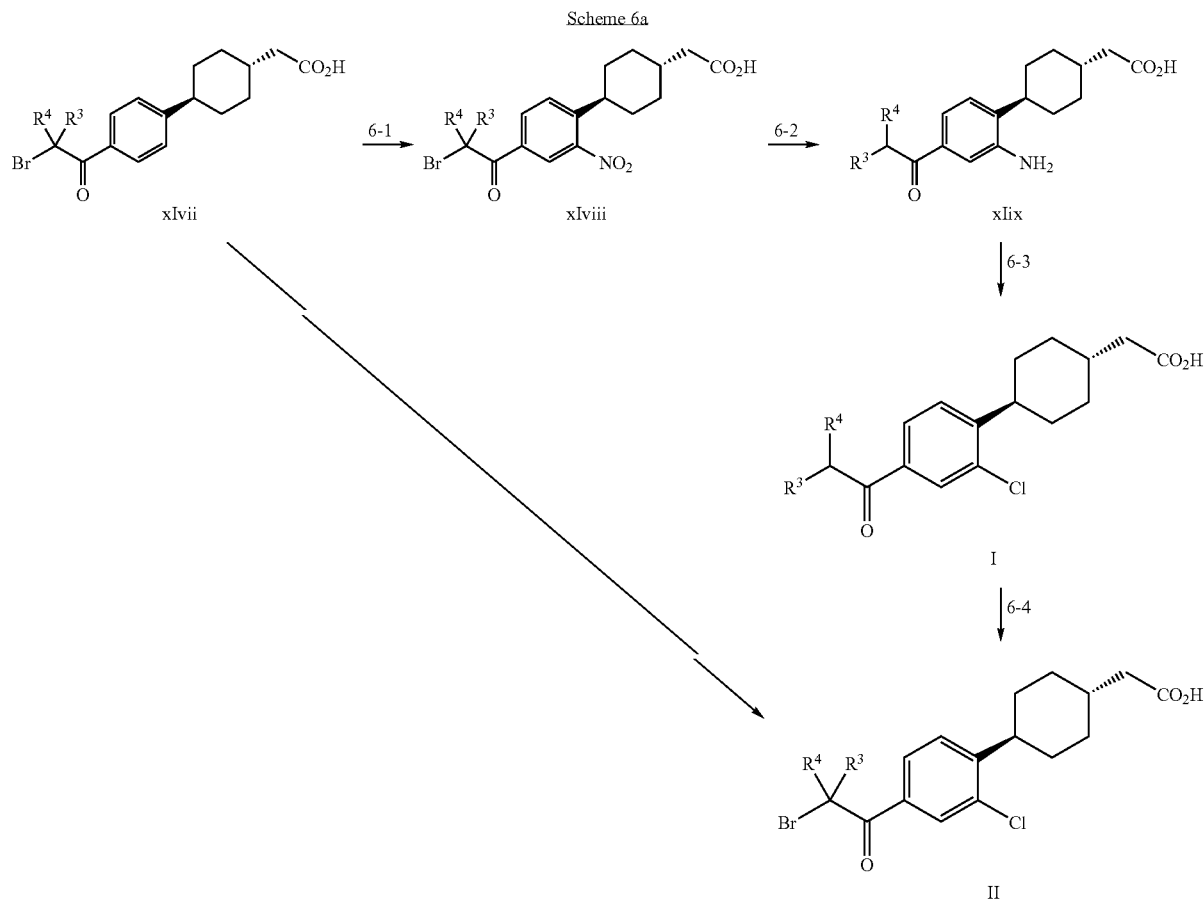

Scheme 6b illustrates the elaboration of intermediates such as xlix to other substituted compounds. For example, compounds of formula lii (wherein $X^{10}$ is F) can be produced from xlix using fluorinating reagents such as nitrosonium tetrafluoroborate, DAST, HF or CsF (generally in solvents such as toluene, benzene, methylene chloride or dichloroethane). Subsequent bromination of lii to produce liii can be accomplished according to known methods. Conversion of either li or liii to target compounds of the formula liv is accomplished via condensation with a suitably substituted pyrimidine (see Example 1).

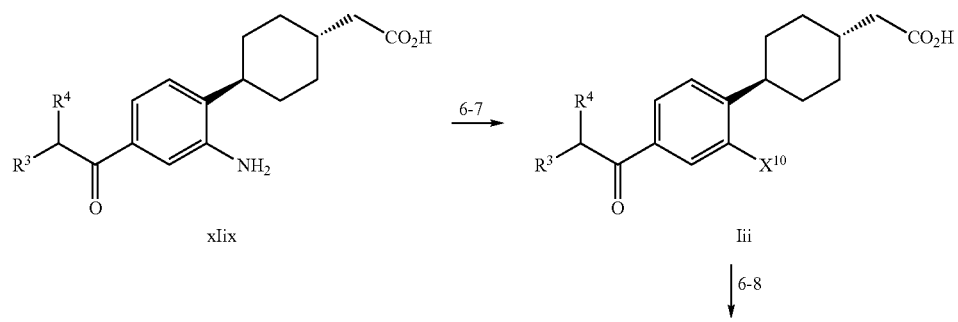

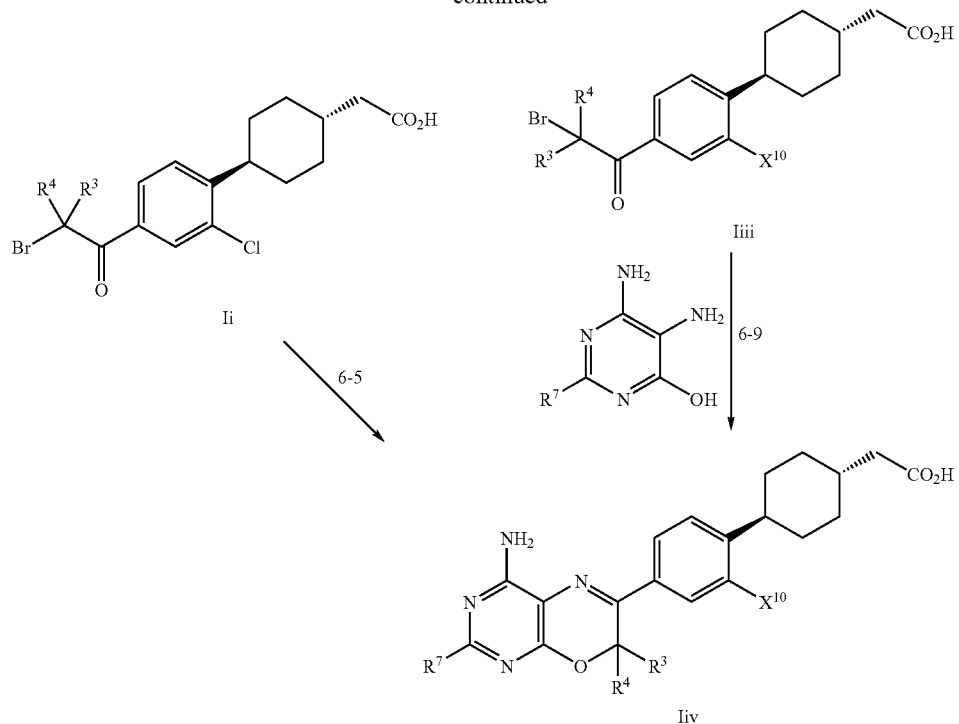

As shown in Scheme 7, compounds of the present invention wherein X is N, Y is CH, Z is O and $W^1$ is a substituted or unsubstituted aryl or heteroaryl can be prepared from a suitably substituted pyrimidine lv (where A is a halogen, e.g., Br, I or a triflate or other suitable substituent known to those skilled in the art) and a substituted or unsubstituted aryl or heteroaryl species lvi (where M is $B(OR^2)$, $Sn(R^3)$ or other suitable metal known to those skilled in the art) by, for example, a palladium catalyzed cross coupling reaction. Those skilled in the art will also appreciate that A and M may be interchanged.

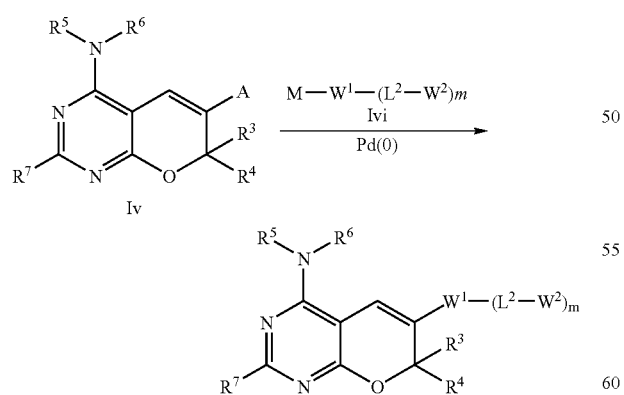

Scheme 8 illustrates a method for the preparation of the intermediate of general structure lv. Condensation of pyrimidine lviii with lvii in a suitable solvent such as acetic acid affords lix. Conversion of the hydroxy moiety to a leaving group, for example, a chloride or bromide with, for example, phosphorus oxychloride or phosphorus oxybromide respectively, is followed by displacement of the leaving group with a suitably substituted amine to afford lv.

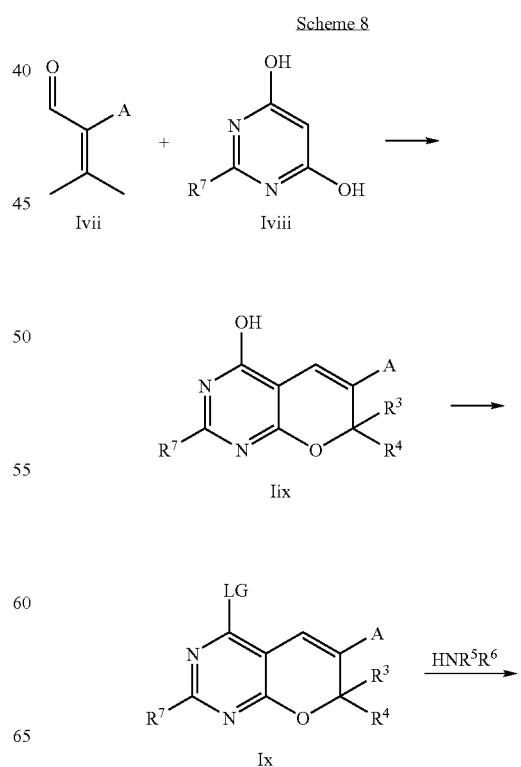

-continued

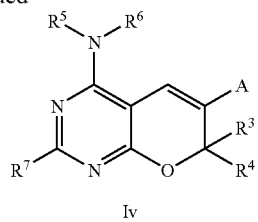

Iv

Compositions

In another aspect, the present invention provides pharmaceutical compositions for modulating DGAT activity in humans and animals that will typically contain a compound of formula I and a pharmaceutically acceptable carrier or diluent.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, patches, creams, ointments, jellies, solutions or suspensions, etc., containing the compounds of the present invention are employed. As used herein, topical application is also meant to include the use of mouth washes and gargles.

The pharmaceutical composition and method of the present invention may further comprise other therapeutically active compounds as noted herein which are usually applied in the treatment of the above-mentioned pathological conditions.

Methods of Use

In yet another aspect, the present invention provides methods of using a compound or composition of the invention to treat or prevent a disease or condition associated with DGAT. Diseases and conditions associated with lipid metabolism and cell proliferation, and complications thereof, can be treated with the subject compounds and compositions. In one group of embodiments, diseases and conditions, including chronic diseases, of humans or other species that can be treated with inhibitors of DGAT function include, but are not limited to, metabolic disorders, such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis and vascular stenosis; neoplastic diseases, such as solid tumors, skin cancer, melanoma, lymphoma and endothelial cancers, e.g., breast cancer, lung cancer, colorectal cancer, stomach cancer, other cancers of the gastrointestinal tract (e.g., esophageal cancer and pancreatic cancer), prostate cancer, kidney cancer, liver cancer, bladder cancer, cervical cancer, uterine cancer, testicular cancer and ovarian cancer; and other diseases and conditions that are sensitive or responsive to modulation of DGAT function.

The methods of the present invention typically involve administering to a subject in need of therapeutic treatment, an effective amount of a compound of formula (I). The dose, frequency and timing of such administering will depend in large part on the selected therapeutic agent, the nature of the condition being treated, the condition of the subject including age, weight and presence of other conditions or disorders, the formulation being administered and the discretion of the attending physician. Preferably, the compositions and compounds of the invention and the pharmaceutically acceptable salts thereof are administered via oral, parenteral or topical routes. Generally, the compounds are administered in dosages ranging from about 2 mg up to about 2,000 mg per day, although variations will necessarily occur depending, as noted above, on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day. The dosage employed for the topical administration will, of course, depend on the size of the area being treated.

Combination Therapy with Additional Active Agents

The present invention further provides methods of using a compound or composition of the invention in combination with one or more additional active agents, depending on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165-71; United Kingdom Prospective Diabetes Study Group: UKPDS 28, *Diabetes Care* (1998) 21: 87-92; Bardin, C. W.,(ed.), CURRENT THERAPY IN ENDOCRINOLOGY AND METABOLISM, $6^{th}$ Edition (Mosby-Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al., *Diabet. Med.* (1996) 13 365-370; Kwiterovich, P. *Am. J. Cardiol* (1998) 82 (12A): 3U-17U).

In particular, the studies provided above indicate that diabetes and hyperlipidemia modulation can be further improved in many instances by the addition of a second agent to the therapeutic regimen. Combination therapy includes administration of a single pharmaceutical dosage formulation which contains a compound having the general structure of formula I and one or more additional active agents, as well as administration of a compound of formula I and each active agent in its own separate pharmaceutical dosage formulation. For example, a compound of formula I and an HMG-CoA reductase inhibitor can be administered to the human subject together in a single oral dosage composition, such as a tablet or capsule, or each agent can be administered in separate oral dosage formulations. Where separate dosage formulations are used, a compound of formula I and one or more additional active agents can be administered at essentially the same time (i.e., concurrently), or at separately staggered times (i.e., sequentially). Combination therapy is understood to include all these regimens.

An example of combination therapy that modulates (prevents the onset of the symptoms or complications associated with) atherosclerosis involves administering a compound of formula I in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the compounds of formula I can be administered in combination with more than one additional active agent, for example, a combination of a compound of formula I with an HMG-CoA reductase inhibitor (e.g., lovastatin, simvastatin and pravastatin) and aspirin, or a compound of formula I with an HMG-CoA reductase inhibitor and a β blocker.

Another example of combination therapy can be seen in treating obesity or obesity-related disorders, wherein the compounds of formula I can be effectively used in combination with, for example, phenylpropanolamine, phentermine, diethylpropion, mazindol; fenfluramine, dexfenfluramine, phentiramine, $β_3$ adrenoceptor agonist agents; sibutramine, gastrointestinal lipase inhibitors (such as orlistat), and leptins. Other agents used in treating obesity or obesity-related disorders can be used in combination with compounds of formula I including, for example, neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

Another example of combination therapy can be seen in modulating diabetes (or treating diabetes and its related symptoms, complications, and disorders), wherein the compounds of formula I can be effectively used in combination with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); dehydroepiandrosterone (also referred to as DHEA or its conjugated sulphate ester, DHEA-$SO_4$); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the active agents discussed above for treating atherosclerosis.

Still another example of combination therapy can be seen in modulating hyperlipidemia (treating hyperlipidemia and its related complications), wherein the compounds of formula I can be effectively used in combination with, for example, statins (such as fluvastatin, lovastatin, pravastatin or simvastatin), bile acid-binding resins (such as colestipol or cholestyramine), nicotinic acid, probucol, betacarotene, vitamin E, or vitamin C.

In accordance with the present invention, a therapeutically effective amount of a compound of formula I can be used for the preparation of a pharmaceutical composition useful for treating diabetes, treating hyperlipidemia, treating hyperuricemia, treating obesity, lowering triglyceride levels, lowering cholesterol levels, raising the plasma level of high density lipoprotein, and for treating, preventing or reducing the risk of developing atherosclerosis.

A further example of combination therapy can be seen in modulating dermatological conditions, wherein compounds of formula I can be effectively used in combination with, for example, acne treatments (e.g., isotretinoin, doxycycline, tetracycline, salicylate) and seborrheic dermatitis treatments (antifungal agents such as climbazole, ketoconazole). Moreover, compounds of formula I can be effectively used to enhance the transdermal delivery of drugs applied topically in the form of a patch, lotion, jellies, cream, etc.

Still another example of combination therapy can be seen in treating nonalcoholic fatty liver disease (NAFLD), wherein compounds of formula I can be effectively used in combination with hepatoprotective agents such as ursodeoxycholic acid and betaine.

Additionally, an effective amount of a compound of formula I and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozil; vitamin $B_6$ and the pharmaceutically acceptable salts thereof; vitamin $B_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, $β_3$ adrenergic receptor agonists; sulfonylureas, biguanides, α-glucosidase inhibitors, other insulin secretogogues, insulin and a hepatoprotective agent can be used together for the preparation of a pharmaceutical composition useful for the above-described treatments.

EXAMPLES $^1$H-NMR spectra were recorded on a Varian Gemini 400 MHz, Jeol Alpha 300 MHz, Bruker DPX 300 MHz, Varian Mercury 400 MHz or Bruker Avance 500 MHz NMR spectrometer. Significant peaks are tabulated and typically include: number of protons, multiplicity (s, singlet; d, doublet; t, triplet; q, quartet; m, multiplet; br s, broad singlet) and coupling constant(s) in Hertz. IR spectra were recorded on a Perkin Elmer 1600 FT-IR or a Perkin Elmer Spectrum One FT-IR. Mass spectrometry results are reported as the ratio of mass over charge, followed by the relative abundance of each ion (in parentheses). Starting materials in the synthesis examples below are either available from commercial sources such as Aldrich Chemical Co., Milwaukee, Wis., USA, or via literature procedures. Abbreviations used in the examples below have their accepted meanings in the chemical literature. For example, THF (tetrahydrofuran), $Et_2O$ (diethyl ether), MeOH (methanol), LDA (lithium diisopropylamide), MeCN (acetonitrile), DMAP (4-dimethyaminopyridine), WSC (1-ethyl-3-(3'-dimethylaminopropyl)carbodiimide), HOBt (1-hydroxybenzotriazole), DBU (1,8-diazabicyclo[5.4.0]undec-7-ene), DME (1,2-dimethoxyethane), DMF (N,N-dimethylformamide), DMSO (dimethyl sulfoxide), AcOH (acetic acid) and AcOEt (ethyl acetate). Other conventional abbreviations are used herein: for example, a methyl group is often provided as an unlabeled terminal "bond", according to accepted practice.

Example 1

This example illustrates the preparation of the compound designated Ex. 1.

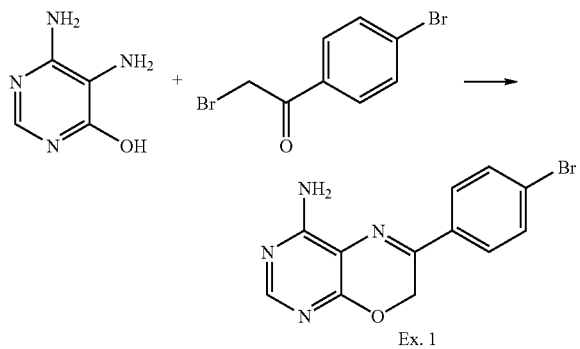

To a suspension of 4,5-diamino-6-hydroxypyrimidine (1.0 g, 7.93 mmol) and 4-bromophenacyl bromide (2.2 g, 7.93 mmol) in EtOH (20 mL) was added NaHCO₃ (666 mg, 7.93 mmol), and the mixture was stirred for 1.5 h at 80° C. After cooling, the reaction mixture was concentrated, and the residue was diluted with CHCl₃ (40 mL). After filtration of insoluble material, the filtrate was concentrated. The residue was triturated with toluene to give the desired compound Ex. 1 (840 mg) as a pale yellow crystal, m.p.: >200° C. IR (cm$^{-1}$): 3291, 3145, 1634, 1586. MS (ESI+): 305, 307 (100). 1H NMR (DMSO-d6, 400 MHz): 5.44 (s, 2H), 7.10 (br s, 2H), 7.69 (d, 2H, J=8.6 Hz), 7.93 (s, 1H), 8.03 (d, 2H, J=8.6 Hz).

Example 1-2 to 1-37

The compounds shown in Table 1 were obtained in the same manner as in Example 1.

Example 2

This example illustrates the preparation of the compound designated Ex. 2.

a)

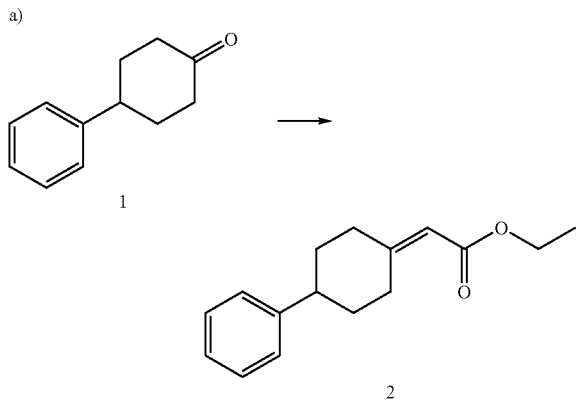

At 0° C., to a solution of triethyl phosphonoacetate (2.6 mL, 12.91 mmol) in DMF(5.5 mL), sodium hydride(60% in oil, 517 mg, 12.91 mmol) was added portionwise, and the reaction mixture was stirred at room temperature for 30 min. A solution of 4-phenylcyclohexanone in DMF (2.0 mL) was added. After stirring for 0.5 h, the mixture was poured into 5% aq. KHSO₄ (10 mL) and extracted with diethyl ether (10 mL). The organic layer was successively washed with water (5 mL) and brine (5 mL), dried over MgSO₄ and concentrated. The residue was purified by column chromatography (hexane/AcOEt=7/1) to give compound 2 (2.0 g) as colorless oil.

b)

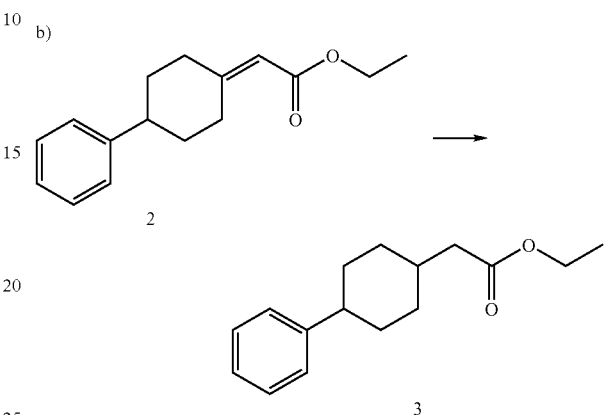

To a stirred solution of 2 (500 mg, 2.05 mmol) in EtOH (5 mL) was added 10% Pd/C (50 mg). The mixture was stirred at room temperature for 1 h under an atmospheric pressure of hydrogen. The catalyst was removed by filtration, and the filtrate was concentrated in vacuo to afford crude compound 3 (491 mg) as colorless oil, which was used for the next reaction without further purification.

c)

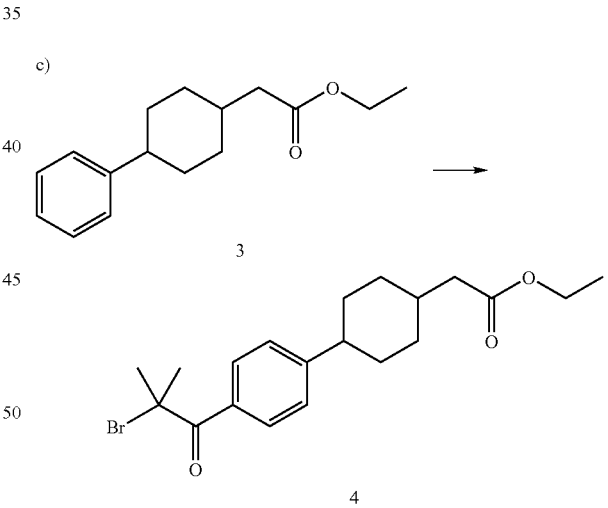

At 0° C., to a solution of compound 3 (271 mg, 1.10 mmol) in CH₂Cl₂ (1.4 mL), anhydrous AlCl₃ (440 mg, 3.30 mmol) was added portionwise and then 2-bromoisobutyryl bromide (0.14 mL, 1.10 mmol) was added dropwise. After stirring for 1 h at 0° C., the mixture was poured into ice water and extracted with CHCl₃ (5 mL). The combined organic layer was successively washed with sat. NaHCO₃ (5 mL) and brine (5 mL), dried over MgSO₄ and concentrated. The residue was purified by column chromatography (hexane/AcOEt=7/1) to give compound 4 (402 mg) as colorless oil.

d)

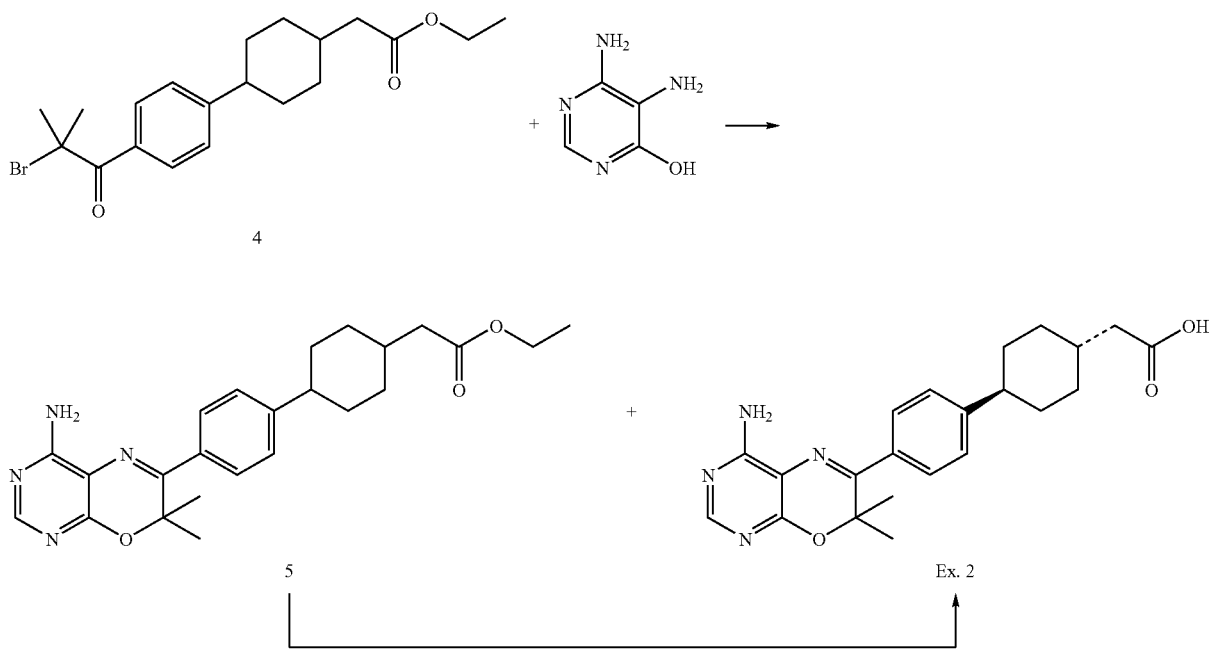

4,5-Diamino-6-hydroxypyrimidine (63.1 mg, 0.50 mmol) was mixed with 1N HCl aq. (0.50 mL, 0.50 mmol), water (2 mL) and EtOH (2 mL) and compound 4 (395 mg, 1.00 mmol) in EtOH (2 mL). The reaction mixture was refluxed (105° C.) for 12 h. The reaction mixture was concentrated to half amount of volume. The residue was adjusted to pH 9-10 with 2N NaOH aq. The resulting mixture was extracted with AcOEt (5 mL). The aqueous layer was adjusted to pH 3-4 with 10% citric acid aq., extracted with AcOEt (5 mL). The organic layer was washed with water (5 mL) and brine (5 mL), dried over $MgSO_4$. Evaporation of the solvent gave a crude Ex. 2 (54 mg, mixture of cis and trans isomers). The first organic layer was washed with water (5 mL) and brine (5 mL), dried over $MgSO_4$. Evaporation of the solvent gave a crude compound 5 (126 mg, mixture of cis and trans isomers), which was used for the next reaction without further purification. To a solution of crude compound 5 in EtOH (1.2 mL), THF (1.8 mL) and water (1.2 mL) was added 2N NaOH aq. (0.45 mL) after stirring at 40° C. for 4 h. The reaction mixture was concentrated to half amount of volume, and added to water (2 mL) and washed with AcOEt (2 mL). The aqueous layer was adjusted to pH 3-4 with 10% citric acid aq., and extracted with AcOEt (5 mL). The organic layer was washed with water (5 mL) and brine (5 mL), dried over $MgSO_4$. Evaporation of the solvent gave a white solid (113 mg). The white solid (113 mg) and crude Ex. 2 (54 mg) were combined and recrystallized from EtOH to give Ex. 2 (92 mg, trans isomer), as a white crystal, m.p.: >270° C. IR ($cm^{-1}$): 3320, 2929, 1702, 1601. MS (ESI+): 395 (100). 1H NMR (DMSO-d6, 300 MHz): 1.10-1.16 (m, 2H), 1.45-1.84 (m, 13H), 2.15 (d, 2H, J=6.0 Hz), 2.54 (m, 1H), 6.97 (br s, 2H), 7.30 (d, 2H, J=8.4 Hz), 7.64 (d, 2H, J=8.4 Hz), 7.94 (s, 1H), 11.95 (br s, 1H).

Example 2-2

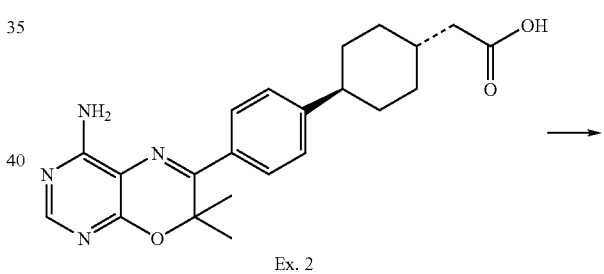

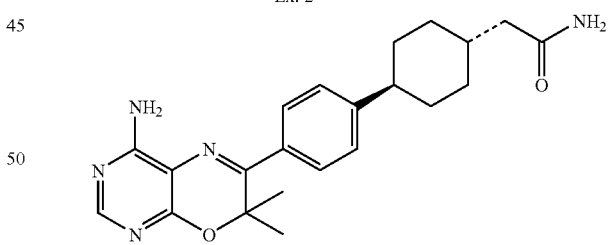

To a solution of Ex. 2 (80 mg, 0.20 mmol) in DMF (2.4 mL) was added HOBt-$H_2O$ (34.2 mg, 0.22 mmol), EDC-HCl (42.8 mg, 0.22 mmol) and 28% ammonia aq. (0.04 mL, 0.81 mmol). The reaction mixture was stirred at room temperature for 70 h. The mixture was poured into sat. $NaHCO_3$ aq. and extracted with AcOEt (3 mL). The organic layer was successively washed with water (3 mL×2), sat. $NaHCO_3$ (3 mL) and brine (3 mL), dried over $MgSO_4$. Evaporation of the solvent gave a white solid (69.5 mg). The solid was slurried with EtOH to give compound Ex. 2-2 (48.2 mg) as a white crystal, m.p.: 224-226° C. IR ($cm^{-1}$):

3348, 2923, 1672, 1604. MS (ESI+): 394 (100). 1H NMR (DMSO-d6, 400 MHz): 1.03-1.22 (m, 8H), 1.4-1.49 (m, 2H), 1.70-1.82 (m, 5H), 2.14 (d, 2H, J=6.9 Hz), 2.54 (m, 1H), 4.11 (br s, 1H), 5.27 (br s, 1H), 6.23 (br s, 2H), 7.25 (d, 2H, J=8.0 Hz), 7.36 (d, 2H, J=8.0 Hz), 7.61 (s, 1H), 11.75 (br s, 1H).

Example 2-3

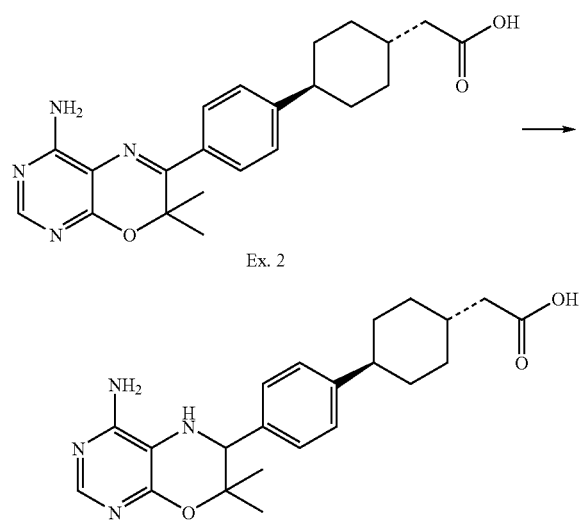

At 0° C., to a solution of Ex. 2 (120 mg, 0.30 mmol) in THF (3.6 mL) and MeOH (3.6 mL), NaBH$_4$ (194 mg, 4.86 mmol) was added portionwise and the reaction mixture was stirred at 0° C. for 20 h. 2N NaOH aq. (0.46 mL, 0.91 mmol) was added and stirred for 30 min at 60° C. The reaction mixture was concentrated to half amount of volume. The residue was added to water (3 mL) and washed with AcOEt (3 mL). The aqueous layer was adjusted to pH 3-4 with 10% citric acid aq., extracted with AcOEt (5 mL). The organic layer was washed with water (5 mL) and brine (5 mL), dried over MgSO$_4$. Evaporation of the solvent gave a white solid (150 mg). The solid was recrystallized from EtOH to give Ex. 2-3 (97 mg) as a white crystal, m.p.: 274-279° C. (decomposed). IR (cm$^{-1}$): 3414, 2927, 1650, 1595. MS (ESI+): 397 (100). 1H NMR (DMSO-d6, 300 MHz): 1.02-1.17 (m, 2H), 1.40-1.53 (m, 2H), 1.61 (s, 6H), 1.66-1.87 (m, 5H), 1.98 (d, 2H, J=7.1 Hz), 2.53 (m, 1H), 6.67 (br s, 1H), 6.89 (br s, 2H), 7.21 (br s, 1H), 7.30 (d, 2H, J=8.1 Hz), 7.63 (d, 2H, J=8.1 Hz), 7.94 (s, 1H).

Example 2-4 a)

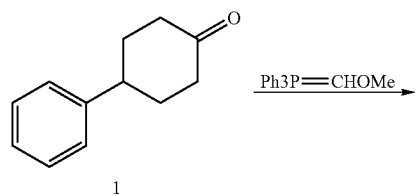

-continued

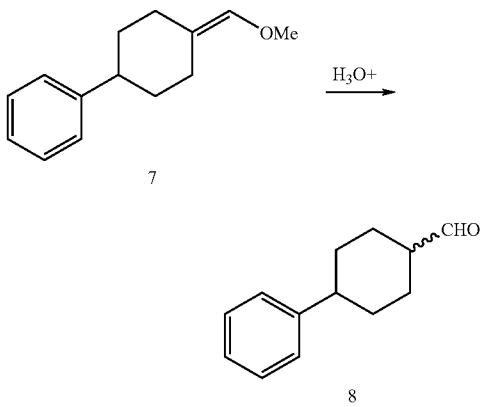

To a stirred suspension of methoxymethyltriphenylphosphonium chloride (3.14 g, 9.2 mmol) in THF (8 mL) was added potassium tert-butoxide (516 mg, 4.6 mmol) under Ar. After 1 h, 4-phenylcyclohexanone (1) (400 mg, 2.3 mmol) was added to the solution. The mixture was stirred for 1 h at room temperature, heated overnight at 70° C. After cooling, the reaction mixture was poured into sat. NaHCO$_3$ (40 mL) and extracted with ether (50 mL). The organic extract was washed with water (40 mL) and brine (40 mL) and dried over Na$_2$SO$_4$, and the solvent was removed to give crude compound 7 (2.19 g), which was used to the next step without further purification.

b)

The crude compound 7 (2.19 g) was mixed with 80% aq. AcOH (25 mL) and heated at 70° C. for 3.5 h with stirring. The reaction mixture was concentrated under reduced pressure. The residue was purified by column chromatography (hexane/AcOEt=20/1) to give compound 8 (395 mg) as colorless oil.

c)

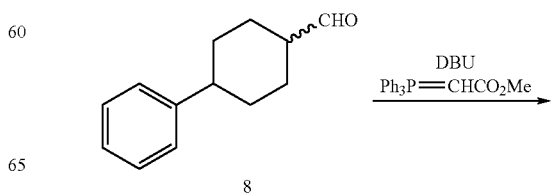

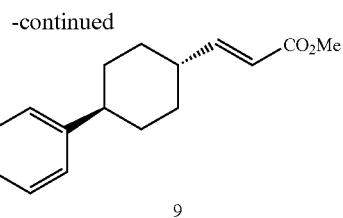

9

To a stirred solution of compound 8 (383 mg, 2.03 mmol) in toluene (20 mL) was added DBU (365 μL, 2.44 mmol) and the mixture was heated at 80° C. for 5 h under Ar. Then to the reaction mixture was added methyl (triphenylphosphoranylidene) acetate (1.2 g, 3.05 mmol) and the mixture was stirred overnight at 100° C. After cooling, the reaction mixture was washed with 5% KHSO$_4$ (10 mL), sat. NaHCO$_3$ (10 mL) and brine (10 mL), and the organic layer was dried over Na$_2$SO$_4$ and concentrated. The residue was purified by column chromatography (hexane/AcOEt=20/1) to give compound 9 (474 mg) as colorless oil.

d)

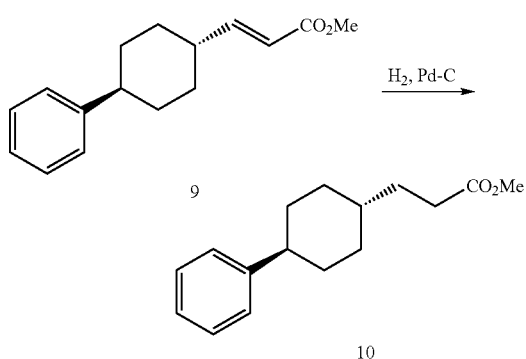

A suspension of 10% palladium on charcoal (50 mg) in a solution of compound 9 (474 mg, 1.94 mmol) in EtOH (15 mL) was hydrogenated under the atmospheric pressure of a hydrogen atmosphere overnight at room temperature. The reaction mixture was filtered, and the filtrate was concentrated to give compound 10 (436 mg) as colorless oil, which was pure enough to be used for the next step without further purification.

e)

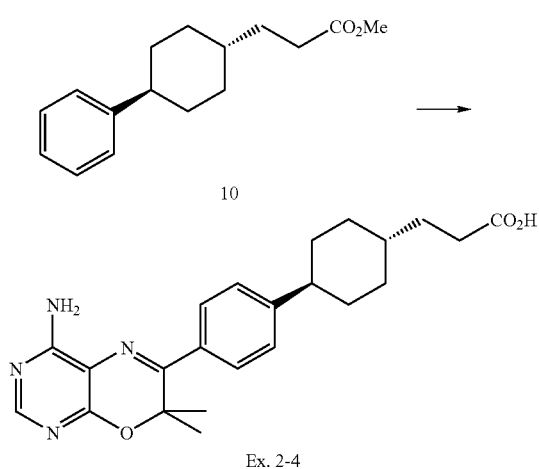

The Example 2 procedure was applied to compound 10 on a 436 mg (1.94 mmol) scale, yielding Ex. 24 (231 mg) as a colorless crystal, m.p.: >250° C. IR (cm$^{-1}$): 3310, 2922, 1702, 1611. MS (ESI+): 409 (100). 1H NMR (DMSO-d6, 400 MHz): 1.04-1.09 (m, 2H), 1.43 (m, 1H), 1.43-1.50 (m, 4H), 1.60 (s, 6H), 1.83 (br d, 4H, J=11.4 (br d, 4H, J=11.4 Hz), 2.25 (t, 2H, d=7.7 Hz), 2.50 (m, 1H), 6.88 (br s, 2H), 7.29 (d, 2H, J=8.3 Hz), 7.63 (d, 2H, J=8.3 Hz), 7.94 (s, 1H), 11.84 (br s, 1H).

Example 2-5

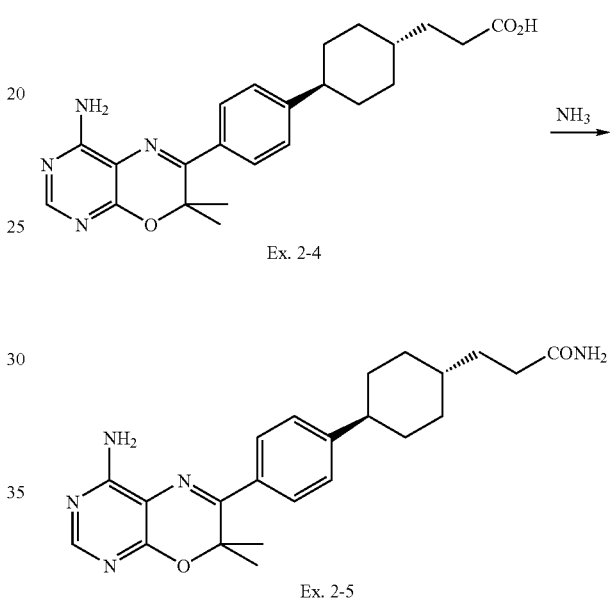

The Example 2-2 procedure was applied to Ex. 2-4 on a 50 mg (0.12 mmol) scale, yielding Ex. 2-5 (41 mg) as a colorless crystal, m.p.: 244-246° C. IR (cm$^{-1}$): 3357, 2920, 1696, 1602. MS (ESI+): 408 (100). 1H NMR (DMSO-d6, 400 MHz): 1.04-1.08 (m, 2H), 1.29 (m, 1H), 1.40-1.49 (m, 4H), 1.60 (s, 6H), 1.83 (br d, 4H, J=10.2 Hz), 2.09 (t, 2H, d=7.4 Hz), 2.50 (m, 1H), 6.60 (br s, 1H), 6.88 (br s, 2H), 7.20 (br s, 1H), 7.29 (d, 2H, J=8.3 Hz), 7.63 (d, 2H, J=8.3 Hz), 7.94 (s, 1H).

Example 2-6

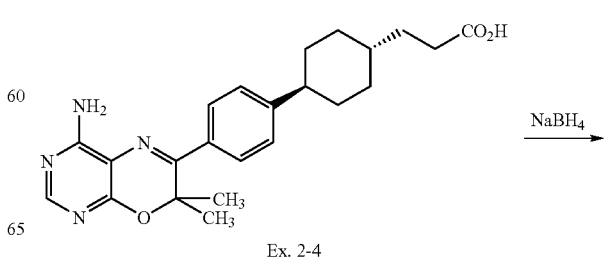

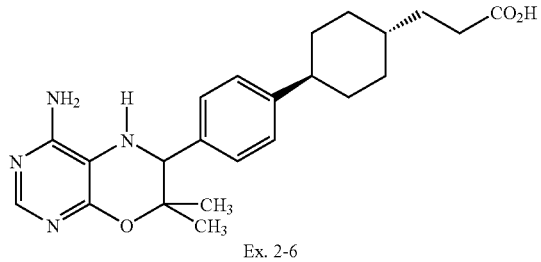

Ex. 2-6

The Example 2-3 procedure was applied to Ex. 2-4 on a 38 mg (0.09 mmol) scale, yielding Ex. 2-6 (19 mg) as a colorless crystal, m.p.: >250° C. IR (cm$^{-1}$): 3348, 2922, 1638, 1595. MS (ESI+): 411 (100). 1H NMR (DMSO-d6, 400 MHz): 1.04-1.09 (m, 2H), 1.08 (s, 3H), 1.22 (s, 3H), 1.32 (m, 1H), 1.43-1.48 (m, 4H), 1.83 (br d, 4H, J=10.7 Hz), 2.24 (t, 2H, d=7.7 Hz), 2.50 (m, 1H), 4.11 (s, 1H), 5.26 (s, 1H), 6.22 (br s, 2H), 7.23 (d, 2H, J=8.1 Hz), 7.35 (d, 2H, J=8.1 Hz), 7.62 (s, 1H), 11.73 (br s, 1H).

Example 2-7 a)

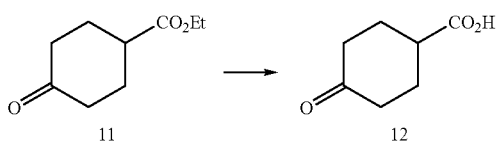

Compound 11 (3 mL, 18.82 mmol) and 30 mL of ethanol and NaOH solution were stirred together at room temperature for 3 h. Solvents were then removed in vacuo, and 12 mL of 2M HCl solution was added. The aqueous layer was extracted with 25 mL of AcOEt, and the extract was washed with brine, dried over MgSO$_4$, and concentrated in vacuo to afford crude compound 12, which was used for the next reaction without further purification.

b)

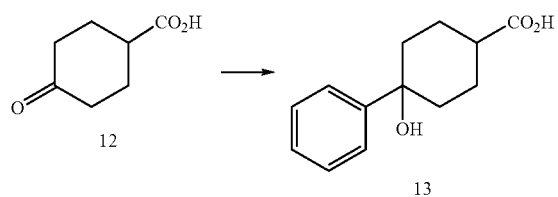

To a stirred solution of crude compound 12 (1.594 g, ca. 11.21 mmol) in 15 mL of THF was added 1.0M PhMgBr (24.7 mL, 24.7 mmol) at 0° C. and stirred for 30 min. After addition of 10 mL of water, the mixture was acidified with 1M HCl solution. The aqueous layer was extracted with 30 mL of AcOEt, and the extract was washed with brine, dried over MgSO$_4$, and concentrated in vacuo to afford crude compound 13, which was used for the next reaction without further purification.

c)

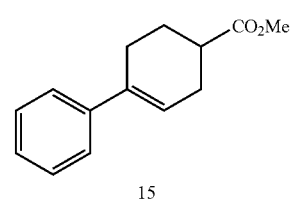

To a stirred suspension of crude compound 13 and K$_2$CO$_3$ (2.01 g, 14.5 mmol) in 10 mL of DMF was added MeI (0.98 mL, 15.7 mmol) and stirred for 3 h. After addition of 15 mL of water, the aqueous layer was extracted with 25 mL of AcOEt, and the extract was washed with water and brine, dried over MgSO$_4$, and concentrated in vacuo to afford crude compound 14, which was used for the next reaction without further purification.

d)

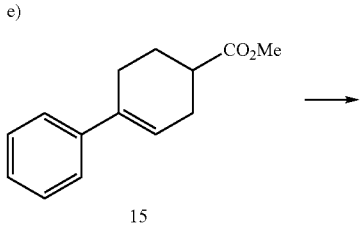

Crude compound 14, 15 mL of CHCl$_3$, trifluoroacetic acid (3.02 mL, 39.4 mmol) and triethylsilane (3.02 mL, 22.5 mmol) were stirred together at 65° C. for 5.5 h. After addition of 25 mL of water, the organic layer was separated, washed with brine, dried over MgSO$_4$, and concentrated in vacuo. The residue was purified by silica gel column chromatography (hexane/AcOEt=10/1) to give compound 15 (1.5 g) as pale yellow oil.

e)

-continued

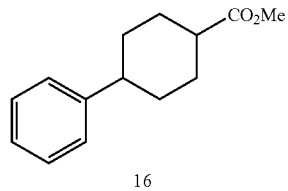

16

To a stirred solution of compound 15 (1.5 g, 6.94 mmol) in 15 mL of MeOH was added 10% Pd/C (240 mg). The mixture was stirred at room temperature for 5 h under an atmospheric pressure of hydrogen. The catalyst was removed by filtration, and filtrate was concentrated in vacuo to afford crude compound 16, which was used for the next reaction without further purification.

f)

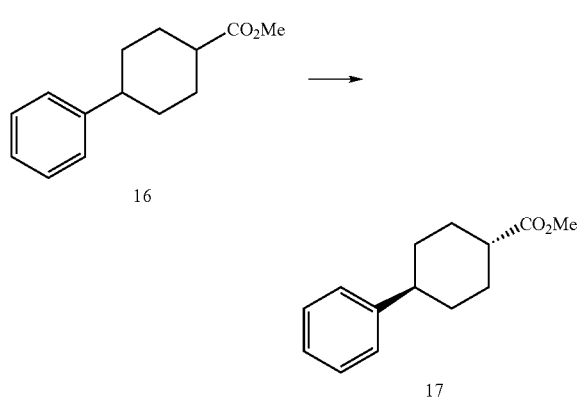

Crude compound 16 and 10 mL of MeOH and 28% MeONa (1.5 mL, 7.3 mmol, methanol solution) were stirred together at 70° C. for 7.5 h. After addition of 30 mL of water, the aqueous layer was extracted with 40 mL of AcOEt, and the extract was washed with water and brine, dried over MgSO$_4$, and concentrated in vacuo to afford crude compound 17 as a mixture of diastereomers (ratio 4:1), which was used for the next reaction without further purification.

g)

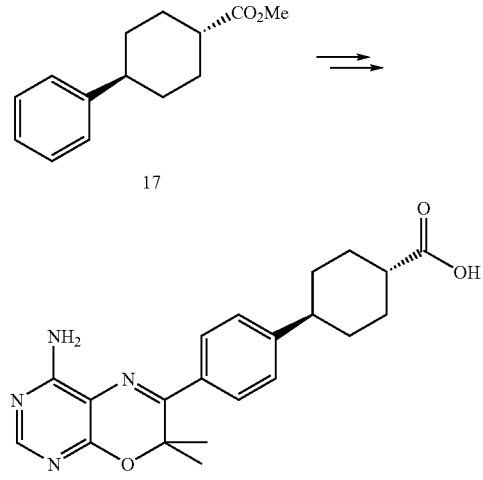

The Example 2-c) and 2-d) procedure was applied to compound 17 on a 69 mg (0.55 mmol) scale, yielding Ex. 2-7 (54 mg) as a colorless crystal, m.p.: >250° C. IR (cm$^{-1}$): 3328, 2931, 1704, 1615. MS (ESI+): 381 (100). 1H NMR (DMSO-d6, 400 MHz): 1.40-1.58 (m, 4H), 1.61 (s, 6H), 1.82-1.92 (m, 2H), 1.97-2.08 (m, 2H), 2.24-2.36 (m, 1H), 2.52-2.61 (m, 1H), 6.91 (br s, 2H), 7.31 (d, 2H, J=8.6 Hz), 7.65 (d, 2H, J=8.6 Hz), 7.95 (s, 1H), 11.92 (br s, 1H).

Examples 2-8 to 2-268

The compounds shown in Table 2 are obtained in the same manner as in Examples 2 through 2-7

Example 3 a)

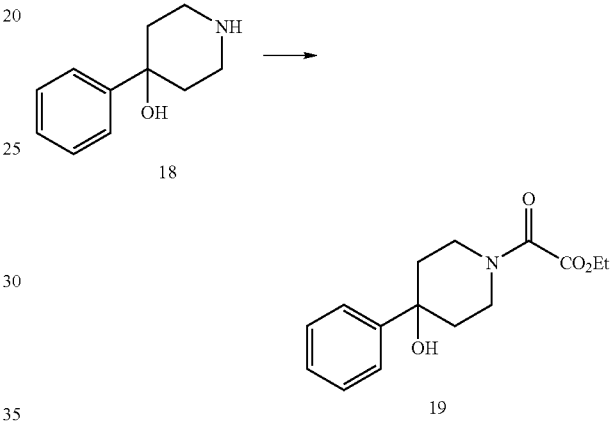

To a stirred solution of 4-hydroxy-4-phenylpiperidine (18) (1.00 g, 5.64 mmol) and Et$_3$N (0.94 mL, 6.77 mmol) in 10 mL of CHCl$_3$ was added ethyl oxalyl chloride (0.63 mL, 5.64 mmol) at 0° C. and stirred for 1 h. After addition of 10 mL of water, the organic layer was separated, dried over MgSO$_4$, and concentrated in vacuo to afford crude compound 19, which was used for the next reaction without further purification.

b)

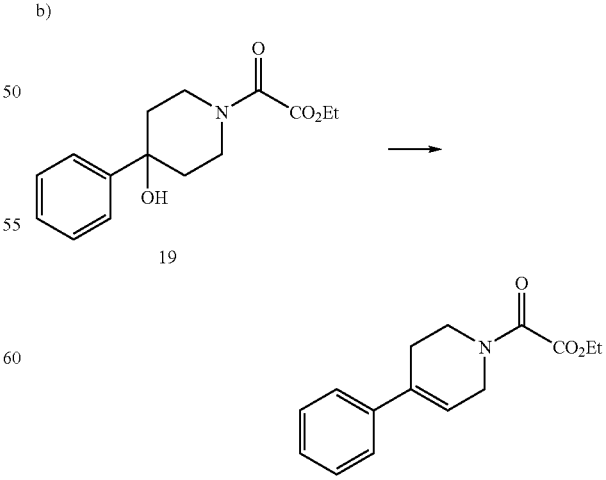

Crude compound 19, 10 mL of CHCl$_3$, trifluoroacetic acid (1.52 mL, 19.7 mmol) and triethylsilane (1.52 mL, 11.3 mmol) were stirred together at 65° C. for 1.5 h. After addition of 15 mL of water, the organic layer was separated, washed with brine, dried over MgSO$_4$, and concentrated in vacuo. The residue was purified by silica gel column chromatography (hexane/AcOEt=9/1) to give compound 20 (1.38 g) as pale yellow oil.

c)

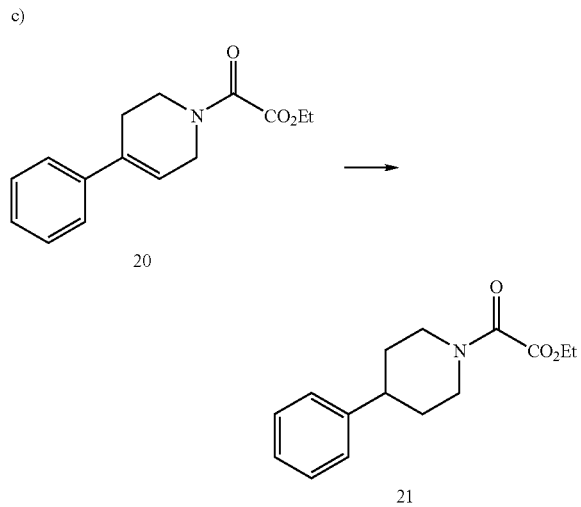

To a stirred solution of compound 20 (1.38 g, 5.32 mmol) in 8 mL of MeOH was added 10% Pd/C (200 mg). The mixture was stirred at room temperature for 5 h under an atmospheric pressure of hydrogen. The catalyst was removed by filtration, and filtrate was concentrated in vacuo to afford crude compound 21, which was used for the next reaction without further purification.

d)

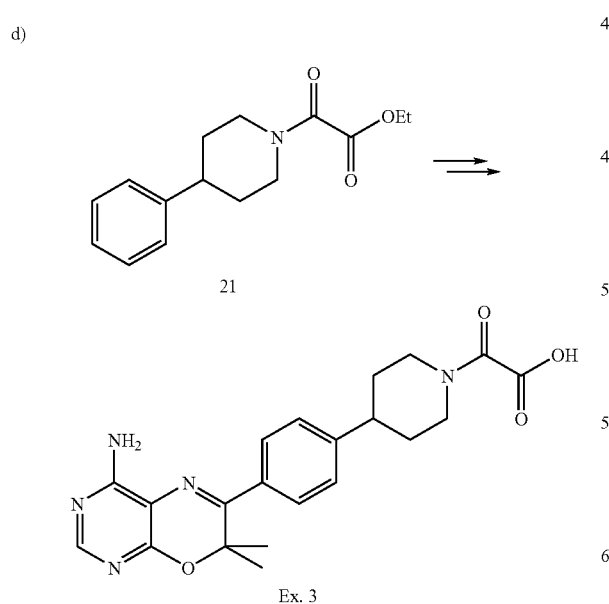

Ex. 3

The Example 2-c) and 2-d) procedure was applied to compound 21 on a 58 mg (0.46 mmol) scale, yielding Ex. 3 (20 mg) as a colorless crystal, m.p.: 188.8-190.9° C. IR (cm$^{-1}$): 1618, 1460, 1440. MS(ESI+): 410 (100). 1H NMR (DMSO-d6, 400 MHz): 1.46-1.67 (m, 2H), 1.6 (s, 6H), 1.81-1.94 (m, 2H), 2.72-2.98 (m, 2H), 3.21-3.34 (m, 1H), 3.63-3.71 (m, 1H), 4.34-4.46 (m, 1H), 6.98 (br s, 2H), 7.33 (d, 2H, J=8.4 Hz), 7.67 (d, 2H, J=8.4 Hz), 7.95 (s, 1H).

Example 3-2 to 3-3

The compounds shown in Table 3 were obtained in the same manner as in Example 3.

Example 4 a)

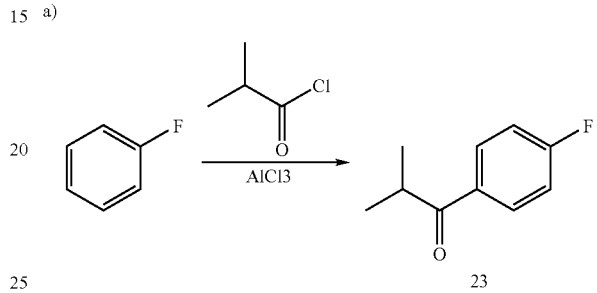

Fluorobenzene (1.78 mL, 18.96 mmol), aluminum chloride (2.53 g, 18.96 mmol) and isobutyryl chloride (1.0 mL, 9.48 mmol) were mixed under Ar and the mixture was stirred at room temperature for 1 h. The reaction mixture was poured into ice water with stirring and extracted with ether (50 mL). The organic extract was washed with sat. NaHCO$_3$ (30 mL) and brine (30 mL) and dried over Na$_2$SO$_4$, and the solvent was removed to give compound 23 (1.47 g) as colorless oil which was pure enough to be used for the next step without further purification.

b)

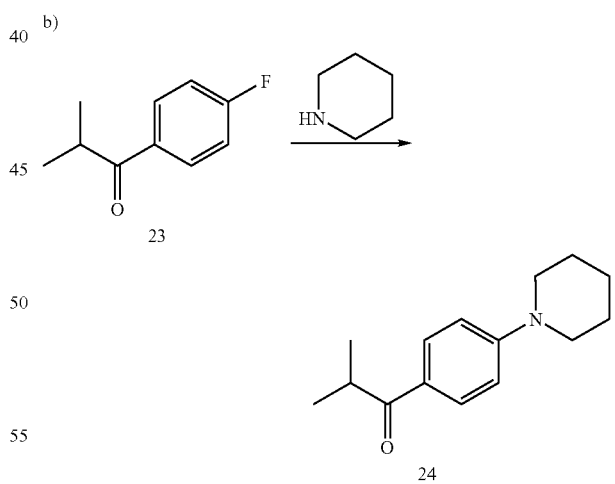

To a solution of compound 23 (50 mg, 0.30 mmol) in DMSO (0.5 mL) was added piperidine (119 μL, 1.2 mmol) and the mixture was heated at 140° C. for 5 h under Ar. After cooling, the reaction mixture was diluted with ether (10 mL) and washed with 5% KHSO$_4$ (10 mL), water (10 mL) and brine (10 mL). The organic layer was dried over Na$_2$SO$_4$, and the solvent was removed to give compound 24 (65 mg) as colorless oil, which was pure enough to be used for the next step without further purification.

c)

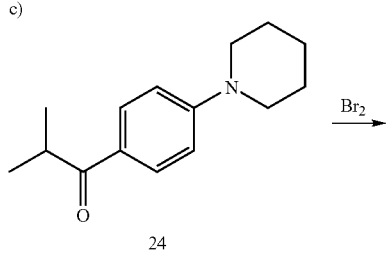

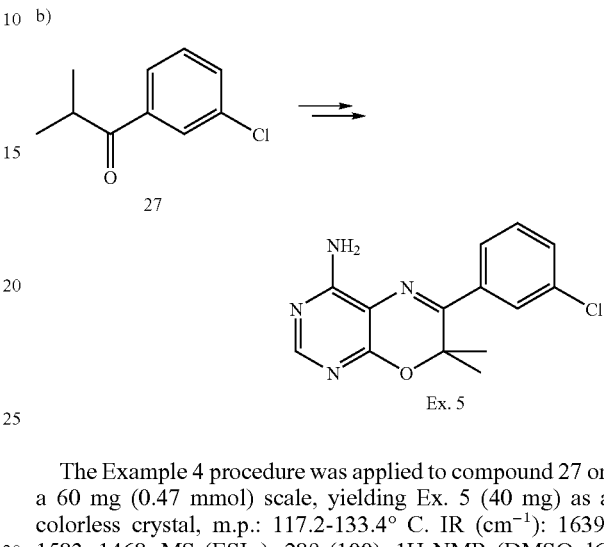

To a solution of compound 24 (64 mg, 0.28 mmol) in DME (1 mL) were added 25% HBr—AcOH (100 μl, 0.31 mmol) and Br$_2$ (15.7 μl, 0.31 mmol) successively and the mixture was stirred at room temperature for 30 min. To the reaction mixture was added 4,5-diamino-6-hydroxypyrimidine (17.5 mg, 0.14 mmol), 1N HCl (140 μl, 0.14 mmol), EtOH (1 mL), and water (1 mL) and the mixture was refluxed overnight. After cooling, EtOH was removed under reduced pressure, and the residue was diluted with AcOEt (10 mL) and washed with 1N NaOH (10 mL) and brine (10 mL). The organic layer was dried over Na$_2$SO$_4$ and concentrated. The residue was purified by thin-layer chromatography using as eluent CHCl$_3$-MeOH (9:1) to afford Ex. 4 (40 mg) as a pale yellow crystal, m.p.: 191-193° C. IR (cm$^{-1}$): 3318, 2933, 1606, 158. MS (ESI+): 338 (100). 1H NMR (DMSO-d6, 400 MHz): 1.58-1.62 (m, 6H), 1.62 (s, 6H), 3.26 (br s, 4H), 6.79 (br s, 2H), 7.29 (d, 2H, J=9.0 Hz), 7.63 (d, 2H, J=9.0 Hz), 7.91 (s, 1H).

Example 4-2 to 4-7

The compounds shown in Table 4 were obtained in the same manner as in Example 4

Example 5 a)

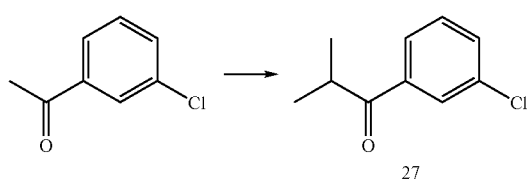

3-Chloroacetophenone (0.5 mL, 3.85 mmol), powdered KOH (2.16 g, 38.5 mmol), 18-crown-6 (102 mg, 0.385 mmol), methyl iodide (1.92 mL, 30.8 mmol) and 12 mL of toluene were stirred together at room temperature for 3 days. After addition of 30 mL of water, the aqueous layer was extracted with 20 mL of AcOEt, and the extract was washed with brine, dried over MgSO$_4$, and concentrated in vacuo to afford crude compound 27, which was used for the next reaction without further purification.

b)

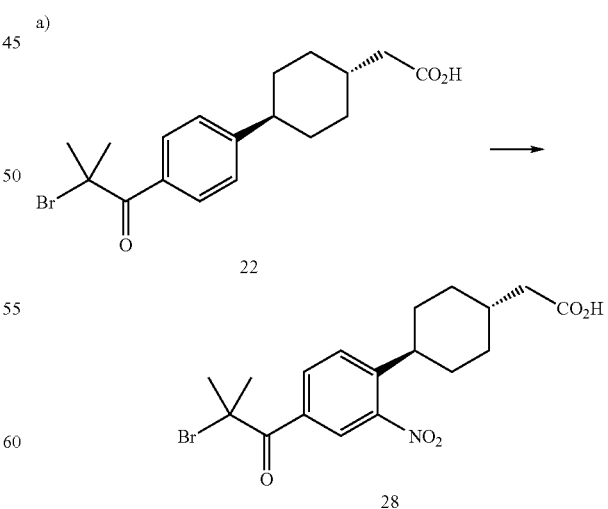

The Example 4 procedure was applied to compound 27 on a 60 mg (0.47 mmol) scale, yielding Ex. 5 (40 mg) as a colorless crystal, m.p.: 117.2-133.4° C. IR (cm$^{-1}$): 1639, 1583, 1468. MS (ESI+): 289 (100). 1H NMR (DMSO-d6, 400 MHz): 1.60 (s, 6H), 7.01 (br s, 2H), 7.48 (t, 1H, J=5.9 Hz), 7.55 (ddd, 1H, J=5.9, 1.3, 0.8 Hz), 7.67 (ddd, 1H, J=5.9, 1.3, 0.8 Hz), 7.76 (t, 1H, J=1.3 Hz), 7.97 (s, 1H).

Example 5-2 to 5-3

The compounds shown in Table 5 were obtained in the same manner as in Example 5.

Example 6 a)

To a stirred solution of compound 22 (20.0 g, 54.5 mmol) in 160 mL of CHCl$_3$ was added dropwise 96% sulfuric acid (12.1 mL, 218 mmol) and 60% nitric acid (4.56 mL, 59.9 mmol) at 0° C. and stirred at same temperature for 30 min. The reaction mixture was then poured into crashed ice (150 g). The organic layer was washed with water (50 mL) and brine (50 mL), dried over Mg2SO4, and concentrated in vacuo. The residue was purified by crystallization from AcOEt/Heptane (1/2,120 mL), to give compound 28 (18.4 g) as a pale yellow crystal.

temperature for 1 h. After addition of 2N HCl, the mixture was extracted with AcOEt (100 mL). The extract was successively washed with 1N HCl (50 mL), water (50 mL), and brine (50 mL), dried over Mg2SO4, and concentrated in vacuo. The residue was purified by silica gel column chromatography (CHCl3/AcOEt=10/1~4/1) to give compound 30 (7.40 g) as a pale yellow crystal.

b)

d)

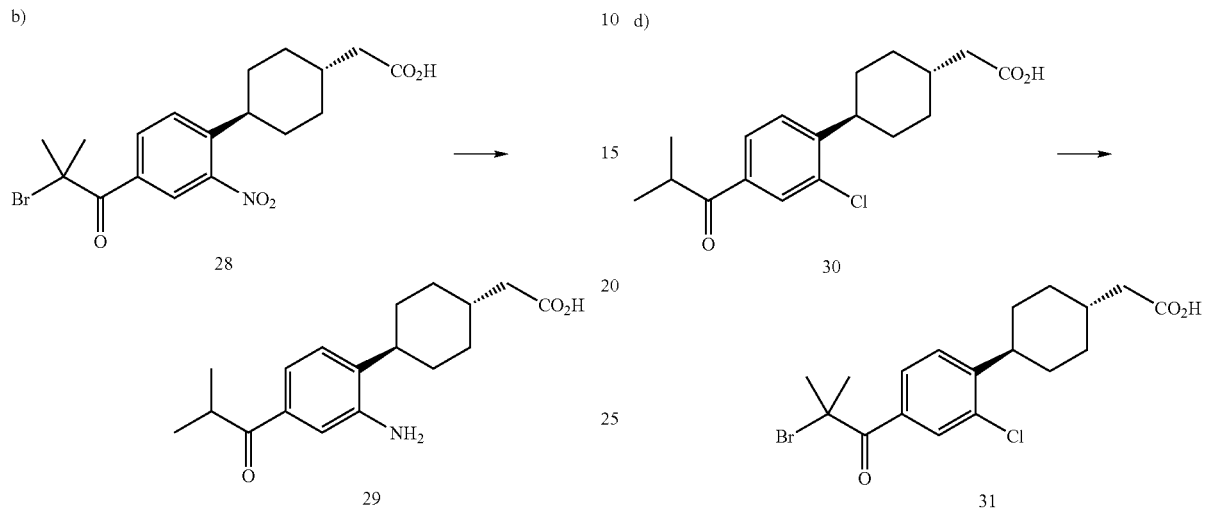

To a stirred suspension of Zn (15.9 g, 218 mmol) in 150 mL of acetic acid, compound 28 (15.0 g, 36.4 mmol) was added portionwise at 0° C. and stirred at room temperature for 1 hr, then stirred at 60° C. for another 30 min. The mixture was cooled to ambient temperature, filtered, and the filtrate was concentrated in vacuo. To the residue was added AcOEt (150 mL), washed with water (50 mL) and brine (50 mL), dried over Mg2SO4, and concentrated in vacuo. The residue was purified by crystallization from EtOH/H₂O (3/1, 50 mL), to give compound 29 (9.36 g) as a white crystal.

To a stirred solution of compound 30 (100 mg, 0.31 mmol) in 1 mL of DME was added 25% HBr—AcOH solution (89 mL, 0.372 mmol) and bromine (19 mL, 0.37 mmol) at 0° C. and stirred for 7 hr at room temperature. After addition of water, the mixture was extracted with AcOEt, the organic layer was washed with water and brine, dried over Mg2SO4. Evaporation of the solvent gave crude compound 31 (112 mg) as a pale yellow solid, which was used for the next reaction without further purification.

c)

e)

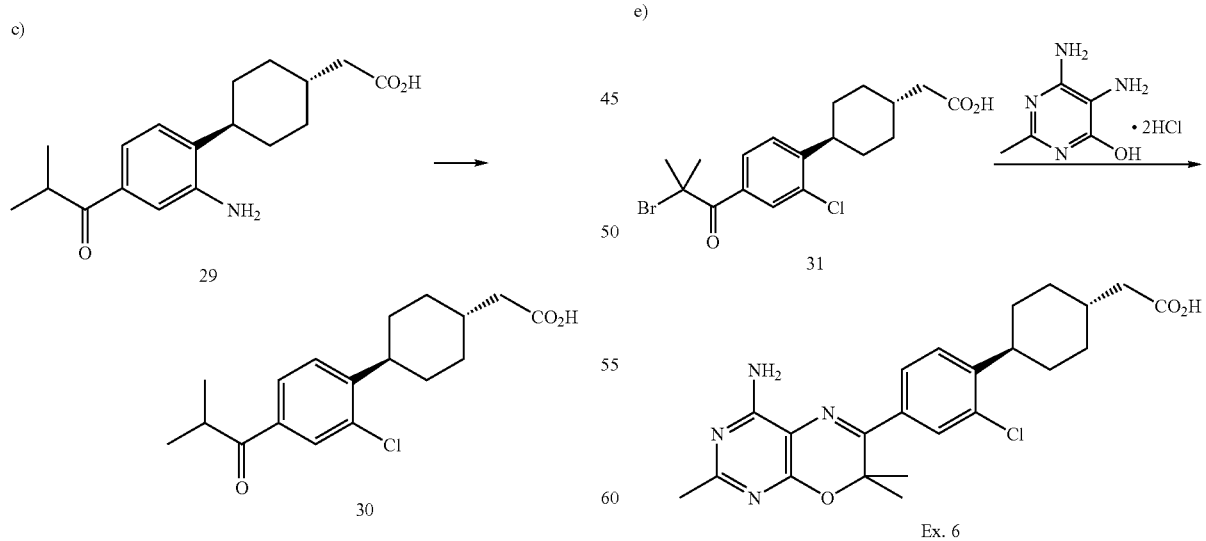

To a stirred suspension of cupper chloride(II) (6.30 g, 44.5 mmol) in 135 mL of acetone was added tert-butyl nitrite (5.88 mL, 44.5 mmol) at 0° C., then added portionwise compound 29 (9.00 g, 29.7 mmol) and stirred at same temperature for 2 h. Then the mixture was stirred at room To a solution of compound 31 (461 mg, 1.07 mmol) in EtOH (4 mL) was added 4,5-diamino-6-hydroxy-2-methylpyrimidine dihydrochloride (457 mg, 2.14 mmol) and water (1.3 mL), and refluxed for 12 h. After cooling, to the reaction mixture was added 4N NaOH (2.5 mL, 10.0 mmol) and refluxed for 1 hr. After cooling, the reaction mixture was adjusted to pH 4 with 4N HCl and stirred for 1 hr. The deposited solid was collected by filtration, washed with water, and dried in vacuo to give Ex. 6 (354 mg) as an orange solid.

f)

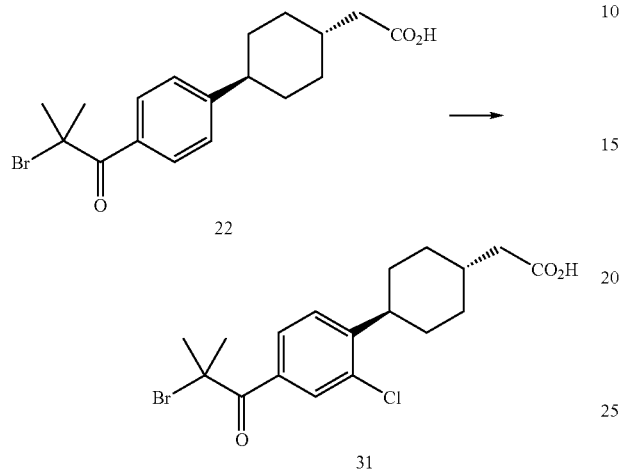

An alternative preparation of 31: To a stirred solution of compound 22 (100 mg, 0.272 mmol) in sulfuryl chloride (0.219 mL, 2.72 mmol) was added aluminum chloride (127 mg, 0.953 mmol) and catalytic amount of S2Cl2 at 0° C. and stirred for 2 h. The reaction mixture was then poured into ice water (30 g) and extracted with AcOEt (30 mL). The organic layer was washed with water (20 mL), brine (20 mL), dried over Mg2SO4. Evaporation of the solvent gave crude compound 31, which was used for the next reaction above, without further purification.

Example 6-9 a)

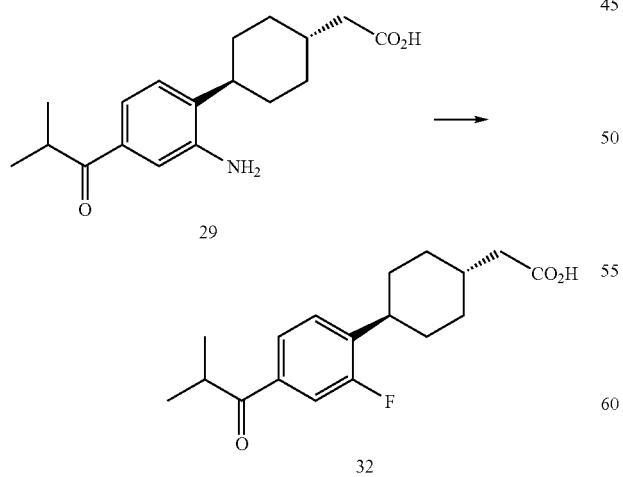

To a suspension of compound 29 (1.0 g, 3.29 mmol) in 15 mL of toluene was added nitrosonium tetrafluoroborate (462 mg, 3.95 mmol) under argon at 0° C. After stirring for 30 min at 0° C., the mixture was heated to 120° C. and stirred for 1 hr. After cooling, the solution was diluted with AcOEt, and the organic layer was washed with water, dried over Na2SO4, and concentrated in vacuo. The residue was purified by silica gel column chromatography (AcOEt/CHCl3/hexane=1/1/1) to give compound 32 (381 mg) as a pale yellow crystal.

b)

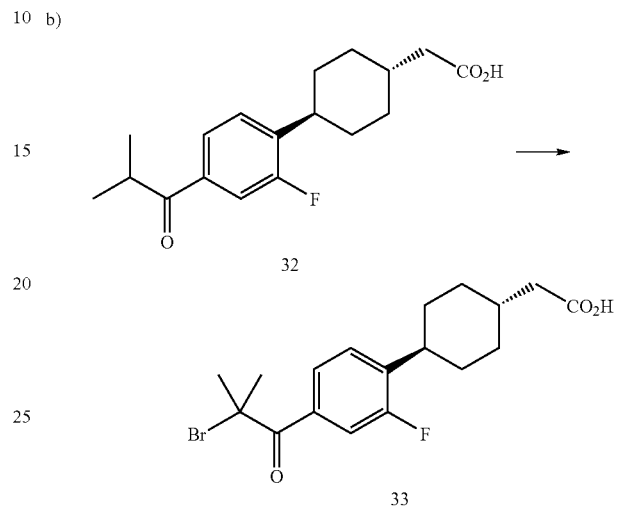

To a stirred solution of compound 32 (381 mg, 1.24 mmol) in 4 mL of DME was added 25% HBr—AcOH solution (356 mL, 1.49 mmol) and bromine (76 mL, 1.49 mmol) at 0° C. and stirred for 5 min at 0° C. and for 30 min at room temperature. After addition of water, the mixture was extracted with AcOEt, the organic layer was washed with brine, dried over Na2SO4. Evaporation of the solvent gave crude compound 33 (454 mg) as a pale yellow solid, which was used for the next reaction without further purification.

c)

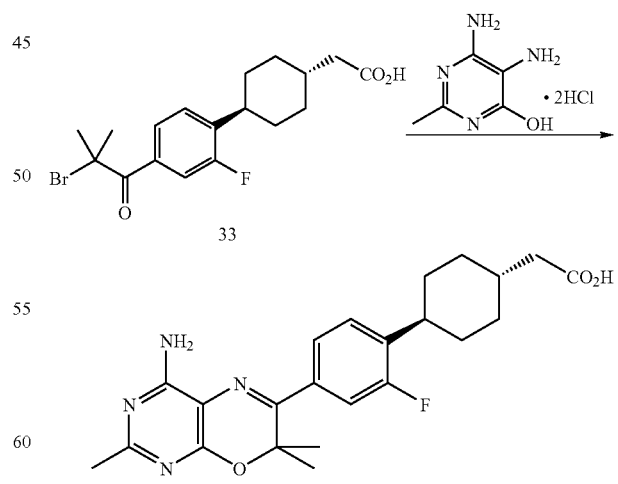

To a solution of compound 33 (454 mg, 1.18 mmol) in EtOH (6 mL) was added 4,5-diamino-6-hydroxy-2-methylpyrimidine dihydrochloride (502 mg, 2.36 mmol) and water (2 mL), and refluxed for 12 h. After cooling, to the reaction mixture was added 2N NaOH (5.9 mL, 11.8 mmol) and reflux for 3 hr. After cooling, the reaction mixture was adjusted to pH 4 with 2N HCl and stirred for 1 hr. The deposited solid was collected by filtration, washed with water, and dried in vacuo to give Ex. 6-9 (477 mg) as a pale yellow solid.

Example 6-2 to 6-25

The compounds shown in Table 6 were obtained in the same manner as in Examples 6 and 6-9.

Example 7 a)

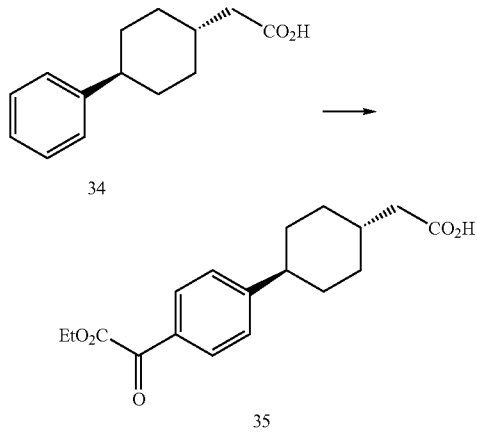

To a stirred mixture of AlCl$_3$ (6.41 g, 48.1 mmol) in 30 mL of CH$_2$Cl$_2$ was added Ethyl oxalyl chloride(1.58 mL, 14.2 mmol) and compound 34 (3.0 g, 14.2 mmol) at 0° C. and stirred at 0° C.~room temperature for 2 h. After the reaction mixture was poured into ice, 10 mL of AcOEt was added to the mixture and conc.HCl was added until suspended solution became clear. The organic layer was separated, and concentrated in vacuo. The residue was purified by silica gel column chromatography (hexane/AcOEt=3/1~1/1) to give compound 35 (3.36 g) as a white solid.

b)

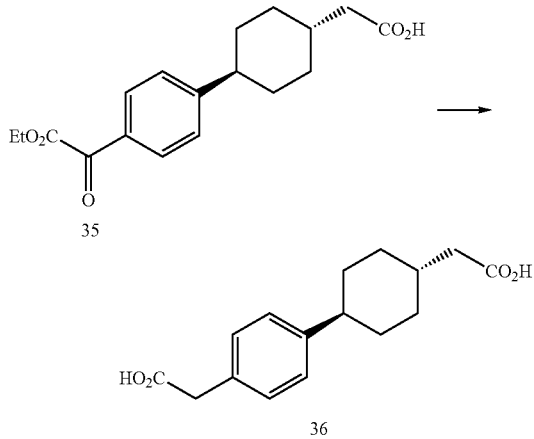

The mixture of compound 35 (3.36 g, 10.5 mmol) and KOH (2.0 g, 35.8 mmol) and N2H4.H2O (1.38 mL, 28.5 mmol) in tri(ethylene glycol) (30 mL) was stirred at 175° C. for 1 h. After cooling to room temperature, 2N HCl (30 mL, 60 mmol) and water (40 mL) was added and the deposited solid was collected by filtration to give compound 36 (2.58 g) as a pale yellow solid.

c)

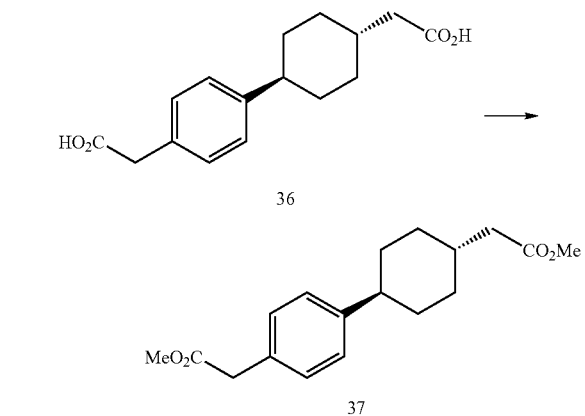

To a stirred mixture of compound 36 (2.57 g, 9.3 mmol) in 30 mL of MeOH was added SOCl2 (1.7 mL, 23.3 mmol) at 0° C. and stirred at room temperature for 4 h. The reaction mixture was concentrated in vacuo, then the residue was purified by silica gel column chromatography (hexane/AcOEt=5/1 3/1) to give compound 37 (2.13 g) as a white solid.

d)

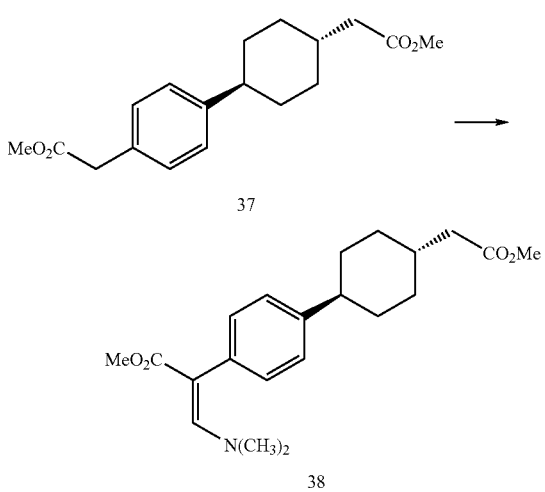

The mixture of compound 37 (2.13 g, 7.0 mmol) and N,N-dimethylformamide diethyl acetal (6.8 mL, 39.7 mmol) was stirred at 130° C. for 3 days. Then toluene (20 mL) was added and the reaction mixture was concentrated in vacuo to give crude compound 38, which was then used for the next reaction without further purification.

e)

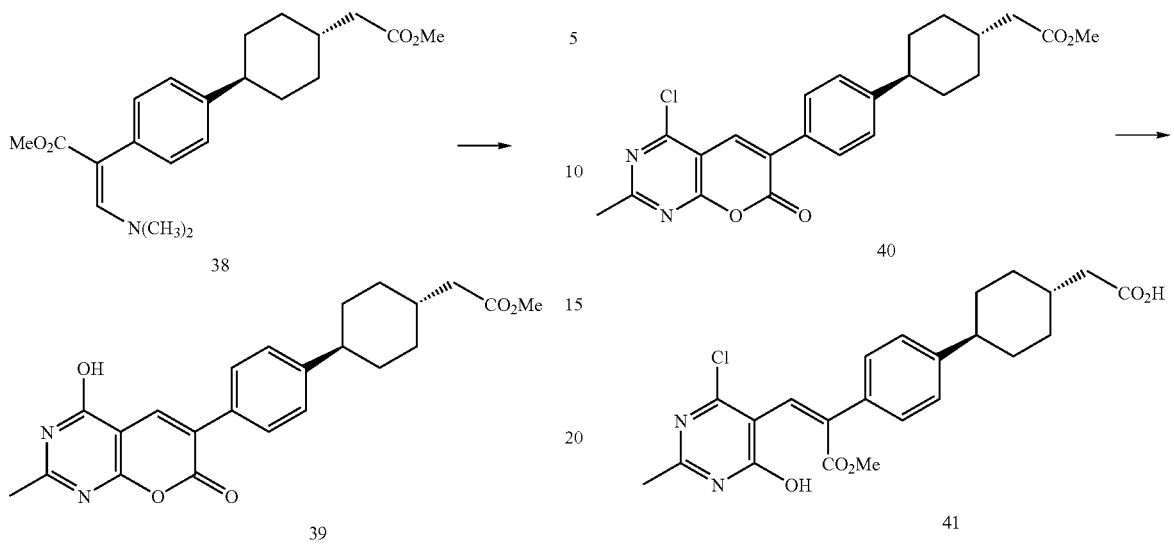

The mixture of compound 38 (crude, 7.0 mmol) and 4,6-Dihydroxy-2-methylpyrimidine (883 mg, 7.0 mmol) in AcOH (20 mL) was stirred at 110° C. for 4 h. After the reaction mixture was concentrated in vacuo, EtOH (10 mL) and water (8 mL) was added and the deposited solid was collected by filtration to give compound 39 (1.12 g) as a brown solid.

f)

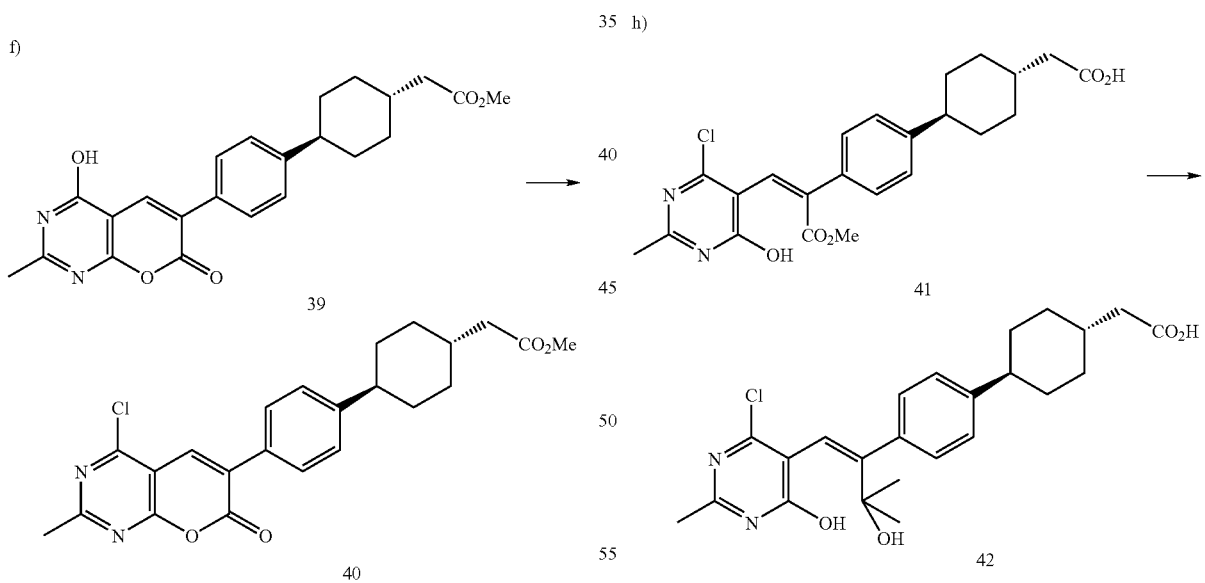

The mixture of compound 39 (200 mg, 0.49 mmol) and $POCl_3$ (1 mL) was stirred at 90° C. for 3 h. Then the reaction mixture was poured into ice and the product was extracted with AcOEt (3 mL), and the organic layer was successively washed with water (2 mL) and brine (2 mL). The organic layer was dried over $MgSO_4$, and concentrated in vacuo. The residue was purified by silica gel column chromatography (hexane/AcOEt=2/1) to give compound 40 (174 mg) as an orange solid.

g)

The mixture of compound 40 (124 mg, 0.30 mmol) and 4N NaOH (0.41 mL, 1.65 mmol) in MeOH (5 mL) was stirred at room temperature for 19 h and then stirred at 60° C. for 2.5 h. After cooling to room temperature, 2N HCl (2 mL, 4 mmol) and water (10 mL) was added and the deposited solid was collected by filtration to give compound 41 (100 mg) as a pale yellow solid.

h)

To a stirred solution of 0.93M MeMgBr in THF (1.2 mL, 1.12 mmol) was added the suspended solution of compound 41 (100 mg, 0.23 mmol) in THF (1.5 mL), and stirred at room temperature for 3 h. After addition of water (1 mL) and 2N HCl (2 mL), the product was extracted with AcOEt (3 mL), and the organic layer was successively washed with brine (2 mL). The organic layer was dried over $MgSO_4$, and concentrated in vacuo to give crude compound 42, which was then used for the next reaction without further purification.

i)

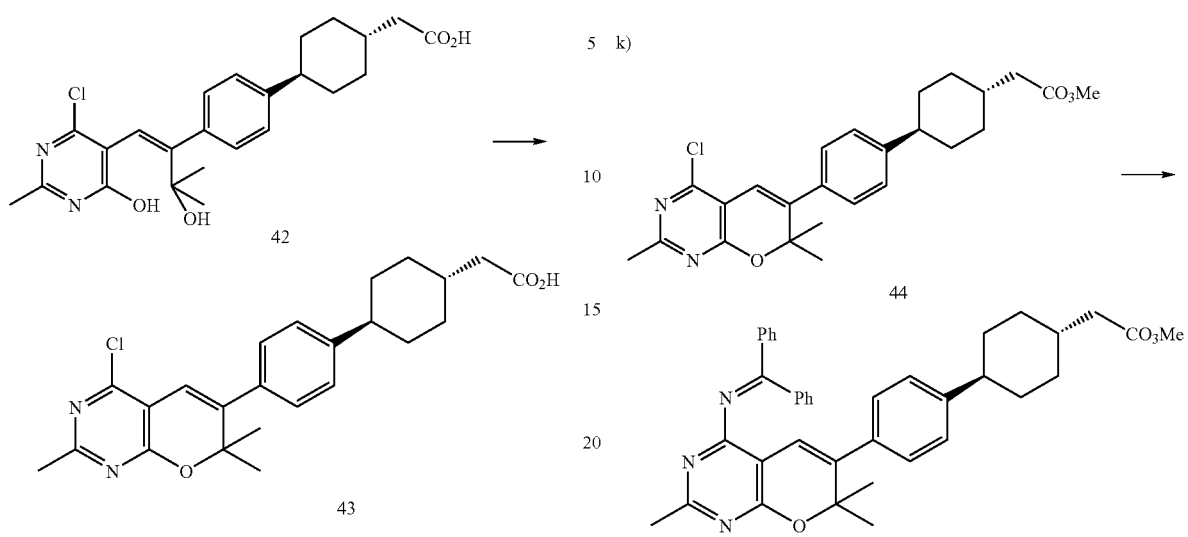

The mixture of compound 42 (crude, 0.23 mmol) and AcOH (2 mL) was stirred at 100° C. for 40 min. After cooling to room temperature, water (3 mL) was added to the reaction mixture and the product was extracted with AcOEt (3 mL), then the organic layer was successively washed with water (2 mL) and brine (2 mL). The organic layer was dried over $MgSO_4$, and concentrated in vacuo. The residue was purified by silica gel column chromatography ($CHCl_3$/MeOH=40/1~20/1) to give compound 43 (54 mg) as a orange solid.

j)

To a stirred suspension of compound 43 (52 mg, 0.12 mmol) and K2CO3 (50 mg, 0.37 mmol) in DMF (1.5 mL) was added MeI (0.023 mL, 0.37 mmol), and the mixture was stirred at room temperature for 3 h. After addition of water (3 mL), the product was extracted with AcOEt (3 mL), and the organic layer was successively washed with water (2 mL) and brine (2 mL). The organic layer was dried over $MgSO_4$, and concentrated in vacuo. The residue was purified by silica gel column chromatography (Hexane/AcOEt=4/1) to give compound 44 (46 mg) as a white solid.

k)

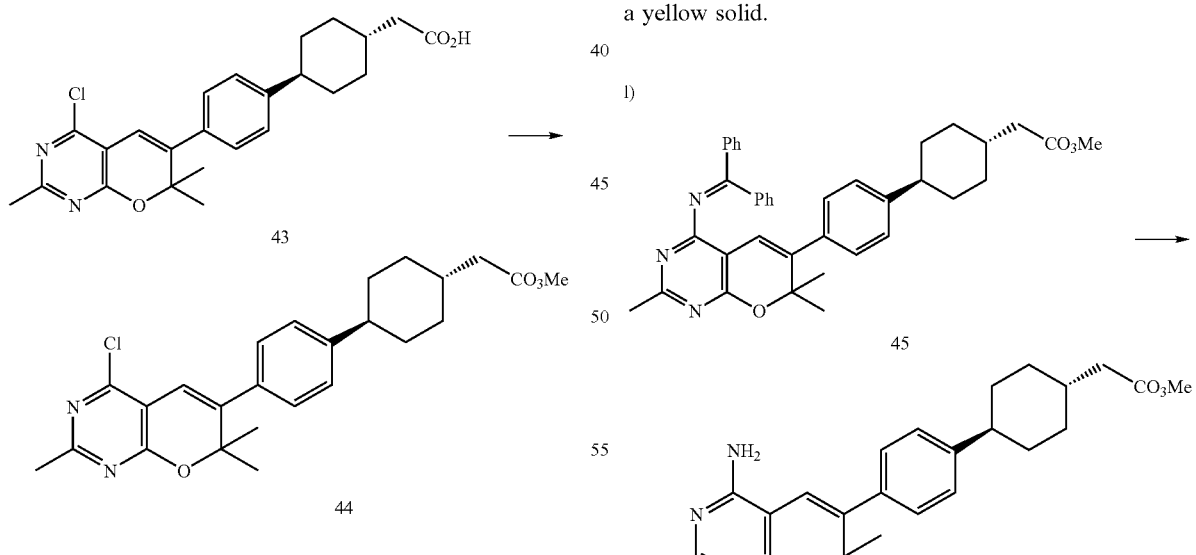

To a stirred solution of compound 44 (134 mg, 0.30 mmol) in toluene (4 mL) was added Benzophenone imine (0.255 mL, 1.52 mmol) and Pd(OAc)2 (14 mg, 0.061 mmol) and (S)-(−)-BINAP (57 mg, 0.091 mmol) and CsCO3 (198 mg, 0.61 mmol), and the mixture was stirred at 110° C. for 23 h. After addition of water (3 mL), the product was extracted with AcOEt (3 mL), and the organic layer was successively washed with brine (2 mL). The organic layer was dried over $MgSO_4$, and concentrated in vacuo. The residue was purified by silica gel column chromatography (Hexane/AcOEt=4/1~2/1) to give compound 45 (88 mg) as a yellow solid.

l)

To a stirred solution of compound 45 (85 mg, 0.145 mmol) in THF (2 mL) was added conc.HCl (0.050 mL), and the mixture was stirred at room temperature for 1 h. After addition of 4N NaOH (0.14 mL), the product was extracted with AcOEt (5 mL), and the organic layer was successively washed with water (4 mL) and brine (4 mL). The organic layer was concentrated in vacuo, thus obtained residue was purified by silica gel column chromatography (CHCl₃/MeOH=50/1) to give compound 46 (57 mg) as a yellow solid.

m)

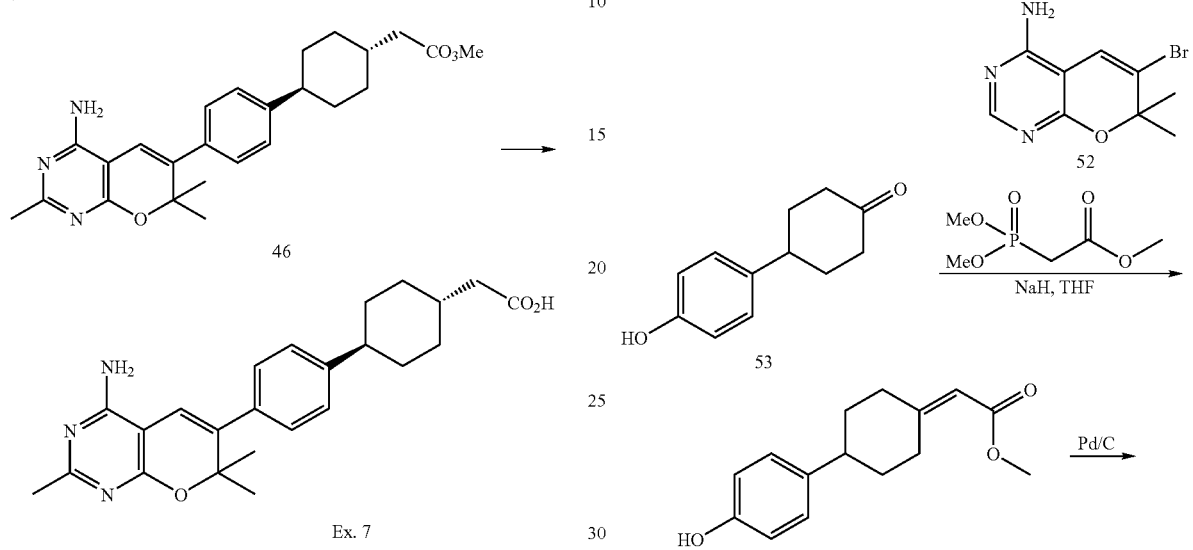

Ex. 7

To a stirred mixture of compound 46 (55 mg, 0.13 mmol) in mixed solvent (2 mL of THF and 3 mL of MeOH) was added 1N NaOH (0.43 mL, 0.43 mmol), and the mixture was stirred at 80° C. for 4 h. After the reaction mixture was concentrated in vacuo, 2N HCl (0.25 mL, 0.5 mmol) and EtOH (1 mL) was added to the mixture and the deposited solid was collected by filtration to give Ex. 7 (38 mg) as a pale yellow solid.

Example 7-4

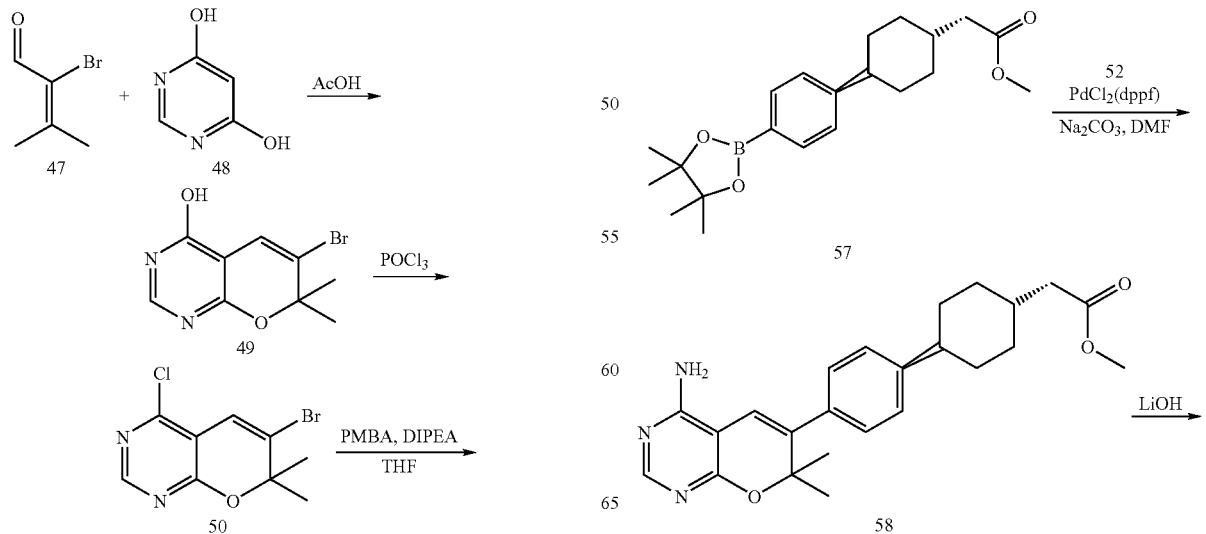

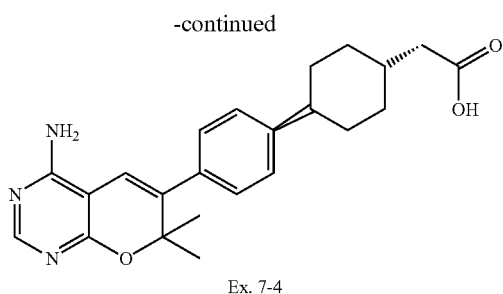

Ex. 7-4

Compound 49. A mixture of 47 (10.0 g, 89.2 mmol) and 48 (14.5 g, 89.2 mmol) in AcOH (100 mL) was heated at 100° C. for 24 h. The solvent was removed in vacuo and the resulting brown residue was purified by flash chromatography (silica gel 4% MeOH/CH$_2$Cl$_2$) to provide 49 as a yellow solid (12.04 g). $^1$H NMR (DMSO-d$_6$) δ 8.02 (s, 1H), 6.71 (s, 1H), 1.53 (s, 6H). Mass Spectrum (ESI+) m/e=257 and 259 (M+1).

Compound 50. A solution of 49 (2.13 g, 8.29 mmol) in POCl$_3$ (10 mL) was heated at 100° C. for 1 h, cooled to r.t. and poured over ice. The resulting solution was extracted with EtOAc (3×75 mL). The organic layers were pooled, washed with brine, dried (MgSO$_4$), filtered, and concentrated in vacuo to provide 50 as a yellow oil (2.28 g). $^1$H NMR (DMSO-d$_6$) δ 8.49 (s, 1H), 7.00 (s, 1H), 1.64 (s, 6H). Mass Spectrum (ESI+) m/e=275, 277, and 279 (M+1).

Compound 51. Diisopropylethylamine (1.9 mL, 10.9 mmol) was added to a solution of 50 (2.0 g, 7.26 mmol) and 4-methoxybenzylamine (2.83 mL, 21.8 mmol) in THF (20 mL). The reaction mixture was heated at reflux for 16 h, cooled to r.t., diluted with water (20 mL) and extracted with EtOAc (3×75 mL). The organic layers were pooled, washed with brine, dried (MgSO$_4$), filtered, and concentrated in vacuo to provide a yellow solid. Purification by flash chromatography (silica gel, 50% EtOAc/hexane) provided 51 as an off-white solid (2.14 g). $^1$H NMR (DMSO-d$_6$) δ 8.05 (s, 1H), 7.79 (m, 1H), 7.21 (d, J=8.7 Hz, 2H), 7.08 (s, 1H), 6.87 (d, J=8.7 Hz, 2H), 4.50 (d, J=5.7 Hz, 2H), 3.71 (s, 3H), 1.50 (s, 6H). Mass Spectrum (ESI+) m/e=376, and 378 (M+1).

Compound 52. A solution of 51 (620 mg, 1.65 mmol) in TFA (20 mL) was heated at 50° C. for 7 h. The solvent was removed in vacuo and the resulting oil was dissolved in EtOAc (30 mL), washed with saturated aqueous NaHCO$_3$ (2×50 mL), brine, dried (MgSO$_4$), filtered, and concentrated in vacuo to provide a yellow solid. The solid was sonicated in Et$_2$O (5 mL) and collected by vacuum filtration to provide 52 as an off-white solid (388 mg). $^1$H NMR (DMSO-d$_6$) δ 7.97 (s, 1H), 7.10 (s, 1H), 7.00 (s, 2H), 1.52 (s, 6H). Mass Spectrum (ESI+) m/e=256 and 258 (M+1).

Compound 54. A 60% suspension in mineral oil of NaH (211 mg, 5.23 mmol) was added to a solution of 53 (1.0 g, 5.26 mmol) in anhydrous THF (25 mL) at 0° C. under a nitrogen atmosphere. In a separate flask trimethyl phosphonoacetate (1.02 mL, 6.31 mmol) was added to a suspension of NaH (315 mg, 7.88 mmol) in anhydrous THF (25 mL) at 0° C. under a nitrogen atmosphere. After 15 min., the two mixtures were warmed to r.t. and stirred for 30 min. The solution containing the ketone was added to the phosphonate solution via cannula. The reaction mixture was stirred at r.t. for 5 h, quenched with water (50 mL) and extracted with EtOAc (3×50 mL). The organic layers were pooled, washed with brine, dried (MgSO$_4$), filtered, and concentrated in vacuo to provide 54 as a white solid (1.25 g). $^1$H NMR (DMSO-d$_6$) δ 9.12 (s, 1H), 7.01 (d, J=8.4 Hz, 2H), 6.66 (d, J=8.4 Hz, 2H), 5.70 (s, 1H), 3.82 (m, 1H), 3.62 (s, 3H), 2.70 (m, 1H), 2.33 (m, 2H), 2.01 (m, 1H), 1.92 (m, 2H), 1.47 (m, 2H). Mass Spectrum (ESI+) m/e=247 (M+1).

Compound 55. A mixture of 54 (5.18 g, 21.0 mmol) and 10% Pd/C (500 mg) in EtOAc (150 mL) was stirred at r.t. under a hydrogen atmosphere for 20 h. The reaction mixture was filtered through celite and concentrated in vacuo to provide a yellow solid. Recrystallization from EtOAc (6 mL) provided 55 as colorless prisms with a 20:1 trans/cis ratio (2.96 g). $^1$H NMR (DMSO-d$_6$) δ 9.08 (s, 1H), 6.99 (d, J=8.5 Hz, 2H), 6.65 (d, J=8.5 Hz, 2H), 3.60 (s, 3H), 2.33 (dt, J=3.0 and 12.1 Hz, 1H), 2.23 (d, J=6.9 Hz, 2H), 1.75 (m, 5H), 1.38 (m, 2H), 1.11 (m, 2H). Mass Spectrum (ESI+) m/e=249 (M+1).

Compound 56. Triethylamine (421 µL, 3.02 mmol) was added dropwise to a solution of 55 (500 mg, 2.02 mmol) and trifluoromethanesulfonic anhydride (424 µL, 2.52 mmol) in anhydrous CH$_2$Cl$_2$ (20 mL) at 0° C. under a nitrogen atmosphere. The reaction mixture was warmed to r.t. and stirred for 4.5 h, poured into water (30 mL) and the layers were separated. The organic layers were pooled, washed with saturated aqueous NaHCO$_3$, brine, dried (MgSO$_4$), filtered, and concentrated in vacuo to provide 56 as an off-white solid (765 mg). $^1$H NMR (DMSO-d$_6$) δ 7.42 (d, J=8.7 Hz, 2H), 7.38 (d, J=8.7 Hz, 2H), 3.60 (s, 3H), 2.57 (m, 1H), 2.25 (d, J=6.6 Hz, 2H), 1.79 (m, 5H), 1.47 (m, 2H), 1.14 (m, 2H). Mass Spectrum (ESI+) m/e=381 (M+1).

Compound 57. A 50 mL round-bottomed flask was charged with 56 (1.35 g, 3.55 mmol), KOAc (1.05 g, 10.6 mmol), bis(pinacolato)diboron (991 mg, 3.90 mmol), PdCl$_2$(dppf) (87 mg, 0.107 mmol), and dppf(59 mg, 0.107 mmol). The flask was consecutively filled with nitrogen and evacuated three times. Anhydrous dioxane (25 mL) was added and the reaction mixture was heated at 80° C. for 17 h. The reaction mixture was cooled to r.t., diluted with EtOAc (50 mL), washed with brine, dried (MgSO$_4$), filtered, and concentrated in vacuo to provide a brown oil. Purification by flash chromatography (silica gel, 15% EtOAc/hexane) provided 57 as a white solid (914 mg). $^1$H NMR (DMSO-d$_6$) δ 7.59 (d, J=7.8 Hz, 2H), 7.24 (d, J=7.9 Hz, 2H), 3.60 (s, 3H), 2.45 (m, 1H), 2.25 (d, J=6.8 Hz, 2H), 1.78 (m, 5H), 1.46 (m, 2H), 1.28 (s, 12H), 1.14 (m, 2H). Mass Spectrum (ESI+) m/e=359 (M+1).

Compound 58. A mixture of 52 (1.12 g, 4.38 mmol), 57 (2.0 g, 6.57 mmol), PdCl$_2$(dppf) (107 mg, 0.132 mmol), and 2M aqueous Na$_2$CO$_3$ (11 mL) in DMF (30 mL) was heated at 80° C. under a nitrogen atmosphere for 24 h. The solution was diluted with water (75 mL) and the resulting precipitate was collected by vacuum filtration to provide an off-white solid. Purification by flash chromatography (silica gel, 5% MeOH/CH$_2$Cl$_2$) provided 58 as a white solid (1.09 g). $^1$H NMR (DMSO-d$_6$) δ 7.95 (s, 1H), 7.29 (d, J=8.0 Hz, 2H), 7.24 (d, J=8.1 Hz, 2H), 6.86 (s, 2H), 6.57 (s, 1H), 3.61 (s, 3H), 2.47 (m, 1H), 2.25 (d, J=6.7 Hz, 2H), 1.79 (m, 5H), 1.51 (s, 6H), 1.44 (m, 2H), 1.16 (m, 2H). Mass Spectrum (ESI+) m/e=408.5 (M+1).

Ex. 7-4. A solution of 58 (130 mg, 0.319 mmol) in MeOH (12 mL) and 10% aqueous LiOH (4 mL) was heated at 100° C. for 4 h. The MeOH was removed in vacuo and the resulting aqueous solution was acidified with 1N HCl to pH 4. The precipitate was collected by vacuum filtration to provide Ex. 7-4 as an off-white solid (111 mg). $^1$H NMR (DMSO-d$_6$) δ 8.09 (s, 1H), 7.33 (bs, 2H), 7.30 (d, J=8.1 Hz, 2H), 7.26 (d, J=8.1 Hz, 2H), 6.61 (s, 1H), 2.47 (m, 1H), 2.15 (d, J=6.9 Hz, 2H), 1.82 (m, 4H), 1.74 (m, 1H), 1.55 (s, 6H), 1.51 (m, 2H), 1.13 (m, 2H). Mass Spectrum (ESI+) m/e=394 (M+1).

Example 7-5

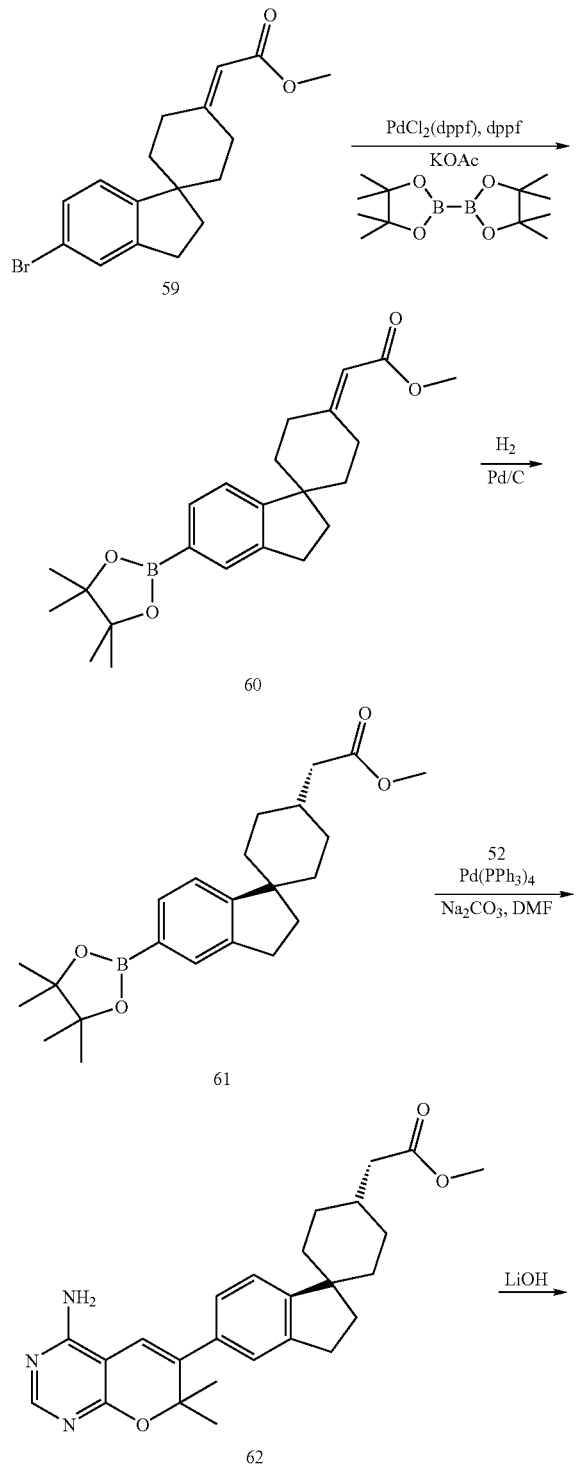

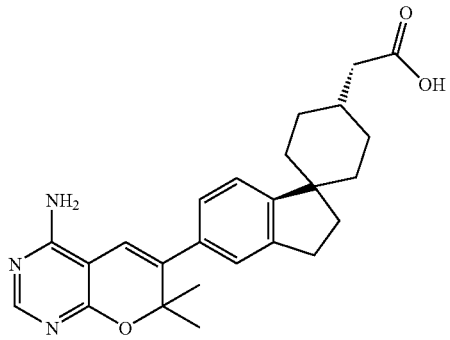

Ex. 7-5

Compound 60. A 100 mL round-bottomed flask was charged with 59 (2.54 g, 7.58 mmol), bis(pinacolato)diboron (2.41 g, 9.47 mmol), KOAc (2.23 g, 22.7 mmol), PdCl$_2$(dppf) (186 mg, 0.227 mmol), and dppf (126 mg, 0.227 mmol). The flask was consecutively filled with nitrogen and evacuated three times. Anhydrous dioxane (70 mL) was added and the reaction mixture was heated at 80° C. for 17 h. The reaction mixture was diluted with EtOAc (75 mL) and washed with water, brine, dried (MgSO$_4$), filtered, and concentrated in vacuo to provide a brown oil. Purification by flash chromatography (silica gel, 5% EtOAc/hexane) provided 60 as a white solid (2.02 g). $^1$H NMR (DMSO-d$_6$) δ 7.52 (s, 1H), 7.47 (d, J=7.6 Hz, 1H), 7.18 (d, J=7.5 Hz, 1H), 5.74 (s, 1H), 3.71 (m, 1H), 3.62 (s, 3H), 2.89 (t, J=7.4 Hz, 2H), 2.41 (m, 1H), 2.32 (m, 1H), 2.13 (m, 3H), 1.66 (m, 4H), 1.28 (s, 12H). Mass Spectrum (ESI+) m/e=383 (M+1).

Compound 61. A mixture of 60 (2.02 g, 5.28 mmol) and 10% Pd/C (562 mg) in MeOH (50 mL) was stirred at r.t. under a hydrogen atmosphere for 21 h. The reaction mixture was filtered through celite and concentrated in vacuo to provide a colorless oil. Crystallization from MeOH, followed by recrystallization from CH$_2$Cl$_2$ with MeOH diffusion provided 61 as white needles with a 20:1 trans/cis ratio (600 mg). $^1$H NMR (DMSO-d$_6$) δ 7.70 (s, 1H), 7.68 (d, J=7.7 Hz, 1H), 7.18 (d, J=7.5 Hz, 1H), 3.71 (s, 3H), 2.90 (t, J=7.3 Hz, 2H), 2.29 (d, J=7.0 Hz, 2H), 1.99 (t, J=7.4 Hz, 2H), 1.90 (m, 1H), 1.76 (m, 2H), 1.68 (m, 2H), 1.60 (m, 2H), 1.35 (s, 12H), 1.25 (m, 2H). Mass Spectrum (ESI+) m/e=385 (M+1).

Compound 62. A mixture of 52 (100 mg, 0.391 mmol), 61 (150 mg, 0.391 mmol), Pd(PPh$_3$)$_4$ (23 mg, 0.020 mmol), and 2M aqueous Na$_2$CO$_3$ (1 mL) in DMF (10 mL) was heated at 80° C. for 3.5 h. The reaction mixture was diluted with EtOAc (75 mL), washed with water (3×50 mL), brine, dried (MgSO$_4$), filtered, and concentrated in vacuo to provide a yellow solid. Purification by flash chromatography (silica gel, 5% MeOH/CH$_2$Cl$_2$) provided 62 as a white solid (103 mg). $^1$H NMR (DMSO-d$_6$) δ 7.95 (s, 1H), 7.18 (m, 3H), 6.84 (s, 2H), 6.56 (s, 1H), 3.61 (s, 3H), 2.85 (t, J=7.3 Hz, 2H), 2.28 (d, J=7.0 Hz, 2H), 1.95 (t, J=7.3 Hz, 2H), 1.79 (m, 1H), 1.65 (m, 5H), 1.51 (s, 6H), 1.49 (m, 1H), 1.23 (m, 2H). Mass Spectrum (ESI+) m/e=434 (M+1).

Ex. 7-5. A solution of 62 (103 mg, 0.238 mmol) in MeOH (9 mL) and 10% aqueous LiOH (3 mL) was heated at 100° C. for 2 h. The MeOH was removed in vacuo and the resulting aqueous layer was acidified to pH 1 with 1N HCl. The resulting precipitate was collected by vacuum filtration to provided Ex. 7-5 as an off-white solid (73 mg). $^1$H NMR (DMSO-d$_6$) δ 8.14 (s, 1H), 7.50 (bs, 2H), 7.20 (m, 3H), 6.61

(s, 1H), 2.86 (t, J=7.2 Hz, 2H), 2.17 (d, J=6.8 Hz, 2H), 1.96 (t, J=7.3 Hz, 2H), 1.71 (m, 1H), 1.67 (m, 2H), 1.63 (m, 3H), 1.56 (s, 6H), 1.50 (m, 2H), 1.22 (m, 2H). Mass Spectrum (ESI+) m/e=420 (M+1).

The compounds shown in Table 7 were obtained in the same manner as in Examples 7, 7-4 and 7-5.

Example 8

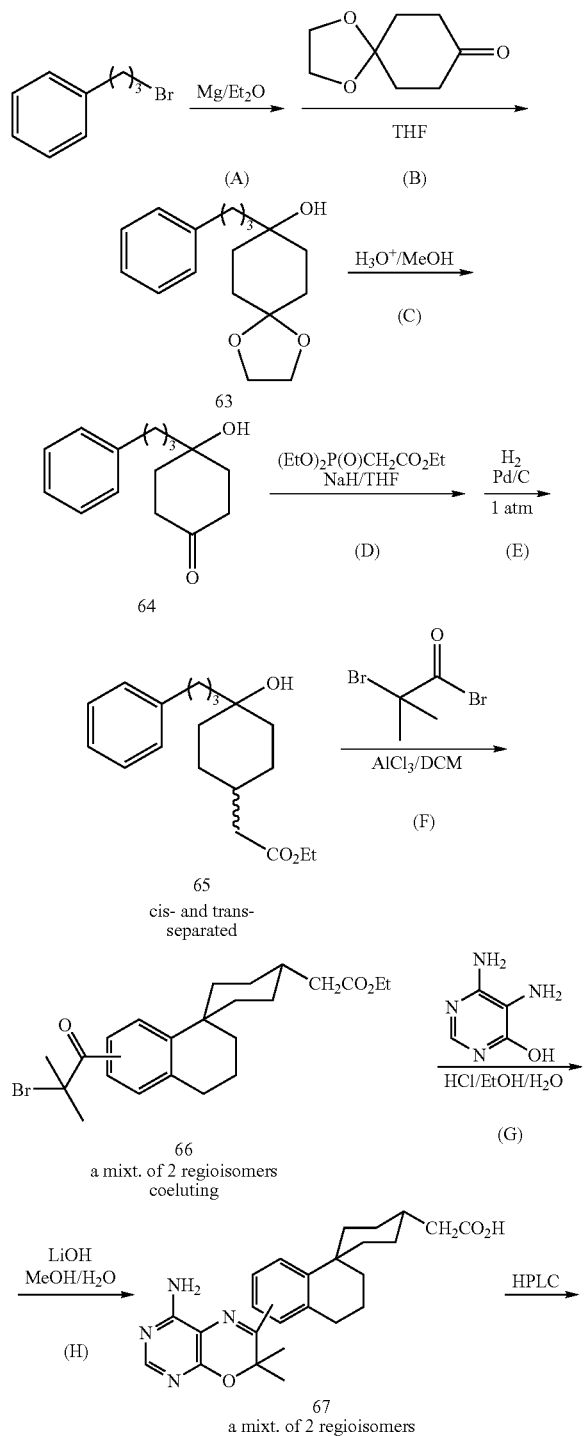

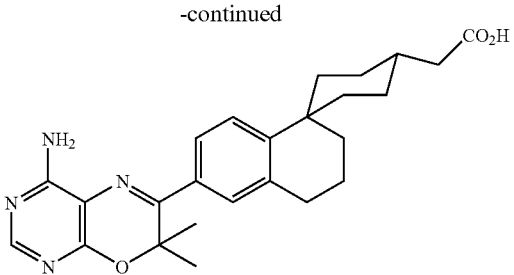

Ex. 8

Steps (A), (B) and (C). Into a flame-dried 1L 3-necked round bottom flask equipped with a magnetic stirrer, a reflux condenser and an addition funnel was placed magnesium turnings (1.1 equiv., 8.8 g) and diethyl ether (60 mL) under a nitrogen atmosphere. A diethyl ether solution of 1-bromo-3-phenylpropane (322.4 mmol, 65.5 g) was added via addition funnel at such a rate that a gentle reflux was maintained throughout the addition, about 1 h 10 min. A few particles of iodine were introduced at the beginning of the addition to initiate the reaction. Upon completion of the addition of the bromide, the reaction mixture was heated at reflux for 1 h, allowed to cool to room temperature and further cooled in an ice bath. A solution of 1,4-cyclohexanedione monoethylene ketal (1 equiv., 51.91 g) in THF (100 mL) was slowly added to the ice-cooled mixture via addition funnel with stirring over 1 h 30 min. The mixture was continuously stirred for 30 min. in the ice bath and overnight at ambient temperature. The reaction mixture was pre-cooled in an ice bath and mixture of ice and 4N aqueous HCl was added. The mixture was stirred until magnesium all dissolved, the layers were separated and the aqueous layer was extracted with diethyl ether (2×). The combined organics were washed with brine to neutral, dried over anhydrous sodium sulfate and concentrated in vacuo. The residue was taken onto the next step, in which it was hydrolyzed in a refluxing mixture with MeOH (400 mL) and 3 N aqueous $H_2SO_4$ (100 mL) for 6 h. The reaction mixture was cooled, concentrated in vacuo, diluted with ice water and extracted with EtOAc (2×). The combined organics were washed with brine (2×), dried over anhydrous sodium sulfate and concentrated in vacuo. Column chromatography (EtOAc/hexanes, 35/65) of the residue provided the desired hydroxyketone 64 (30 g). $^1$H NMR (CDCl$_3$) δ 1.45 (br s, 1H), 1.59-1.63 (m, 2H), 1.73-1.83 (m, 4H), 1.93-1.97 (m, 2H), 2.20-2.28 (m, 2H), 2.65-2.76 (m, 4H), 7.19-7.24 (m, 3H), 7.28-7.33 (m, 2H). Mass Spectrum (CI+) m/e=215.1 (M+1).

Step (D). To a flame-dried single-necked round bottom flask in an ice bath was placed NaH (a 60% dispersion in mineral oil) (1 equiv., 0.66 g) and subsequently charged with THF (20 mL) under a nitrogen atmosphere. To this was dropwise added trimethyl phosphonoacetate (1 equiv., 2.89 g/2.75 mL) via syringe. When hydrogen evolution appeared complete, a solution of hydroxyketone 64 (15.5 mmol, 3.33 g) in THF (40 mL) was slowly introduced via addition funnel. The reaction mixture was stirred at ambient temperature overnight. The reaction was quenched with saturated aqueous NH$_4$Cl followed by water and extracted with EtOAc (2×). The combined organics were washed with brine (2×), dried over anhydrous sodium sulfate and concentrated in vacuo. Column chromatography of the residue (EtOAc/hexanes, 30/70) provided the desired hydroxyacrylate (3.5 g). $^1$H NMR (CDCl$_3$) δ 1.16 (s, 1H), 1.29 (t, J=7.1 Hz, 3H), 1.51-1.61 (m, 4H), 1.70-1.80 (m, 4H), 2.10-2.14 (m, 1H), 2.43-2.59 (m, 2H), 2.65 (t, J=7.5 Hz, 2H), 3.46-3.50 (m, 1H), 4.16 (q, J=7.1 Hz, 2H), 5.65 (s, 1H), 7.19-7.22 (m, 3H), 7.28-7.32 (m, 2H).

Step (E). The hydroxyacrylate (15.5 mmol) obtained above was hydrogenated over palladium (10% on charcoal) (10 mol %) in EtOAc (60 mL) using hydrogen gas at an atmospheric pressure over 10 h. The Pd/C was filtered off by a layer of celite and the filtrate was concentrated in vacuo. The product contained a mixture of two conformers (ratio 3:1) of the desired tertiary hydroxyl ester 65, which were separated by column chromatography (EtOAc/hexanes, 20/80) and characterized by the following spectral data. In practice, the conformeric mixture was further elaborated without separation. $^1$H NMR (major conformer, CDCl$_3$) δ 1.06 (s, 1H), 1.27 (t, J=7.1 Hz, 3H), 1.33-1.42 (m, 4H), 1.46-1.51 (m, 2H), 1.55-1.66 (m, 4H), 1.68-1.76 (m, 3H), 2.23 (d, J=7.0 Hz, 2H), 2.63 (t, J=7.6 Hz, 2H) 4.14 (q, J=7.1 Hz, 2H), 7.18-7.23 (m, 3H), 7.28-7.32 (m, 2H). Mass Spectrum (CI+) m/e=287.1 (M+1); $^1$H NMR (minor conformer, CDCl$_3$) δ 1.07-1.15 (m, 2H), 1.22 (s, 1H), 1.27 (t, J=7.1 Hz, 3H), 1.39-1.44 (m, 2H), 1.54-1.58 (m, 2H), 1.67-1.75 (m, 6H), 1.88 (m, 1H), 2.22 (d, J=7.1 Hz, 2H), 2.65 (t, J=7.6 Hz, 2H), 4.14 (q, J=7.1 Hz, 2H), 7.18-7.22 (m, 3H), 7.29-7.32 (m, 2H). Mass Spectrum (CI+) m/e=287.1 (M+1).

Steps (F), (G) and (H). To a flame-dried 50 mL single-necked round bottom flask in an ice-salt bath was placed AlCl$_3$ (2.5 equiv., 1.43 g) followed by dropwise addition of 2-bromoisobutyryl bromide (2 equiv., 2.01 g/1.08 mL) under a nitrogen atmosphere. The mixture was stirred for about 5 min., and CH$_2$Cl$_2$ (8 mL) was introduced. After another 5 min, a CH$_2$Cl$_2$ (20 mL) solution of the conformeric mixture of tertiary hydroxyl ester 65 (4.3 mmol, 1.23 g) was dropwise added. The reaction mixture was continuously stirred in the ice-salt bath for 1 h. A mixture of ice and 2 N aqueous HCl was added and the mixture was stirred until all dissolved and extracted with CH$_2$Cl$_2$ (2×). The combined organics were washed with brine (3×), dried over anhydrous sodium sulfate and concentrated in vacuo. The residue contained mainly two acylation regioisomers in a ratio of about 4 to 1, which were cyclized with 4,5-diamino-6-hydroxypyrimidine hemisulfate (0.5 equiv., 0.63 g) in the presence of 2N aqueous HCl (2.2 equiv., 4 mL) in 3:1 EtOH-H$_2$O (40 mL). The mixture was refluxed for about 12 h. The mixture was cooled, diluted with saturated aqueous NH$_4$Cl and extracted with EtOAc (2×). The combined organics were washed with saturated aqueous NH$_4$Cl (2×), dried over anhydrous sodium sulfate and concentrated in vacuo. The product was hydrolyzed by LiOH.H$_2$O (5 equiv., 0.73 g) in 3:1 MeOH-H$_2$O (20 mL). Using the same workup used in the preceding cyclization step, a mixture of two major regioisomers (67) was obtained. The major isomer (1.2 g) was obtained by recrystallization (EtOAc/CH$_2$Cl$_2$/MeOH). The desired isomer (Ex. 8) (200 mg) was obtained by preparatory HPLC of the mother liquor. $^1$H NMR (CDCl$_3$) (a single conformer, trans-) δ 1.35-1.43 (m, 2H), 1.69-1.88 (m, 16H), 1.96 (m, 1H), 2.36 (d, J=7.0 Hz, 2H), 2.83 (t, J=6.0 Hz, 2H), 7.34 (d, J=1.6 Hz, 1H), 7.42 (dd, J=8.4, 1.6 Hz, 1H), 7.49 (d, J=8.4 Hz, 1H), 8.16 (s, 1H). Mass Spectrum (CI+) m/e=435.2 (M+1).

Example 8-2

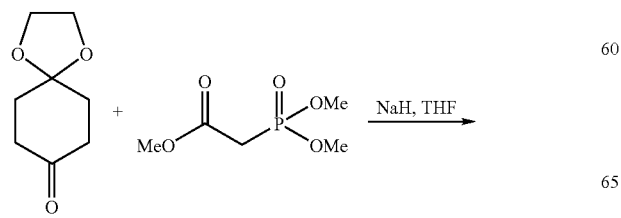

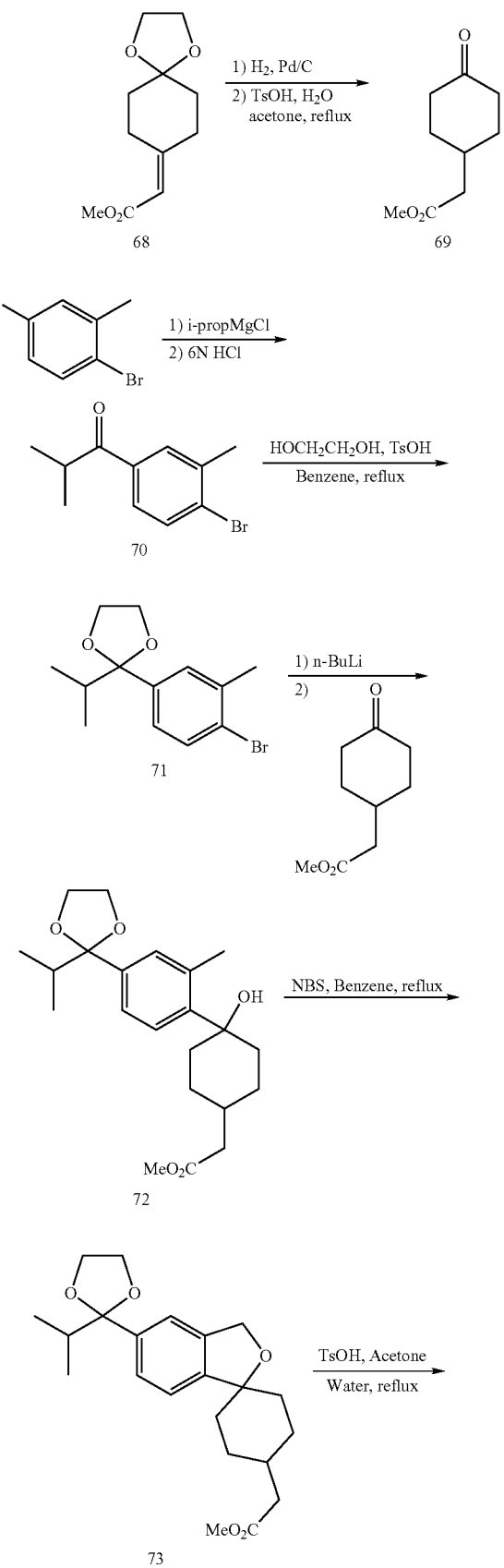

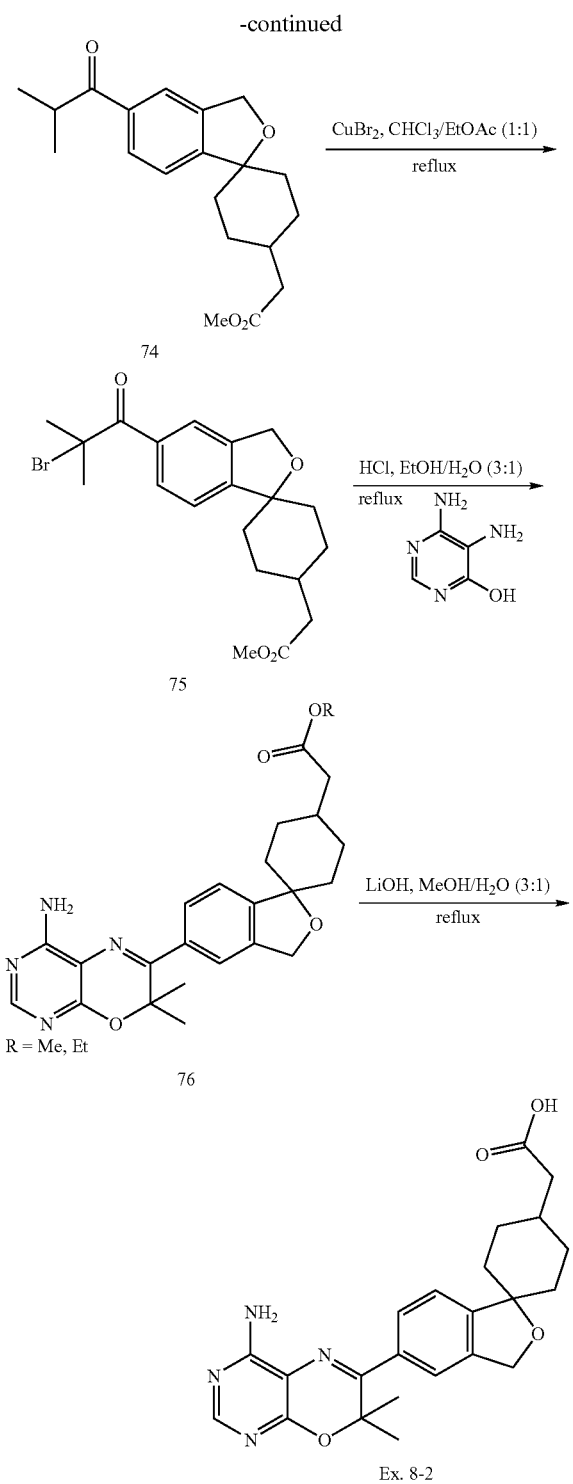

Ex. 8-2

Compound 69. Trimethyl phosphonoacetate (10.36 mL, 64.0 mmol) was added to a suspension of NaH in anhydrous THF (500 mL) at 0° C. under a nitrogen atmosphere. After 30 min. at 0° C., a solution of 1,4-cyclohexanedione monoethylene ketal (10.0 g, 64.0 mmol) in anhydrous THF (50 mL) was added via cannula. The reaction mixture was warmed to ambient temperature and stirred for 12 h. The reaction was quenched with water and the THF was removed in vacuo. The aqueous layer was extracted with EtOAc and the organic layers were pooled, washed with brine, dried (MgSO$_4$), filtered, and concentrated in vacuo to provide 68 as a colorless oil. 10% Pd/C was added to a solution of 68 in 95% EtOH (200 mL). The reaction mixture was stirred under a hydrogen atmosphere for 20 h, filtered through celite, and concentrated in vacuo to provide a colorless oil. p-Toluenesulfonic acid monohydrate (1.21 g, 6.40 mmol) was added to a solution of the oil in acetone (200 mL) and water (50 mL) and the reaction mixture was heated at reflux for 24 h. The acetone was removed in vacuo and the aqueous solution was extracted with EtOAc. The organic layers were pooled, washed with brine, dried (MgSO$_4$), filtered, and concentrated in vacuo to provide 69 as a colorless liquid (5.86 g). $^1$H NMR (CDCl$_3$) δ 1.46 (m, 2H), 2.08 (m, 2H), 2.25-2.33 (m, 3H), 2.37 (m, 4H), 3.68 (s, 3H). Mass Spectrum (ESI+) m/e=171.1 (M+H).

Compound 70. Isopropylmagnesium chloride (25.5 mL, 51.0 mmol) was added via syringe to a solution of 4-bromo-3-methylbenzonitrile (5.0 g, 25.5 mmol) in anhydrous Et$_2$O (50 mL) at 0° C. under a nitrogen atmosphere. The reaction mixture was heated at reflux for 12 h. The reaction mixture was cooled to 0° C. and quenched with 6 N HCl. After stirring at ambient temperature for 12 h, the layers were separated and the aqueous solution was extracted with EtOAc. The organic extracts were pooled, washed with brine, dried (MgSO$_4$), filtered, and concentrated in vacuo to provide a brown oil. Flash chromatography (silica gel, 2% EtOAC/hexanes) provided 70 as a colorless oil (3.69 g). $^1$H NMR (DMSO-d$_6$) δ 1.08 (d, J=6.8 Hz, 6H), 2.41 (s, 3H), 3.62 (m, 1H), 7.68 (d, J=8.4 Hz, 1H), 7.73 (d, J=8.3 Hz, 1H), 7.92 (s, 1H). Mass Spectrum (ESI+) m/e=241.1 and 243.1 (M+H).

Compound 71. p-Toluenesulfonic acid monohydrate (360 mg, 1.89 mmol) was added to a solution of 70 (4.57 g, 18.9 mmol) and ethylene glycol (8.45 mL, 0.152 mol) in benzene (50 mL). The reaction mixture was heated at reflux for 20 h while removing water using a Dean-Stark trap. The solution was washed with saturated aqueous NaHCO$_3$, brine, dried (MgSO$_4$), filtered and concentrated in vacuo to provide a colorless oil. Flash chromatography (silica gel, 2% EtOAc/hexanes) provided 71 as a colorless oil (4.86 g). $^1$H NMR (DMSO-d$_6$) δ 0.79 (d, J=6.8 Hz, 6H), 2.03 (m, 1H), 2.34 (s, 3H), 3.63 (m, 2H), 3.92 (m, 2H), 7.07 (dd, J=2.2 and 8.2 Hz, 1H), 7.30 (d, J=2.1 Hz, 1H), 7.52 (d, J=8.2 Hz, 1H). Mass Spectrum (ESI+) m/e=285.0 and 287.1 (M+H).

Compound 72. n-BuLi (5.4 mL, 13.5 mmol) was added to a solution of 71 (3.50 g, 12.3 mmol) in anhydrous THF (20 mL) at −78° C. The solution was stirred at −78° C. for 30 min. and added to a solution of 69 (2.30 g, 13.5 mmol) in anhydrous THF (20 mL) at −78° C. The reaction mixture was warmed to ambient temperature and stirred for 12 h. The reaction was quenched with saturated aqueous NH$_4$Cl and the layers were separated. The aqueous layer was extracted with EtOAc and the organic extracts were pooled, washed with brine, dried (MgSO$_4$), filtered and concentrated in vacuo to provide a yellow oil. Flash chromatography (silica gel, 15% EtOAc/hexanes) provided 72 as a colorless oil as a mixture of cis and trans isomers (2.24 g). $^1$H NMR (CDCl$_3$) δ 0.88 (d, J=6.8 Hz, 6H), 0.88 (d, J=6.8 Hz, 6H), 1.60-2.40 (m, 24H), 2.60 (s, 3H), 2.62 (s, 3H), 3.66 (s, 3H), 3.68 (s, 3H), 3.75 (m, 4H), 3.98 (m, 4H), 7.15-7.26 (m, 4H), 7.33 (m, 2H). Mass Spectrum (ESI+) m/e=359.2 ([M−H$_2$O]+H).

Compound 73. A solution of NBS (260 mg, 1.46 mmol) and 72 (500 mg, 1.33 mmol) in benzene (100 mL) was heated at reflux for 24 h. The reaction mixture was cooled to ambient temperature, washed with water, brine, dried (MgSO₄), filtered and concentrated in vacuo to provide a brown oil. Flash chromatography (silica gel, 10% EtOAc/hexanes) provided 73 as a yellow oil as a mixture of cis and trans isomers (187 mg). ¹H NMR (DMSO-d₆) δ 0.88 (d, J=6.8 Hz, 6H), 0.89 (d, J=6.8 Hz, 6H), 1.54-2.10 (m, 20H) 2.28 (d, J=7.0 Hz, 2H), 2.43 (d, J=7.3 Hz, 2H), 3.68 (s, 3H), 3.70 (s, 3H), 3.76 (m, 4H), 3.97 (m, 4H), 5.02 (s, 2H), 5.03 (s, 2H), 7.00 (d, J=7.8 Hz, 1H), 7.22 (m, 3H), 7.28 (m, 2H). Mass Spectrum (ESI+) m/e=375.1 (M+H).

Compound 74. A solution of 73 (450 mg, 1.20 mmol) and p-toluenesulfonic acid monohydrate (23.0 mg, 0.120 mmol) in acetone (25 mL) and water (5 mL) was heated at reflux for 24 h. The acetone was removed in vacuo and the aqueous solution was extracted with EtOAc. The organic layers were pooled, washed with brine, dried (MgSO₄), filtered and concentrated in vacuo to provide a yellow oil as a mixture of cis and trans isomers (366 mg). ¹H NMR (DMSO-d₆) δ 1.09 (d, J=6.8 Hz, 6H), 1.09 (d, J=6.8 Hz, 6H), 1.40-1.83 (m, 18H) 2.25 (d, J=7.0 Hz, 2H), 2.53 (d, J=7.4 Hz, 2H), 3.59 (s, 3H), 3.60 (s, 3H), 3.63 (m, 2H), 4.98 (s, 4H), 7.38 (d, J=7.9 Hz, 1H), 7.60 (d, J=7.9 Hz, 1H), 7.87 (m, 4H). Mass Spectrum (ESI+) m/e=331.2 (M+H).

A mixture of 74 (400 mg, 1.21 mmol) and CuBr₂ (811 mg, 3.63 mmol) in CHCl₃ (25 mL) and EtOAc (25 mL) was heated at reflux for 5 h. The solvent was removed in vacuo and the residue was partitioned between EtOAc and water. The layers were separated and the aqueous solution was extracted with EtOAc. The organic layers were pooled, washed with brine, dried (MgSO₄), filtered, and concentrated in vacuo to provide 75 as a yellow oil. 4,5-Diamino-6-hydroxypyrimidine hemisulfate (170 mg, 0.486 mmol) and 2 N HCl (535 μL, 1.07 mmol) were added to a solution of 75 (398 mg, 0.972 mmol) in EtOH (18 mL) and water (6 mL). The reaction mixture was heated at reflux for 23 h and quenched with saturated aqueous NH₄Cl. The solution was extracted with EtOAc and the organic layers were pooled, washed with brine, dried (MgSO₄), filtered, and concentrated in vacuo to provide 76 as an orange foam (360 mg). Lithium hydroxide monohydrate (173 mg, 4.12 mmol) was added to a solution of 76 (360 mg, 0.825 mmol) in MeOH (18 mL) and water (6 mL). The reaction mixture was heated at reflux for 18 h and quenched with NH₄Cl. The solution was acidified with HCl and extracted with EtOAc. The organic layers were pooled, washed with brine, dried (MgSO₄), filtered, and concentrated in vacuo to provide Ex. 8-2 as a yellow solid (146 mg), as a mixture of cis and trans isomers which were separated by reverse phase HPLC. ¹H NMR (major isomer, DMSO-d₆) δ 1.50 (m, 5H), 1.61 (s, 6H), 1.82 (m, 4H), 2.40 (d, J=7.3 Hz, 2H), 4.97 (s, 2H), 7.53 (d, J=7.9 Hz, 1H), 7.60 (d, J=8.0 Hz, 1H), 7.62 (s, 1H), 7.99 (s, 1 H). Mass Spectrum (CI+) m/e=423.2 (M+1). ¹H NMR (minor isomer, DMSO-d₆) δ 1.40 (m, 2H), 1.60 (s, 6H), 1.64 (m, 4H), 1.75 (m, 3H), 2.15 (d, J=6.9 Hz, 2H), 4.97 (s, 2H), 7.30 (d, J=8.5 Hz, 1H), 7.61 (m, 2H), 7.98 (s, 1H). Mass Spectrum (CI+) m/e=423.2 (M+1).

Example 8-3

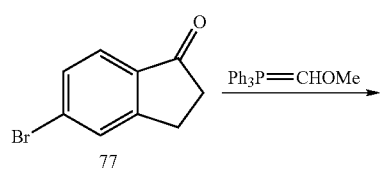

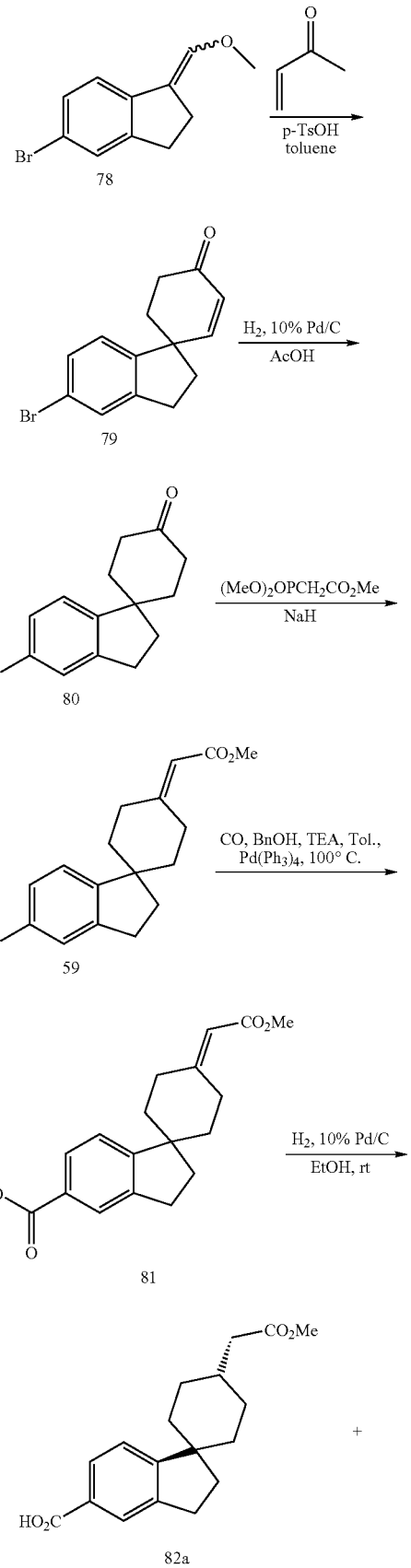

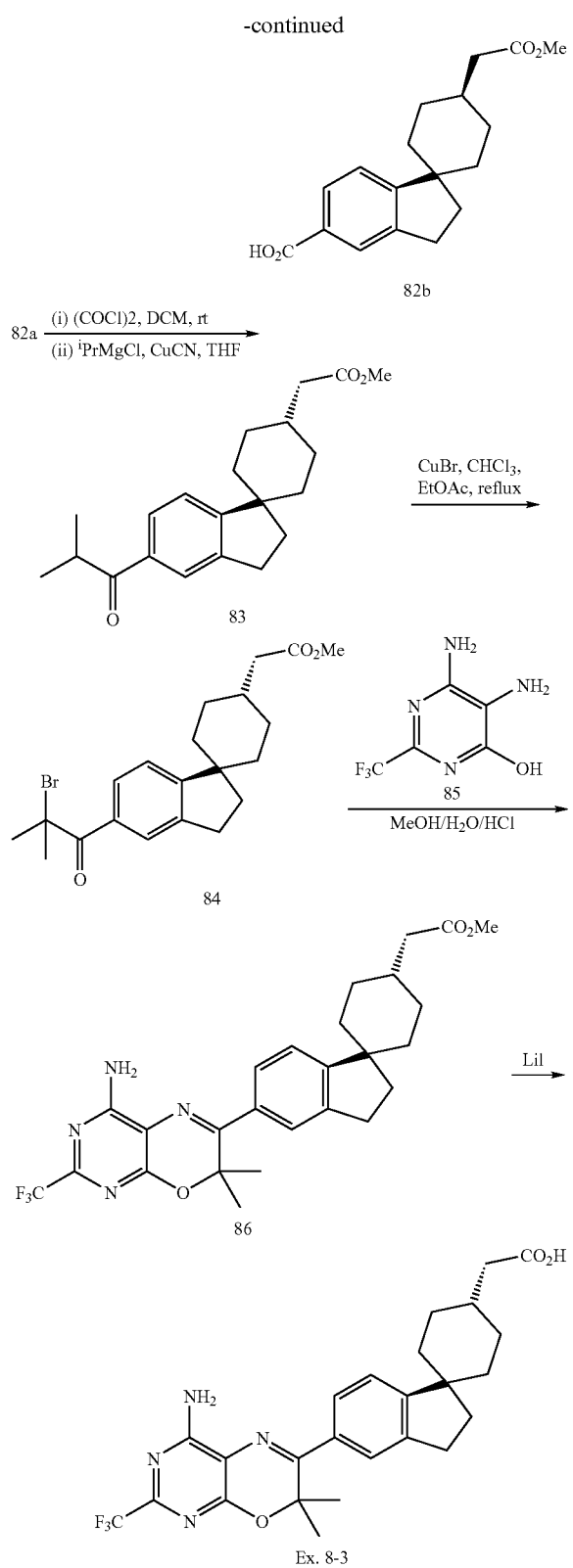

Compound 78. To a stirred suspension of potassium tert-butoxide (16.2 g, 142 mmol) in 1,4-dioxane (300 mL) was added (methoxymethyl)triphenyl-phosphonium chloride (48.5 g, 142 mmol) at r.t. under $N_2$. After stirring for 2 h, 5-bromoindanone (77, 13 g, 61.6 mmol) in dioxane (170 mL) was added to the solution at r.t. under $N_2$. The mixture was stirred for 2 h at r.t., poured into water (500 mL) and extracted with EtOAc (500 mL). The organic layer was separated, washed with brine, dried over $Na_2SO_4$, and concentrated in vacuo. To the residue was added hexane:EtOAc (2:1 (500 mL)). The mixture was stirred at r.t., filtered and the precipitate washed with 2× hexane:EtOAc (2:1 (500 mL)). The filtrate was concentrated in vacuo and the residue distilled (700 mm torr at 145-150° C.) to give compound 78 as a light yellow solid of the cis and trans mixture (14.5 g). $^1$H NMR (CDCl$_3$) δ 2.70-2.80 (m, 2H, major and minor isomers), 2.94-3.00 (m, 2H, major and minor isomers), 3.75 (s, 3H, major and minor isomers), 6.20 (t, J=1.8 Hz, 1H, minor isomer only), 6.65 (t, J=2.6 Hz, 1H, major isomer only), 7.12 (d, J=8.2 Hz, 1H, major isomer only), 7.22-7.34 (m, 2H, major and minor isomers), 7.68 (d, J=8.2 Hz, 1H, minor isomer only).

Compound 79. To a stirred solution of 78 (14.5 g, 60.8 mmol) in toluene (60 mL) was added methylvinyl ketone (6.0 mL, 68 mmol) and p-toluenesulfonic acid monohydrate (1.2 g, 6.3 mmol) at r.t. The mixture was heated at 100° C. for 18 h under $N_2$, allowed to cool to r.t. and poured into sat. aqueous NaHCO$_3$ solution (200 mL). The organic layer was separated and washed with brine. The aqueous layer was extracted with EtOAc and the organic layer was separated and washed with brine. The organic layer was dried over $Na_2SO_4$ and concentrated in vacuo. The residue was recrystallized from EtOH:H$_2$O (2:1 (168 mL)), filtered and dried in vacuo at 60° C. to give 79 as a pale yellow solid (9.90 g). $^1$H NMR (CDCl$_3$) δ 2.09-2.24 (m, 3H), 2.29-2.32 (m, 1H), 2.54 (dd, J=7.2, 6.3 Hz, 2H), 2.99-3.12 (m, 2H), 6.10 (d, J=10.1 Hz, 1H), 6.76 (d, J=10.1 Hz, 1H), 6.99 (d, J=8.1 Hz, 1H), 7.35 (d, J=8.1 Hz, 1H), 7.44 (s, 1H).

Compound 80. To a stirred solution of 79 (153.4 g, 0.55 M) in acetic acid (3.7 L) was added 10% Pd/C (30 g). The mixture was stirred under an atmosphere of hydrogen for 4 h and filtered through silica gel (washing with acetic acid followed by DCM). The filtrate was concentrated in vacuo to afford 80 as a white solid (150.51 g). $^1$H NMR (CDCl$_3$) δ 1.90-1.97 (m, 2H), 2.02-2.12 (m, 2H), 2.26 (t, J=7.3 Hz, 2H), 2.43-2.61 (m, 4H), 3.01 (t, J=7.3 Hz, 2H), 7.04 (d, J=8.1 Hz, 1H), 7.32-7.35 (m, 1H), 7.40 (s, 1H).

Compound 59. To a stirred solution of trimethyl phosphonoacetate (116.45 g, 640 mmol.) in anhydrous THF (2.2 L) under an atmosphere of $N_2$ at 0° C. was added portionwise over 7 min. sodium hydride (25.6 g of a 60% dispersion in mineral oil, 640 mmol.). The mixture was stirred at 0° C. for 30 min. and allowed to warm to r.t. over 30 min. A solution of 80 (149 g, 533 mmol.) in anhydrous THF (375 mL) was added over 10 min. The mixture was stirred at r.t. for 90 min. and saturated aqueous NH$_4$Cl (500 mL) was added. The mixture was stirred for 5 min. and concentrated in vacuo to remove the THF. The aqueous phase was washed with diethyl ether (1 L and 500 mL). The combined organic fractions were washed with brine solution, dried (MgSO$_4$) and concentrated in vacuo. Trituration of the resulting oily residue afforded a white solid which was collected by filtration and washed with hexane to give 59 (62.0 g). The mother liquor was concentrated in vacuo and the residue recrystallized from EtOAc/hexane at 0° C. to afford additional 59 (38.3 g). A further three iterations of the above recrystallization method afforded additional 59 (40.5 g). $^1$H NMR (CDCl$_3$) δ 1.68-1.78 (m, 4H), 2.11-2.21 (m, 3H), 2.31-2.46 (m, 2H), 2.95 (t, J=7.4 Hz, 2H), 3.73 (s, 3H), 3.82-3.87 (m, 2H), 5.73 (s, 1H), 6.99 (d, J=8.0 Hz, 2H), 7.29-7.32 (m, 1H), 7.37 (s, 1H).

Compound 82a. To a 5 L 3-necked round bottom flask containing 59 (140 g, 418 mmol) was added Et$_3$N (280 mL, 2.03 mol), benzyl alcohol (420 mL, 4.06 mmol) and toluene (1.4 L). The resulted solution was purged with CO for 5 min. before addition of Pd(PPh$_3$)$_4$ (9.34 g, 8 mmol). The reaction was heated to 90° C. for 8 h with purging of CO. The mixture was stirred in an ice bath for 30 min. and filtered, and the precipitate washed with EtOAc. The filtrate was washed with water, brine and dried over sodium sulfate. The solvents and the excess benzyl alcohol were removed in vacuo. The residue was dissolved in DCM (50 mL) and hexane (50 mL) and filtered through a funnel filled with silica gel (500 g). The pad was washed with hexane/EtOAc (gradient elution: 9/1 to 1/1). Concentration in vacuo afforded 81 as yellow oil (160 g). Compound 81 was dissolved in EtOH (12 L) and Pd on carbon (10%, 20 g) was added. The mixture was stirred under an atmosphere of hydrogen for 2 days, filtered through a pad of celite and concentrated in vacuo to give a white solid (120 g). To the crude product was added EtOAc (200 mL) and the mixture was heated to reflux for 1 min. and filtered. The filtrate was reheated to reflux and hexane was added slowly. The resulting mixture was cooled slowly to r.t. to afford a white crystalline solid which was collected by filtration (44 g of the trans isomer 82a). The mother liquor was concentrated and recrystallization from EtOAc: hexane afforded an additional 16 g of 82a. $^1$H NMR (CDCl$_3$) δ 1.23-1.27 (m, 2H), 1.59-1.90 (m, 7H), 2.03 (t, J=7.4 Hz, 2H), 2.28 (d, J=7.0 Hz, 2H), 2.93 (t, J=7.4 Hz, 2H), 3.70 (s, 3H), 7.21 (d, J=7.9 Hz, 1H), 7.93 (s, 1H), 7.95 (d, J=7.9 Hz, 1H). Mass Spectrum (ESI+) m/e=303 (M+1).

Compound 83. DMF (200 µL) was added to a solution of 82a (57.23 g, 0.189 mol) and oxalyl chloride (19.8 mL, 0.227 mol) in CH$_2$Cl$_2$ (500 mL) at 0° C. under a nitrogen atmosphere. The reaction mixture was stirred at 0° C. for 15 min. and at r.t. for 3 h. The solvent was removed in vacuo to provide the acid chloride as an off-white solid (60.3 g). A three-necked 2 liter round-bottomed flask was charged with CuCN (4.19 g, 46.8 mmol) and anhydrous THF (500 mL) and cooled to −25° C. To this stirred suspension was added a 2M solution of isopropylmagnesium chloride (46.8 mL, 93.5 mmol in THF) dropwise while maintaining an internal temperature between −25 and −22° C. To this solution was added a solution of the acid chloride (preparation described above) (10 g, 31.2 mmol) in anhydrous THF (50 mL) dropwise while maintaining an internal temperature between −20 and −17° C. The reaction mixture was stirred at −15° C. for 1 h and quenched with 10% NH$_4$OH in saturated aqueous NH$_4$Cl (300 mL). This solution was warmed to r.t. and the layers were separated. The organic layer was washed with 10% NH$_4$OH in saturated aqueous NHCl (2×300 mL), brine (1×300 mL), dried (MgSO$_4$), filtered, and concentrated in vacuo to provide 83 as an off-white solid (10.08 g). $^1$H NMR (CDCl$_3$) δ 7.83 (m, 2H), 7.22 (d, J=8.4 Hz, 1H), 3.72 (s, 3H), 3.54-3.58 (m, 1H), 2.94 (t, J=7.4 Hz, 2H), 2.30 (d, J=7.0 Hz, 2H), 2.04 (t, J=7.4 Hz, 2H), 1.92 (m, 1H), 1.78 (m, 2H), 1.69-1.64 (m, 4H), 1.28 (m, 2H), 1.23 (d, J=6.8 Hz, 6H). Mass Spectrum (ESI+) m/e=329 (M+1).

Compound 84. A solution of 83 (5 g, 15.2 mmol) in EtOAc (100 mL) and chloroform (100 mL) was treated with CuBr$_2$ (10 g, 44.8 mmol) and the mixture was heated at reflux for 8 h before being cooled to r.t. The reaction mixture was filtered and washed with EtOAc. The filtrate was washed with water, brine and dried over sodium sulfate. The solvents were removed in vacuo and hexane (20 mL) was added. A white solid 84 was formed with stirring and collected by filtration (5 g). Additional 84 (0.76 g) was obtained by crystallization from the mother liquor at 0° C. $^1$H NMR (CDCl$_3$) δ 1.25-1.28 (m, 2H), 1.61-1.92 (m, 7H), 2.03-2.06 (m, 8H), 2.29 (d, J=7.0 Hz, 2H), 2.94 (t, J=7.4 Hz, 2H), 3.72 (s, 3H), 7.19 (d, J=8.0 Hz, 1H), 7.99 (s, 1H), 8.05 (d, J=8.0 Hz, 1H). Mass Spectrum (ESI+) m/e=407 and 409 (M+1).

Compound 86. To 84 (0.5 g, 1.23 mmol.) and 4,5-diamino-6-hydroxy-2-trifluoromethylpyrimidine (85, J. A. Barone et al., *J Med. Chem.*, 1969, 6, 39; P. D. Landauer et al., *J. Chem. Soc.*, 1953, 3721.) (0.26 g, 1.34 mmol) was added methanol (13 mL), 2N HCl (2 mL) and water (5 mL). The mixture was heated at reflux for 24 h, cooled and concentrated in vacuo. To the residue was added water (10 mL) and the resulting precipitate was collected by filtration, washed with pentane and dried under vacuum to afford 86 (375 mg) as a white solid. $^1$H NMR (DMSO-d$_6$) δ 1.18-1.27 (m, 2H), 1.48-1.86 (m, 13H), 1.98 (t, J=7.3 Hz, 2H), 2.28 (d, J=7.2 Hz, 2H), 2.89 (t, J=7.1 Hz, 2H), 3.61 (s, 3H), 7.28 (d, J=8.0 Hz, 1H), 7.53 (d, J=8.0 Hz, 1H), 7.58 (s, 1H).

Ex. 8-3. To a stirred solution of 86 (100 mg, 0.199 mmol) in DMF (1 mL) was added anhydrous lithium iodide (670 mg, 5 mmol). The mixture was heated at 125-130° C. for 24 h and poured into water (20 mL). The resulting precipitate was collected by filtration and washed with water. The precipitate was recrystallized from ethanol to afford Ex. 8-3 (70 mg) as a white solid. $^1$H NMR (DMSO-d$_6$) δ 1.17-1.26 (m, 2H), 1.48-1.82 (m, 16H), 1.98 (t, J=7.4 Hz, 2H), 2.18 (d, J=6.8 Hz, 2H), 2.90 (t, J=7.2 Hz, 2H), 7.28 (d, J=8.1 Hz, 1H), 7.37 (brs, 1H), 7.53 (d, J=8.1 Hz, 1H), 7.58 (s, 1H), 7.80 (brs, 1H), 12.05 (brs, 1H).

Example 8-4

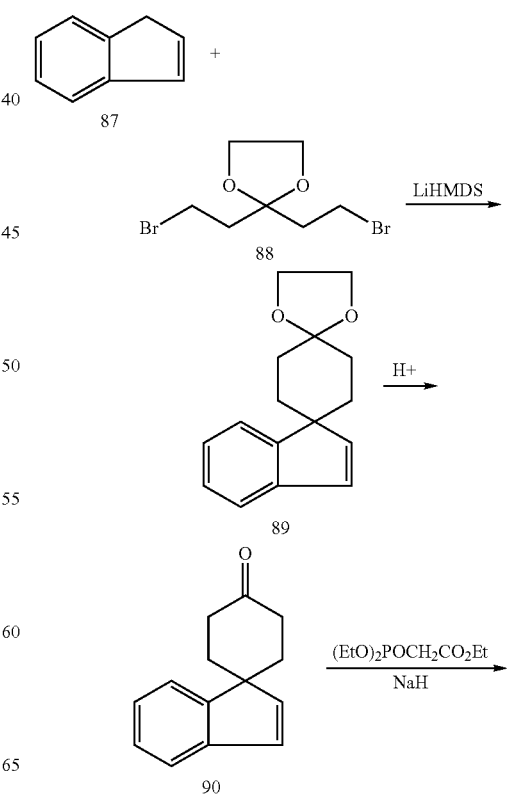

-continued
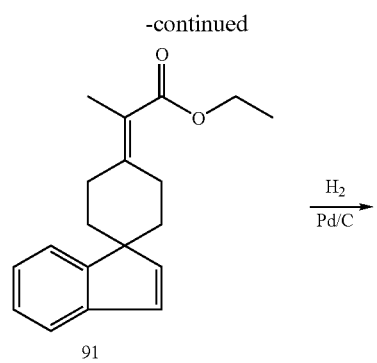
91
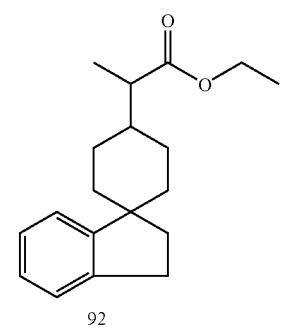
92
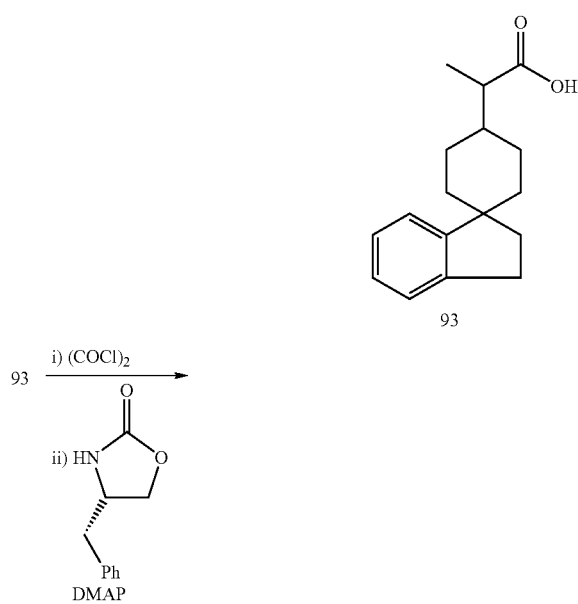
93
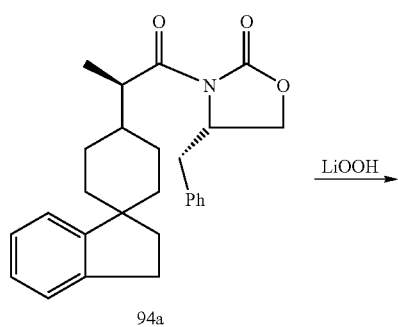
94a
-continued
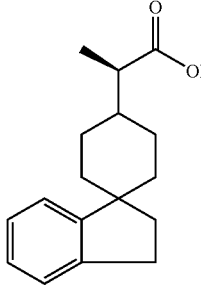
95a
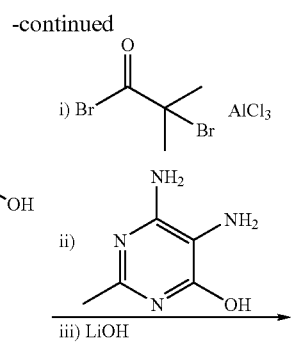
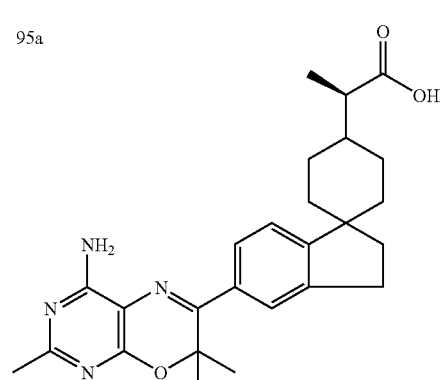
Ex. 8-4
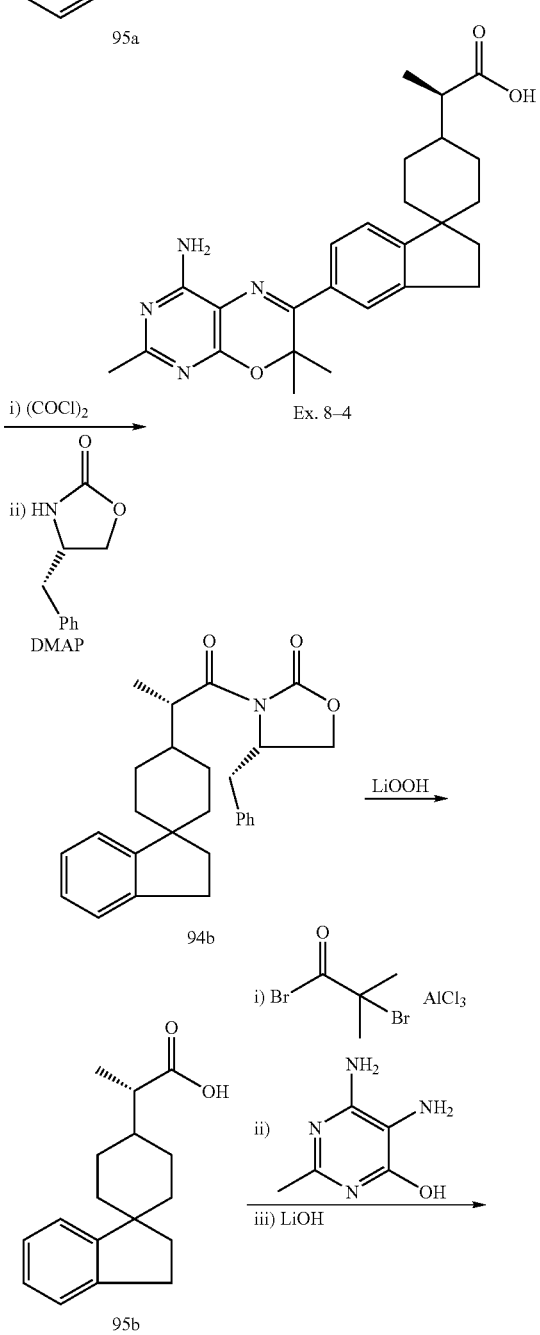
95b

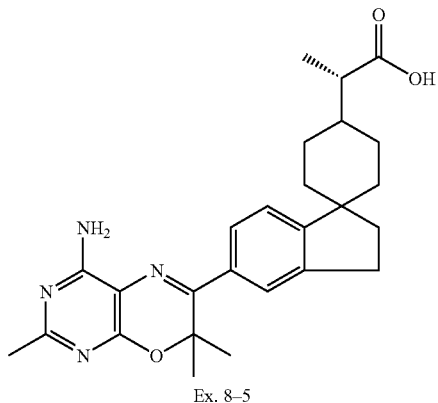

Ex. 8–5

Compound 89. A dried 500 mL single-necked round bottom flask was charged with indene 87 (8.91 g, 76.65 mmol) and THF (60 mL). The solution was stirred and cooled by an ice bath. To the flask was added lithium bis(trimethylsilyl)amide (153.3 mL, 1.0 M in THF, 153.3 mmol) through a syringe over a period of 30 min. The resulting mixture was stirred at 0° C. for 30 min., and transferred by a cannula to a stirred solution of the dibromoketal 88 (20.0 g, 66.23 mmol) in THF at 0° C. over 30 min. After addition, the reaction mixture was stirred for 2 h at 0° C. and 30 min. at r.t. The solvent was evaporated in vacuo and the residue was purified by silica gel chromatography (hexane/EtOAc 25/1 to 15/1; gradient elution) to give compound 89 (15.0 g) as light yellow crystals. $^1$H NMR (CDCl$_3$) δ 1.43 (d, J=13.5 Hz, 2H), 1.88-1.99 (m, 4H), 2.20 (d, J=4.0, 13.0 Hz, 2H), 4.06 (s, 4H), 6.78 (d, J=6.0, 1H), 6.85 (d, J=6.0, 1H), 7.20-7.27 (m, 2H), 7.34 (d, J=7.5, 1H), 7.42 (d, J=7.5, 1H). Mass Spectrum (ESI+) m/e=243 (M$^+$+1).

Compound 90. To the solution of 89 (15.0 g, 62 mmol) in MeOH (350 mL) was added 3M H$_2$SO$_4$ (60 mL). The reaction mixture was heated at reflux for 7 h under a nitrogen atmosphere. The mixture was cooled to r.t. and the MeOH removed in vacuo. The mixture was diluted with ice water and extracted with EtOAc (100 mL×3), washed with water (25 mL×2) and brine (20 mL) and dried over MgSO$_4$. Concentration in vacuo gave a crude product which was purified by silica gel column chromatography (hexane/EtOAc 20/1) to give compound 90 (10.0 g) as a white solid. $^1$H NMR (CDCl$_3$) δ 1.76 (m, 2H), 2.34 (m, 2H), 2.68 (m, 4H), 6.90 (d, J=6.0, 1H), 6.95 (d, J=6.0, 1H), 7.25-7.51 (m, 4H). Mass Spectrum (ESI+) m/e=199 (M+1)

Compound 91. A suspension of NaH (60% dispersion in mineral oil) (2.45 g, 61.25 mmol) in THF (200 mL) in a 500 mL pre-dried flask was cooled to 0° C. under a nitrogen atmosphere. To the flask was added a solution of triethyl 2-phosphonopropionate (14.60 g, 61.25 mmol) in THF (10 mL) dropwise at 0° C. over 15 min. The mixture was stirred at 0° C. for 15 min. and a solution of 90 (7.8 g, 39.20 mmol) in THF (50 mL) was added through an additional funnel dropwise over 25 min. After addition, the mixture was stirred at r.t. overnight. The reaction was quenched with aqueous saturated NH$_4$Cl solution and was extracted with EtOAc, washed with water and brine, and dried over MgSO$_4$. Evaporation of solvent gave a crude product which was purified by silica gel column chromatography (hexane/EtOAc 20/1) to give compound 91 (10.0 g) as a white solid. $^1$H NMR (CDCl$_3$) δ 1.35 (t, J=7.1 Hz, 3H), 1.50-1.1.60 (m, 2H), 1.98 (s, 3H), 1.95-2.05 (m, 2H), 2.25-2.48 (m, 2H), 2.75-2.90 (m, 1H), 3.10-3.25 (m, 1H), 4.25 (q, J=7.1 Hz, 2H), 6.81 (d, J=5.7, 1H), 6.93 (d, J=5.7, 1H), 7.20-7.36 (m, 4H).

Compound 92. 91 (5.6 g, 19.72 mmol) was dissolved in EtOAc (60 mL) and was hydrogenated over palladium (10% on charcoal) using hydrogen gas at an atmospheric pressure for 24 h. The mixture was filtered through celite and the filtrate was concentrated in vacuo to give product 92 (5.4 g) as colorless oil which was used directly in the next reaction without further purification. $^1$H NMR (CDCl$_3$) δ 1.18 (d, J=7.0 Hz, 3H), 1.30 (t, J=7.1 Hz, 3H), 1.61-1.85 (m, 9H), 1.98 (t, J=7.5 Hz, 2H), 2.31 (m, 1H), 2.89 (t, J=7.4 Hz, 2H), 4.14-4.19 (m, 2H), 7.05-7.20 (m, 4H).

Compound 93. 92 (2.63 g, 9.21 mmol) was dissolved in MeOH/THF/H$_2$O (40 mL, 5/2/1). To the above solution was added lithium hydroxide monohydrate (1.93 g, 46.0 mmol) and the mixture was stirred at 50° C. overnight. MeOH was removed in vacuo and the reaction mixture was acidified with 2N HCl. The mixture was extracted with EtOAc (25 mL×3), washed with water, brine and dried over MgSO$_4$. Evaporation of solvent gave a crude product which was purified by silica gel column chromatography (hexane/EtOAc 8/1) to give compound 93 (2.38 g) as a white solid. $^1$H NMR (CDCl$_3$) δ 1.24 (d, J=7.02 Hz, 3H), 1.61-1.85 (m, 1OH), 1.95-2.0 (m, 2H), 2.3-2.4 (m, 1H), 2.88-2.92 (m, 2H), 7.05-7.20 (m, 4H). Mass Spectrum (ESI+) m/e=258 (M).

Compound 94a and 94b. To 93 (2.2 g, 8.53 mmol) in CH$_2$Cl$_2$ at 0° C. under a nitrogen atmosphere was added (COCl)$_2$ (0.82 mL, 9.38 mmol) and a drop of DMF. The reaction was stirred at 0° C. for 1 h. To this generated acid chloride solution was added a solution of (S)-(−)-4-benzyl-2-oxazolidione (1.66 g, 9.37 mmol), DMAP (1.09 g, 8.92 mmol) and triethylamine (1.88 mL, 13.49 mmol) in CH$_2$Cl$_2$ dropwise at 0° C. under a nitrogen atmosphere. After addition, the mixture was stirred at r.t. for 2 h. The reaction was quenched by addition of saturated aqueous NH$_4$Cl, extracted with EtOAc (25 mL×3), washed with water (10 mL×2), brine and dried over MgSO$_4$. Concentration in vacuo gave a crude product which was purified by silica gel column chromatography (hexane/EtOAc 19/1 to 10/1) to give compound 94a (926 mg) and 94b (1.27 g). NB: stereochemical assignment of 94a and 94b is arbitrary. Compound 94a: $^1$H NMR (CDCl$_3$) δ 1.26 (d, J=6.9 Hz, 3H), 1.61-1.80 (m, 2H), 1.80-1.95 (m, 7H), 1.99 (t, J=7.3 Hz, 2H), 2.80 (dd, J=9.6, J=13.3 Hz, 1H), 2.91 (t, J=7.4 Hz, 2H), 3.33 (dd, J=3.2, 13.3 Hz, 1H), 3.71-3.75 (m, 1H), 4.15-4.23 (m, 2H), 4.70-4.78 (m, 1H), 7.05-7.37 (m, 9H). Mass Spectrum (ESI+) m/e=418 (M+1). [α]$^{26}$=+54.85 (c=0.60, CH$_2$Cl$_2$). Compound 94b: $^1$H NMR (CDCl$_3$) δ 1.21 (d, J=6.9 Hz, 3H), 1.25-1.95 (m, 9H), 2.01 (t, J=7.4 Hz, 2H), 2.75 (m, 1H), 2.90 (t, J=7.3 Hz, 2H), 3.32-3.41 (m, 1H), 3.73-3.78 (m, 1H), 4.12-4.22 (m, 2H), 4.73-4.77 (m, 1H), 7.05-7.39 (m, 9H). Mass Spectrum (ESI+) m/e=418 (M+1). [α]$^{26}$=+10.12 (c=0.60, CH$_2$Cl$_2$)

Compound 95a. To a stirred solution of 94a (900 mg, 2.16 mmol) in THF (30 mL) and H$_2$O (10 mL) was added H$_2$O$_2$ (30%, 1.8 mL, 17.7 mmol) and lithium hydroxide monohydrate (360 mg, 8.55 mmol) at 0° C. The reaction was allowed to warm to r.t. overnight and quenched with saturated aqueous $Na_2SO_3$ solution and acidified with 10% HCl. The mixture was extracted with EtOAc (15 mL×3), washed with water (5 mL×2), brine and dried over $MgSO_4$. Concentration in vacuo gave a crude product which was purified by silica gel column chromatography (hexane/EtOAc 8/1) to give compound 95a (500 mg) as a white solid. $^1H$ NMR ($CDCl_3$) δ 1.24 (d, J=7.0 Hz, 3H), 1.61-1.85 (m, 1OH), 1.95-2.0 (m, 2H), 2.30-2.40 (m, 1H), 2.88-2.92 (m, 2H), 7.05-7.20 (m, 4H). Mass Spectrum (ESI+) m/e=258 (M)

Compound 95b. Compound 95b (ent-95a) was prepared from 94b in a similar manner to that described for the conversion of 94a to 95a above.

Ex. 8-4. To a suspension of anhydrous $AlCl_3$ (484 mg, 3.63 mmol) in $CH_2Cl_2$ (5 mL) was added 2-bromoisobutyryl bromide (0.21 mL, 1.70 mmol) dropwise at 0° C. under a nitrogen atmosphere. After the mixture was stirred for 5 min., a solution of compound 95a (376 mg, 1.46 mmol) in $CH_2Cl_2$ (20 mL) was added dropwise. After stirring at 0° C. for 1 h, the mixture was poured into ice water and extracted with $CH_2Cl_2$ (15 mL×3). The combined organic layer was successively washed with water, saturated $NaHCO_3$ and brine, dried over $MgSO_4$ and concentrated in vacuo. To the residue was added 2-methyl-4,5-diamino-6-hydroxypyrimidine (PD Landauer et al., *J. Chem. Soc.*, 1953, 3721)(250 mg, 1.54 mmol), 1N HCl (5 mL, 5 mmol), water (5 mL) and EtOH (25 mL). The reaction mixture was heated at reflux overnight. The reaction mixture was cooled to r.t. and EtOH was removed by evaporation. The residue was diluted with saturated aqueous $NH_4Cl$ solution and extracted with EtOAc (15 mL×3). The combined organic layer was successively washed with water and brine, dried over $MgSO_4$ and concentrated in vacuo. To the residue was added MeOH/THF/$H_2O$ (15 mL, 1/1/1) and lithium hydroxide monohydrate (200 mg, 4.77 mmol) and the mixture was stirred at 45° C. for 40 h. MeOH was removed in vacuo and the residue was acidified with 2N HCl. This mixture was extracted with EtOAc (15 mL×3), washed with water, brine and dried over $MgSO_4$. Concentration in vacuo gave a crude product which was purified by HPLC (reverse phase) to give compound Ex. 8-4 (65.6 mg) as a white solid. $^1H$ NMR (DMSO-$d_6$) δ 1.07 (d, J=7.0 Hz, 3H), 1.15-1.35 (m, 1H), 1.50-1.81 (m, 6H), 1.63 (s, 6H), 1.96 (t, J=7.5 Hz, 2H), 2.21 (m, 1H), 2.34 (s, 3H), 2.45-2.55 (m, 2H), 2.88 (t, J=7.5, 2H), 7.25 (m, 1H), 7.51-7.54 (m, 4H), 12.0 (bs, 1H). Mass Spectrum (ESI+) m/e=449 (M+1).

Ex 8-5. Compound Ex. 8-5 (ent-Ex. 84) was prepared in a similar manner to the preparation of Ex. 8-4 from 95a above.

Example 8-6

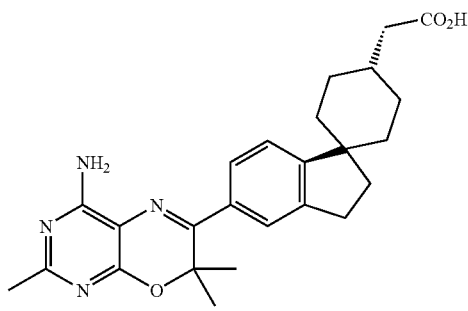

This compound was obtained in the same manner as in Example 8. $^1H$ NMR (DMSO-$d_6$) δ 1.14-1.23 (m, 2H), 1.47-1.80 (m, 15H), 1.96 (t, J=7.3 Hz, 2H), 2.15 (d, J=7.0 Hz, 2H), 2.32 (s, 3H), 2.87 (t, J=7.3 Hz, 2H), 7.10 (s, br, 2H), 7.24 (d, J=7.8 Hz, 1H), 7.43-7.50 (m, 2H).

Example 8-7

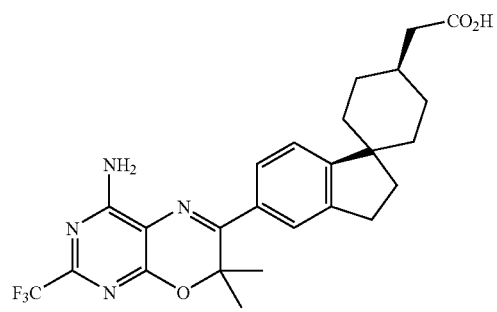

This compound was obtained in the same manner as in Example 8. $^1H$ NMR (DMSO-$d_6$) δ 1.39-1.45 (m, 2H), 1.47-1.55 (m, 2H), 1.60-1.75 (m, 10H), 1.94 (t, J=7.2 Hz, 2H), 2.03 (m, 1H), 2.38 (d, J=7.3 Hz, 2H), 2.87 br, 1H), 7.44 (d, J=8.0 Hz, 1H), 7.52 (d, J=8.0 Hz, 1H), 7.57 (s, 1H), 7.77 (s, br, 1H).

Example 9

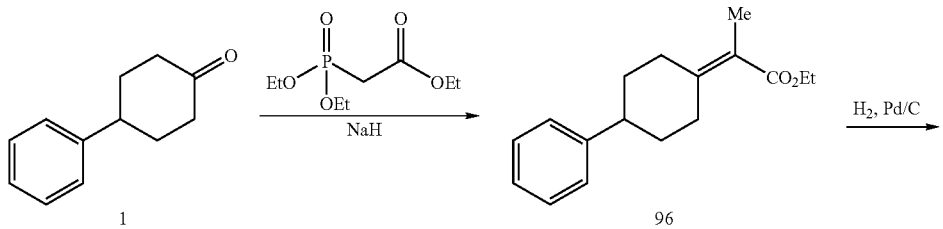

-continued
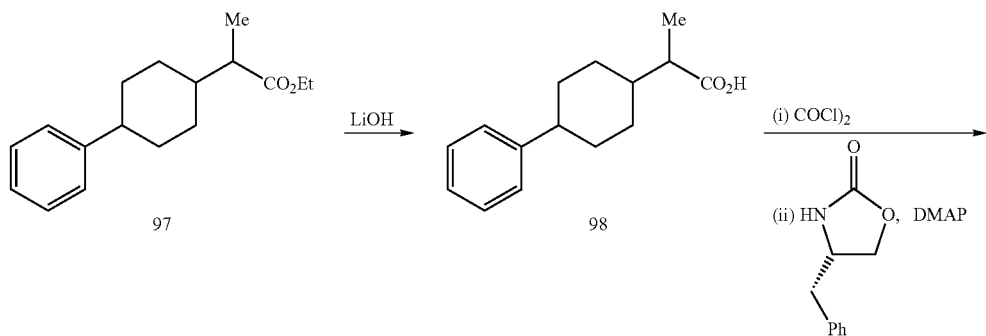
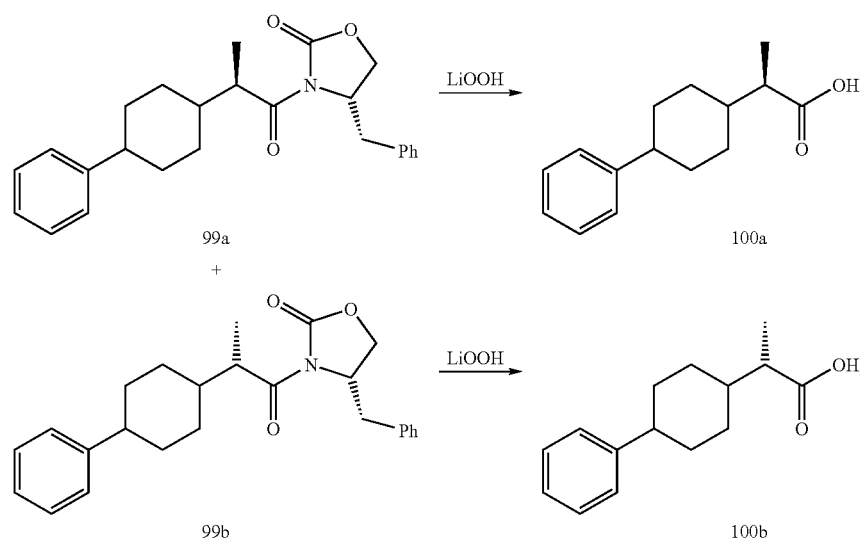
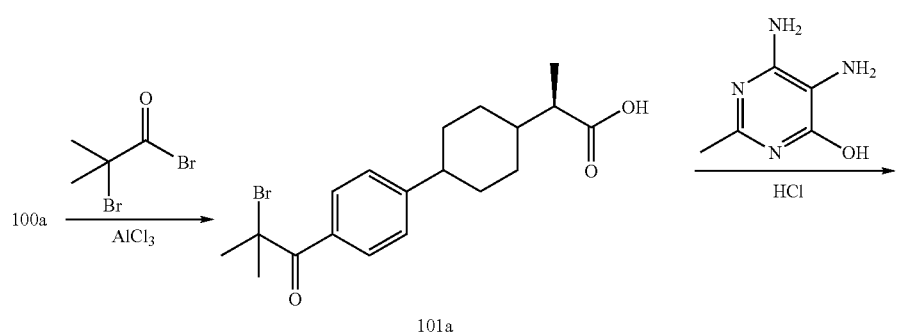
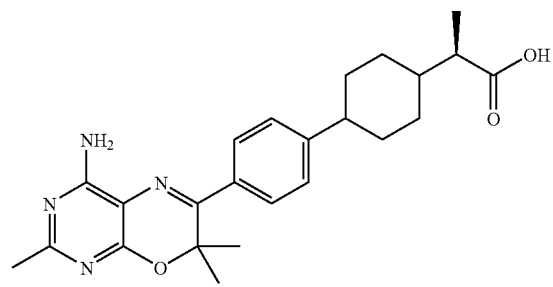
Ex. 9

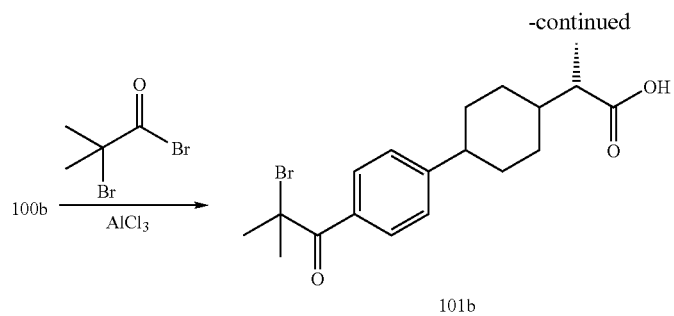
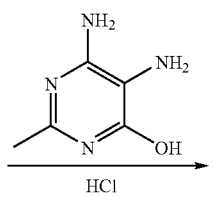
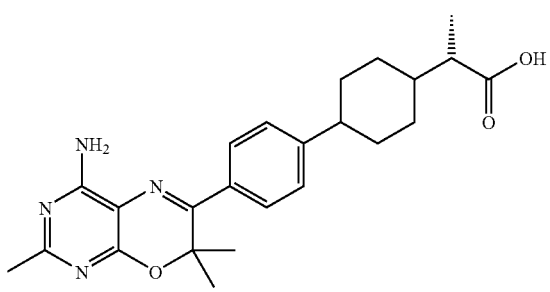

Ex. 9-2

Compound 97. Compound 96 was prepared from 4-phenylcyclohexanone and triethylphosphonopropionate in a similar manner to that described for the conversion of 1 to 2 (Example 2). Compound 97 was prepared from 96 in a similar manner to that described for the conversion of 2 to 3 (Example 2).

Compound 98. To a stirred solution of 97 (2.86 g, 11 mmol) in methanol (83 mL) was added lithium hydroxide (2.62 g, 110 mol) in water (28 mL). The mixture was heated at reflux for 2 h and allowed to cool to r.t., and the methanol was removed in vacuo. The aqueous solution was washed with diethyl ether, acidified to pH 1 with 1N HCl and extracted with diethyl ether (3×). The combined organics were dried (MgSO$_4$), filtered and concentrated in vacuo to afford 98 (2.31 g) as a white solid. $^1$H NMR (CDCl$_3$) δ 1.23 (d, J=7.2 Hz, 3H), 1.29-1.33 (m, 2H), 1.42-1.59 (m, 2H), 1.69-1.80 (m, 2H), 1.85-2.00 (m, 3H), 2.30-2.39 (m, 1H), 2.45-2.60 (m, 1H), 7.21-7.34 (m, 5H).

Compounds 99a and 99b. To a stirred solution of 98 (13.5 g, 58.1 mmol) in DCM (225 mL) was added 3 drops of DMF. The mixture was cooled to 0° C. and oxalyl chloride (5.58 mL, 63.91 mmol) was added dropwise. The mixture was stirred at r.t. for 2 h and added dropwise to a separate vessel containing (S)-4-benzyl-2-oxazolidinone (10.81 g, 61 mmol), DMAP (7.1 g, 58.1 mmol), Et$_3$N (20.24 mL, 145.3 mmol) and DCM (100 mL) at 0° C. The mixture was allowed to warm to r.t. and stirred at r.t. for 12 h. Water (300 mL) was added. The organic layer was separated and washed with 1N HCl (200 mL), saturated aqueous sodium bicarbonate (200 mL) and brine, and dried (MgSO$_4$), filtered and concentrated in vacuo. The residue was purified by flash chromatography (silica gel 5-40% EtOAc in hexane; gradient elution) to provide 99a (11.48 g) as white crystals and 99b (10.75 g) as a white foam. NB: the stereochemical assignment of 99a and 99b is arbitrary. Compound 99a: $^1$H NMR (CDCl$_3$) δ 1.17-1.34 (m, 5H), 1.45-2.01 (m, 7H), 2.49 (tt, J=12.3 Hz, J=3.5 Hz, 1H), 2.81 (dd, J=9.6 Hz, J=13.2 Hz, 1H), 3.33 (dd, J=3.2 Hz, J=13.4 Hz, 1H), 3.74 (quin, J=7.0 Hz, 1H), 4.19-4.25 (m, 2H), 4.70-4.76 (m, 1H), 7.19-7.39 (m, 10H). Compound 99b: $^1$H NMR (CDCl$_3$) δ 1.21 (d, J=6.9 Hz, 3H), 1.25-2.02 (m, 9H), 2.51 (tt, J=12.1 Hz, J=3.4 Hz, 1H), 2.74 (dd, J=10.0 Hz, J=13.2 Hz, 1H), 3.40 (dd, J=3.4 Hz, J=13.2 Hz, 1H), 3.78 (quin, J=6.8 Hz, 1H), 4.12-4.21 (m, 2H), 4.72-4.79 (m, 1H), 7.19-7.39 (m, 10H).

Compound 100a. To a stirred solution of 99a (10.48 g, 26.8 mmol) in THF (400 mL) and water (125 mL) at 0° C. was added lithium hydroxide (1.28 g, 53.6 mmol) and 3% hydrogen peroxide (10.7 mL). The mixture was stirred at 0° C. for 75 min. and an aqueous solution of sodium sulfite (14.75 g in 80 mL of water) was added followed by 0.5 M aqueous sodium bicarbonate (270 mL). The aqueous layer was washed with DCM and acidified to pH 1 with 5N HCl and extracted with EtOAc. The ethyl acetate layer was dried (MgSO$_4$), filtered and concentrated in vacuo to afford 100a (1 g) as a white solid.

Additional material could be obtained from the DCM layer. $^1$H NMR (CDCl$_3$) δ 1.22 (d, J=7.2 Hz, 3H), 1.23-1.33 (m, 2H), 1.50-1.56 (m, 2H), 1.58-1.65 (m, 1H), 1.87-2.01 (m, 4H), 2.38 (quin, J=6.8 Hz, 1H), 2.50 (tt, J=3.2 Hz, J=12.0 Hz, 1H), 7.18-7.33 (m, 5H).

Compound 100b. Compound 100b (ent-100a) was prepared from 99b in a similar manner to the preparation of 100a from 99a above.

Compound 101a. Compound 101a was prepared from 100a in a similar manner to that described for the conversion of 3 to 4 (Example 2). ¹H NMR (CDCl₃) δ 1.23 (d, J=7.2 Hz, 3H), 1.29-1.33 (m, 2H), 1.42-1.59 (m, 2H), 1.69-1.80 (m, 2H), 1.85-2.00 (m, 3H), 2.30-2.39 (m, 1H), 2.45-2.60 (m, 1H), 7.21-7.34 (m, 5H).

Compound 101b. Compound 101b (ent-101a) was prepared from 100b in a similar manner to the preparation of 101a from 100a above.

Ex. 9. Ex. 9 was prepared from 101a and 4,5-diamino-6-hydroxy-2-methylpyrimidine (P. D. Landauer et al., *J. Chem. Soc.*, 1953, 3721.) in a similar manner to that described for the conversion of 4 to Ex. 2. ¹H NMR (CDCl₃) δ 1.24 (d, J=6.8 Hz, 3H), 1.25-1.30 (m, 2H), 1.48-1.59 (m, 3H), 1.71 (s, 6H), 1.91-2.00 (m, 4H), 2.36-2.40 (m, 1H), 2.46 (s, 3H), 2.51-2.57 (m, 1H), 7.27 (d, J=8.4 Hz, 2H), 7.55 (d, J=8.4 Hz, 2H). Mass Spectrum (ESI+) m/e=423.3 (M+1).

Ex. 9-2. Ex. 9-2 (ent-Ex. 9) was prepared from 101b in a similar manner to the preparation of Ex. 9 from 101a above.

Example 9-3

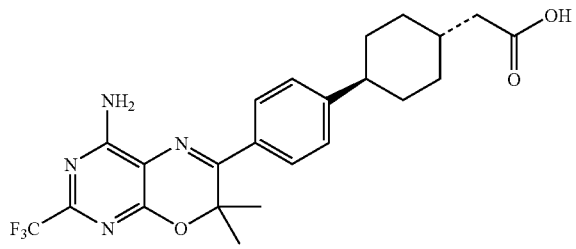

This compound was obtained in the same manner as in Example 9. ¹H NMR (DMSO-d₆) δ 1.10-1.20 (m, 2H), 1.42-1.90 (m, 13H), 2.17 (d, J=6.8 Hz, 2H), 2.45-2.60 (m, 1H), 7.34 (d, J=8 Hz, 2H), 7.36 (brs, 1H), 7.71 (d, J=8 Hz, 2H), 7.74 (brs, 1H), 12.04 (brs, 1H).

The compounds provided in Table 10 were prepared by combinations of the methods provided above.

TABLE 1

| New Ex. No. | MOLSTRUCTURE | m p | NMR(δ) | solvent |
|---|---|---|---|---|
| 1 | | >200 | 5.44(s, 2H), 7.10(brs, 2H), 7.69(d, 2H, J=8.6Hz), 7.93(s, 1H), 8.03(d, 2H, J=8.6Hz). | DMSO-d6, 400 MHz |
| 1-2 | | >220 | 5.46(s, 2H), 7.08(brs, 2H), 7.35(t, 2H, J=7.5Hz), 7.94(s, 1H), 8.15–8.19(m, 2H) | DMSO-d6, 400 |
| 1-3 | | >220 | 5.46(s, 2H), 7.12(brs, 2H), 7.57(d, 2H, J=6.0Hz), 7.94(s, 1H), 8.13(d, 2H, J=9.0Hz) | DMSO-d6, 400 |
| 1-4 | | 217–219 | 2.39(s, 3H), 5.43(s, 2H), 7.03(brs, 2H), 7.32(d, 2H, J=6.0Hz), 7.93(s, 1H), 7.99(d, 2H, J=6.0Hz) | DMSO-d6, 400 |
| 1-5 | | | 5.22(s, 2H), 7.02(brs, 2H), 7.45(t, 1H, J=6.0Hz), 7.53(t, 1H, J=4.5Hz), 7.64(d, 1H, J=6.0Hz), 7.76(d, 1H, J=6.0Hz), 7.99(s, 1H) | DMSO-d6, 400 |

TABLE 1-continued
| New Ex. No. | MOLSTRUCTURE | m p | NMR(δ) | solvent |
|---|---|---|---|---|
| 1-6 | 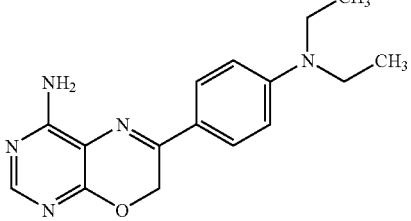 | 206dec. | 1.14(t, 6H, J=6.0Hz), 3.44(q, 4H, J=5.0Hz), 5.34(s, 2H), 6.72(d, 2H, J=6.0Hz), 6.84(brs, 2H), 7.88(s, 1H), 7.90(d, 2H, J=9.0Hz) | DMSO-d6, 400 |
| 1-7 | 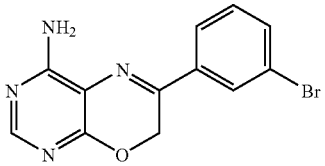 | >220 | 5.45(s, 2H), 7.19(brs, 2H), 7.46(t, 1H, J=6.0Hz), 7.72(d, 1H, J=6.0Hz), 7.95(s, 1H), 8.01(d, 1H, J=6.0Hz), 8.39(s, 1H) | DMSO-d6, 400 |
| 1-8 | 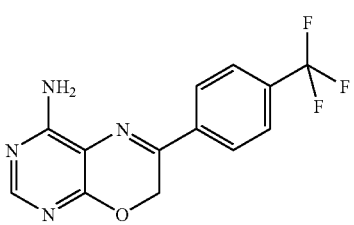 | >220 | 5.51(s, 2H), 7.19(brs, 2H), 7.86(d, 2H, J=6.0Hz), 7.96(s, 1H), 8.30(d, 2H, J=6.0Hz) | DMSO-d6, 400 |
| 1-9 | 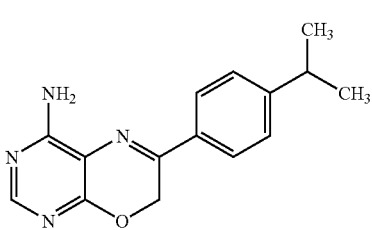 | 176–178 | 1.23(d, 6H, J=6.0Hz), 2.93–3.00(m, 1H), 5.42(s, 2H), 7.01(brs, 2H), 7.36(d, 2H, J=6.0Hz), 7.92(s, 1H), 7.99(d, 2H, J=6.0Hz) | DMSO-d6, 400 |
| 1-10 | 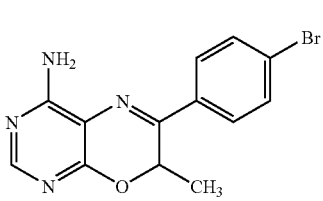 | 222–224 | 1.33(d, 3H, J=6.0Hz), 5.98(q, 1H, J=6.0Hz), 7.14(brs, 2H), 7.69(d, 2H, J=6.0Hz), 7.95(s, 1H), 8.09(d, 2H, J=6.0Hz) | DMSO-d6, 400 |
| 1-11 | 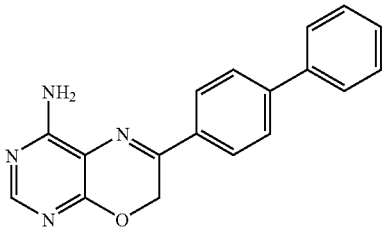 | >250 | 5.49(s, 2H), 7.08(brs, 2H), 7.39–7.43(m, 1H), 7.49–7.52(m, 2H), 7.76–7.81(m, 4H), 7.93(s, 1H), 8.18(d, 2H, J=6.0Hz) | DMSO-d6, 400 |

TABLE 1-continued

| New Ex. No. | MOLSTRUCTURE | m p | NMR(δ) | solvent |
|---|---|---|---|---|
| 1-12 | | 191–193 | 3.84(s, 3H), 5.40(s, 2H), 6.98(brs, 2H), 7.03(d, 2H, J=6.0Hz), 7.90(s, 1H), 8.05(d, 2H, J=6.0Hz) | DMSO-d6, 400 |
| 1-13 | | >250 | 5.52(s, 2H), 7.25(brs, 2H), 7.96(s, 1H), 8.30(d, 2H, J=6.0Hz), 8.34(d, 2H, J=6.0Hz) | DMSO-d6, 400 |
| 1-14 | | >220 | 2.25(s, 3H), 5.40(s, 2H), 7.05(brs, 2H), 7.70(d, 2H, J=9.0Hz), 8.03(d, 2H, J=9.0Hz) | DMSO-d6, 300 |
| 1-15 | | 75–77 | 5.05(s, 2H), 5.58(brs, 2H), 6.06(dd, 1H, J=1.1, 8.0 Hz), 6.32(dd, 1H, J=1.1, 8.0 Hz), 6.85(t, 1H, J=8.0 Hz), 7.69(d, 2H, J=8.6 Hz), 8.04(d, 2H, J=8.6 Hz). | DMSO-d6, 300 |
| 1-16 | | 215 | 5.56(s, 2H), 7.22(br, 2H), 7.51–7.55(m, 1H), 7.95–8.00(m, 2H), 8.52–8.55(m, 1H), 8.65–8.67(m, 1H) | DMSO-d6, 300 |
| 1-17 | | >220 | 5.49(s, 2H), 7.21(brs, 2H), 7.51–7.55(m, 1H), 7.94(s, 1H), 8.44–8.48(m, 1H), 8.68–8.70(m, 1H), 9.27(s, 1H) | DMSO-d6, 300 |
| 1-18 | | >220 | 5.48(s, 2H), 7.28(br, 2H), 7.96(s, 1H), 8.01(d, 2H, J=6.0Hz), 8.73(d, 2H, J=6.0Hz) | DMSO-d6, 300 |

TABLE 1-continued

| New Ex. No. | MOLSTRUCTURE | m p | NMR(δ) | solvent |
|---|---|---|---|---|
| 1-19 | | 191–193 | 1.21(t, 3H, J=7.5Hz), 2.68(q, 2H, J=7.0Hz), 5.43(s, 2H), 7.07(brs, 2H), 7.34(d, 2H, J=9.0Hz), 7.92(s, 1H), 8.01(d, 2H, J=9.0Hz) | DMSO-d6, 300 |
| 1-20 | | 189–192 | 0.90(t, 3H, J=7.5Hz), 1.56–1.68(m, 2H), 2.60–2.65(m, 2H), 5.43(s, 2H), 7.07(brs, 2H), 7.32(d, 2H, J=9.0Hz), 7.92(s, 1H), 8.01(d, 2H, J=9.0Hz) | DMSO-d6, 300 |
| 1-21 | | 183–186 | 0.91(t, 3H, J=7.5Hz), 1.27–1.37(m, 2H), 1.53–1.63(m, 2H), 2.62–2.67(m, 2H), 5.43(s, 2H), 7.08(brs, 2H), 7.32(d, 2H, J=9.0Hz), 7.92(s, 1H), 8.00(d, 2H, J=9.0Hz) | DMSO-d6, 400 |
| 1-22 | | 142 | 1.14–1.45(m, 5H), 1.61–1.85(m, 5H), 2.23–2.30(m, 1H), 4.89(s, 2H), 6.74(brs, 2H), 7.87(s, 1H) | DMSO-d6, 400 |
| 1-23 | | 209–212 | 5.47(s, 2H), 7.17(brs, 2H), 7.49(d, 2H, J=6.0Hz), 7.94(s, 1H), 8.22(d, 2H, J=6.0Hz) | DMSO-d6, 300 |
| 1-24 | | | 5.35(s, 2H), 6.95(brs, 2H), 7.35(d, 2H, J=6.0Hz), 7.52(d, 2H, J=3.0Hz), 7.92(s, 1H) | DMSO-d6, 300 |
| 1-25 | | 219–221 | 1.23–1.51(m, 5H), 1.69–1.85(m, 5H), 2.55–2.63(m, 1H), 5.43(s, 2H), 7.06(brs, 2H), 7.92(s, 1H), 8.00(d, 2H, J=9.0Hz) | DMSO-d6, 300 |

TABLE 1-continued

| New Ex. No. | MOLSTRUCTURE | m p | NMR(δ) | solvent |
|---|---|---|---|---|
| 1-26 | | >220 | 5.25(s, 2H), 6.24(brs, 2H), 6.55(brs, 2H), 7.63(d, 2H, J=12.0Hz), 7.92(d, 2H, J=12.0Hz) | DMSO-d6, 400 |
| 1-27 | | >220 | 5.45(s, 2H), 7.29(brs, 2H), 7.77(d, 1H, J=9.0Hz), 7.94(s, 1H), 8.02(d, 1H, J=9.0Hz), 8.46(s, 1H) | DMSO-d6, 300 |
| 1-28 | | 218–220 | 5.22(s, 2H), 7.17(brs, 2H), 7.57-7.60(m, 1H), 7.75–7.79(m, 2H), 7.99(s, 1H) | DMSO-d6, 300 |
| 1-29 | | >220 | 5.35(s, 2H), 7.18(brs, 2H), 7.65(d, 2H, J=9.0Hz), 7.92(d, 2H, J=6.0Hz), 10.67(brs, 1H) | DMSO-d6, 400 |
| 1-30 | | >220 | 3.04(s, 6H), 5.27(s, 2H), 6.73(brs, 2H), 7.63(d, 2H, J=6.0Hz), 7.94(d, 2H, J=6.0Hz) | DMSO-d6, 400 |
| 1-31 | | 190–192 | 5.17(s, 2H), 8.01(s, 1H) | DMSO-d6, 300 |
| 1-32 | | >200 | 4.07(dd, 1H, J=7.6, 10.7Hz), 4.33(dd, 1H, J=1.6, 10.7Hz), 4.48(m, 1H), 5.19(brs, 1H), 6.27(brs, 2H), 7.40(d, 2H, J=8.6 Hz), 7.58(s, 1H), 7.60(d, 2H, J=8.6Hz). | DMSO-d6, 400MHz |

TABLE 1-continued

| New Ex. No. | MOLSTRUCTURE | m p | NMR(δ) | solvent |
|---|---|---|---|---|
| 1-33 | | | 0.99(d, 3H, J=6.0Hz), 4.54(brs, 2H), 5.36(br, 1H), 6.36(br, 2H), 7.28(d, 2H, J=6.0Hz), 7.58(d, 2H, J=9.0Hz), 7.65(s, 1H) | DMSO-d6, 300 |
| 1-34 | | 232–233 | 2.16(s, 3H), 4.03–4.08(m, 1H), 4.29–4.32(m, 1H), 4.42–4.45(m, 1H), 4.99(brs, 1H), 6.19(brs, 2H), 7.40(d, 2H, J=6.0Hz), 7.59(d, 2H, J=9.0Hz) | DMSO-d6, 400 |
| 1-35 | | >220 | 4.56–4.73(m, 2H), 5.46–5.49(m, 1H), 7.26(d, 2H, J=9.0Hz), 7.60(d, 2H, J=9.0Hz), 8.30(s, 1H), 11.94(brs, 1H) | DMSO-d6, 300 |
| 1-36 | | 198–200 | 4.09–4.15(m, 1H), 4.34–4.38(m, 1H), 4.54(brs, 1H), 5.23(brs, 1H), 6.35(brs, 2H), 7.45(d, 1H, J=12.0Hz), 7.63(s, 1H), 7.69(d, 1H, J=9.0Hz), 7.74(s, 1H) | DMSO-d6, 300 |
| 1-37 | | >220 | 4.02–4.09(m, 1H), 4.34–4.38(m, 1H), 4.80(brs, 1H), 5.28(brs, 1H), 6.35(brs, 2H), 7.51(s, 2H), 7.64(s, 1H), 7.70(s, 1H) | DMSO-d6, 300 |

TABLE 2

| New Ex. No. | MOLSTRUCTURE | m p | NMR(δ) | solvent |
|---|---|---|---|---|
| 2 | (structure with NH₂-pyrido-oxazine, dimethyl, phenyl-cyclohexyl-CH₂COOH) | >270 | 1.07–1.21(m,2H), 1.42–1.84(m, 13H), 2.15(d, 2H, J=6.0Hz), 2.53–2.56(m, 1H), 6.97(brs, 2H), 7.31(d, 2H, J=9.0Hz), 7.65(d, 2H, J=9.0Hz), 7.95(s, 1H), 11.96(brs, 1H) | DMSO-d6, 300 |
| 2-2 | (structure with NH₂-pyrido-oxazine, dimethyl, phenyl-cyclohexyl-CH₂CONH₂) | 224–226 | 1.02–1.17(m, 2H), 1.4–1.53(m, 2H), 1.61(s,6H), 1.66–1.87(m, 5H), 1.98(d, 2H, J=7.12Hz), 2.53(m, 1H), 6.67(br, 1H), 6.89(br, 2H), 7.21(br, 1H), 7.3(d, 2H, J=8.12Hz), 7.63(d, 2H, J=8.12Hz), 7.94(s, 1H) | DMSO-d6, 400 |
| 2-3 | (structure with NH₂-pyrido-dihydrooxazine NH, dimethyl, phenyl-cyclohexyl-CH₂COOH) | 273–279 | 1.03–1.22(m, 8H), 1.4–1.49(m, 2H), 1.7–1.82(m, 5H), 2.14(d, 2H, J=6.93Hz), 2.54(m, 1H), 4.11(br, 1H), 5.27(br, 1H), 6.23(br, 2H), 7.25(d, 2H, J=8.07Hz), 7.36(d, 2H, J=8.04Hz), 7.61(s, 1H), 11.75(br, 1H) | DMSO-d6, 300 |

TABLE 2-continued

| New Ex. No. | MOLSTRUCTURE | m p | NMR(δ) | solvent |
|---|---|---|---|---|
| 2-4 | (structure) | >250 | 1.04–1.09(m, 2H), 1.43(m, 1H), 1.43–1.50(m, 4H), 1.60(s, 6H), 1.83(brd, 4H, J=11.4Hz), 2.25(t, 2H, d=7.7Hz), 2.50(m, 1H), 6.88(brs, 2H), 7.29(d, 2H, J=8.3 Hz), 7.63(d, 2H, J=8.3 Hz), 7.94(s, 1H), 11.84(brs, 1H). | DMSO-d6, 400 MHz |
| 2-5 | (structure) | 244–246 | 1.04–1.08(m, 2H), 1.29(m, 1H), 1.40–1.49(m, 4H), 1.60(s, 6H), 1.83(brd, 4H, J=10.2Hz), 2.09(t, 2H, d=7.4Hz), 2.50(m, 1H), 6.60(brs, 1H), 6.88(brs, 2H), 7.20(brs, 1H), 7.29(d, 2H, J=8.3 Hz), 7.63(d, 2H, J=8.3Hz), 7.94(s, 1H). | DMSO-d6, 400 MHz |
| 2-6 | (structure) | >250 | 1.04–1.09(m, 2H), 1.08(s, 3H), 1.22(s, 3H), 1.32(m, 1H), 1.43–1.48(m, 4H), 1.83(brd, 4H, J=10.7Hz), 2.24(t, 2H, d=7.7 Hz), 2.50(m, 1H), 4.11(s, 1H), 5.26(s, 1H), 6.22(brs, 2H), 7.23(d, 2H, J=8.1Hz), 7.35(d, 2H, J=8.1Hz), 7.62(s, 1H), 11.73(brs, 1H). | DMSO-d6, 400 MHz |

TABLE 2-continued

| New Ex. No. | MOLSTRUCTURE | m p | NMR(δ) | solvent |
|---|---|---|---|---|
| 2-7 | ![structure] | >250 | 1.42–1.55(m, 4H), 1.60(s, 6H), 1.81–1.91(m, 2H), 1.95–2.06(m, 2H), 2.23–2.33(m, 1H), 2.52–2.60(m, 1H), 6.90(br, 2H), 7.30(d, 2H, J=8.1Hz), 7.64(d, 2H, J=8.1Hz), 7.95(s, 1H) | DMSO-d6, 400 MHz |
| 2-8 | ![structure] | >220 | 1.07(s, 3H), 1.23(s, 3H), 4.17(brs, 1H), 5.31(brs. 1H), 6.26(brs, 2H), 7.35–7.47(m, 5H), 7.63(s, 1H) | DMSO-d6, 300 |
| 2-9 | ![structure] | 189–190 | 1.60(s, 6H), 6.93(brs, 2H), 7.44–7.50(m, 3H), 7.69–7.71(m, 2H), 7.96(s, 1H) | DMSO-d6, 400 |
| 2-10 | ![structure] | 201–203 | 1.60(s, 6H), 7.03(brs, 2H), 7.65(d, 2H, J=9.0Hz), 7.70(d, 2H, J=9.0Hz), 7.96(s, 1H) | DMSO-d6, 300 |

TABLE 2-continued

| New Ex. No. | MOLSTRUCTURE | m p | NMR(δ) | solvent |
|---|---|---|---|---|
| 2-11 | (4-Br-phenyl, CH3, CH3, acetyl-N, pyrido-oxazine) | >220 | 1.22(s, 3H), 1.47(s, 3H), 5.38(s, 2H), 6.99(d, 2H, J=6.0Hz), 7.55(d, 2H, J=6.0Hz), 8.35(s, 1H), 11.94(brs, 1H) | DMSO-d6, 400 |
| 2-12 | (4-Br-phenyl, CH3, CH3, NH2, pyrido-oxazine) | >220 | 1.05(s, 3H), 1.23(s, 3H), 4.20(brs, 1H), 5.33(brs, 1H), 6.26(brs, 2H), 7.40(d, 2H, J=9.0Hz), 7.60(d, 2H, J=6.0Hz), 7.63(s, 1H) | DMSO-d6, 300 |
| 2-13 | (4-Br-phenyl, spirocyclopentyl, NH2, pyrido-oxazine) | 184–186 | 1.79–1.86(m, 2H), 2.01–2.08(m, 1H), 2.13–2.19(m, 1H), 7.05(brs, 2H), 7.61(d, 2H, J=6.0Hz), 7.66(d, 2H, J=6.0Hz), 7.95(s, 1H) | DMSO-d6, 400 |
| 2-14 | (4-Br-phenyl, spirocyclopentyl, NH2, pyrido-oxazine) | 226–233 | 1.29–1.76(m, 4H), 4.37(brs, 1H), 5.51 (brs, 1H), 6.23(brs, 2H), 7.27(d, 2H, J=6.0Hz), 7.55(d, 2H, J=6.0Hz), 7.63(s, 1H) | DMSO-d6, 300 |
| 2-15 | (4-Cl-phenyl, CH3, CH3, NH2, pyrido-oxazine) | 210–211 | 1.60(s, 6H), 7.05(brs, 2H), 7.52(d, 2H, J=9.0Hz), 7.77(d, 2H, J=9.0Hz), 7.96(s, 1H) | DMSO-d6, 300 |

TABLE 2-continued

| New Ex. No. | MOLSTRUCTURE | m p | NMR(δ) | solvent |
|---|---|---|---|---|
| 2-16 | (4-methylphenyl pyridopyrazine derivative) | 161–162 | 1.60(s, 6H),2.36(s, 3H), 6.97(brs, 2H), 7.27(d, 2H, J=9.0Hz), 7.63(d, 2H, J=9.0Hz), 7.95(s, 1H) | DMSO-d6, 300 |
| 2-17 | (4-fluorophenyl pyridopyrazine derivative) | 189–190 | 1.60(s, 6H), 7.01(brs, 2H), 7.29(dd, 2H, J=9.0, 9.0Hz), 7.81(dd, 2H, J=9.0, 9.0Hz), 7.96(s, 1H) | DMSO-d6, 300 |
| 2-18 | (4-cyclohexylphenyl pyridopyrazine derivative) | 186–187 | 1.21–1.47(m, 5H), 1.60(s, 6H), 1.70–1.82(m, 5H), 2.54–2.58(m, 1H), 6.89(brs, 2H), 7.29(d, 2H, J=6.0Hz), 7.64(d, 2H, J=9.0Hz), 7.94(s, 1H) | DMSO-d6, 400 |
| 2-19 | (4-chlorophenyl pyridopyrazine derivative) | >230 | 1.05(s, 3H), 1.23(s, 3H), 4.21(brs, 1H), 5.33(brs, 1H), 6.28(brs, 2H), 7.46(s, 4H), 7.63(s,1H) | DMSO-d6, 300 |

TABLE 2-continued

| New Ex. No. | MOLSTRUCTURE | m p | NMR(δ) | solvent |
|---|---|---|---|---|
| 2-20 | (4-methylphenyl pyrido-oxazine with NH2) | >230 | 1.06(s, 3H), 1.21(s, 3H), 2.31(s, 3H), 4.12(brs, 1H), 5.26(brs, 1H), 6.27(brs, 2H), 7.20(d, 2H, J=6.0Hz), 7.34(d, 2H, J=9.0Hz), 7.62(s, 1H) | DMSO-d6, 300 |
| 2-21 | (4-fluorophenyl pyrido-oxazine with NH2) | >230 | 1.06(s, 3H), 1.23(s, 3H), 4.20(brs, 1H), 5.28(brs, 1H), 6.22(brs, 2H), 7.22(dd, 2H, J=6.0, 6.0Hz), 7.48(dd, 2H, J=6.0, 6.0Hz), 7.63(s, 1H) | DMSO-d6, 400 |
| 2-22 | (4-cyclohexylphenyl pyrido-oxazine with NH2) | >230 | 1.08(s, 3H), 1.22(s, 3H), 1.26–1.46(m, 5H), 1.69–1.83(m, 5H), 2.47–2.54(m, 1H),4.11(brs, 1H), 5.28(brs, 1H), 6.25(brs, 2H), 7.25(d, 2H, J=9.0Hz), 7.37(d, 2H, J=9.0Hz), 7.61(s, 1H) | DMSO-d6, 300 |
| 2-23 | (4-methoxyphenyl pyrido-oxazine with NH2) | 183–184 | 1.61(s, 6H), 3.82(s, 3H), 6.87(brs, 2H), 6.99(d, 2H, J=6.0Hz), 7.71(d, 2H, J=6.0Hz), 7.94(s, 1H) | DMSO-d6, 400 |

TABLE 2-continued

| New Ex. No. | MOLSTRUCTURE | m p | NMR(δ) | solvent |
|---|---|---|---|---|
| 2-24 | (4-methoxyphenyl substituted pyrido-oxazine with NH2) | 225–226 | 1.06(s, 3H), 1.21(s, 3H), 3.76(s, 3H), 4.11(brs, 1H), 5.23(brs, 1H), 6.26(brs, 2H), 6.96(d, 2H, J=9.0Hz), 7.38(d, 2H, J=9.0Hz), 7.62(s, 1H) | DMSO-d6, 300 |
| 2-25 | (4-hydroxyphenyl substituted pyrido-oxazine with NH2) | 245–246 | 1.60(s, 6H), 6.82(d, 2H, J=9.0Hz), 6.91(brs, 2H), 7.62(d, 2H, J=6.0Hz), 7.93(s, 1H), 9.94(s, 1H) | DMSO-d6, 300 |
| 2-26 | (4-cyclohexylphenyl substituted pyrimido-oxazine with NH2 and CH3) | 226–227 | 1.19–1.46(m, 5H), 1.58(s, 6H), 1.69–1.82(m, 5H), 2.25(s, 3H), 2.52–2.58(m, 1H), 6.86(brs, 2H), 7.29(d, 2H, J=9.0Hz), 7.63(d, 2H, J=9.0Hz) | DMSO-d6, 300 |
| 2-27 | (biphenyl substituted pyrido-oxazine with NH2) | 218–219 | 1.66(s, 6H), 7.02(brs, 2H), 7.39–7.53(m, 3H), 7.73–7.77(m, 4H), 7.83–7.86(m, 2H), 7.97(s, 1H) | DMSO-d6, 300 |

TABLE 2-continued

| New Ex. No. | MOLSTRUCTURE | m p | NMR(δ) | solvent |
|---|---|---|---|---|
| 2-28 | ![structure] | >250 | 1.65(s, 6H), 6.97(brs, 2H), 7.77(d, 2H, J=3.0Hz), 7.88(s, 4H), 7.97(s, 1H), 8.68(d, 2H, J=3.0Hz) | DMSO-d6, 300 |
| 2-29 | ![structure] | 231–232 | 1.66(s, 6H), 7.02(brs, 2H), 7.51–7.55(m, 1H), 7.83(d, 2H, J=9.0Hz), 7.88(d, 2H, J=9.0Hz), 7.98(s, 1H), 8.14–8.18(m, 1H), 8.61–8.63(m, 1H), 8.97–8.98(m, 1H) | DMSO-d6, 300 |
| 2-30 | ![structure] | 210–211 | 1.65(s, 6H), 2.96(s, 6H), 6.83(d, 2H, J=9.0Hz), 6.99(brs, 2H), 7.60(d, 2H, J=6.0Hz), 7.67(d, 2H, J=6.0Hz), 7.78(d, 2H, J=9.0Hz), 7.96(s, 1H) | DMSO-d6, 300 |

TABLE 2-continued

| New Ex. No. | MOLSTRUCTURE | m p | NMR(δ) | solvent |
|---|---|---|---|---|
| 2-31 | (4-oxocyclohexyl phenyl pyridopyrazine structure) | >240 | 1.61(s, 6H), 1.89–2.13(m, 4H), 2.26–2.34(m, 2H), 2.55–2.62(m, 2H), 3.09–3.17(m, 1H), 6.97(brs, 2H), 7.39(d, 2H, J=9.0Hz), 7.68(d, 2H, J=9.0Hz), 7.95(s, 1H) | DMSO-d6, 300 |
| 2-32 | (cyclohexyloxy phenyl structure) | 174–175 | 1.26–1.58(m, 7H), 1.61(s, 6H), 1.70–1.76(m, 2H), 1.92–1.96(m, 2H), 6.86(brs, 2H), 6.97(d, 2H, J=8.0Hz), 7.68(d, 2H, J=8.0Hz), 7.93(s, 1H) | DMSO-d6, 400 |
| 2-33 | (ethyl phenyl structure) | 185–186 | 0.91(t, 3H, J=8.0Hz), 1.57–1.66(m, 2H), 1.60(s, 6H), 2.61(t, 2H, J=8.0Hz), 6.89(br, 2H), 7.27(d, 2H, J=8.0Hz), 7.63(d, 2H, J=8.0Hz), 7.95(s, 1H) | DMSO-d6, 400 MHz |
| 2-34 | (tert-butyl phenyl structure) | 220–220 | 1.33(s, 9H), 1.67(s, 6H), 7.49(d, 2H, J=8.0Hz), 7.58(br, 2H), 7.70(d, 2H, J=8.0Hz), 8.15(s, 1H) | DMSO-d6, 400 MHz |

TABLE 2-continued

| New Ex. No. | MOLSTRUCTURE | m p | NMR(δ) | solvent |
|---|---|---|---|---|
| 2-35 | (4-ethylphenyl substituted pyrido-pyrimidine oxazine with gem-dimethyl and NH2) | 135–136 | 1.21(t, 3H, J=7.0Hz), 1.60(s, 6H), 2.66(q, 2H, J=7.0Hz), 6.90(br, 2H), 7.29(d, 2H, J=8.0Hz), 7.64(d, 2H, J=8.0Hz), 7.95(s, 1H) | DMSO-d6, 400 MHz |
| 2-36 | (4-isopropylphenyl substituted analog) | 175–179 | 1.23(d, 6H, J=8.0Hz), 1.61(s, 6H), 2.91–2.98(m, 1H), 6.89(br, 2H), 7.32(d, 2H, J=8.0Hz), 7.64(d, 2H, J=8.0Hz), 7.95(s, 1H) | DMSO-d6, 400 MHz |
| 2-37 | (4-n-butylphenyl substituted analog) | 157–160 | 0.91(t, 3H, J=8.0Hz), 1.27–1.36(m, 2H), 1.54–1.61(m, 2H), 1.60(s, 6H), 2.63(t, 2H, J=8.0Hz), 6.90(br, 2H), 7.27(d, 2H, J=8.0Hz), 7.63(d, 2H, J=8.0Hz), 7.95(s, 1H) | DMSO-d6, 400 MHz |
| 2-38 | (4-ethoxyphenyl substituted analog) | 189–190 | 1.35(t, 3H, J=6.0Hz), 1.61(s, 6H), 4.10(q, 2H, J=6.7Hz), 6.87(brs, 2H), 6.97(d, 2H, J=8.0Hz), 7.70(d, 2H, J=12.0Hz), 7.93(s, 1H) | DMSO-d6, 400 |

TABLE 2-continued

| New Ex. No. | MOLSTRUCTURE | m p | NMR(δ) | solvent |
|---|---|---|---|---|
| 2-39 | (structure) | 207–208 | 1.21(t, 3H, J=7.5Hz), 1.49–1.69(m, 8H), 1.93–2.08(m, 3H), 2.33–2.45(m, 2H), 2.84–2.94(m, 1H), 3.85–3.90(m, 1H), 4.09(q, 2H, J=7.0Hz), 5.72(s, 1H), 6.97(brs, 2H), 7.33(d, 2H, J=9.0Hz), 7.65(d, 2H, J=6.0Hz), 7.95(s, 1H) | DMSO-d6, 300 |
| 2-40 | (structure) | >250 | 1.46–1.63(m, 8H), 1.97–2.04(m, 3H), 2.32–2.38(m, 2H), 2.84–2.94(m, 1H), 3.85–3.90(m, 1H), 5.64(s, 1H), 6.90(brs, 2H), 7.32(d, 2H, J=8.0Hz), 7.64(d, 2H, J=8.0Hz), 7.94(s, 1H), 11.80(brs, 1H) | DMSO-d6, 400 |
| 2-41 | (structure) | 201–209 | 0.93(d, 3H, J=6.5Hz), 1.03–1.13(m, 2H), 1.39–1.57(m, 3H), 1.62(s, 6H), 1.76–1.87(m, 4H), 2.49–2.58(m, 1H), 6.91(br, 2H), 7.31(d, 2H, J=8.4Hz), 7.76(d, 2H, J=8.4Hz), 7.98(s, 1H) | DMSO-d6, 400 MHz |

TABLE 2-continued

| New Ex. No. | MOLSTRUCTURE | m p | NMR(δ) | solvent |
|---|---|---|---|---|
| 2-42 | (structure) | 226–227 | 1.60(s, 6H), 1.64–1.74(m, 2H), 1.89–2.16(m, 6H), 2.75–2.81(m, 1H), 6.90(brs, 2H), 7.33(d, 2H, J=8.0Hz), 7.66(d, 2H, J=8.0Hz), 7.95(s, 1H) | DMSO-d6, 400 |
| 2-43 | (structure) | 246–248 | 1.23–1.35(m, 2H), 1.43–1.56(m, 2H), 1.60(s, 6H), 1.75–1.81(m, 2H), 1.90–1.96(m, 2H), 2.46–2.54(m, 1H), 4.60(d, 1H, J=6.0Hz), 6.97(brs, 2H), 7.30(d, 2H, J=9.0Hz), 7.64(d, 2H, J=9.0Hz), 7.95(s, 1H) | DMSO-d6, 300 |
| 2-44 | (structure) | | 1.40–1.60(m, 2H), 1.60(s, 6H), 1.90–2.00(m, 3H), 2.25–2.40(m, 2H), 2.85(s, 3H), 3.00(s, 3H), 3.13(m, 1H), 5.89(s, 1H), 6.90(brs, 2H), 7.31(d, 2H, J=8.3 Hz), 7.64(d, 2H, J=8.3Hz), 7.94(s, 1H). | DMSO-d6, 400 MHz |

TABLE 2-continued

| New Ex. No. | MOLSTRUCTURE | m p | NMR(δ) | solvent |
|---|---|---|---|---|
| 2-45 | | 142–144 | 1.40–1.60(m, 2H), 1.60(s, 6H), 1.90–2.00(m, 3H), 2.25–2.40(m, 2H), 2.80(m, 1H), 4.13(m, 1H), 4.30(d, 2H, J=6.0Hz), 5.89(s, 1H), 6.90(brs, 2H), 7.20–7.33(m, 6H), 7.64(d, 2H, J=8.3Hz), 7.94(s, 1H), 8.30(brt, 1H, J=6.0Hz). | DMSO-d6, 400 MHz |
| 2-46 | | | 1.45–1.57(m, 2H), 1.60(s, 6H), 1.84–2.00(m, 3H), 2.23–2.36(m, 2H), 2.75–2.89(m, 1H), 5.67(s, 1H), 6.77(brs, 1H), 6.97(brs, 2H), 7.26(brs, 1H), 7.32(d, 2H, J=9.0Hz), 7.66(d, 2H, J=9.0Hz), 7.95(s, 1H) | DMSO-d6, 300 |
| 2-47 | | 229–230 | 1.03(t, 3H, J=7.5Hz), 1.45–1.58(m, 3H), 1.60(s, 6H), 1.81–2.32(m, 5H), 2.73–2.89(m, 1H), 3.05–3.14(m, 2H), 5.65(s, 1H), 6.97(brs, 2H), 7.32(d, 2H, J=9.0Hz), 7.65(d, 2H, J=6.0Hz), 7.80–7.84(m, 1H), 7.95(s, 1H) | DMSO-d6, 300 |

TABLE 2-continued

| New Ex. No. | MOLSTRUCTURE | m p | NMR(δ) | solvent |
|---|---|---|---|---|
| 2-48 | | | 1.45–1.58(m, 3H), 1.60(s, 6H), 1.84–2.02(m, 3H), 2.22–2.36(m, 2H), 2.80–2.89(m, 1H), 3.12–3.19(m, 2H), 3.38–3.43(m, 2H), 4.07–4.14(m, 0.5H), 4.65–4.70(m, 0.5H), 5.68(s, 1H), 6.97(brs, 2H), 7.32(d, 2H, J=9.0Hz), 7.65(d, 2H, J=9.0Hz), 7.84(t, 1H, J=6.0Hz), 7.95(s, 1H) | DMSO-d6, 300 |
| 2-49 | | | 0.88–1.09(m, 2H), 1.27–1.59(m, 3H), 1.68(s, 6H), 1.78–1.88(m, 4H), 2.33–2.47(m, 1H), 2.63–2.73(m, 2H), 2.77–2.88(m, 2H), 3.08(t, 2H, J=7.0Hz), 4.68(s, 2H), 6.99(t, 1H, J=5.8Hz), 7.11(d, 2H, J=8.3Hz), 7.26(s, 2H), 7.43(d, 2H, J=8.3Hz) | DMSO-d6, 300 MHz |
| 2-50 | | | 1.41–1.60(m, 2H), 1.60(s, 6H), 1.91–2.03(m, 3H), 2.16–2.42(m, 9H), 2.79–2.86(m, 1H), 2.96–3.05(m, 1H), 3.42–3.49(m, 1H), 3.49(br, 3H), 5.87(s, 1H), 6.89(br, 2H), 7.31(d, 2H, J=8.6Hz), 7.64(d, 2H, J=8.6Hz), 7.94(s, 1H) | DMSO-d6, 400 MHz |

TABLE 2-continued

| New Ex. No. | MOLSTRUCTURE | m p | NMR(δ) | solvent |
|---|---|---|---|---|
| 2-51 | (structure with aminopyrido-oxazine, phenyl, cyclohexylidene, CH₂C(O)N-CH₂CH₂-N(CH₃)₂) | | 1.43–1.59(m, 2H), 1.60(s, 6H), 1.87–2.01(m, 3H), 2.18(s, 6H), 2.28–2.34(m, 4H), 2.79–2.88(m, 1H), 3.18(q, 2H, J=6.4Hz), 4.05–4.10(m, 1H), 5.67(s, 1H), 6.89(br, 2H), 7.31(d, 2H, J=8.1Hz), 7.64(d, 2H, J=8.1Hz), 7.69(t, 1H, J=6.4Hz), 7.94(s, 1H) | DMSO-d6, 400 MHz |
| 2-52 | (structure with aminopyrido-oxazine, phenyl, cyclohexylidene, CH₂C(O)N-CH₂-C(O)O-C(CH₃)₃) | 212–215 | 1.41(s, 9H), 1.47–1.63(m, 2H), 1.60(s, 6H), 1.88–2.03(m, 3H), 2.28–2.34(m, 2H), 2.82–2.89(m, 1H), 3.74(d, 2H, J=6.1Hz), 3.98–4.06(m, 1H), 5.72(s, 1H), 6.90(br, 2H), 7.31(d, 2H, J=8.1Hz), 7.64(d, 2H, J=8.1Hz), 7.94(s, 1H), 8.11(t, 1H, J=6.1Hz) | DMSO-d6, 400 MHz |
| 2-53 | (structure with aminopyrido-oxazine, biphenyl, CH₂COOH) | >270 | 1.65(s, 6H), 3.64(s, 2H), 7.04(brs, 2H), 7.39(d, 2H, J=9.0Hz), 7.69(d, 2H, J=9.0Hz), 7.75(d, 2H, J=9.0Hz), 7.84(d, 2H, J=9.0Hz), 12.32(brs, 1H) | DMSO-d6, 300 |

TABLE 2-continued

| New Ex. No. | MOLSTRUCTURE | m p | NMR(δ) | solvent |
|---|---|---|---|---|
| 2-54 | | 267(dec.) | 1.12(s, 3H), 1.28(s, 3H), 3.62(s, 2H), 4.22(brs, 1H), 5.35(brs, 1H), 6.27(brs, 2H), 7.36(d, 2H, J=9.0Hz), 7.54(d, 2H, J=9.0Hz), 7.65(d, 2H, J=9.0Hz), 7.64(s, 1H), 7.70(d, 2H, J=9.0Hz) | DMSO-d6, 300 |
| 2-55 | | >250 | 1.49(s, 6H), 1.60(s, 6H), 6.98(brs, 2H), 7.40(d, 2H, J=8.4 Hz), 7.68(d, 2H, J=8.4Hz), 7.95(s, 1H), 12.4(brs, 1H). | DMSO-d6, 300 MHz |
| 2-56 | | | | |
| 2-57 | | | | |

TABLE 2-continued

| New Ex. No. | MOLSTRUCTURE | m p | NMR(δ) | solvent |
|---|---|---|---|---|
| 2-58 | (structure) | 251–252 | 1.01–1.13(m, 2H), 1.39–1.53(m, 3H), 1.60(s, 6H), 1.82–1.91(m, 2H, J=6.0Hz), 2.89(s, 3H), 6.94(brs, 2H), 7.01(t, 1H, J=6.0Hz), 7.32(d, 2H, J=9.0Hz), 7.65(d, 2H, J=9.0Hz), 7.95(s, 1H) | DMSO-d6, 300 |
| 2-59 | (structure) | >250 | 1.04–1.12(m, 2H), 1.43–1.60(m, 3H), 1.60(s, 6H), 1.77–1.83(m, 4H), 2.38(d, 2H, J=6.9Hz), 2.49(m, 1H), 5.24(s, 1H), 6.88(brs, 2H), 7.29(d, 2H, J=8.3 Hz), 7.62(d, 2H, J=8.3Hz), 7.94(s, 1H), 9.20(brs, 1H), 11.20(brs, 1H). | DMSO-d6, 400 MHz |
| 2-60 | (structure) | 173–175 | a mixture of keto- and enol-form; 1.04–1.12(m, 2H), 1.43–1.60(m, 2H), 1.60(s, 6H), 1.70(m, 1H), 1.81–1.85(m, 4H), 2.33(d, 1H, J=6.9Hz) and 2.37(d, 1H, J=6.9 Hz), 2.50(m, 1H), 3.85(s, 1H) and 5.00(s, 0.5H), 6.88(brs, 2H), 7.29(d, 2H, J=8.3Hz), 7.64(d, 2H, J=8.3Hz), 7.95(s, 1H), 12.40(brs, 0.5H). | DMSO-d6, 400 MHz |

TABLE 2-continued

| New Ex. No. | MOLSTRUCTURE | m p | NMR(δ) | solvent |
|---|---|---|---|---|
| 2-61 | | 159–162 | 0.97–1.13(m, 2H), 1.35–1.52(m, 3H), 1.60(s, 6H), 1.76–1.87(m, 4H), 2.46–2.59(m, 1H), 2.91(t, 2H, J=6.0Hz), 5.02(s, 2H), 6.94(br, 2H), 7.23–7.40(m, 8H), 7.64(d, 2H, J=7.7Hz), 7.95(s, 1H) | DMSO-d6, 300 MHz |
| 2-62 | | >230 | 1.25–1.40(m, 2H), 1.45–1.55(m, 2H), 1.60(s, 6H), 1.83(brd, 2H, J=12.6Hz), 2.11(brd, 2H, J=9.6 Hz), 2.55(m, 1H), 3.35(m, 1H), 4.05(s, 2H), 6.88(brs, 2H), 7.29(d, 2H, J=8.3Hz), 7.63(d, 2H, J=8.3Hz), 7.94(s, 1H), 12.30(brs, 1H). | DMSO-d6, 400 MHz |
| 2-63 | | | 0.99–1.08(m, 2H), 1.24–1.34(m, 1H), 1.39–1.51(m, 2H), 1.60(s, 6H), 1.76–1.92(m, 4H), 2.44(d, 2H, J=6.6Hz), 2.47–2.56(m, 1H), 6.89(br, 2H), 7.30(d, 2H, J=8.2Hz), 7.63(d, 2H, J=8.2Hz), 7.95(s, 1H) | DMSO-d6, 400 MHz |

TABLE 2-continued

| New Ex. No. | MOLSTRUCTURE | m p | NMR(δ) | solvent |
|---|---|---|---|---|
| 2-64 | | >230 | 1.04–1.20(m, 2H), 1.43–1.50(m, 3H), 1.60(s, 6H), 1.75–1.88(m, 5H), 2.02(m, 1H), 2.51(m, 1H), 4.60(m, 1H), 6.88(brs, 2H), 7.30(d, 2H, J=8.3Hz), 7.63(d, 2H, J=8.3Hz), 7.94(s, 1H), 12.02(brs, 1H). | DMSO-d6, 400 MHz |
| 2-65 | | 243–244 | 1.05–1.14(m, 2H), 1.33(s, 6H), 1.38–1.51(m, 2H), 1.60(s, 6H), 1.76–1.85(m, 5H), 2.00(d, 2H, J=6.0Hz), 2.54–2.55(m, 1H), 6.94(brs, 2H), 7.31(d, 2H, J=9.0Hz), 7.64(d, 2H, J=9.0Hz), 7.95(s, 1H),7.98(s, 1H) | DMSO-d6, 300 MHz |
| 2-66 | | 176–177 | 1.59(s, 6H), 1.72–1.77(m, 4H), 2.72–2.82(m, 4H), 6.92(br, 2H), 7.11(d, 1H, J=7.7Hz), 7.40(d, 1H, J=7.7Hz), 7.39(s, 1H), 7.95(s, 1H) | DMSO-d6, 300 MHz |
| 2-67 | | >250 | 0.80–0.96(m, 2H), 1.11(s, 3H), 1.41–1.65(m, 4H), 1.62(s, 6H), 1.65–1.79(m, 1H), 1.96(d, 2H, J=7.0Hz), 2.31–2.41(m, 2H), 6.95(br, 2H), 7.44(d, 2H, J=8.4Hz), 7.70(d, 2H, J=8.4Hz), 7.95(s, 1H), 11.86(brs, 1H) | DMSO-d6, 300 MHz |

TABLE 2-continued

| New Ex. No. | MOLSTRUCTURE | m p | NMR(δ) | solvent |
|---|---|---|---|---|
| 2-68 | | >250 | 1.53–1.90(m, 5H), 1.59(s, 6H), 2.40–2.52(m, 2H), 2.66–2.82(m, 3H), 6.93(br, 2H), 7.13(d, 1H, J=7.7Hz), 7.44(d, 1H, J=7.7Hz), 7.50(s, 1H), 7.95(s, 1H), 12.15(brs, 1H) | DMSO-d6, 300 MHz |
| 2-69 | | >250 | 1.06(d, 3H, J=7.1Hz), 1.11–1.28(m, 2H), 1.43–1.52(m, 2H), 1.55–1.65(m, 1H), 1.61(s, 6H), 1.71–1.91(m, 4H), 2.15–2.23(m, 1H), 2.49–2.56(m, 1H), 6.92(br, 2H), 7.31(d, 2H, J=8.1Hz), 7.64(d, 2H, J=8.1Hz), 7.95(s, 1H), 11.97(brs, 1H) | DMSO-d6, 400 MHz |
| 2-70 | | 212–214 | 1.04–1.20(m, 2H), 1.43–1.50(m, 2H), 1.60(s, 6H), 1.61(m, 1H), 1.75–1.88(m, 4H), 2.51(m, 1H), 3.11(d, 2H, J=7.2Hz), 3.95(s, 2H), 6.88(brs, 2H), 7.29(d, 2H, J=8.3Hz), 7.64(d, 2H, J=8.3Hz), 7.94(s, 1H), 10.68(brs, 1H). | DMSO-d6, 400 MHz |
| 2-71 | | >250 | 1.59(s, 6H), 3.10–3.21(m, 4H), 3.26–3.34(m, 1H), 6.94(br, 2H), 7.28(d, 1H, J=7.7Hz), 7.48(d, 1H, J=7.7Hz), 7.55(s, 1H), 12.29(brs, 1H) | DMSO-d6, 300 MHz |

TABLE 2-continued

| New Ex. No. | MOLSTRUCTURE | m p | NMR(δ) | solvent |
|---|---|---|---|---|
| 2-72 | (structure) | >250 | 1.59(s, 6H), 2.42(d, 2H, J=7.3Hz), 2.57–2.80(m, 3H), 3.04–3.15(m, 2H), 6.92(br, 2H), 7.26(d, 1H, J=8.1Hz), 7.46(d, 1H, J=8.1Hz), 7.53(s, 1H), 7.95(s, 1H), 12.06(brs, 1H) | DMSO-d6, 300 MHz |
| 2-73 | (structure) | >250 | 1.03–1.13(m, 2H), 1.08(s, 3H), 1.22(s, 3H), 1.32(s, 6H), 1.36–1.48(m, 2H), 1.67–1.86(m, 5H), 1.99(d, 2H, J=6.6Hz), 2.42–2.50(m, 1H), 4.11(s, 1H), 5.25(s, 1H), 6.20(br, 2H), 7.24(d, 2H, J=8.1Hz), 7.35(d, 2H, J=8.1Hz), 7.61(s, 1H), 7.94(s, 1H), 11.93(brs, 1H) | DMSO-d6, 400 MHz |
| 2-74 | (structure) | >250 | 1.11–1.27(m, 2H), 1.36–1.54(m, 2H), 1.60(s, 6H), 1.68–1.87(m, 5H), 2.50–2.61(m, 1H), 2.83(d, 2H, J=7.0Hz), 6.93(br, 2H), 7.30(d, 2H, J=8.4Hz), 7.64(d, 2H, J=8.4Hz), 7.95(s, 1H) | DMSO-d6, 300 MHz |
| 2-75 | (structure) | 244–245 | 1.03(s, 3H), 1.26(s, 3H), 1.33–1.43(m, 4H), 1.46(s, 3H), 1.68–1.80(m, 6H), 2.52–2.55(m, 1H), 5.16(s, 1H), 6.23(brs, 2H), 7.23(d, 2H, J=9.0Hz), 7.53(d, 2H, J=9.0Hz), 7.61(s, 1H) | DMSO-d6, 300 MHz |

TABLE 2-continued

| New Ex. No. | MOLSTRUCTURE | m p | NMR(δ) | solvent |
|---|---|---|---|---|
| 2-76 | | >250 | 1.11–1.27(m, 2H), 1.36–1.51(m, 2H), 1.68–1.87(m, 5H), 2.41–2.52(m, 1H), 2.83(d, 2H, J=6.6Hz), 4.11(s, 1H), 5.25(s, 1H), 6.20(br, 2H), 7.23(d, 2H, J=8.1Hz), 7.35(d, 2H, J=8.1Hz), 7.61(s, 1H), 15.98(brs, 1H) | DMSO-d6, 400 MHz |
| 2-77 | | 137–139 | 1.04–1.34(m, 4H), 1.43–1.50(m, 2H), 1.60(s, 6H), 1.63–1.88(m, 7H), 2.23(d, 2H, J=7.2Hz), 2.51(m, 1H), 3.00(m, 1H), 3.15(m, 1H), 3.68–3.75(m, 2H), 3.94(m, 1H), 4.65(brs, 1H), 6.88(brs, 2H), 7.30(d, 2H, J=8.3 Hz), 7.63(d, 2H, J=8.3Hz), 7.94(s, 1H). | DMSO-d6, 400 MHz |
| 2-78 | | 185–187 | 1.04–1.20(m, 2H), 1.12(s, 6H), 1.31(d, 2H, J=5.4Hz), 1.43–1.50(m, 3H), 1.60(s, 6H), 1.75–1.95(m, 4H), 2.51(m, 1H), 4.01(s, 1H), 6.88(brs, 2H), 7.29(d, 2H, J=8.3Hz), 7.63(d, 2H, J=8.3Hz), 7.94(s, 1H). | DMSO-d6, 400 MHz |

TABLE 2-continued

| New Ex. No. | MOLSTRUCTURE | m p | NMR(δ) | solvent |
|---|---|---|---|---|
| 2-79 | (structure) | 207–208 | 1.00–1.14(m, 2H), 1.34–1.51(m, 5H), 1.80–1.91(m, 4H), 2.53–2.57(m, 1H), 3.43–3.49(m, 2H), 4.27(brs, 1H), 6.92(brs, 2H), 7.30(d, 2H, J=9.0Hz), 7.64(d, 2H, J=9.0Hz), 7.95(s, 1H) | DMSO-d6, 300 |
| 2-80 | (structure) | 271–272 | 0.98–1.24(m, 2H), 1.33–1.64(m, 10H), 1.76–1.98(m, 5H), 2.52–2.58(m, 1H), 3.98–4.03(m, 1H), 6.04(brs, 1H), 6.91(brs, 2H), 7.31(d, 2H, J=8.0Hz), 7.64(d, 2H, J=8.0Hz), 7.95(s, 1H) | DMSO-d6, 400 |
| 2-81 | (structure) | | 1.00–1.11(m, 5H), 1.22(s, 3H), 1.33–1.49(m, 5H), 1.75–1.85(m, 4H), 2.41–2.49(m, 1H), 3.43–3.49(m, 2H), 4.11(brs, 1H), 4.28–4.33(m, 1H), 5.26(brs, 1H), 6.22(brs, 2H), 7.24(d, 2H, J=9.0Hz), 7.36(d, 2H, J=9.0Hz), 7.62(s, 1H) | DMSO-d6, 300 |

TABLE 2-continued

| New Ex. No. | MOLSTRUCTURE | m p | NMR(δ) | solvent |
|---|---|---|---|---|
| 2-82 | (structure with piperidine) | 209–210 | 1.06–1.17(m, 2H), 1.32–1.52(m, 6H), 1.58–1.90(m, 11H), 1.61(s, 6H), 2.54–2.63(m, 1H), 2.77–2.89(m, 2H), 2.99–3.10(m, 2H), 7.03(brs, 2H), 7.31(d, 2H, J=9.0Hz), 7.65(d, 2H, J=9.0Hz), 7.98(s, 1H) | DMSO-d6, 300 MHz |
| 2-83 | (structure with pyrrolidine) | 142–143 | 1.04–1.16(m, 2H), 1.37–1.54(m, 6H), 1.60(brs, 6H), 1.79–2.02(m, 9H), 2.54–2.60(m, 1H), 2.91–3.03(m, 2H), 3.07–3.22(m, 2H), 7.03(brs, 2H), 7.31(d, 2H, J=9.0Hz), 7.66(d, 2H, J=9.0Hz), 7.98(brs, 1H) | DMSO-d6, 300 MHz |
| 2-84 | (structure with 4-hydroxypiperidine) | 217–218 | 1.02–1.14(m, 2H), 1.33–1.49(m, 10H), 1.60(s, 6H), 1.69–1.86(m, 9H), 2.54–2.58(m, 1H), 2.71–2.81(m, 2H), 3.42–3.52(m, 1H), 4.56(brs, 1H), 6.92(brs, 2H), 7.30(d, 2H, J=9.0Hz), 7.64(d, 2H, J=9.0Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-85 | | 115–116 | 1.04–1.18(m, 2H), 1.34–1.51(m, 6H), 1.58–1.66(m, 2H), 1.60(s, 6H), 1.80–1.96(m, 7H), 2.38–2.49(m, 2H), 2.51–2.60(m, 1H), 2.68–2.80(m, 2H), 4.80(brs, 1H), 6.92(brs, 2H), 7.18–7.34(m, 5H), 7.49(d, 2H, J=9.0Hz), 7.65(d, 2H, J=9.0Hz), 7.95(s, 1H) | DMSO-d6, 300 MHz |
| 2-86 | | 190–191 | 1.01–1.23(m, 4H), 1.30–1.57(m, 7H), 1.60(s, 6H), 1.74–1.86(m, 7H), 2.25–2.31(m, 2H), 2.53–2.57(m, 1H), 2.80–2.86(m, 2H), 3.30(s, 2H), 6.91(brs, 2H), 7.14–7.30(m, 7H), 7.64(d, 2H, J=9.0Hz), 7.95(s, 1H) | DMSO-d6, 300 MHz |
| 2-87 | | 221–222 | 1.02–1.14(m, 4H), 1.31–1.64(m, 9H), 1.60(s, 6H), 1.78–1.87(m, 7H), 2.27–2.37(m, 2H), 2.54–2.57(m, 1H), 2.80–2.90(m, 2H), 3.40–3.46(m, 2H), 4.29(t, 1H, J=4.5Hz), 6.92(brs, 2H), 7.30(d, 2H, J=9.0Hz), 7.64(d, 2H, J=9.0Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-88 | | 175–176 | 1.05–1.13(m, 2H), 1.34–1.50(m, 6H), 1.60(s, 6H), 1.79–1.85(m, 5H), 2.31–2.45(m, 8H), 2.53–2.57(m, 1H), 3.46(s, 2H), 6.92(brs, 2H), 7.24–7.35(m, 7H), 7.64(d, 2H, J=9.0Hz), 7.95(s, 1H) | DMSO-d6, 300 MHz |
| 2-89 | | | 1.47–1.67(m, 6H), 1.70(s, 6H), 1.74–1.86(m, 3H), 1.88–2.07(m, 4H), 2.17–2.27(m, 1H), 2.44–2.61(m, 3H), 2.64–2.74(m, 1H), 5.40(br, 2H), 7.34(br, 2H), 7.55(br, 2H), 8.14(s, 1H) | CDCl3, 400 MHz |
| 2-90 | | | 1.34–1.65(m, 10H), 1.61(s, 6H), 1.81–1.99(m, 5H), 2.14–2.27(m, 1H), 2.31–2.45(m, 3H), 2.68–2.83(m, 1H), 6.90(br, 2H), 7.31(br, 2H), 7.65(br, 2H), 7.95(s, 1H) | DMSO-d6, 400 MHz |

TABLE 2-continued

| New Ex. No. | MOLSTRUCTURE | m p | NMR(δ) | solvent |
|---|---|---|---|---|
| 2-91 | | | 1.04–1.13(m, 2H), 1.38–1.58(m, 3H), 1.60(s, 6H), 1.75–1.95(m, 3H), 2.51(m, 1H), 3.01(brt, 2H, J=6.4Hz), 3.80(d, 2H, J=5.6Hz), 5.41(brt, 1H, J=5.6Hz), 6.90(brs, 2H), 7.28(d, 2H, J=8.3Hz), 7.62(d, 2H, J=8.3Hz), 7.69(brt, 1H, J=6.4Hz), 7.93(s, 1H). | DMSO-d6, 400 MHz |
| 2-92 | | 113–115 | 1.04–1.17(m, 2H), 1.43–1.50(m, 2H), 1.60(s, 6H), 1.80–1.84(m, 5H), 2.19(s, 3H), 2.23–2.31(m, 6H), 2.51(m, 1H), 3.43–3.48(m, 4H), 6.91(brs, 2H), 7.30(d, 2H, J=8.3Hz), 7.63(d, 2H, J=8.3Hz), 7.95(s, 1H). | DMSO-d6, 300 MHz |
| 2-93 | | 146–147 | 1.03–1.20(m, 2H), 1.37–1.88(m, 19H), 2.22(d, 2H, J=6.0Hz), 2.53–2.58(m, 1H), 3.39–3.46(m, 4H), 6.92(brs, 2H), 7.31(d, 2H, J=9.0Hz), 7.64(d, 2H, J=9.0Hz), 7.95(s, 1H) | DMSO-d6, 300 |

TABLE 2-continued

| New Ex. No. | MOLSTRUCTURE | m p | NMR(δ) | solvent |
|---|---|---|---|---|
| 2-94 | (structure) | 232–233 | 1.06–1.19(m, 2H), 1.41–1.63(m, 8H), 1.71–1.91(m, 9H), 2.16(d, 2H, J=6.0Hz), 2.51–2.59(m, 1H), 3.28–3.31(m, 2H), 3.41(t, 2H, J=6.0Hz), 6.92(brs, 2H), 7.31(d, 2H, J=9.0Hz), 7.64(d, 2H, J=9.0Hz), 7.95(s, 1H) | DMSO-d6, 300 |
| 2-95 | (structure) | 199–200 | 1.08–1.21(m, 2H), 1.41–1.56(m, 2H), 1.60(s, 6H), 1.74–1.87(m, 4H), 2.25(d, 2H, J=9.0Hz), 3.41–3.59(m, 10H), 6.93(brs, 2H), 7.31(d, 2H, J=9.0Hz), 7.64(d, 2H, J=9.0Hz), 7.95(s, 1H) | DMSO-d6, 300 |
| 2-96 | (structure) | 112–113 | 0.89–1.18(m, 4H), 1.32–1.55(m, 4H), 1.60(s, 6H), 1.67–1.83(m, 7H), 2.22(d, 2H, J=6.0Hz), 2.52–2.57(m, 1H), 2.92–3.02(m, 2H), 3.41–3.47(m, 2H), 3.84–3.92(m, 2H), 4.33–4.42(m, 2H), 6.93(brs, 2H), 7.31(d, 2H, J=9.0Hz), 7.64(d, 2H, J=9.0Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-97 | | 225–226 | 1.06–1.18(m, 2H), 1.41–1.53(m, 2H), 1.60(s, 6H), 1.74–1.83(m, 5H), 2.23(d, 2H, J=6.0Hz), 2.33–2.42(m, 6H), 2.53–2.58(m, 1H), 3.43–3.54(m, 6H), 4.41(t, 1H, J=6.0Hz), 6.93(brs, 2H), 7.31(d, 2H, J=9.0Hz), 7.64(d, 2H, J=9.0Hz), 7.95(s, 1H) | DMSO-d6, 300 MHz |
| 2-98 | | 131–133 | 1.04–1.13(m, 2H), 1.16(s, 6H), 1.38–1.58(m, 2H), 1.59(s, 6H), 1.65–1.85(m, 5H), 1.97(d, 2H, J=6.8Hz), 2.51(m, 1H), 3.36(d, 2H, J=5.9Hz), 4.89(t, 1H, J=5.9 Hz), 6.92(brs, 2H), 7.24(s, 1H), 7.27(d, 2H, J=8.3Hz), 7.61(d, 2H, J=8.3Hz), 7.92(s, 1H). | DMSO-d6, 400 MHz |
| 2-99 | | 113–115 | a mixture of 2 conformers; 1.04–1.13(m, 2H), 1.38–1.58(m, 2H), 1.60(s, 6H), 1.65–1.85(m, 5H), 2.20–2.28(m, 2H), 2.51(m, 1H), 2.82 and 3.01(s, 3H), 3.30–3.51(m, 4H), 4.60 and 4.77(brt, 1H, J=5.6Hz), 6.92(brs, 2H), 7.29(d, 2H, J=8.3Hz), 7.62(d, 2H, J=8.3Hz), 7.93(s, 1H). | DMSO-d6, 400 MHz |

| New Ex. No. | MOLSTRUCTURE | m p | NMR(δ) | solvent |
|---|---|---|---|---|
| 2-100 | (structure) | 184–185 | 1.03–1.21(m, 2H), 1.39–1.55(m, 2H), 1.62(s, 6H), 1.71–1.95(m, 8H), 2.13–2.36(m, 2H), 2.43–2.59(m, 1H), 3.22–3.52(m, 4H), 3.85–4.02(m, 1H), 4.67–4.92(m, 1H), 6.91(br, 2H), 7.31(d, 2H, J=8.4Hz), 7.64(d, 2H, J=8.4Hz), 7.95(s, 1H) | DMSO-d6, 300 MHz |
| 2-101 | (structure) | 237–239 | 1.02–1.20(m, 2H), 1.37–1.57(m, 2H), 1.60(s, 6H), 1.69–1.95(m, 7H), 2.09–2.20(m, 2H), 2.44–2.59(m, 1H), 3.33–3.54(m, 2H), 4.20–4.38(m, 2H), 4.80–5.00(m, 1H), 6.92(br, 2H), 7.31(d, 2H, J=8.4Hz), 7.64(d, 2H, J=8.4Hz), 7.95(s, 1H) | DMSO-d6, 300 MHz |
| 2-102 | (structure) | 214–215 | 0.84(t, 3H, J=7.3Hz), 1.02–1.19(m, 2H), 1.34–1.53(m, 4H), 1.60(s, 6H), 1.69–1.86(m, 5H), 1.99(d, 2H, J=6.6Hz), 2.48–2.57(m, 1H), 3.00(q, 2H, J=6.6Hz), 6.93(br, 2H), 7.30(d, 2H, J=8.4Hz), 7.64(d, 2H, J=8.4Hz), 7.74(t, 1H, J=6.6Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-103 | | 231–232 | 1.02–1.22(m, 2H), 1.39–1.57(m, 2H), 1.60(s, 6H), 1.69–1.97(m, 5H), 2.08–2.21(m, 2H), 2.47–2.59(m, 1H), 3.29–3.56(m, 4H), 4.15–4.41(m, 2H), 4.81–5.00(m, 1H), 6.89(br, 2H), 7.31(d, 2H, J=8.4Hz), 7.64(d, 2H, J=8.4Hz), 7.95(s, 1H) | DMSO-d6, 300 MHz |
| 2-104 | | 186–188 | 1.00–1.55(m, 7H), 1.60(s, 6H), 1.78–1.94(m, 4H), 2.46–2.61(m, 1H), 2.85(s, 3H), 4.05(s, 1.4H), 4.08(s, 0.6H), 6.92(br, 2H), 7.30(d, 2H, J=8.1Hz), 7.64(d, 2H, J=8.1Hz), 7.95(s, 1H) | DMSO-d6, 300 MHz |
| 2-105 | | >250 | 1.52–1.92(m, 8H), 1.61(s, 6H), 2.49–2.65(m, 1H), 2.76(s, 1.8H), 2.79(s, 1.2H), 4.06(s, 0.6H), 4.16(s, 0.4H), 4.25–4.47(m, 1H), 6.93(br, 2H), 7.33(brd, 2H, J=8.2Hz), 7.65(d, 2H, J=8.2Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-106 | | 250–252 | 1.03–1.22(m, 2H), 1.39–1.58(m, 2H), 1.60(s, 6H), 1.69–1.92(m, 5H), 2.12(d, 2H, J=6.6Hz), 2.45–2.58(m, 1H), 3.16–3.41(m, 3H), 3.55–3.60(m, 1H), 3.94–4.09(m, 2H), 4.84(br, 1H), 4.92(br, 1H), 6.93(br, 2H), 7.31(d, 2H, J=8.1Hz), 7.64(d, 2H, J=8.1Hz), 7.95(s, 1H) | DMSO-d6, 300 MHz |
| 2-107 | | >250 | 1.07–1.18(m, 2H), 1.41–1.53(m, 2H), 1.59(s, 6H), 1.71–1.86(m, 5H), 2.15(d, 2H, J=4.0Hz), 2.24(s, 3H), 2.51–2.57(m, 1H), 6.84(brs, 2H), 7.28(d, 2H, J=8.0Hz), 7.61(d, 2H, J=8.0Hz), 12.04(brs, 1H) | DMSO-d6, 400 MHz |
| 2-108 | | 202–203 | 1.06–1.16(m, 2H), 1.36–1.48(m, 2H), 1.59–1.84(m, 5H), 1.59(s, 6H), 2.51–2.56(m, 1H), 3.86(d, 2H, J=8.0Hz), 6.89–7.15(m, 1H), 6.91(brs, 2H), 7.27(d, 2H, J=8.0Hz), 7.62(d, 2H, J=8.0Hz), 7.93(s, 1H) | DMSO-d6, 400 MHz |

TABLE 2-continued

| New Ex. No. | MOLSTRUCTURE | m p | NMR(δ) | solvent |
|---|---|---|---|---|
| 2-109 | | >230 | 1.15–1.35(m, 2H), 1.37–1.58(m, 3H), 1.60(s, 6H), 1.80–1.95(m, 5H), 2.51(m, 1H), 2.75(d, 2H, J=9.3Hz), 6.91(brs, 2H), 7.03–7.22(m, 2H), 7.30(d, 2H, J=8.3 Hz), 7.39–7.57(m, 2H), 7.63(d, 2H, J=8.3Hz), 7.95(s, 1H), 12.19(brs, 1H). | DMSO-d6, 400 MHz |
| 2-110 | | 155–156 | 1.01–1.18(m, 2H), 1.38–1.59(m, 2H), 1.60(s, 6H), 1.72–1.86(m, 5H), 2.34(d, 2H, J=6.0Hz), 2.54–2.58(m, 1H), 4.05(d, 2H, J=6.0Hz), 5.04(t, 1H, J=6.0Hz), 6.91(brs, 2H), 7.31(d, 2H, J=9.0Hz), 7.64(d, 2H, J=9.0Hz), 7.95(s, 1H) | DMSO-d6, 300 MHz |
| 2-111 | | >250 | 1.04–1.21(m, 2H), 1.38–1.58(m, 2H), 1.66(s, 6H), 1.70–1.89(m, 5H), 2.29(d, 2H, J=6.4Hz), 2.45–2.58(m, 1H), 2.96–3.13(m, 4H), 3.60–3.77(m, 4H), 7.32(d, 2H, J=8.3Hz), 7.65(br, 2H), 7.68(d, 2H, J=8.3Hz), 8.16(s, 1H), 9.32(br, 2H) | DMSO-d6, 300 MHz |

| New Ex. No. | MOLSTRUCTURE | m p | NMR(δ) | solvent |
|---|---|---|---|---|
| 2-112 | (structure) | >250 | 1.31–1.58(m, 4H), 1.60(s, 6H), 1.82–1.91(m, 2H), 2.06–2.16(m, 2H), 2.53–2.65(m, 1H), 2.77–2.88(m, 1H), 3.30(s, 2H), 6.93(brs, 2H), 7.31(d, 2H, J=6.0Hz), 7.64(d, 2H, J=6.0Hz), 7.94(s, 1H), 12.40(brs, 1H) | DMSO-d6, 300 |
| 2-113 | (structure) | 172–173 | 1.04–1.13(m, 2H), 1.34–1.46(m, 2H), 1.59(s, 6H), 1.78–1.84(m, 5H), 2.23(s, 3H), 2.36(d, 2H, J=8.0Hz), 2.51–2.58(m, 1H), 6.58(s, 1H), 6.92(brs, 2H), 7.28(d, 2H, J=8.0Hz), 7.62(d, 2H, J=8.0Hz), 7.93(s, 1H) | DMSO-d6, 400 MHz |
| 2-114 | (structure) | 250 | 1.04–1.22(m, 2H), 1.16(d, 6H, J=6.1Hz), 1.38–1.68(m, 4H), 1.60(s, 6H), 1.80–1.97(m, 5H), 2.49–2.62(m, 1H), 2.63–2.70(m, 1H), 6.93(br, 2H), 7.31(d, 2H, J=8.4Hz), 7.65(d, 2H, J=8.4Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-115 | (structure) | 127–135 | 0.99–1.23(m, 6H), 1.17(t, 3H, J=7.1Hz), 1.36–1.52(m, 2H), 1.60(s, 6H), 1.72–1.94(m, 8H), 2.45–2.59(m, 1H), 2.79–2.94(m, 2H), 3.81–3.89(m, 2H), 4.02(q, 2H, J=7.1Hz), 6.93(br, 2H), 7.30(d, 2H, J=8.4Hz), 7.64(d, 2H, J=8.4Hz), 7.95(s, 1H) | DMSO-d6, 300 MHz |
| 2-116 | (structure) | >250 | 0.93–1.22(m, 6H), 1.32–1.52(m, 4H), 1.60(s, 6H), 1.74–1.95(m, 7H), 2.20–2.34(m, 1H), 2.41(d, 2H, J=6.4Hz), 2.47–2.58(m, 1H), 3.27–3.39(m, 1H), 4.44(d, 1H, J=4.5Hz), 6.95(br, 2H), 7.29(d, 2H, J=8.3Hz), 7.63(d, 2H, J=8.3Hz), 7.95(s, 1H) | DMSO-d6, 300 MHz |
| 2-117 | (structure) | >250 | 1.07–1.18(m, 2H), 1.43–1.53(m, 2H), 1.55(s, 6H), 1.70–1.85(m, 5H), 2.15(d, 2H, J=8.0Hz), 2.51–2.55(m, 1H), 6.21(brs, 2H), 6.31(d, 1H, J=8.0Hz), 7.29(d, 2H, J=8.0Hz), 7.49(d, 1H, J=8.0Hz), 7.60(d, 2H, J=8.0Hz), 11.94(brs, 1H) | DMSO-d6, 400 MHz |

TABLE 2-continued

| New Ex. No. | MOLSTRUCTURE | m p | NMR(δ) | solvent |
|---|---|---|---|---|
| 2-118 | | 215–216 | 1.08–1.23(m, 2H), 1.38–1.50(m, 2H), 1.59(s, 6H), 1.68–1.83(m, 5H), 2.52–2.55(m, 1H), 2.58(d, 2H, J=4.0Hz), 2.62(s, 3H), 6.95(brs, 2H), 7.06(s, 1H), 7.28(d, 2H, J=8.0Hz), 7.62(d, 2H, J=8.0Hz), 7.93(s, 1H) | DMSO-d6, 400 MHz |
| 2-119 | | >250 | 1.08–1.18(m, 2H), 1.26(s, 9H), 1.35–1.49(m, 2H), 1.60(s, 6H), 1.75–1.85(m, 5H), 2.38(d, 2H, J=4.0Hz), 2.52–2.58(m, 1H), 6.55(brs, 1H), 6.94(brs, 2H), 7.29(d, 2H, J=12.0Hz), 7.62(d, 2H, J=8.0Hz), 7.93(s, 1H) | DMSO-d6, 400 MHz |
| 2-120 | | 226–227 | 0.68–1.19(m, 7H), 1.36–1.54(m, 2H), 1.59(s, 6H), 1.74–1.88(m, 5H), 2.33(d, 2H, J=4.0Hz), 2.53–2.56(m, 1H), 6.50(s, 1H), 6.94(brs, 2H), 7.28(d, 2H, J=8.0Hz), 7.62(d, 2H, J=8.0Hz), 7.93(s, 1H) | DMSO-d6, 400 MHz |
| 2-121 | | | 1.14–1.34(m, 2H), 1.37–1.58(m, 3H), 1.60(s, 6H), 1.80–1.95(m, 5H), 2.51(m, 1H), 2.71(d, 2H, J=9.3Hz), 3.77(s, 3H), 6.74(dd, 1H, J=2.2, 8.4Hz), 6.91(brs, 2H), 6.99(d, 1H, J=2.2Hz), 7.30(d, 2H, J=8.3Hz), 7.35(d, 1H, J=8.4 Hz), 7.64(d, 2H, J=8.3Hz), 7.95(s, 1H), 12.05(brs, 1H). | DMSO-d6, 300 MHz |

TABLE 2-continued

| New Ex. No. | MOLSTRUCTURE | m p | NMR(δ) | solvent |
|---|---|---|---|---|
| 2-122 | (structure with Cl-benzimidazole) | >230 | 1.15–1.33(m, 2H), 1.37–1.58(m, 3H), 1.60(s, 6H), 1.80–1.95(m, 5H), 2.51(m, 1H), 2.75(d, 2H, J=9.3Hz), 6.92(brs, 2H), 7.14(d, 1H, J=8.4Hz), 7.30(d, 2H, J=8.3 Hz), 7.39–7.55(m, 2H), 7.63(d, 2H, J=8.3Hz), 7.95(s, 1H), 12.37(brs, 1H). | DMSO-d6, 300 MHz |
| 2-123 | (structure with phenyl-imidazole) | 230–231 | 1.09–1.19(m, 2H), 1.41–1.52(m, 2H), 1.59(s, 6H), 1.76–1.88(m, 5H), 2.53–2.58(m, 1H), 3.18(d, 2H, J=12.0Hz), 6.71(brs, 1H), 6.93(brs, 2H), 7.27–7.42(m, 5H), 7.62(d, 2H, J=8.0Hz), 7.88(d, 2H, J=8.0Hz), 7.93(s, 1H) | DMSO-d6, 400 MHz |
| 2-124 | (structure with F-benzimidazole) | >230 | 1.14–1.33(m, 2H), 1.37–1.58(m, 3H), 1.60(s, 6H), 1.70–2.03(m, 5H), 2.51(m, 1H), 2.73(d, 2H, J=7.0Hz), 6.72–7.13(m, 3H), 7.17–7.35(m, 3H), 7.44(brs, 1H), 7.62(d, 2H, J=8.3Hz), 7.93(s, 1H), 12.30(brs, 1H). | DMSO-d6, 400 MHz |

TABLE 2-continued

| New Ex. No. | MOLSTRUCTURE | m p | NMR(δ) | solvent |
|---|---|---|---|---|
| 2-125 | | | 0.97–1.11(m, 2H), 1.34–1.54(m, 12H), 1.60(s, 6H), 1.78–1.95(m, 4H), 2.53–2.58(m, 1H), 2.76–2.83(m, 2H), 6.94(brs, 2H), 7.30(d, 2H, J=9.0Hz), 7.57(brs, 1H), 7.65(d, 2H, J=9.0Hz), 7.95(s, 1H), 10.76(brs, 1H) | DMSO-d6, 300 |
| 2-126 | | 234–235 | 0.93–1.50(m, 4H), 1.60(s, 6H), 1.72–1.91(m, 5H), 2.16(d, 2H, J=6.0Hz), 2.57–2.68(m, 1H), 6.95(brs, 2H), 7.29(d, 2H, J=6.0Hz), 7.64(d, 2H, J=6.0Hz), 7.95(s, 1H), 11.94(brs, 1H) | DMSO-d6, 300 |
| 2-127 | | 228–230 | 1.03–1.17(m, 2H), 1.39–1.51(m, 2H), 1.58–1.67(m, 7H), 1.82–1.95(m, 4H), 2.09(s, 3H), 2.51–2.59(m, 2H), 3.06–3.10(m, 2H), 6.11(brs, 1H), 6.94(brs, 2H), 7.31(d, 2H, J=9.0Hz), 7.45–7.49(m, 1H), 7.65(d, 2H, J=9.0Hz), 7.95(s, 1H) | DMSO-d6, 300 |

| New Ex. No. | MOLSTRUCTURE | m p | NMR(δ) | solvent |
|---|---|---|---|---|
| 2-128 | (structure) | 253–254 | 0.98–1.13(m, 2H), 1.35–1.51(m, 3H), 1.60(s, 6H), 1.77–1.88(m, 7H), 2.52–2.58(m, 1H), 2.91–2.95(m, 2H), 6.93(brs, 2H), 7.30(d, 2H, J=6.0Hz), 7.63(d, 2H, J=6.0Hz), 7.82(t, 1H, J=6.0Hz), 7.95(s, 1H) | DMSO-d6, 300 |
| 2-129 | (structure) | 206–207 | 0.93–1.08(m, 2H), 1.32–1.47(m, 3H), 1.60(s, 6H), 1.76–1.85(m, 4H), 2.39(s, 3H), 2.51–2.54(m, 1H), 2.57–2.62(m, 2H), 6.93(brs, 2H), 7.29(d, 2H, J=9.0Hz), 7.41(d, 2H, J=9.0Hz), 7.54(t, 1H, J=6.0Hz), 7.64(d, 2H, J=9.0Hz), 7.69(d, 2H, J=9.0Hz), 7.95(s, 1H) | DMSO-d6, 300 |
| 2-130 | (structure) | 226–227 | 0.96–1.11(m, 2H), 1.37–1.55(m, 3H), 1.60(s, 6H), 1.79–1.96(m, 4H), 2.53–2.57(m, 1H), 2.74–2.79(m, 2H), 6.43(s, 2H), 6.50(t, 1H, J=6.0Hz), 6.93(brs, 2H), 7.31(d, 2H, J=9.0Hz), 7.65(d, 2H, J=9.0Hz), 7.95(s, 1H) | DMSO-d6, 300 |

TABLE 2-continued

| New Ex. No. | MOLSTRUCTURE | m p | NMR(δ) | solvent |
|---|---|---|---|---|
| 2-131 | | 230–231 | 0.99–1.13(m, 2H), 1.35–2.01(m, 18H), 2.51–2.58(m, 1H), 2.77–2.86(m, 2H), 2.96–3.01(m, 2H), 3.49–3.53(m, 1H), 6.93(brs, 2H), 7.30(d, 2H, J=9.0Hz), 7.64(d, 2H, J=9.0Hz), 7.91–7.97(m, 2H) | DMSO-d6, 300 |
| 2-132 | | 217–218 | 0.98–1.14(m, 2H), 1.37–1.98(m, 16H), 2.53–2.58(m, 1H), 2.72–2.85(m, 2H), 2.96–3.00(m, 2H), 3.71(t, 1H, J=7.5Hz), 4.16(brs, 1H), 4.65(brs, 1H), 6.93(brs, 2H), 7.30(d, 2H, J=9.0Hz), 7.64(d, 2H, J=9.0Hz), 7.94–7.98(m, 2H) | DMSO-d6, 300 |
| 2-133 | | >230 | 1.61(s, 6H), 1.60–1.75(m, 8H), 2.18(m, 1H), 2.37(d, 2H, J=7.2 Hz), 2.60(m, 1H), 6.94(brs, 2H), 7.34(d, 2H, J=8.3Hz), 7.64(d, 2H, J=8.3Hz), 7.95(s, 1H). | DMSO-d6, 300 MHz |

TABLE 2-continued

| New Ex. No. | MOLSTRUCTURE | m p | NMR(δ) | solvent |
|---|---|---|---|---|
| 2-134 | | 225–226 | 1.07–1.18(m, 2H), 1.42–1.53(m, 2H), 1.58(s, 6H), 1.77–1.85(m, 5H), 1.91(s, 3H), 2.20(d, 2H, J=4.0Hz), 2.24(s, 3H), 2.54–2.57(m, 1H), 3.22(s, 3H), 6.81(brs, 2H), 7.28(d, 2H, J=8.0Hz), 7.61(d, 2H, J=12.0Hz), 11.66 and 11.93(brs, 1H) | DMSO-d6, 400 MHz |
| 2-135 | | 229–230 | 1.01–1.13(m, 2H), 1.17(s, 6H), 1.41–1.51(m, 2H), 1.58(s, 6H), 1.68–1.84(m, 5H), 1.98(d, 2H, J=8.0Hz), 2.24(s, 3H), 2.52–2.56(m, 1H), 3.38(d, 2H, J=4.0Hz), 4.90(t, 1H, J=4.0Hz), 6.80(brs, 2H), 7.26(brs, 1H), 7.28(d, 2H, J=8.0Hz), 7.60(d, 2H, J=8.0Hz) | DMSO-d6, 400 MHz |
| 2-136 | | 210–211 | 1.07–1.19(m, 2H), 1.42–1.52(m, 2H), 1.58(s, 6H), 1.76–1.86(m, 5H), 2.12(d, 2H, J=8.0Hz), 2.24(s, 3H), 2.51–2.56(m, 1H), 3.15–3.26(m, 2H), 3.35–3.39(m, 1H), 3.54–3.58(m, 1H), 3.95–4.06(m, 2H), 4.87(d, 1H, J=4.0Hz), 4.95(d, 1H, J=4.0Hz), 6.80(brs, 2H), 7.28(d, 2H, J=8.0Hz), 7.60(d, 2H, J=8.0Hz) | DMSO-d6, 400 MHz |

TABLE 2-continued

| New Ex. No. | MOLSTRUCTURE | m p | NMR(δ) | solvent |
|---|---|---|---|---|
| 2-137 | | >250 | 1.13–1.24(m, 2H), 1.38–1.50(m, 2H), 1.57(s, 6H), 1.73–1.83(m, 5H), 2.24(s, 3H), 2.82(d, 2H, J=8.0Hz), 3.35–3.39(m, 1H), 6.81(brs, 2H), 7.27(d, 2H, J=8.0Hz), 7.60(d, 2H, J=8.0Hz) | DMSO-d6, 400 MHz |
| 2-138 | | 235–238 | 0.96–1.13(m, 2H), 1.35–1.55(m, 3H), 1.58(s, 6H), 1.75–1.89(m, 4H), 2.24(s, 3H), 2.47.2.61(m, 1H), 3.01(t, 2H, J=6.0Hz), 3.80(d, 2H, J=6.0Hz), 5.42(t, 1H, J=6.0Hz), 6.82(br, 2H), 7.29(d, 2H, J=8.3Hz), 7.61(d, 2H, J=8.3Hz), 7.69(t, 1H, J=6.0Hz) | DMSO-d6, 300 MHz |
| 2-139 | | 249–250 | 1.03(s, 6H), 1.06–1.08(m, 2H), 1.36–1.48(m, 3H), 1.58(s, 6H), 1.81(m, 4H), 2.25(s, 3H), 2.66(m, 2H), 3.37(d, 2H, J=5.3Hz), 4.86(t, 1H, J=5.3Hz), 6.80(brs, 2H), 7.29(d, 2H, J=8.3Hz), 7.44(t, 1H, J=5.6Hz), 7.62(d, 2H, J=8.3Hz). | DMSO-d6, 300 MHz |

TABLE 2-continued

| New Ex. No. | MOLSTRUCTURE | m p | NMR(δ) | solvent |
|---|---|---|---|---|
| 2-140 | | 223–224 | 0.98–1.10(m, 2H), 1.37–1.48(m, 3H), 1.58(s, 6H), 1.82(m, 4H), 2.25(s, 3H), 2.25(t, 2H, J=6.5Hz), 2.95(m, 2H), 3.61(dt, 1H, J=6.5Hz, 5.3Hz), 4.53(t, 1H, J=5.3Hz), 6.80(brs, 2H), 7.29(d, 2H, J=8.3Hz), 7.61(d, 2H, J=8.3Hz), 7.78(t, 1H, J=5.3Hz), | DMSO-d6, 300 MHz |
| 2-141 | | 221–223 | 0.97–1.15(m, 2H), 1.24(s, 6H), 1.25–1.53(m, 5H), 1.58(s, 6H), 1.76–1.93(m, 4H), 2.25(s, 3H), 2.45–2.62(m, 1H), 3.12(q, J=6.4Hz, 2H), 5.28(s, 1H), 6.83(brs, 2H), 7.28(d, J=8.3Hz, 2H), 7.53–7.61(m, 1H), 7.61(d, J=8.3Hz, 2H). | DMSO-d6, 300 MHz |
| 2-142 | | 142–144 | 0.99–1.19(m, 2H), 1.34–1.58(m, 3H), 1.60(s, 6H), 1.67–1.89(m, 5H), 2.08(d, 2H, d=6.9Hz), 2.24(s, 3H), 2.51(m, 1H), 3.63(d, 2H, J=5.5Hz), 6.81(brs, 2H), 6.96(brs, 1H), 7.24(brs, 1H), 7.30(d, 2H, J=8.3Hz), 7.62(d, 2H, J=8.3Hz), 7.95(t, 1H, J=5.5Hz). | DMSO-d6, 300 MHz |

TABLE 2-continued

| New Ex. No. | MOLSTRUCTURE | m p | NMR(δ) | solvent |
|---|---|---|---|---|
| 2-143 | | 196–198 | a mixture of 2 conformers; 1.02–1.22(m, 2H), 1.34–1.58(m, 3H), 1.58(s, 6H), 1.72–1.92(m, 5H), 2.13 and 2.27(d, 2H, d=6.9Hz), 2.24(s, 3H), 2.51(m, 1H), 2.81 and 3.03(s, 3H), 3.98 and 4.09(s, 2H), 6.82(brs, 2H), 7.28(d, 2H, J=8.3Hz), 7.62(d, 2H, J=8.3Hz) 11.70(brs, 1H). | DMSO-d6, 300 MHz |
| 2-144 | | >230 | a mixture of 2 conformers; 0.99–1.20(m, 2H), 1.34–1.58(m, 3H), 1.58(s, 6H), 1.73–1.92(m, 5H), 2.12 and 2.26(d, 2H, d=6.9Hz), 2.24(s, 3H), 2.51(m, 1H), 2.79 and 3.98(s, 3H), 3.85 and 3.92(s, 2H), 6.82(brs, 2H), 6.96 and 7.14(brs, 1H), 7.29(d, 2H, J=8.3 Hz), 7.27 and 7.43(brs, 1H), 7.61(d, 2H, J=8.3Hz). | DMSO-d6, 400 MHz |
| 2-145 | | >250 | 0.55(s, 3H), 1.21(s, 3H), 1.55(s, 6H), 1.95–2.02(m, 1H), 2.14–2.36(m, 4H), 2.24(s, 3H), 3.14–3.20(m, 1H), 6.83(brs, 2H), 7.16(d, 2H, J=8.0Hz), 7.62(d, 2H, J=8.0Hz) | DMSO-d6, 400 MHz |

TABLE 2-continued

| New Ex. No. | MOLSTRUCTURE | m p | NMR(δ) | solvent |
|---|---|---|---|---|
| 2-146 | (structure) | >250 | 1.58(s, 6H), 1.74–1.82(m, 2H), 2.24(s, 3H), 2.37(d, 2H, J=8.0Hz), 2.44–2.60(m, 4H), 3.36–3.43(m, 1H), 6.80(brs, 2H), 7.27(d, 2H, J=8.0Hz), 7.61(d, 2H, J=8.0Hz), 11.98(brs, 1H) | DMSO-d6, 400 MHz |
| 2-147 | (structure) | >230 | 1.05–1.20(m, 2H), 1.38–1.52(m, 2H), 1.58(s, 6H), 1.73–1.87(m, 5H), 2.24(s, 3H), 2.29(d, 2H, 6.9Hz), 2.51(m, 1H), 6.81(brs, 2H), 7.28(d, 2H, J=8.3Hz), 7.61(d, 2H, J=8.3Hz), 11.07(s, 1H), 11.10(brs, 1H). | DMSO-d6, 400 MHz |
| 2-148 | (structure) | >250 | 1.13–1.24(m, 2H), 1.43–1.55(m, 2H), 1.58(s, 6H), 1.82–1.85(m, 4H), 2.24(s, 3H), 2.38–2.41(m, 2H), 2.50–2.58(m, 1H), 6.82(br, 1H), 7.30(d, 2H, J=9.0Hz), 7.62(d, 2H, J=9.0Hz), 11.96(brs, 1H), 15.85(br, 1H) | DMSO-d6, 300 MHz |

TABLE 2-continued

| New Ex. No. | MOLSTRUCTURE | m p | NMR(δ) | solvent |
|---|---|---|---|---|
| 2-149 | (structure) | 237–238 | 1.58(s, 6H), 1.60–1.71(m, 4H), 2.04–2.23(m, 3H), 2.23(s, 3H), 2.24(s, 3H), 2.40–2.46(m, 2H), 3.35–3.41(m, 1H), 6.81(brs, 2H), 7.25(d, 2H, J=8.0Hz), 7.61(d, 2H, J=8.0Hz), 11.99(brs, 1H) | DMSO-d6, 400 MHz |
| 2-150 | (structure) | 228–229 | 0.99–1.10(m, 2H), 1.25(s, 6H), 1.37–1.48(m, 2H), 1.58(s, 6H), 1.76–1.85(m, 5H), 2.24(s, 3H), 2.53–2.57(m, 1H), 2.96–2.99(m, 2H), 5.32(s, 1H), 6.81(brs, 2H), 7.28(d, 2H, J=8.0Hz), 7.58(brs, 1H), 7.60(d, 2H, J=8.0Hz) | DMSO-d6, 400 MHz |
| 2-151 | (structure) | >250 | 1.11–1.23(m, 2H), 1.42–1.52(m, 2H), 1.57(s, 6H), 1.77–1.86(m, 5H), 2.25(s, 3H), 2.44(d, 2H, J=8.0Hz), 2.53–2.62(m, 1H), 6.81(brs, 2H), 7.28(d, 2H, J=8.0Hz), 7.61(d, 2H, J=8.0Hz), 12.70(brs, 1H) | DMSO-d6, 400 MHz |

TABLE 2-continued

| New Ex. No. | MOLSTRUCTURE | m p | NMR(δ) | solvent |
|---|---|---|---|---|
| 2-152 | (structure) | 225–226 | 1.11–1.23(m, 2H), 1.41–1.49(m, 2H), 1.57(s, 6H), 1.76–1.84(m, 5H), 2.24(s, 3H), 2.44(d, 2H, J=8.0Hz), 2.53–2.61(m, 1H), 6.82(brs, 2H), 7.28(d, 2H, J=8.0Hz), 7.61(d, 2H, J=8.0Hz), 12.69(brs, 1H) | DMSO-d6, 400 MHz |
| 2-153 | (structure) | | 1.11–1.24(m, 2H), 1.40–1.51(m, 2H), 1.58(s, 6H), 1.77–1.87(m, 5H), 2.24(s, 3H), 2.46(d, 2H, J=8.0Hz), 2.52–2.58(m, 1H), 6.81(brs, 2H), 7.28(d, 2H, J=8.0Hz), 7.61(d, 2H, J=8.0Hz), 11.41(brs, 1H) | DMSO-d6, 400 MHz |
| 2-154 | (structure) | 229–233 | 1.00–1.11(m, 2H), 1.37–1.58(m, 3H), 1.65(s, 6H), 1.76–1.87(m, 4H), 2.49–2.57(m, 1H), 2.99–3.04(m, 2H), 3.81(d, 2H, J=6.0Hz), 5.42(t, 1H, J=6.0Hz), 7.32(d, 2H, J=6.0Hz), 7.69(d, 2H, J=6.0Hz) | DMSO-d6, 300 MHz |

TABLE 2-continued

| New Ex. No. | MOLSTRUCTURE | m p | NMR(δ) | solvent |
|---|---|---|---|---|
| 2-155 | | | 1.01–1.22(m, 2H), 1.34–1.52(m, 2H), 1.57(s, 6H), 1.68–1.89(m, 4H), 2.24(s, 3H), 2.37(d, 2H, d=6.9Hz), 2.50(m, 1H), 5.23(s, 1H), 6.81(brs, 2H), 7.27(d, 2H, J=8.3Hz), 7.60(d, 2H, J=8.3Hz), 9.25(brs, 1H), 11.20(brs, 1H). | DMSO-d6, 400 MHz |
| 2-156 | | >250 | 1.09–1.23(m, 2H), 1.15(t, 3H, J=8.0Hz), 1.43–1.52(m, 2H), 1.57(s, 6H), 1.71–1.90(m, 5H), 2.24(s, 3H), 2.44(d, 2H, J=8.0Hz), 2.53–2.58(m, 1H), 3.58(q, 2H, J=8.0Hz), 6.80(brs, 2H), 7.28(d, 2H, J=8.0Hz), 7.60(d, 2H, J=8.0Hz), 11.34(s, 1H) | DMSO-d6, 400 MHz |
| 2-157 | | | 1.11–1.24(m, 2H), 1.44–1.54(m, 2H), 1.58(s, 6H), 1.68–1.87(m, 5H), 2.24(s, 3H), 2.53–2.57(m, 1H), 3.51(d, 2H, J=8.0Hz), 6.80(brs, 2H), 7.29(d, 2H, J=8.0Hz), 7.61(d, 2H, J=8.0Hz), 12.28(brs, 1H) | DMSO-d6, 400 MHz |

TABLE 2-continued

| New Ex. No. | MOLSTRUCTURE | m p | NMR(δ) | solvent |
|---|---|---|---|---|
| 2-158 | (structure) | 240–241 | 1.03–1.14(m, 2H), 1.41–1.53(m, 2H), 1.58–1.71(m, 1H), 1.58(s, 6H), 1.77–1.86(m, 4H), 2.25(s, 3H), 2.50–2.58(m, 1H), 3.04(d, 2H, J=9.0Hz), 3.56(t, 2H, J=7.5Hz), 4.27(t, 2H, J=7.5Hz), 6.80(br, 1H), 7.29(d, 2H, J=6.0Hz), 7.63(d, 2H, J=9.0Hz) | DMSO-d6, 300 MHz |
| 2-159 | (structure) | 148(dec.) | 1.01–1.13(m, 2H), 1.39–1.51(m, 2H), 1.58–1.69(m, 1H), 1.58(s, 6H), 1.76–1.86(m, 4H), 2.25(s, 3H), 2.50–2.57(m, 1H), 3.11(d, 2H, J=6.0Hz), 3.95(s, 2H), 6.81(br, 1H), 7.29(d, 2H, J=9.0Hz), 7.62(d, 2H, J=6.0Hz) | DMSO-d6, 300 MHz |
| 2-160 | (structure) | 185–186 | 1.00–1.13(m, 2H), 1.30–1.51(m, 6H), 1.58(s, 6H), 1.79–1.87(m, 4H), 2.24(s, 3H), 2.50–2.58(m, 1H), 0.00–0.00(m, 2H), 3.17(q, 2H, J=7.0Hz), 3.78(d, 2H, J=6.0Hz), 5.40(t, 1H, J=6.0Hz), 6.80(br, 2H), 7.29(d, 2H, J=9.0Hz), 7.62(d, 2H, J=9.0Hz), 7.66(t, 1H, J=6.0Hz) | DMSO-d6, 300 MHz |

TABLE 2-continued

| New Ex. No. | MOLSTRUCTURE | m p | NMR(δ) | solvent |
|---|---|---|---|---|
| 2-161 | (structure) | 219–221 | 0.95–1.12(m, 2H), 1.35–1.52(m, 3H), 1.58(s, 6H), 1.73–1.91(m, 4H), 2.24(s, 3H), 2.47–2.57(m, 1H), 2.86(t, 2H, J=6.2Hz), 5.33(br, 2H), 5.98(t, 1H, J=5.7Hz), 6.80(br, 2H), 7.29(d, 2H, J=8.3Hz), 7.61(d, 2H, J=8.3Hz) | DMSO-d6, 300 MHz |
| 2-162 | (structure) | 216–250 | 0.95–1.11(m, 2H), 1.36–1.53(m, 3H), 1.58(s, 6H), 1.76–1.90(m, 4H), 2.24(s, 3H), 2.45–2.56(m, 1H), 2.91(d, 2H, J=6.8Hz), 3.56(t, 2H, J=8.5Hz), 4.13(t, 2H, J=8.5Hz), 6.79(br, 2H), 7.29(d, 2H, J=8.3Hz), 7.61(d, 2H, J=8.3Hz) | DMSO-d6, 300 MHz |
| 2-163 | (structure) | 219–221 | 0.82(s, 3H), 0.83(s, 3H), 0.98–1.14(m, 2H), 1.35–1.54(m, 3H), 1.58(s, 6H), 1.76–1.88(m, 4H), 2.24(s, 3H), 2.44–2.56(m, 1H), 2.94–3.10(m, 2H), 3.16–3.34(m, 2H), 3.73(d, 1H, J=5.7Hz), 4.48(t, 1H, J=5.7Hz), 5.31(d, 1H, J=5.7Hz), 6.79(br, 2H), 7.29(d, 2H, J=8.3Hz), 7.61(d, 2H, J=8.3Hz), 7.68(t, 1H, J=5.8Hz) | DMSO-d6, 300 MHz |

TABLE 2-continued

| New Ex. No. | MOLSTRUCTURE | m p | NMR(δ) | solvent |
|---|---|---|---|---|
| 2-164 | | 222–225 | 0.96–1.14(m, 2H), 1.35–1.61(m, 4H), 1.58(s, 6H), 1.75–1.89(m, 5H), 2.24(s, 3H), 2.46–2.59(m, 1H), 2.99(t, 2H, J=6.6Hz), 3.45–3.54(m, 2H), 3.95(dt, 1H, J=5.7, 3.8Hz), 4.42(t, 1H, J=5.7Hz), 5.39(d, 1H, J=5.7Hz), 6.81(br, 2H), 7.29(d, 2H, J=8.3Hz), 7.61(d, 2H, J=8.3Hz), 7.68(t, 1H, J=6.2Hz) | DMSO-d6, 300 MHz |
| 2-165 | | >250 | a mixture of 2 conformers; 1.02–1.15(m, 2H), 1.37–1.48(m, 2H), 1.57(s, 6H), 1.78–1.85(m, 5H), 2.24(s, 3H), 2.27(d, 2H, J=4.0Hz), 2.52–2.55(m, 1H), 3.30 and 3.56(s, 3H), 5.12(brs, 1H), 6.81(brs, 2H), 7.27(d, 2H, J=8.0Hz), 7.60(d, 2H, J=8.0Hz), 10.64(brs, 1H) | DMSO-d6, 400 MHz |
| 2-166 | | 225–233 | 0.98–1.13(m, 2H), 1.35–1.51(m, 2H), 1.58(s, 6H), 1.63–1.87(m, 6H), 2.21–2.32(m, 1H), 2.24(s, 3H), 2.45–2.60(m, 1H), 3.06(d, 2H, J=7.1Hz), 3.17–3.35(m, 2H), 4.04–4.16(m, 1H), 5.45(br, 1H), 6.82(br, 2H), 7.29(d, 2H, J=8.3Hz), 7.62(d, 2H, J=8.3Hz) | DMSO-d6, 300 MHz |

TABLE 2-continued

| New Ex. No. | MOLSTRUCTURE | m p | NMR(δ) | solvent |
|---|---|---|---|---|
| 2-167 | (structure) | | 0.90(s, 3H), 0.99–1.14(m, 2H), 1.08(s, 3H), 1.30–1.51(m, 2H), 1.58(s, 6H), 1.62–1.90(m, 5H), 2.24(s, 3H), 2.45–2.59(m, 1H), 2.95–3.12(m, 4H), 3.74(d, 1H, J=5.7Hz), 5.41(d, 1H, J=5.7Hz), 6.79(br, 2H), 7.28(d, 2H, J=8.3Hz), 7.61(d, 2H, J=8.3Hz) | DMSO-d6, 300 MHz |
| 2-168 | (structure) | | 1.13–1.31(m, 2H), 1.38–1.58(m, 2H), 1.58(s, 6H), 1.74–1.92(m, 5H), 2.25(s, 3H), 2.50(m, 1H), 258(d, 2H, d=6.9Hz), 3.72(s, 3H), 6.80(brs, 2H), 7.29(d, 2H, J=8.3Hz), 7.62(d, 2H, J=8.3Hz). | DMSO-d6, 300 MHz |
| 2-169 | (structure) | >230 | 1.10–1.25(m, 2H), 1.38–1.53(m, 2H), 1.57(s, 6H), 1.69–1.87(m, 5H), 2.24(s, 3H), 2.50(m, 1H), 2.54(d, 2H, d=6.9Hz), 3.58(s, 3H), 6.80(brs, 2H), 7.27(d, 2H, J=8.3Hz), 7.60(d, 2H, J=8.3Hz), 10.66(brs, 1H). | DMSO-d6, 400 MHz |

TABLE 2-continued

| New Ex. No. | MOLSTRUCTURE | m p | NMR(δ) | solvent |
|---|---|---|---|---|
| 2-170 | (structure) | 228–229 | 1.05–1.15(m, 2H), 1.38–1.48(m, 2H), 1.58(s, 6H), 1.66–2.01(m, 7H), 2.24(s, 3H), 2.51–2.55(m, 1H), 3.08–3.30(m, 6H), 3.85–3.90(m, 2H), 4.97(d, 1H, J=4.0Hz), 6.80(brs, 2H), 7.27(d, 2H, J=8.0Hz), 7.61(d, 2H, J=12.0Hz) | DMSO-d6, 400 MHz |
| 2-171 | (structure) | | 1.09–1.28(m, 2H), 1.38–1.80(m, 3H), 1.69(s, 6H), 1.84–2.04(m, 4H), 2.44(s, 3H), 2.48–2.60(m, 1H), 3.09(d, 2H, J=6.0Hz), 3.38–3.53(m, 4H), 4.59(s, 1H), 5.50(br, 2H), 7.24(d, 2H, J=8.3Hz), 7.54(d, 2H, J=8.3Hz) | CDCl3, 300 MHz |
| 2-172 | (structure) | >250 | 1.04–1.09(m, 2H), 1.43(m, 1H), 1.43–1.50(m, 4H), 1.60(s, 6H), 1.80–1.90(m, 4H), 5.24(s, 1H), 6.88(brs, 2H), 7.29(d, 2H, J=8.3 Hz), 7.62(d, 2H, J=8.3Hz), 7.94(s, 1H), 9.20(brs, 1H), 11.20(brs, 1H). | DMSO-d6, 400 MHz |

TABLE 2-continued

| New Ex. No. | MOLSTRUCTURE | m p | NMR(δ) | solvent |
|---|---|---|---|---|
| 2-173 | (structure) | 218–219 | 1.02–1.13(m, 2H), 1.40–1.49(m, 5H), 1.60(s, 6H), 1.81–1.85(m, 4H), 2.53–2.57(m, 1H), 2.89(s, 3H), 2.96–3.02(m, 2H), 6.88–6.97(m, 3H), 7.31(d, 2H, J=9.0Hz), 7.65(d, 2H, J=9.0Hz), 7.95(s, 1H) | DMSO-d6, 300 MHz |
| 2-174 | (structure) | 238–239 | 0.99–1.14(m, 2H), 1.31–1.52(m, 5H), 1.60(s, 6H), 1.79(s, 3H), 1.80–1.86(m, 4H), 2.53–2.59(m, 1H), 3.05–3.12(m, 2H), 6.93(brs, 2H), 7.30(d, 2H, J=9.0Hz), 7.65(d, 2H, J=9.0Hz), 7.77(t, 1H, J=4.5Hz), 7.95(s, 1H) | DMSO-d6, 300 MHz |
| 2-175 | (structure) | 230–231 | 0.91–1.06(m, 2H), 1.27–1.45(m, 5H), 1.60(s, 6H), 1.67–1.82(m, 4H), 2.39(s, 3H), 2.44–2.49(m, 1H),2.74–2.80(m, 2H),6.93(brs, 2H), 7.28(d, 2H, J=9.0Hz), 7.41(d, 2H, J=9.0Hz), 7.45(t, 1H, J=7.5Hz),7.64(d, 2H, J=9.0Hz), 7.69(d, 2H, J=9.0Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-176 | | 196–198 | 0.98–1.14(m, 2H), 1.29–1.65(m, 11H), 1.76–1.93(m, 4H), 2.51–2.58(m, 1H), 3.14–3.21(m, 2H), 3.79(d, 2H, J=6.0Hz), 5.39(t, 1H, J=6.0Hz), 6.92(brs, 2H), 7.30(d, 2H, J=9.0Hz), 7.62–7.67(m, 3H), 7.95(s, 1H) | DMSO-d6, 300 MHz |
| 2-177 | | 198–200 | 0.84(t, 3H, J=7.4Hz), 0.97–1.12(m, 2H), 1.18–1.53(m, 7H), 1.60(s, 6H), 1.76–1.88(m, 4H), 2.57(m, 1H), 2.99(q, 2H, J=6.5Hz), 6.94(br, 2H), 7.29(d, 2H, J=8.3Hz), 7.64(d, 2H, J=8.3Hz), 7.75(t, 1H, J=6.5Hz), 7.95(s, 1H) | DMSO-d6, 300 MHz |
| 2-178 | | 143–160 | 1.03–1.17(m, 2H), 1.25–1.56(m, 5H), 1.64(s, 6H), 2.30(t, 1.2H, J=7.7Hz), 2.39(t, 0.8H, J=7.7Hz), 2.51–2.62(m, 1H), 3.17–3.54(m, 5H), 3.89–4.00(m, 1H), 4.77(br, 0.6H), 4.95(br, 0.4H), 6.99(br, 2H), 7.33(d, 2H, J=8.3Hz), 7.67(d, 2H, J=8.3Hz), 7.98(s, 1H) | DMSO-d6, 300 MHz |

TABLE 2-continued

| New Ex. No. | MOLSTRUCTURE | m p | NMR(δ) | solvent |
|---|---|---|---|---|
| 2-179 | | 168–170 | 0.98–1.16(m, 2H), 1.25–1.55(m, 5H), 1.60(s, 6H), 1.75–1.94(m, 4H), 2.24–2.44(m, 2H), 2.48–2.60(m, 1H), 2.81(s, 1.5H), 3.00(s, 1.5H), 3.25–3.41(m, 2H), 3.43–3.55(m, 2H), 4.60(br, 0.5H), 4.78(br, 0.5H), 6.92(br, 2H), 7.30(d, 2H, J=8.4Hz), 7.64(d, 2H, J=8.4Hz), 7.95(s, 1H) | DMSO-d6, 300 MHz |
| 2-180 | | 200–202 | 0.98–1.55(m, 9H), 1.60(s, 6H), 1.61–1.94(m, 6H), 2.33(t, 2H, J=7.8Hz), 2.48–2.59(m, 1H), 2.90–3.04(m, 1H), 3.07–3.20(m, 1H), 3.60–3.75(m, 2H), 3.85–4.03(m, 1H), 4.71(br, 1H), 6.92(br, 2H), 7.30(d, 2H, J=8.4Hz), 7.64(d, 2H, J=8.4Hz), 7.95(s, 1H) | DMSO-d6, 300 MHz |
| 2-181 | | 83–207 | 1.02–1.14(m, 2H), 1.24–1.51(m, 5H), 1.60(s, 6H), 1.77–1.91(m, 4H), 2.16–2.37(m, 8H), 2.46–2.54(m, 1H), 3.38–3.50(m, 4H), 6.93(br, 2H), 7.29(d, 2H, J=8.3Hz), 7.64(d, 2H, J=8.3Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-182 | | 167–169 | 0.99–1.13(m, 2H), 1.27–1.50(m, 6H), 1.55–1.69(m, 9H), 1.76–2.00(m, 5H), 2.51–2.57(m, 1H), 2.80–2.87(m, 2H), 3.09–3.16(m, 2H), 3.49–3.53(m, 1H), 6.94(brs, 2H), 7.29(d, 2H, J=6.0Hz), 7.63(d, 2H, J=6.0Hz), 7.88–7.92(m, 1H), 7.95(s, 1H) | DMSO-d6, 300 |
| 2-183 | | 201–203 | 0.98–1.13(m, 2H), 1.24–1.70(m, 13H), 1.77–1.98(m, 5H), 2.51–2.58(m, 1H), 2.71–2.87(m, 2H), 3.07–3.16(m, 2H), 3.70(t, 1H, J=7.5Hz), 4.17(brs, 1H), 4.67(d, 1H, J=3.0Hz), 6.92(brs, 2H), 7.30(d, 2H, J=90Hz), 7.64(d, 2H, J=9.0Hz), 7.92(t, 1H, J=45Hz), 7.95(s, 1H) | DMSO-d6, 300 |
| 2-184 | | >250 | 1.03–1.17(m, 2H), 1.37–1.54(m, 5H), 1.60(s, 6H), 1.78–1.90(m, 4H), 2.08(s, 3H), 2.53–2.59(m, 1H), 3.19–3.25(m, 2H), 6.12(brs, 1H), 6.94(brs, 2H), 7.30(d, 2H, J=9.0Hz), 7.34–7.39(m, 1H), 7.64(d, 2H, J=9.0Hz), 7.95(s, 1H) | DMSO-d6, 300 |

TABLE 2-continued
| New Ex. No. | MOLSTRUCTURE | m p | NMR(δ) | solvent |
|---|---|---|---|---|
| 2-185 | 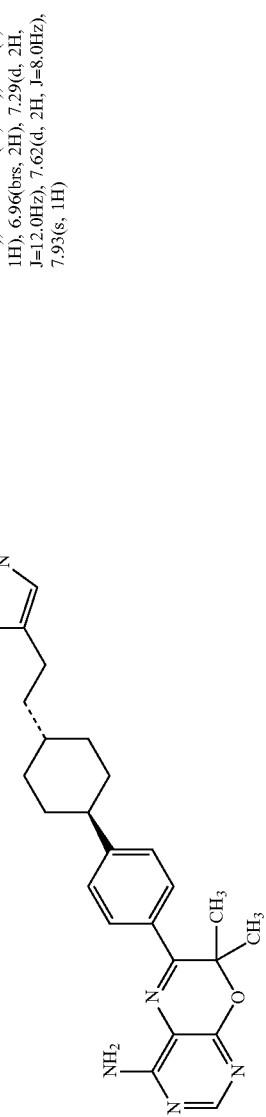 | 193–194 | 1.02–1.14(m, 2H), 1.27–1.51(m, 6H), 1.60(s, 6H), 1.80–1.89(m, 4H), 2.20(s, 3H), 2.44–2.46(m, 2H), 2.52–2.56(m, 1H), 6.53(s, 1H), 6.96(brs, 2H), 7.29(d, 2H, J=12.0Hz), 7.62(d, 2H, J=8.0Hz), 7.93(s, 1H) | DMSO-d6, 400 MHz |
| 2-186 | 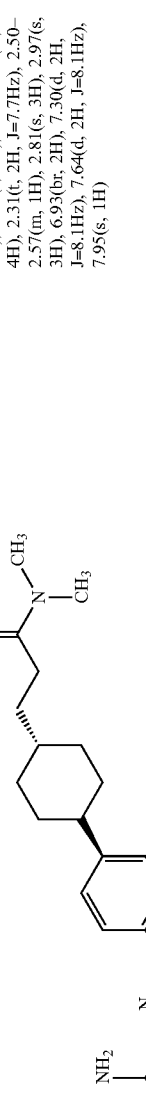 | 200–201 | 0.98–1.13(m, 2H), 1.25–1.51(m, 5H), 1.60(s, 6H), 1.77–1.90(m, 4H), 2.31(t, 2H, J=7.7Hz), 2.50–2.57(m, 1H), 2.81(s, 3H), 2.97(s, 3H), 6.93(br, 2H), 7.30(d, 2H, J=8.1Hz), 7.64(d, 2H, J=8.1Hz), 7.95(s, 1H) | DMSO-d6, 300 MHz |
| 2-187 | 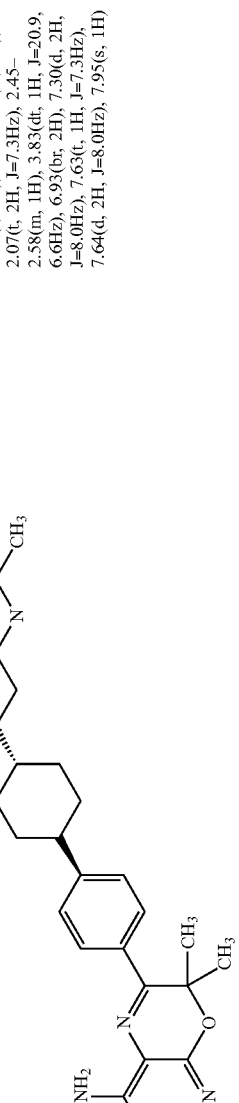 | 206–208 | 0.96–1.11(m, 2H), 1.04(d, 6H, J=6.6Hz), 1.20–1.51(m, 5H), 1.60(s, 6H), 1.76–1.92(m, 4H), 2.07(t, 2H, J=7.3Hz), 2.45–2.58(m, 1H), 3.83(dt, 1H, J=20.9, 6.6Hz), 6.93(br, 2H), 7.30(d, 2H, J=8.0Hz), 7.63(t, 1H, J=7.3Hz), 7.64(d, 2H, J=8.0Hz), 7.95(s, 1H) | DMSO-d6, 300 MHz |

TABLE 2-continued

| New Ex. No. | MOL STRUCTURE | m p | NMR(δ) | solvent |
|---|---|---|---|---|
| 2-188 | (structure) | 173–175 | 0.99(t, 1.5H, J=7.1Hz), 1.01–1.15(m, 2H), 1.10(t, 1.5H, J=7.1Hz), 1.22–1.54(m, 5H), 1.60(s, 6H), 1.76–1.87(m, 4H), 2.29(t, 1H, J=7.7Hz), 2.32(t, 1H, J=7.7Hz), 2.46–2.58(m, 1H), 2.78(s, 1.5H), 2.94(s, 1.5H), 3.26–3.37(m, 2H), 6.92(br, 2H), 7.30(d, 2H, J=8.4Hz), 7.64(d, 2H, J=8.4Hz), 7.95(s, 1H) | DMSO-d6, 300 MHz |
| 2-189 | (structure) | 192-194 | 0.96–1.13(m, 2H), 1.00(t, 3H, J=7.0Hz), 1.11(t, 3H, J=7.0Hz), 1.25–1.52(m, 5H), 1.60(s, 6H), 1.75–1.92(m, 4H), 2.30(t, 2H, J=7.7Hz), 2.49–2.59(m, 1H), 3.22–3.34(m, 4H), 6.94(br, 2H), 7.30(d, 2H, J=8.4Hz), 7.64(d, 2H, J=8.4Hz), 7.95(s, 1H) | DMSO-d6, 300 MHz |
| 2-190 | (structure) | 210–212 | 0.80(t, 1.5H, J=7.3Hz), 0.84(t, 1.5H, J=7.3Hz), 0.98–1.15(m, 2H), 1.22–1.57(m, 8H), 1.60(s, 6H), 1.74–1.91(m, 4H), 2.28–2.37(m, 2H), 2.47–2.59(m, 1H), 2.79(s, 1.5H), 2.95(s, 1.5H), 3.24(q, 2H, J=7.3Hz), 6.93(br, 2H), 7.30(d, 2H, J=8.4Hz), 7.64(d, 2H, J=8.4Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-191 | (structure) | >250 | 1.00–1.11(m, 2H), 1.25–1.35(m, 1H), 1.43–1.50(m, 4H), 1.58(s, 6H), 1.78–1.86(m, 4H), 2.22–2.28(m, 2H), 2.24(s, 3H), 6.82(brs, 2H), 7.29(d, 2H, J=9.0Hz), 7.62(d, 2H, J=9.0Hz), 11.99(brs, 1H) | DMSO-d6, 300 MHz |
| 2-192 | (structure) | >250 | 0.99–1.12(m, 2H), 1.22–1.33(m, 1H), 1.42–1.52(m, 4H), 1.58(s, 6H), 1.80–1.84(m, 4H), 2.24(s, 3H), 2.32(t, 2H, J=7.5Hz), 3.23(s, 3H), 6.81(brs, 2H), 7.29(d, 2H, J=9.0Hz), 7.62(d, 2H, J=9.0Hz), 11.66(brs, 1H) | DMSO-d6, 300 MHz |
| 2-193 | (structure) | >240 | 0.95–1.12(m, 2H), 1.17(s, 6H), 1.21–1.30(m, 1H), 1.36–1.49(m, 4H), 1.58(s, 6H), 1.77–1.87(m, 4H), 2.09(t, 2H, J=7.5Hz), 2.24(s, 3H), 2.47–2.58(m, 1H), 3.37(d, 2H, J=6.0Hz), 4.88(t, 1H, J=6.0Hz), 6.80(br, 2H), 7.24(brs, 1H), 7.29(d, 2H, J=9.0Hz), 7.62(d, 2H, J=9.0Hz) | DMSO-d6, 300 MHz |

TABLE 2-continued

| New Ex. No. | MOLSTRUCTURE | m p | NMR(δ) | solvent |
|---|---|---|---|---|
| 2-194 | | 230–231 | 0.99–1.12(m, 2H), 1.25–1.36(m, 1H), 1.37–1.52(m, 4H), 1.58(s, 6H), 1.79–1.87(m, 4H), 2.22(t, 2H, J=7.5Hz), 2.24(s, 3H), 2.49–2.57(m, 1H), 3.17(dd, 1H, J=12.0, 6.0Hz), 3.25(dd, 1H, J=12.0, 6.0Hz), 3.36(dd, 1H, J=12.0, 6.0Hz), 3.57(dd, 1H, J=12.0, 6.0Hz), 3.94–4.01(m, 1H), 4.01–4.08(m, 1H), 4.86(d, 1H, J=6.0Hz), 4.93(d, 1H, J=6.0Hz), 6.81(br, 1H), 7.29(d,2H, J=9.0Hz), 7.62(d, 2H, J=9.0Hz) | DMSO-d6, 300 MHz |
| 2-195 | | 250(deg.) | 1.06–1.13(m, 2H), 1.43–154(m, 5H), 1.58(s, 6H), 1.84(m, 4H), 2.24(s, 3H), 2.55(d, 2H, J=7.5Hz), 6.83(brs, 2H), 7.29(d, 2H, J=8.3Hz), 7.62(d, 2H, J=8.3Hz). | DMSO-d6, 400 MHz |
| 2-196 | | 2111(deg.) | 1.06–1.13(m, 2H), 1.44–154(m, 5H), 1.58(s, 6H), 1.84(m, 4H), 2.24(s, 3H), 2.55(d, 2H, J=7.5Hz), 6.82(brs, 2H), 7.29(d, 2H, J=8.3Hz), 7.62(d, 2H, J=8.3Hz). | DMSO-d6, 300 MHz |

TABLE 2-continued

| New Ex. No. | MOLSTRUCTURE | m p | NMR(δ) | solvent |
|---|---|---|---|---|
| 2-197 | | 250(deg.) | 1.04–1.15(m, 2H), 1.36–1.49(m, 5H), 1.58(s, 6H), 1.86(m, 4H), 2.24(m, 2H), 2.54(m, 1H), 2.66(m, 2H), 3.69(s, 3H), 6.82(brs, 2H), 7.29(d, 2H, J=8.3Hz), 7.62(d, 2H, J=8.3Hz). | DMSO-d6., 300 MHz |
| 2-198 | | >250 | 1.04–1.11(m, 2H), 1.39–1.52(m, 5H), 1.58(s, 6H), 1.86(m, 4H), 2.24(s, 3H), 2.64(m, 2H), 3.57(s, 3H), 4.86(t, 1H, J=5.3Hz), 6.83(brs, 2H), 7.29(d, 2H, J=8.3Hz), 7.44(t, 1H, J=5.6Hz), 7.62(d, 2H, J=8.3Hz). | DMSO-d6., 300 MHz |
| 2-199 | | 198–200 | 1.10–1.15(m, 2H), 1.43–1.50(m, 3H), 1.69(s, 6H), 1.78(m, 2H), 1.94(m, 4H), 2.47(s, 3H), 2.67(m, 1H), 2.90(m, 2H), 5.74(brs, 2H), 7.25(d, 2H, J=8.3Hz), 7.54(d, 2H, J=8.3Hz). | CDCl3, 300 MHz |

TABLE 2-continued

| New Ex. No. | MOLSTRUCTURE | m p | NMR(δ) | solvent |
|---|---|---|---|---|
| 2-200 | | >250 | 1.04–1.19(m, 3H), 1.37–1.52(m, 2H), 1.58(s, 6H), 1.62–1.69(m, 2H), 1.79–1.91(m, 4H), 2.24(s, 3H), 2.47–2.58(m, 1H), 2.93(t, 2H, J=7.5Hz), 6.81(brs, 2H), 7.29(d, 2H, J=9.0Hz), 7.62(d, 2H, J=9.0Hz) | DMSO-d6, 300 MHz |
| 2-201 | | >250 | 1.03–1.15(m, 2H), 1.27–1.41(m, 1H), 1.39–1.53(m, 4H), 1.58(s, 6H), 1.81–1.87(m, 4H), 2.24(s, 3H), 2.46–2.53(m, 2H), 2.57(br, 1H), 6.81(br, 1H), 7.29(d, 2H, J=9.0Hz), 7.62(d, 2H, J=9.0Hz), 11.96(brs, 1H), 15.78(br, 1H) | DMSO-d6, 300 MHz |
| 2-202 | | >225 | 1.02–1.18(m, 2H), 1.11(s, 6H), 1.34–1.53(m, 5H), 1.58(s, 6H), 1.69–1.85(m, 4H), 2.24(s, 3H), 2.43–2.53(m, 1H), 6.81(br, 2H), 7.28(d, 2H, J=8.3Hz), 7.61(d, 2H, J=8.3Hz), 12.03(brs, 1H) | DMSO-d6, 300 MHz |

TABLE 2-continued

| New Ex. No. | MOLSTRUCTURE | m p | NMR(δ) | solvent |
|---|---|---|---|---|
| 2-203 | | 235–237 | 1.35–1.55(m, 4H), 1.60(s, 6H), 1.77–1.79(m, 4H), 2.15–2.25(m, 1H), 2.48–2.61(m, 1H), 3.11(q, 2H, J=6.0Hz), 3.39(q, 2H, J=6.0Hz), 4.64(t, 1H, J=6.0Hz), 6.97(br, 2H), 7.31(d, 2H, J=8.4Hz), 7.65(d, 2H, J=8.4Hz), 7.74(t, 1H, J=6.0Hz), 7.95(s, 1H) | DMSO-d6., 300 MHz |
| 2-204 | | >250 | 1.43–1.54(m, 4H), 1.60(s, 6H), 1.81–1.95(m, 4H), 2.10–2.24(m, 1H), 2.49–2.63(m, 1H), 6.70(brs, 1H), 6.95(br, 2H), 7.23(brs, 1H), 7.31(d, 2H, J=8.4Hz), 7.65(d, 2H, J=8.4Hz), 7.95(s, 1H) | DMSO-d6., 300 MHz |
| 2-205 | | >250 | 1.41–1.59(m, 4H), 1.61(s, 6H), 1.81–1.91(m, 4H), 2.21–2.31(m, 1H), 2.54–2.60(m, 1H), 3.74(d, 2H, J=5.6Hz), 6.97(br, 2H), 7.31(d, 2H, J=8.1Hz), 7.65(d, 2H, J=8.1Hz), 7.96(s, 1H), 8.04(t, 1H, J=5.6Hz) | DMSO-d6., 400 MHz |

TABLE 2-continued

| New Ex. No. | MOLSTRUCTURE | m p | NMR(δ) | solvent |
|---|---|---|---|---|
| 2-206 | (structure) | >250 | 1.08(s, 3H), 1.22(s, 3H), 1.41–1.54(m, 4H), 1.80–1.88(m, 2H), 1.96–2.04(m, 2H), 2.22–2.30(m, 1H), 2.47–2.55(m, 1H), 4.11(s, 1H), 5.27(d, 2H, J=8.1Hz), 6.23(s, 2H), 7.25(d, 2H, J=8.1Hz), 7.36(d, 2H, J=8.1Hz), 7.62(s, 1H) | DMSO-d6, 400 MHz |
| 2-207 | (structure) | >250 | 1.45–1.65(m, 7H), 1.60(s, 6H), 1.80–1.95(m, 6H), 2.50–2.78(m, 3H), 3.05–3.26(m, 1H), 3.86–4.30(m, 2H), 6.90(brs, 2H), 7.30(d, 2H, J=9.0Hz), 7.64(d, 2H, J=9.0Hz), 7.95(s, 1H), 12.05(brs, 1H) | DMSO-d6, 300 MHz |
| 2-208 | (structure) | 193–194 | 1.45–1.65(m, 4H), 1.60(s, 6H), 1.80–1.95(m, 7H), 2.08–2.19(m, 2H), 2.53–2.63(m, 1H), 3.55–3.63(m, 2H), 4.21–4.25(m, 1H), 6.95(brs, 2H), 7.32(d, 2H, J=9.0Hz), 7.66(d, 2H, J=9.0Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-209 | (structure) | >250 | 1.23–1.36(m, 2H), 1.48–1.57(m, 2H), 1.60(s, 6H), 1.79(s, 3H), 1.83–1.92(m, 4H), 2.53–2.58(m, 1H), 3.55–3.66(m, 1H), 6.94(brs, 2H), 7.33(d, 2H, J=9.0Hz), 7.65(d, 2H, J=9.0Hz), 7.76(d, 1H, J=6.0Hz), 7.95(s, 1H) | DMSO-d6, 300 MHz |
| 2-210 | (structure) | >250 | 1.24–1.48(m, 4H), 1.58(s, 6H), 1.69–1.76(m, 4H), 2.39(s, 3H), 2.41–2.46(m, 1H), 2.98–3.08(m, 1H), 6.93(brs, 2H), 7.27(d, 2H, J=9.0Hz), 7.40(d, 2H, J=9.0Hz), 7.61(d, 2H, J=9.0Hz), 7.65(d, 1H, J=6.0Hz), 7.73(d, 2H, J=9.0Hz), 7.94(s, 1H) | DMSO-d6, 300 MHz |
| 2-211 | (structure) | >250 | a mixture of 2 conformers: 1.25 and 1.27(s, 3H), 1.42–1.57(m, 4H), 1.61(s, 6H), 1.79–1.91(m, 4H), 2.21–2.30(m, 1H), 2.52–2.63(m, 1H), 4.14–4.25(m, 1H), 6.96(brs, 2H), 7.32(d, 2H, J=9.0Hz), 7.65(d, 2H, J=6.0Hz), 7.96(s, 1H), 8.04(d, 1H, J=6.0Hz) | DMSO-d6, 300 MHz |

TABLE 2-continued

| New Ex. No. | MOLSTRUCTURE | m p | NMR(δ) | solvent |
|---|---|---|---|---|
| 2-212 | | >250 | 1.33(s, 6H), 1.42–1.54(m, 4H), 1.60(s, 6H), 1.81–1.88(m, 4H), 2.17–2.25(m, 1H), 2.53–2.59(m, 1H), 6.97(brs, 2H), 7.31(d, 2H, J=9.0Hz), 7.65(d, 2H, J=9.0Hz), 7.90(brs, 1H), 7.96(s, 1H) | DMSO-d6, 300 MHz |
| 2-213 | | >250 | 1.45–1.57(m, 4H), 1.61(s, 6H), 1.84–1.91(m, 4H), 2.30–2.37(m, 1H), 2.53–2.60(m, 1H), 3.60–3.70(m, 2H), 4.25–4.31(m, 1H), 4.91(brs, 1H), 6.97(brs, 2H), 7.32(d, 2H, J=9.0Hz), 7.66(d, 2H, J=9.0Hz), 7.85(d, 1H, J=9.0Hz), 7.96(s, 1H) | DMSO-d6, 300 MHz |
| 2-214 | | >250 | a mixture of 2 conformers: 1.49–1.63(m, 4H), 1.61(s, 6H), 1.80–1.89(m, 4H), 2.81 and 3.09(s, 3H), 3.98 and 4.20(s, 2H), 6.93(brs, 2H), 7.31 and 7.33(d, 2H, J=9.0Hz), 7.65 and 7.66(d, 2H, J=9.0Hz), 7.95(s, 1H) | DMSO-d6, 300 MHz |

TABLE 2-continued
| New Ex. No. | MOLSTRUCTURE | m p | NMR(δ) | solvent |
|---|---|---|---|---|
| 2-215 | 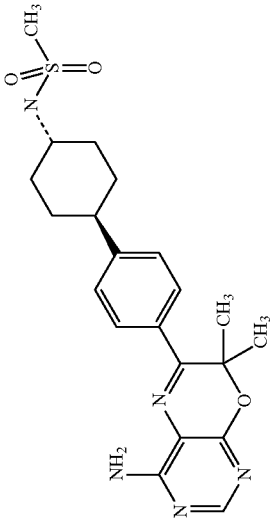 | >250 | 1.34–1.44(m, 2H), 1.51–1.58(m, 2H), 1.60(s, 6H), 1.78–1.87(m, 2H), 1.97–2.06(m, 2H), 2.51–2.56(m, 1H), 2.93(s, 3H), 3.19–3.23(m, 1H), 6.90(brs, 2H), 7.03(d, 1H, J=6.0Hz), 7.31(d, 2H, J=6.0Hz), 7.64(d, 2H, J=6.0Hz), 7.95(s, 1H) | DMSO-d6, 400 |
| 2-216 | 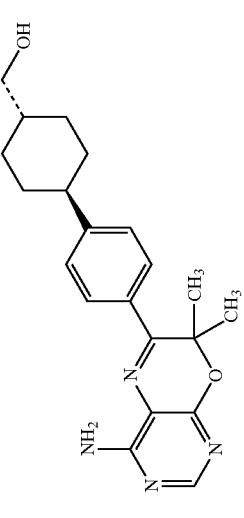 |  | 1.01–1.10(m, 2H), 1.40–1.49(m, 3H), 1.60(s, 6H), 1.83–1.87(m, 4H), 2.52–2.55(m, 1H), 3.22–3.28(m, 2H), 6.90(brs, 2H), 7.30(d, 2H, J=8.0Hz), 7.63(d, 2H, J=8.0Hz), 7.94(s, 1H) | DMSO-d6, 400 |
| 2-217 | 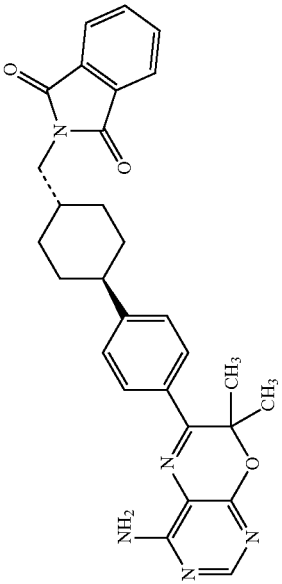 | 225–227 | 1.09–1.20(m, 2H), 1.36–1.46(m, 2H), 1.58(s, 6H), 1.76–1.81(m, 5H), 2.52–2.56(m, 1H), 3.48(d, 2H, J=8.0Hz), 6.89(brs, 2H), 7.27(d, 2H, J=12.0Hz), 7.61(d, 2H, J=12.0Hz), 7.82–7.88(m, 4H), 7.92(s, 1H) | DMSO-d6, 400 MHz |

TABLE 2-continued

| New Ex. No. | MOLSTRUCTURE | m p | NMR(δ) | solvent |
|---|---|---|---|---|
| 2-218 | | 212 | 1.32–1.54(m, 4H), 1.60(s, 6H), 1.81–1.85(m, 2H), 2.05–2.10(m, 2H), 2.53–2.56(m, 1H), 3.09–3.18(m, 1H), 6.46(s, 2H), 6.54(d, 1H, J=9.0Hz), 6.94(brs, 2H), 7.31(d, 2H, J=6.0Hz), 7.64(d, 2H, J=6.0Hz), 7.95(s, 1H) | DMSO-d6, 300 MHz |
| 2-219 | | 243–248 | 1.08(s, 3H), 1.22(s, 3H), 1.44–1.62(m, 4H), 1.69–1.90(m, 4H), 2.45–2.58(m, 1H), 2.63–2.77(m, 1H), 2.81(s, 1.2H), 3.08(s, 1.8H), 4.11(s, 0.6H), 4.18(s, 0.4H), 5.26(s, 1H), 6.20(br, 2H), 7.26(d, 2H, J=8.1Hz), 7.37(d, 2H, J=8.1Hz), 7.61(s, 1H), 12.48(brs, 1H) | DMSO-d6, 400 MHz |
| 2-220 | | >250 | 1.16–1.29(m, 2H), 1.43–1.56(m, 2H), 1.61(s, 6H), 1.80–2.11(m, 5H), 2.53–2.59(m, 1H), 2.94(d, 2H, J=6.0Hz), 6.79(s, 2H), 6.93(brs, 2H), 7.31(d, 2H, J=9.0Hz), 7.66(d, 2H, J=9.0Hz), 7.95(s, 1H) | DMSO-d6, 300 |

TABLE 2-continued

| New Ex. No. | MOLSTRUCTURE | m p | NMR(δ) | solvent |
|---|---|---|---|---|
| 2-221 | (structure) | >250 | 1.08(s, 3H), 1.16–1.27(m, 5H), 1.43–1.52(m, 2H), 1.80–2.08(m, 5H), 2.46–2.49(m, 1H), 2.93(d, 2H, J=8.0Hz), 4.11(brs, 1H), 5.25(brs, 1H), 6.20(brs, 2H), 6.76(s, 2H), 7.24(d, 2H, J=8.0Hz), 7.36(d, 2H, J=8.0Hz), 7.61(s, 1H) | DMSO-d6, 400 |
| 2-222 | (structure) | >250 | 1.07(s, 3H), 1.22(s, 3H), 1.24–1.53(m, 4H), 1.75–2.11(m, 4H), 2.41–2.48(m, 1H), 3.05–3.17(m, 1H), 4.11(brs, 1H), 5.26(brs, 1H), 6.21(brs, 2H), 6.45(brs, 2H), 6.52(d, 1H, J=12.0Mz), 7.24(d, 2H, J=8.0Hz), 7.35(d, 2H, J=8.0Hz), 7.60(s, 1H) | DMSO-d6, 300 MHz |
| 2-223 | (structure) | | 1.00–1.11(m, 5H), 1.22(s, 3H), 1.37–1.48(m, 3H), 1.77–1.85(m, 4H), 2.43–2.48(m, 1H), 3.24–3.27(m, 2H), 4.11(brs, 1H), 4.30–4.32(m, 1H), 5.26(brs, 1H), 6.20(brs, 2H), 7.24(d, 2H, J=8.0Hz), 7.36(d, 2H, J=8.0Hz), 7.61(s, 1H) | DMSO-d6, 400 |

TABLE 2-continued

| New Ex. No. | MOLSTRUCTURE | m p | NMR(δ) | solvent |
|---|---|---|---|---|
| 2-224 | (structure) | | 0.94–1.06(m, 2H), 1.36–1.60(m, 6H), 1.76–1.93(m, 4H), 2.03–2.13(m, 2H), 2.25–2.35(m, 3H), 2.52–2.56(m, 1H), 6.91(brs, 2H), 7.30(d, 2H, J=12.0Hz), 7.64(d, 2H, J=12.0Hz), 7.94(s, 1H) | DMSO-d6, 400 |
| 2-225 | (structure) | 169–171 | 0.92–1.08(m, 2H), 1.29–2.15(m, 2H), 2.53–2.58(m, 1H), 2.64–2.73(m, 2H), 3.38–3.48(m, 1H), 4.47–4.51(m, 1H), 6.91(brs, 2H), 7.30(d, 2H, J=9.0Hz), 7.64(d, 2H, J=9.0Hz), 7.95(s, 1H) | DMSO-d6, 300 |
| 2-226 | (structure) | | 0.97–1.11(m, 2H), 1.40–1.68(m, 11H), 1.79–2.01(m, 7H), 2.18–2.31(m, 2H), 2.39–2.47(m, 2H), 2.62–2.74(m, 2H), 4.75(brs, 1H), 6.92(brs, 2H), 7.18–7.36(m, 5H), 7.49(d, 2H, J=9.0Hz), 7.65(d, 2H, J=9.0Hz), 7.95(s, 1H) | DMSO-d6, 300 |
| 2-227 | (structure) | 198–200 | 0.91–1.69(m, 21H), 1.77–1.94(m, 4H), 2.05–2.16(m, 1H), 2.53–2.61(m, 1H), 2.74–2.89(m, 2H), 3.40–3.46(m, 2H), 4.30(brs, 1H), 6.91(brs, 2H), 7.30(d, 2H, J=9.0Hz), 7.65(d, 2H, J=9.0Hz), 7.95(s, 1H) | DMSO-d6, 300 |

TABLE 2-continued

| New Ex. No. | MOLSTRUCTURE | m p | NMR(δ) | solvent |
|---|---|---|---|---|
| 2-228 | | 119–120 | 0.91–1.65(m, 19H), 1.75–1.90(m, 6H), 2.11(brs, 1H), 2.55–2.58(m, 1H), 2.72–2.91(m, 2H), 6.91(brs, 2H), 7.15–7.33(m, 7H), 7.64(d, 2H, J=9.0Hz), 7.95(s, 1H) | DMSO-d6, 300 |
| 2-229 | | 160–162 | 0.97–1.11(m, 2H), 1.39–1.97(m, 19H), 2.27–2.63(m, 3H), 3.24(brs, 2H), 6.91(brs, 2H), 7.30(d, 2H, J=6.0Hz), 7.64(d, 2H, J=6.0Hz), 7.95(s, 1H) | DMSO-d6, 300 |
| 2-230 | | | 0.91–1.10(m, 2H), 1.37–1.63(m, 11H), 1.78–1.92(m, 5H), 2.06–2.42(m, 10H), 2.52–2.59(m, 1H), 6.91(brs, 2H), 7.30(d, 2H, J=9.0Hz), 7.64(d, 2H, J=9.0Hz), 7.95(s, 1H) | DMSO-d6, 300 |
| 2-231 | | | 0.95–1.07(m, 2H), 1.37–1.65(m, 11H), 1.78–1.91(m, 4H), 2.15–2.23(m, 2H), 2.32–2.47(m, 6H), 3.45–3.51(m, 2H), 6.91(brs, 2H), 7.25–7.35(m, 7H), 7.64(d, 2H, J=9.0Hz), 7.95(s, 1H) | DMSO-d6, 300 |

TABLE 2-continued

| New Ex. No. | MOLSTRUCTURE | m p | NMR(δ) | solvent |
|---|---|---|---|---|
| 2-232 | (structure) | 171–172 | 0.98–1.08(m, 2H), 1.39(s, 9H), 1.41–1.51(m, 2H), 1.60(s, 6H), 1.80–1.91(m, 5H), 2.13(brs, 2H), 2.26–2.32(m, 4H), 2.48–2.53(m, 4H), 2.52–2.57(m, 1H), 6.90(brs, 2H), 7.28(d, 2H, J=8.0Hz), 7.62(d, 2H, J=8.0Hz), 7.93(s, 1H) | DMSO-d6, 400 MHz |
| 2-233 | (structure) | 224–229 | 1.06(d, 3H, J=6.0Hz), 1.09–1.31(m, 3H), 1.36–1.52(m, 2H), 1.61(s, 6H), 1.71–1.82(m, 1H), 1.90–1.93(m, 2H), 2.01–2.47(m, 1H), 3.37–3.46(m, 1H), 6.93(br, 2H), 7.30(d, 2H, J=8.4Hz), 7.64(d, 2H, J=8.4Hz), 7.95(s, 1H) | DMSO-d6, 400 MHz |
| 2-234 | (structure) | 226–230 | 1.37–1.67(m, 4H), 1.61(s, 6H), 1.78–1.92(m, 4H), 2.46–2.60(m, 1H), 3.62–3.78(m, 1H), 3.79(s, 2H), 6.93(br, 2H), 7.33(d, 2H, J=8.4Hz), 7.48(d, 1H, J=8.4Hz), 7.65(d, 2H, J=8.4Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-235 | (structure) | 201–202 | 1.46–1.66(m, 4H), 1.61(s, 6H), 1.71–1.93(m, 8H), 2.43–2.63(m, 2H), 3.26–3.35(m, 2H), 3.43–3.54(m, 2H), 6.93(br, 2H), 7.31(d, 2H, J=8.4Hz), 7.65(d, 2H, J=8.4Hz), 7.95(s, 1H) | DMSO-d6., 300 MHz |
| 2-236 | (structure) | 220–224 | 1.33–1.89(m, 14H), 1.61(s, 6H), 2.51(s, 2H), 3.36(s, 4H), 6.92(br, 2H), 7.31(d, 2H, J=8.1Hz), 7.65(d, 2H, J=8.1Hz), 7.95(s, 1H) | DMSO-d6., 300 MHz |
| 2-237 | (structure) | 250–252 | 1.16–1.39(m, 2H), 1.46–1.92(m, 8H), 1.61(s, 6H), 2.51–2.81(m, 2H), 2.87–3.05(m, 1H), 3.12–3.25(m, 1H), 3.62–3.99(m, 4H), 4.64–4.78(m, 1H), 6.93(br, 2H), 7.31(d, 2H, J=8.4Hz), 7.65(d, 2H, J=8.4Hz), 7.95(s, 1H) | DMSO-d6., 300 MHz |

TABLE 2-continued

| New Ex. No. | MOLSTRUCTURE | m p | NMR(δ) | solvent |
|---|---|---|---|---|
| 2-238 | (structure) | 190–191 | 1.48–1.65(m, 4H), 1.61(s, 6H), 1.72–1.92(m, 4H), 2.20(s, 3H), 2.22–2.38(m, 4H), 2.51–2.75(m, 2H), 3.41–3.55(m, 4H), 6.93(br, 2H), 7.31(d, 2H, J=8.4Hz), 7.65(d, 2H, J=8.4Hz), 7.95(s, 1H) | DMSO-d6., 300 MHz |
| 2-239 | (structure) | 233–235 | 1.47.1.67(m, 4H), 1.57(s, 6H), 1.70–1.92(m, 4H), 2.47–2.77(m, 2H), 3.37–3.65(m, 8H), 6.92(br, 2H), 7.31(d, 2H, J=8.4Hz), 7.65(d, 2H, J=8.4Hz), 7.95(s, 1H) | DMSO-d6., 300 MHz |
| 2-240 | (structure) | 233–235 | 0.95–1.09(m, 2H), 1.37–1.65(m, 3H), 1.60(s, 6H), 1.77–1.96(m, 4H), 2.19(brd, 2H, J=7.0Hz), 2.39–2.49(m, 4H), 2.50–2.61(m, 1H), 3.07–3.14(m, 4H), 6.91(br, 2H), 7.30(d, 2H, J=8.4Hz), 7.64(d, 2H, J=8.4Hz), 7.95(s, 1H) | DMSO-d6., 300 MHz |

TABLE 2-continued

| New Ex. No. | MOLSTRUCTURE | m p | NMR(δ) | solvent |
|---|---|---|---|---|
| 2-241 | (structure) | 120–126 | 0.96–1.10(m, 2H), 0.99(d, 6H, J=6.6Hz), 1.41–1.65(m, 3H), 1.60(s, 6H), 1.81–1.93(m, 4H), 2.15(brd, 2H, J=7.0Hz), 2.27–2.38(m, 4H), 2.49–2.59(m, 1H), 2.80–2.89(m, 1H), 3.40–3.51(m, 4H), 6.92(br, 2H), 7.30(d, 2H, J=8.4Hz), 7.64(d, 2H, J=8.4Hz), 7.95(s, 1H) | DMSO-d6, 300 MHz |
| 2-242 | (structure) | 171–172 | 0.98–1.08(m, 2H), 1.39(s, 9H), 1.41–1.51(m, 2H), 1.60(s, 6H), 1.80–1.91(m, 5H), 2.13(brs, 2H), 2.26–2.32(m, 4H), 2.48–2.53(m, 4H), 2.52–2.57(m, 1H), 6.90(brs, 2H), 7.28(d, 2H, J=8.0Hz), 7.62(d, 2H, J=8.0Hz), 7.93(s, 1H) | DMSO-d6, 400 MHz |
| 2-243 | (structure) | 208–210 | a mixture of 2 conformers; 1.02–1.13(m, 2H), 1.38–1.58(m, 2H), 1.59(s, 6H), 1.61–1.91(m, 5H), 2.51(m, 1H), 2.85 and 2.87(s, 3H), 3.06 and 3.20(d, 2H, J=6.8 Hz), 4.06 and 4.07(brs, 2H), 4.30 and 4.35(brs, 1H), 6.91(brs, 2H), 7.27(d, 2H, J=8.3Hz), 7.61(d, 2H, J=8.3Hz), 7.92(s, 1H). | DMSO-d6, 400 MHz |

TABLE 2-continued

| New Ex. No. | MOLSTRUCTURE | m p | NMR(δ) | solvent |
|---|---|---|---|---|
| 2-244 | | 208–209 | 0.94–1.05(m, 2H), 1.41–1.50(m, 2H), 1.60(s, 6H), 1.79–1.90(m, 5H), 2.08(d, 2H, J=8.0Hz), 2.23–2.29(m, 4H), 2.69–2.71(m, 4H), 6.92(brs, 2H), 7.28(d, 2H, J=8.0Hz), 7.62(d, 2H, J=8.0Hz), 7.93(s, 1H) | DMSO-d6., 400 MHz |
| 2-245 | | 180–182 | 0.82(t, 3H, J=7.4Hz), 1.04–1.13(m, 2H), 1.37–1.58(m, 5H), 1.60(s, 6H), 1.80–1.95(m, 4H), 2.01–2.18(m, 2H), 2.19–2.39(m, 4H), 2.51(m, 1H), 2.95(q, 2H, J=7.4Hz), 3.20–3.28(m, 4H), 6.40(brs, 1H), 6.91(brs, 2H), 7.28(d, 2H, J=8.3Hz), 7.62(d, 2H, J=8.3Hz), 7.93(s, 1H). | DMSO-d6., 400 MHz |
| 2-246 | | 158–160 | 1.04–1.13(m, 2H), 1.37–1.58(m, 3H), 1.59(s, 6H), 1.80–1.95(m, 4H), 2.01–2.18(m, 2H), 2.19–2.39(m, 4H), 2.51(m, 1H), 3.20–3.28(m, 4H), 5.89(brs, 2H), 6.91(brs, 2H), 7.27(d, 2H, J=8.3 Hz), 7.61(d, 2H, J=8.3Hz), 7.92(s, 1H). | DMSO-d6., 400 MHz |
| 2-247 | | 205–206 | 0.98–1.07(m, 2H), 1.43–1.51(m, 2H), 1.60(s, 6H), 1.80–1.92(m, 5H), 2.14(d, 2H, J=8.0Hz), 2.28–2.36(m, 4H), 2.52–2.58(m, 1H), 3.43–3.48(m, 4H), 4.07(d, 2H, J=6.0Hz), 4.33(t, 1H, J=6.0Hz), 6.93(brs, 2H), 7.28(d, 2H, J=8.0Hz), 7.63(d, 2H, J=8.0Hz), 7.93(s, 1H) | DMSO-d6., 400 MHz |

TABLE 2-continued

| New Ex. No. | MOLSTRUCTURE | m p | NMR(δ) | solvent |
|---|---|---|---|---|
| 2-248 | | 207–208 | 1.00–1.04(m, 2H), 1.30(s, 6H), 1.79–1.93(m, 5H), 2.13(d, 2H, J=8.0Hz), 2.30–2.35(m, 4H), 2.53–2.58(m, 1H), 3.79–3.97(m, 4H), 6.92(brs, 2H), 7.28(d, 2H, J=8.0Hz), 7.63(d, 2H, J=12.0Hz), 7.93(s, 1H) | DMSO-d6, 400 MHz |
| 2-249 | | 202–203 | 0.97–1.06(m, 2H), 1.43–1.52(m, 2H), 1.60(s, 6H), 1.81–1.92(m, 5H), 1.98(s, 3H), 2.14(d, 2H, J=8.0Hz), 2.26–2.36(m, 4H), 2.52–2.56(m, 1H), 3.38–3.45(m, 4H), 6.93(brs, 2H), 7.28(d, 2H, J=8.0Hz), 7.63(d, 2H, J=12.0Hz), 7.93(s, 1H) | DMSO-d6, 400 MHz |
| 2-250 | | 220–240 | 1.43–1.69(m, 4H), 1.61(s, 6H), 1.73–1.92(m, 4H), 2.36–2.64(m, 2H), 3.13–3.41(m, 3H), 3.65(dd, 1H, J=5.9, 9.9Hz), 3.96–4.11(m, 2H), 4.85(br, 1H), 4.92(br, 1H), 6.93(br, 2H), 7.32(d, 2H, J=8.4Hz), 7.65(d, 2H, J=8.4Hz), 7.95(s, 1H) | DMSO-d6, 300 MHz |

TABLE 2-continued

| New Ex. No. | MOLSTRUCTURE | m p | NMR(δ) | solvent |
|---|---|---|---|---|
| 2-251 | (structure) | 159–164 | .09(m, 2H), 1.39–1.72(m, 8H), 1.60(s, 6H), 1.77–1.93(m, 6H), 1.97–2.16(m, 2H), 2.45–2.61(m, 1H), 2.76–2.89(m, 1H), 6.67(br, 1H), 6.91(br, 2H), 7.17(br, 1H), 7.30(d, 2H, J=8.1Hz), 7.64(d, 2H, J=8.1Hz), 7.95(s, 1H) | DMSO-d6, 300 MHz |
| 2-252 | (structure) | 209–211 | 1.04(t, 3H, J=7.4Hz), 1.20–1.29(m, 2H), 1.46–1.58(m, 2H), 1.60(s, 6H), 1.80–1.95(m, 4H), 2.01–2.07(m, 2H), 2.51(m, 1H), 2.92–3.01(m, 4H), 6.90(brs, 1H), 7.96(brt, 1H, J=5.6Hz), 7.29(d, 2H, J=8.3Hz), 7.63(d, 2H, J=8.3Hz), 7.94(s, 1H). | DMSO-d6, 400 MHz |
| 2-253 | (structure) | 248(dec.) | 1.03–1.17(m, 2H), 1.38–1.64(m, 8H), 1.78–1.96(m, 4H), 2.55(d, J=9.0Hz), 3.22(s, 2H), 3.30(s, 2H), 6.92(brs, 2H), 7.30(d, 2H, J=6.0Hz), 7.64(d, 2H, J=6.0Hz), 7.95(s, 1H), 12.40(brs, 1H) | DMSO-d6, 300 |

TABLE 2-continued
| New Ex. No. | MOLSTRUCTURE | m p | NMR(δ) | solvent |
|---|---|---|---|---|
| 2-254 | 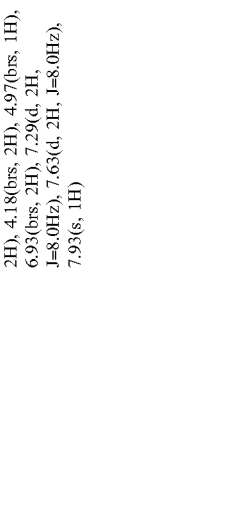 | 213–214 | 1.39–1.52(m, 4H), 1.60(s, 6H), 1.85–1.93(m, 4H), 2.52–2.68(m, 2H), 4.18(brs, 2H), 4.97(brs, 1H), 6.93(brs, 2H), 7.29(d, 2H, J=8.0Hz), 7.63(d, 2H, J=8.0Hz), 7.93(s, 1H) | DMSO-d6, 400 MHz |
| 2-255 | 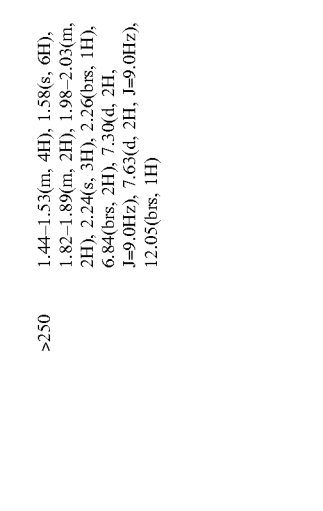 | >250 | 1.44–1.53(m, 4H), 1.58(s, 6H), 1.82–1.89(m, 2H), 1.98–2.03(m, 2H), 2.24(s, 3H), 2.26(brs, 1H), 6.84(brs, 2H), 7.30(d, 2H, J=9.0Hz), 7.63(d, 2H, J=9.0Hz), 12.05(brs, 1H) | DMSO-d6, 300 MHz |
| 2-256 | 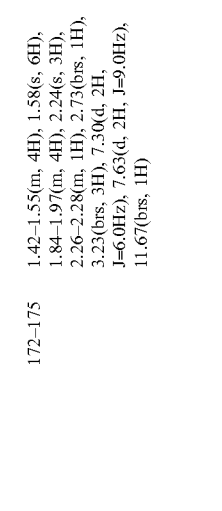 | 172–175 | 1.42–1.55(m, 4H), 1.58(s, 6H), 1.84–1.97(m, 4H), 2.24(s, 3H), 2.26–2.28(m, 1H), 2.73(brs, 1H), 3.23(brs, 3H), 7.30(d, 2H, J=6.0Hz), 7.63(d, 2H, J=9.0Hz), 11.67(brs, 1H) | DMSO-d6, 300 MHz |

TABLE 2-continued

| New Ex. No. | MOLSTRUCTURE | m p | NMR(δ) | solvent |
|---|---|---|---|---|
| 2-257 | (structure) | 220–225 | 1.18(s, 6H), 1.36–1.56(m, 4H), 1.58(s, 6H), 1.79–1.87(m, 4H), 2.15–2.22(m, 1H), 2.24(s, 3H), 2.55–2.59(m, 1H), 3.37(d, 2H, J=6.0Hz), 4.90(t, 1H, J=6.0Hz), 6.82(br, 2H), 7.18(brs, 1H), 7.29(d, 2H, J=9.0Hz), 7.63(d, 2H, J=9.0Hz) | DMSO-d6, 300 MHz |
| 2-258 | (structure) | >250 | 1.44–1.61(m, 4H), 1.58(s, 6H), 1.75–1.88(m, 4H), 2.25(s, 3H), 2.41–2.51(m, 2H), 2.54–2.62(m, 1H), 3.18(dd, 1H, J=12.0, 6.0Hz), 3.37(dd, 1H, J=12.0, 6.0Hz), 3.65(dd, 1H, J=9.0, 6.0Hz), 3.96–4.02(m, 1H), 4.02–4.10(m, 1H), 4.87(d, 1H, J=6.0Hz), 4.95(d, 1H, J=6.0Hz), 6.83(br, 1H), 7.31(d, 2H, J=9.0Hz), 7.63(d, 2H, J=9.0Hz) | DMSO-d6, 300 MHz |
| 2-259 | (structure) | 271–277 | 1.05–1.20(m, 2H), 1.36–1.62 (m, 3H), 1.58(s, 6H), 1.77–1.98 (m, 4H), 2.24(s, 3H), 2.47–2.59 (m, 1H), 2.54(d, J=6.0Hz, 2 H), 3.31(s, 2H), 6.81(brs, 2H), 7.29(d, J=9.0Hz, 2H), 7.62(d, J=9.0Hz, 2H), 12.48(s, 1H). | DMSO-d6, 300 MHz |

TABLE 2-continued
| New Ex. No. | MOLSTRUCTURE | m p | NMR(δ) | solvent |
|---|---|---|---|---|
| 2-260 | 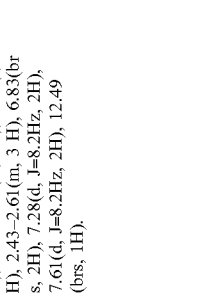 | 235–239 | 1.01–1.21(m, 2H), 1.32–1.54 (m, 3H), 1.41(s, 6H), 1.58(s, 6 H), 1.77–1.97(m, 4H), 2.24(s, 3 H), 2.43–2.61(m, 3 H), 6.83(br s, 2H), 7.28(d, J=8.2Hz, 2H), 7.61(d, J=8.2Hz, 2H), 12.49 (brs, 1H). | DMSO-d6, 300 MHz |
| 2-261 | 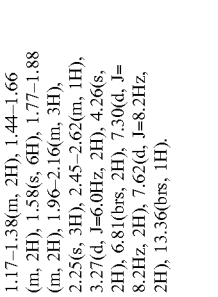 | 225–227 | 1.17–1.38(m, 2H), 1.44–1.66 (m, 2H), 1.58(s, 6H), 1.77–1.88 (m, 2H), 1.96–2.16(m, 3H), 2.25(s, 3H), 2.45–2.62(m, 1H), 3.27(d, J=6.0Hz, 2H), 4.26(s, 2H), 6.81(brs, 2H), 7.30(d, J= 8.2Hz, 2H), 7.62(d, J=8.2Hz, 2H), 13.36(brs, 1H). | DMSO-d6, 300 MHz |
| 2-262 | 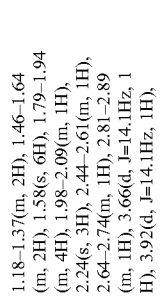 | >166 | 1.18–1.37(m, 2H), 1.46–1.64 (m, 2H), 1.58(s, 6H), 1.79–1.94 (m, 4H), 1.98–2.09(m, 1H), 2.24(s, 3H), 2.44–2.61(m, 1H), 2.64–2.74(m, 1H), 2.81–2.89 (m, 1H), 3.66(d, J=14.1Hz, 1 H), 3.92(d, J=14.1Hz, 1H), 6.80(brs, 2H), 7.29(d, J=8.4 Hz, 2H), 7.61(d, J=8.4Hz, 2 H), 13.06(s, 1H). | DMSO-d6, 400 MHz |

TABLE 2-continued

| New Ex. No. | MOLSTRUCTURE | m p | NMR(δ) | solvent |
|---|---|---|---|---|
| 2-263 | | >250 | 1.59(s, 6H), 1.61–1.75(m, 4H), 1.89–1.99(m, 2H), 2.10–2.21(m, 2H), 2.25(s, 3H), 2.67(br, 1H), 3.09(br, 1H), 6.83(br, 2H), 7.35(d, 2H, J=6.0Hz), 7.65(d, 2H, J=6.0Hz), 16.07(brs, 1H) | DMSO-d6, 300 MHz |
| 2-264 | | >250 | 1.44–1.69(m, 4H), 1.59(s, 6H), 1.89–1.94(m, 2H), 2.00–2.04(m, 2H), 2.25(s, 3H), 2.55–2.66(m, 2H), 3.16–3.18(m, 2H), 6.83(br, 1H), 7.33(d, 2H, J=9.0Hz), 7.64(d, 2H, J=9.0Hz), 11.99(br, 1H) | DMSO-d6, 300 MHz |
| 2-265 | | | | |

TABLE 2-continued

| New Ex. No. | MOLSTRUCTURE | m p | NMR(δ) | solvent |
|---|---|---|---|---|
| 2-266 | | | | |
| 2-267 | | | | |
| 2-268 | | | | |

TABLE 3
| New Ex. No. | MOLSTRUCTURE | m p | NMR(δ) | solvent |
|---|---|---|---|---|
| 3 | | 188–190 | 1.46–1.65(m, 2H), 1.60(s, 6H), 1.81–1.94(m, 2H), 2.73–2.96(m, 2H), 3.22–3.34(m, 1H), 3.63–3.70(m, 1H), 4.33–4.44(m, 1H), 7.00(br, 2H), 7.33(d, 2H, J=8.4 Hz), 7.67(d, 2H, J=8.4 Hz), 7.95(s, 1H) | DMSO-d6, 300 MHz |
| 3-2 | | ClH | 1.63(s, 6H), 1.76–2.02(m, 4H), 2.83–3.11(m, 3H), 3.32–3.47(m, 2H), 7.24(br, 2H), 7.32(d, 2H, J=8.1 Hz), 7.73(d, 2H, J=8.1 Hz), 8.04(s, 1H), 8.69(br, 1H) | DMSO-d6, 300 MHz |
| 3-3 | | 232–237 | 1.39–1.54(m, 2H), 1.60(s, 6H), 1.73–1.84(m, 2H), 2.04(s, 3H), 2.54–2.64(m, 1H), 2.77–2.90(m, 1H), 3.07–3.20(m, 1H), 3.87–3.98(m, 1H), 4.49–4.60(m, 1H), 6.95(br, 2H), 7.33(d, 2H, J=8.4 Hz), 7.66(d, 2H, J=8.4 Hz), 7.96(s, 1H) | DMSO-d6, 300 MHz |
TABLE 4
| New Ex. No. | MOLSTRUCTURE | m p | NMR(δ) | solvent |
|---|---|---|---|---|
| 4 |  | 191–193 | 1.58–1.62(m, 6H), 1.62(s, 6H), 3.26(brs, 4H), 6.79(brs, 2H), 7.29(d, 2H, J=9.0 Hz), 7.63(d, 2H, J=9.0 Hz), 7.91(s, 1H). | DMSO-d6, 400 MHz |

TABLE 4-continued

| New Ex. No. MOLSTRUCTURE | m p | NMR(δ) | solvent |
|---|---|---|---|
| 4-2 | | 1.21–1.30(m, 2H), 1.62(s, 6H), 1.61–1.80(m, 3H), 2.54(d, 2H, J=7.0 Hz), 2.73(brt, 2H, J=12.8 Hz), 3.83(brd, 2H, J=12.8 Hz), 6.79(brs, 2H), 6.91(d, 2H, J=9.0 Hz), 7.17–7.31(m, 5H), 7.62(d, 2H, J=9.0 Hz), 7.91(s, 1H). | DMSO-d6, 400 MHz |
| 4-3 | 176–177 | 1.19(t, 3H, J=6.0 Hz), 1.57–1.69(m, 8H), 1.85–1.92(m, 2H), 2.54–2.61(m, 1H), 2.86–2.95(m, 2H), 3.76–3.83(m, 2H), 4.09(q, 2H, J=7.0 Hz), 6.87(brs, 2H), 6.96(d, 2H, J=9.0 Hz), 7.65(d, 2H, J=6.0Hz), 7.92(s, 1H) | DMSO-d6, 300 |
| 4-4 | >240 | 1.57–1.66(m, 8H), 1.87–1.92(m, 2H), 2.45–2.47(m, 1H), 2.87–2.93(m, 2H), 3.76–3.80(m, 2H), 6.82(brs, 2H), 6.94(d, 2H, J=8.0 Hz), 7.64(d, 2H, J=8.0 Hz), 7.91(s, 1H) | DMSO-d6, 400 |
| 4-5 | 174–175 | 1.21(t, 3H, J=6.0 Hz), 1.62(s, 6H), 3.25–3.27(m, 2H), 3.50–3.53(m, 2H), 4.08(q, 2H, J=6.7 Hz), 6.83(brs, 2H), 6.97(d, 2H, J=12.0 Hz), 7.66(d, 2H, J=8.0 Hz), 7.92(s, 1H) | DMSO-d6, 400 |

TABLE 4-continued

| New Ex. No. MOLSTRUCTURE | m p | NMR(δ) | solvent |
|---|---|---|---|
| 4-6 | 191–196 | 1.63(s, 6H), 1.96–1.99(m, 4H), 3.25–3.31(m, 4H), 6.55(d, 2H, J=8.6 Hz), 6.77(br, 2H), 7.65(d, 2H, J=8.6 Hz), 7.90(s, 1H) | DMSO-d6, 400 MHz |
| 4-7 | 214–219 | 1.62(s, 6H), 3.22(t, 4H, J=4.8 Hz), 3.75(t, 4H, J=4.8 Hz), 6.83(br, 2H), 6.96(d, 2H, J=8.4 Hz), 7.67(d, 2H, J=8.4 Hz), 7.92(s, 1H) | DMSO-d6, 400 MHz |

TABLE 5

| New Ex. No. MOLSTRUCTURE | m p | NMR(δ) | solvent |
|---|---|---|---|
| 5 | 117–133 | 1.60(s, 6H), 7.01(br, 2H), 7.48(t, 1H, J=8.1 Hz), 7.55(ddd, 1H, J=1.0, 2.0, 1.0 Hz), 7.67(dt, 1H, J=8.1, 1.0 Hz), 7.76(t, 1H, J=2.0 Hz), 7.97(s, 1H) | DMSO-d6, 400 MHz |
| 5-2 | 130–131 | 1.58(s, 6H), 5.20(s, 2H), 6.93(br, 2H), 7.15(d, 1H, J=8.3 Hz), 7.25–7.49(m, 8H), 7.97(s, 1H) | DMSO-d6, 400 MHz |
| 5-3 | 151–152 | 1.02–1.33(m, 5H), 1.60(s, 6H), 1.65–1.88(m, 6H), 3.85(d, 2H, J=6.2 Hz), 6.94(br, 2H), 7.05(dd, 1H, J=2.5, 8.0 Hz), 7.17(d, 1H, J=2.5 Hz), 7.23(d, 1H, J=8.0 Hz), 7.35(t, 1H, J=8.0 Hz), 7.97(s, 1H) | DMSO-d6, 400 MHz |

TABLE 6
| New Ex. No. | MOLSTRUCTURE | m p | NMR(δ) | solvent |
|---|---|---|---|---|
| 6 |  | >230 | 1.09–1.22(m, 2H), 1.41–1.56(m, 2H), 1.58(s, 6H), 1.70–1.91(m, 5H), 2.16(d, 2H, d=6.7 Hz), 2.24(s, 3H), 2.92(m, 1H), 6.91(brs, 2H), 7.42(d, 1H, J=8.1 Hz), 7.63(dd, 1H, J=8.1, 1.8 Hz), 7.72(d, 1H, J=1.8 Hz), 12.10(brs, 1H). | DMSO-d6, 400 MHz |
| 6-2 | 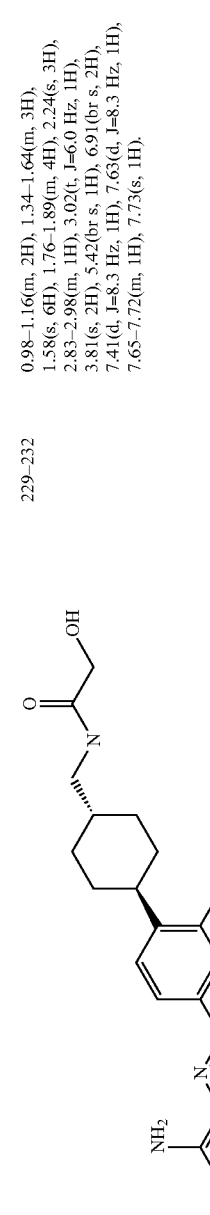 | 229–232 | 0.98–1.16(m, 2H), 1.34–1.64(m, 3H), 1.58(s, 6H), 1.76–1.89(m, 4H), 2.24(s, 3H), 2.83–2.98(m, 1H), 3.02(t, J=6.0 Hz, 1H), 3.81(s, 2H), 5.42(br s, 1H), 6.91(br s, 2H), 7.41(d, J=8.3 Hz, 1H), 7.63(d, J=8.3 Hz, 1H), 7.65–7.72(m, 1H), 7.73(s, 1H). | DMSO-d6, 300 MHz |

TABLE 6-continued

| New Ex. No. | MOLSTRUCTURE | m p | NMR(δ) | solvent |
|---|---|---|---|---|
| 6-3 | | 280(deg.) | 1.15–1.42(m, 5H), 1.56(s, 6H), 1.80(m, 4H), 2.23(s, 3H), 2.13(d, 2H, J=6.8 Hz), 4.97(brs, 2H), 6.75(brs, 2H), 6.82(dd, 1H, J=8.3 Hz, 1.9 Hz), 6.93(d, 1H, J=1.9 Hz), 7.01(d, 1H, J=8.3 Hz). | DMSO-d6, 300 MHz |
| 6-4 | | 177(deg.) | 1.01–1.09(m, 2H), 1.45–1.56(m, 3H), 1.59(s, 6H), 1.70–1.83(m, 6H), 2.13–2.19(m, 4H), 2.25(s, 3H), 2.41–2.46(m, 2H), 3.63–3.69(m, 2H), 6.87(brs, 2H), 7.42(d, 1H, J=8.3 Hz), 7.51(d, 1H, J=1.9 Hz), 7.62(dd, 1H, J=8.3, 1.9 Hz). | DMSO-d6, 300 MHz |
| 6-5 | | >300 | 1.15–1.25(m, 2H), 1.37–1.57(m, 2H), 1.58(s, 6H), 1.65–1.94(m, 5H), 2.24(s, 3H), 2.31(d, J=6.8 Hz, 2H), 2.85–3.01(m, 1H), 6.90(s, 2H), 7.41(d, J=8.3 Hz, 1H), 7.63(dd, J=1.9, 8.3 Hz, 1H), 7.73(d, J=1.9 Hz, 1H), 11.07(s, 1H), 11.17(s, 1H). | DMSO-d6, 300 MHz |

TABLE 6-continued

| New Ex. No. | MOLSTRUCTURE | m p | NMR(δ) | solvent |
|---|---|---|---|---|
| 6-6 | | >282 | 1.13–1.32(m, 2H), 1.39–1.57(m, 2H), 1.58(s, 6H), 1.70–1.96(m, 5H), 2.25(s, 3H), 2.45(d, J=6.8 Hz, 2H), 2.87–3.01(m, 1H), 6.91(s, 2H), 7.42(d, J=8.3 Hz, 1H), 7.64(dd, J=1.9, 8.3 Hz, 1H), 7.74(d, J=1.9 Hz, 1H), 12.17(s, 1H). | DMSO-d6, 300 MHz |
| 6-7 | | >280 | 1.02–1.20(m, 2H), 1.33–1.53(m, 2H), 1.56(s, 6H), 1.65–1.89(m, 5H), 2.14(d, J=6.8 Hz, 2H), 2.24(s, 3H), 2.75–2.89(m, 1H), 6.77(br s, 1H), 7.07(d, J=7.9 Hz, 1H), 7.08(s, 1H), 7.15(d, J=7.9 Hz, 1H), 9.45(s, 1H), 11.99(s, 1H). | DMSO-d6, 300 MHz |
| 6-8 | | 224–225 | 1.02–1.21(m, 2H), 1.31–1.60(m, 2H), 1.35(t, J=6.9 Hz, 3H), 1.58(s, 6H), 1.66–1.89(m, 5H), 2.15(d, J=6.6 Hz, 2H), 2.25(s, 3H), 2.78–2.93(m, 1H), 4.10(q, J=6.9 Hz, 2H), 6.83(br s, 2H), 7.17–7.29(m, 3H), 11.98(s, 1H). | DMSO-d6, 300 MHz |

TABLE 6-continued

| New Ex. No. | MOLSTRUCTURE | m p | NMR(δ) | solvent |
|---|---|---|---|---|
| 6-9 | (structure) | >269 | 1.07–1.23(m, 2H), 1.44–1.63(m, 2H), 1.59(s, 6H), 1.71–1.90(m, 5H), 2.16(d, J=6.8 Hz, 2H), 2.24(s, 3H), 2.70–2.88(m, 1H), 6.88(br s, 2H), 7.34–7.42(m, 1H), 7.46–7.55(m, 2H), 12.02(s, 1H). | DMSO-d6, 300 MHz |
| 6-10 | (structure) | 212–214 | 1.01–1.14(m, 2H), 1.42–1.57(m, 3H), 1.59(s, 6H), 1.81(m, 4H), 2.24(s, 3H), 2.80(m, 1H), 3.02(m, 2H), 3.81(d, 2H, J=6.0 Hz), 5.1(t, 1H, J=6.0 Hz), 6.88(brs, 2H), 7.34–7.40(m, 1H), 7.48–7.54(m, 2H), 7.67–7.71(m, 1H). | DMSO-d6, 300 MHz |
| 6-11 | (structure) | >282 | 1.10–1.31(m, 2H), 1.42–1.64(m, 2H), 1.59(s, 6H), 1.67–1.89(m, 5H), 2.24(s, 3H), 2.44(d, J=6.8 Hz, 2H), 2.75–2.88(m, 1H), 6.89(br s, 1H), 7.33–7.42(m, 1H), 7.47–7.56(m, 2H), 12.16(s, 1H). | DMSO-d6, 300 MHz |

TABLE 6-continued

| New Ex. No. | MOLSTRUCTURE | m p | NMR(δ) | solvent |
|---|---|---|---|---|
| 6-12 | (structure) | 171–173 | 1.03–1.19(m, 2H), 1.34–1.51(m, 2H), 1.58(s, 6H), 1.72–1.85(m, 4H), 2.24(s, 3H), 2.39(d, 2H, d=6.7 Hz), 2.92(m, 1H), 5.23(s, 1H), 6.90(brs, 2H), 7.40(d, 1H, J=8.1 Hz), 7.62(d, 1H, J=8.1 Hz), 7.72(s, 1H), 9.20(brs, 1H), 11.20(brs, 1H). | DMSO-d6, 400 MHz |
| 6-13 | (structure) | >250 | 1.09(t, 3H, J=7.4 Hz), 1.03–1.16(m, 2H), 1.34–1.54(m, 2H), 1.58(s, 6H), 1.76–1.89(m, 4H), 2.25(s, 3H), 2.83–3.08(m, 5H), 5.70(t, 1H, J=5.6 Hz), 5.85(t, 1H, J=5.9 Hz), 6.90(brs, 2H), 7.43(d, 1H, J=8.1 Hz), 7.64(d, 1H, J=8.1 Hz), 7.73(s, 1H). | DMSO-d6, 300 MHz |
| 6-14 | (structure) | 205–209 | 0.88(d, 6H, J=6.0 Hz), 1.01–1.13(m, 2H), 1.37–1.52(m, 3H), 1.58(s, 6H), 1.77–1.87(m, 5H), 2.25(s, 3H), 2.89(t, 2H, J=6.0 Hz), 2.89–2.95(m, 1H), 3.73(d, 2H, J=6.0 Hz), 6.90(br, 2H), 7.13(br, 1H), 7.42(d, 1H, J=9.0 Hz), 7.63(dd, 1H, J=9.0, 3.0 Hz), 7.73(d, 1H, J=3.0 Hz) | DMSO-d6, 300 MHz |

TABLE 6-continued

| New Ex. No. | MOLSTRUCTURE | m p | NMR(δ) | solvent |
|---|---|---|---|---|
| 6-15 | (structure) | 225–228 | 1.00–1.11(m, 2H), 1.36–1.51(m, 3H), 1.58(s, 6H), 1.78–1.86(m, 4H), 2.24(s, 3H), 2.92–2.96(m, 2H), 3.24–3.27(m, 4H), 3.52–3.55(m, 4H), 6.53(t, 1H, J=6.0 Hz), 6.90(br, 1H), 7.42(d, 1H, J=9.0 Hz), 7.63(dd, 1H, J=9.0, 3.0 Hz), 7.73(d, 1H, J=3.0 Hz) | DMSO-d6, 300 MHz |
| 6-16 | (structure) | >250 | 0.98–1.10(m, 2H), 1.36–1.52(m, 3H), 1.58(s, 6H), 1.81–1.85(m, 4H), 2.25(s, 3H), 2.78(s, 6H), 2.89–2.94(m, 3H), 6.25(t, 1H, J=6.0 Hz), 6.89(br, 2H), 7.42(d, 1H, J=9.0 Hz), 7.63(dd, 1H, J=9.0, 3.0 Hz), 7.73(d, 1H, J=3.0 Hz) | DMSO-d6, 300 MHz |
| 6-17 | (structure) | >250 | 1.07–1.19(m, 2H), 1.45–1.54(m, 2H), 1.59(s, 6H), 1.64–1.74(m, 1H), 1.80–1.87(m, 4H), 2.25(s, 3H), 2.91–3.00(m, 1H), 3.05(d, 2H, J=6.0 Hz), 3.56(t, 2H, J=9.0 Hz), 4.27(t, 2H, J=9.0 Hz), 6.90(br, 2H), 7.42(d, 1H, J=9.0 Hz), 7.64(dd, 1H, J=9.0, 3.0 Hz), 7.74(d, 1H, J=3.0 Hz) | DMSO-d6, 300 MHz |

TABLE 6-continued

| New Ex. No. | MOLSTRUCTURE | m p | NMR(δ) | solvent |
|---|---|---|---|---|
| 6-18 | | >250 | 0.99–1.16(m, 2H), 1.25(s, 6H), 1.35–1.53(m, 3H), 1.58(s, 6H), 1.77–1.86(m, 4H), 2.24(s, 3H), 2.86–2.96(m, 1H), 2.99(t, 2H, J=6.0 Hz), 5.32(s, 1H), 6.89(br, 2H), 7.42(d, 1H, J=8.3 Hz), 7.57–7.65(m, 2H), 7.73(d, 1H, J=1.9 Hz) | DMSO-d6, 300 MHz |
| 6-19 | | 225–226 | 1.05–1.19(m, 2H), 1.37–1.51(m, 2H), 1.58(s, 6H), 1.60–1.66(m, 1H), 1.71–1.87(m, 5H), 1.95–2.02(m, 1H), 2.24(s, 3H), 2.89–2.96(m, 1H), 3.09–3.15(m, 1H), 3.20–3.31(m, 4H), 3.85–3.91(m, 2H), 4.97(d, 1H, J=4.0 Hz), 6.90(brs, 2H), 7.40(d, 1H, J=8.0 Hz), 7.62(d, 1H, J=8.0 Hz), 7.72(s, 1H) | DMSO-d6, 400 MHz |
| 6-20 | | 247–248 | 1.07–1.21(m, 2H), 1.44–1.55(m, 2H), 1.65(s, 6H), 1.70–1.90(m, 5H), 2.16(d, 2H, J=8.0 Hz), 2.89–2.98(m, 1H), 7.45(d, 1H, J=8.0 Hz), 7.49 and 7.83(brs, 2H), 7.69(dd, 1H, J=8.0, 4.0 Hz), 7.80(d, 1H, J=4.0 Hz), 12.04(brs, 1H) | DMSO-d6, 400 MHz |

TABLE 6-continued

| New Ex. No. | MOLSTRUCTURE | m p | NMR(δ) | solvent |
|---|---|---|---|---|
| 6-21 | | >250 | 1.06–1.19(m, 2H), 1.41–1.55(m, 2H), 1.66(s, 6H), 1.68–1.75(m, 1H), 1.77–1.89(m, 4H), 2.91–3.01(m, 1H), 3.05(d, 2H, J=6.0 Hz), 3.56(dd, 2H, J=9.0, 9.0 Hz), 4.27(dd, 2H, J=9.0, 6.0 Hz), 7.44(d, 1H, J=6.0 Hz), 7.71(dd, 1H, J=6.0, 3.0 Hz), 7.82(d, 1H, J=3.0 Hz) | DMSO-d6, 300 MHz |
| 6-22 | | 147(dec.) | 1.01–1.14(m, 2H), 1.38–1.53(m, 3H), 1.65(s, 6H), 1.78–1.88(m, 4H), 2.88(t, 1H, J=6.0 Hz), 2.88–2.98(m, 2H), 5.34(brs, 2H), 6.00(t, 1H, J=4.5 Hz), 7.45(d, 1H, J=6.0 Hz), 7.70(dd, 1H, J=9.0, 3.0 Hz), 7.81(d, 1H, J=3.0 Hz) | DMSO-d6, 300 MHz |
| 6-23 | | 160–166 | 0.99–1.13(m, 2H), 1.36–1.51(m, 3H), 1.58(s, 6H), 1.76–1.90(m, 4H), 2.25(s, 3H), 2.86–3.01(m, 1H), 2.88(t, 2H, J=5.8 Hz), 5.34(s, 2H), 5.99(t, 1H, J=5.8 Hz), 6.89(br, 2H), 7.42(d, 1H, J=8.3 Hz), 7.63(dd, 1H, J=1.9, 8.3 Hz), 7.73(d, 1H, J=1.9 Hz) | DMSO-d6, 300 MHz |

TABLE 6-continued
| New Ex. No. | MOLSTRUCTURE | m p | NMR(δ) | solvent |
|---|---|---|---|---|
| 6-24 | 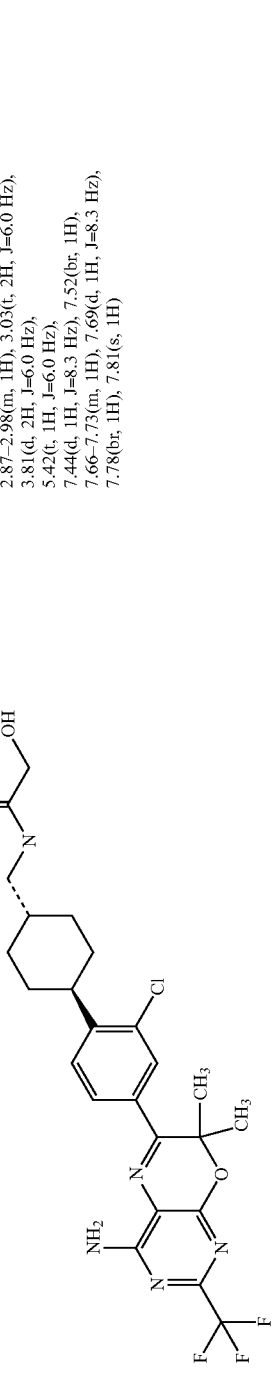 | 213–216 | 0.99–1.18(m, 2H), 1.33–1.62(m, 3H), 1.65(s, 6H), 1.77–1.89(m, 4H), 2.87–2.98(m, 1H), 3.03(t, 2H, J=6.0 Hz), 3.81(d, 2H, J=6.0 Hz), 5.42(t, 1H, J=6.0 Hz), 7.44(d, 1H, J=8.3 Hz), 7.52(br, 1H), 7.66–7.73(m, 1H), 7.69(d, 1H, J=8.3 Hz), 7.78(br, 1H), 7.81(s, 1H) | DMSO-d6, 300 MHz |
| 6-25 | 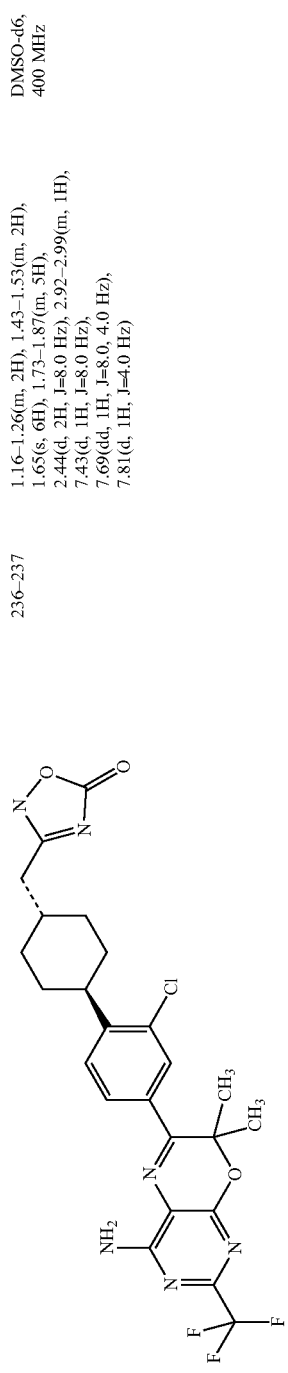 | 236–237 | 1.16–1.26(m, 2H), 1.43–1.53(m, 2H), 1.65(s, 6H), 1.73–1.87(m, 5H), 2.44(d, 2H, J=8.0 Hz), 2.92–2.99(m, 1H), 7.43(d, 1H, J=8.0 Hz), 7.69(dd, 1H, J=8.0, 4.0 Hz), 7.81(d, 1H, J=4.0 Hz) | DMSO-d6, 400 MHz |

TABLE 7

| New Ex. No. | MOLSTRUCTURE | m p | NMR(δ) | solvent |
|---|---|---|---|---|
| 7 | | >225 | 1.04–1.19(m, 2H), 1.39–1.55(m, 2H), 1.49(s, 6H), 1.65–1.89(m, 5H), 2.14(d, 2H, J=7.2 Hz), 2.21(s, 3H), 2.42–2.52(m, 1H), 6.55(s, 1H), 6.78(br, 2H), 7.23(d, 2H, J=8.3 Hz), 7.27(d, 2H, J=8.3 Hz), 12.01(s, 1H) | DMSO-d6, 300 MHz |
| 7-2 | | | 1.05–1.22(m, 2H), 1.13(s, 3H), 1.21(s, 3H), 1.36–1.52(m, 2H), 1.65–1.86(m, 5H), 2.14(d, 2H, J=6.8 Hz), 2.20(s, 3H), 2.38–2.70(m, 3H), 2.98–3.04(m, 1H), 6.45(br, 2H), 7.18(d, 2H, J=8.3 Hz), 7.22(d, 2H, J=8.3 Hz), 11.99(brs, 1H) | DMSO-d6, 300 MHz |
| 7-3 | | >250 | 1.50(s, 6H), 2.32(s, 3H), 6.56(s, 1H), 6.88(br, 2H), 7.20(d, 2H, J=8.4 Hz), 7.26(d, 2H, J=8.4 Hz), 7.95(s, 1H) | DMSO-d6, 300 MHz |
| 7-4 | | | 8.09(s, 1H), 7.33(bs, 2H), 7.30(d, J=8.1 Hz, 2H), 7.26(d, J=8.1 Hz, 2H), 6.61(s, 1H), 2.47(m, 1H), 2.15(d, J=6.9 Hz, 2H), 1.82(m, 4H), 1.74(m, 1H), 1.55(s, 6H), 1.51(m, 2H), 1.13(m, 2H) | DMSO-d6, 400 MHz |
| 7-5 | | | 8.14(s, 1H), 7.50(bs, 2H), 7.20(m, 3H), 6.61(s, 1H), 2.86(t, J=7.2 Hz, 2H), 2.17(d, J=6.8 Hz, 2H), 1.96(t, J=7.3 Hz, 2H), 1.71(m, 1H), 1.67(m, 2H), 1.63(m, 3H), 1.56(s, 6H), 1.50(m, 2H), 1.22(m, 2H) | DMSO-d6, 400 MHz |

TABLE 9

| New Ex. No. | MOLSTRUCTURE | m p | NMR(δ) | solvent |
|---|---|---|---|---|
| 9 | | | 1.24(d, J=6.8 Hz, 3H), 1.25–1.30(m, 2H), 1.48–1.59(m, 3H), 1.71(s, 6H), 1.91–2.00(m, 4H), 2.36–2.40(m, 1H), 2.46(s, 3H), 2.51–2.57(m, 1H), 7.27(d, J=8.4 Hz, 2H), 7.55(d, J=8.4 Hz, 2H) | CDCl3 |
| 9-2 | | | | |
| 9-3 | | | 1.10–1.20(m, 2H), 1.42–1.90(m, 13H), 2.17(d, J=6.8 Hz, 2H), 2.45–2.60(m, 1H), 7.34(d, J=8 Hz, 2H), 7.36(brs, 1H), 7.71(d, J=8 Hz, 2H), 7.74(brs, 1H), 12.04(brs, 1H) | DMSO-d6 |

TABLE 10

| New Ex. No. | MOLSTRUCTURE | m p | NMR(δ) | solvent |
|---|---|---|---|---|
| 10 | | | 0.85(t, J=7.1 Hz, 3H), 1.05–2.02(m, 19H), 6.97(brs, 2H), 7.30(d, J=7.8 Hz, 2H), 7.66(d, J=7.8 Hz, 2H), 7.95(s, 1H), 12.05(s, 1H) | DMSO-d6, 400 MHz |

TABLE 10-continued

| New Ex. No. | MOLSTRUCTURE | m p | NMR(δ) | solvent |
|---|---|---|---|---|
| 10-2 | | | 1.78–1.85(m, 9H), 1.96–2.07(m, 1H), 2.35–2.48(m, 4H), 2.86–2.93(m, 2H), 3.03–4.02(m, 1H), 3.82(brd, J=12 Hz, 1H), 5.81(s, 1H), 7.19(d, J=8.0 Hz, 1H), 7.36–7.40(m, 2H), 8.17(s, 1H) | CDCl3, 400 MHz |
| 10-3 | | | 1.06(s, 6H), 1.14–1.22(m, 2H), 1.40–1.46(m, 2H), 1.61–1.75(m, 10H), 1.82–1.85(m, 2H), 7.3(brs, 2H), 7.31(d, J=7.7 Hz, 2H), 7.64(d, J=7.7 Hz, 2H), 7.99(s, 1H) | DMSO-d6, 400 MHz |
| 10-4 | | | 0.87–0.93(m, 1H), 0.97(t, J=4.9 Hz, 1H), 1.02–1.10(m, 1H), 1.20–1.31(m, 1H), 1.48(dd, J=5.4 Hz, J=2.1 Hz, 1H), 1.57–1.85(m, 10H), 1.91–1.98(m, 1H), 2.63–2.72(m, 1H), 7.29(d, J=8.3 Hz, 2H), 7.69(d, J=8.3 Hz, 2H), 8.05(s, 1H) | DMSO-d6, 400 MHz |
| 10-5 | | | 0.75(m, 2H), 0.99(m, 2H), 1.38–1.62(m, 12H), 1.68–1.87(m, 4H), 6.97(br s, 2H), 7.29(d, J=8.2 Hz, 2H), 7.63(d, J=8.2 Hz, 2H), 7.94(s, 1H), 12.00(s, 1H) | DMSO-d6, 400 MHz |
| 10-6 | | | 1.25–1.55(m, 4H), 1.59(s, 6H), 1.62–1.72(m, 3H), 1.80–1.87(m, 2H), 2.43–2.55(m, 1H), 3.82(br s, 1H), 5.05(brs, 1H), 6.98(brs, 2H), 7.31(d, J=8.2 Hz, 2H), 7.64(d, J=8.2 Hz, 2H), 7.94(s, 1H), 12.03(brs, 1H) | DMSO-d6, 400 MHz |

TABLE 10-continued

| New Ex. No. | MOLSTRUCTURE | m p | NMR(δ) | solvent |
|---|---|---|---|---|
| 10-7 | | | 1.5–1.85(m, 6H), 1.80(s, 6H), 2.06(m, 2H), 2.22(m, 2H), 2.72–2.90(m, 2H), 5.67(s, 1H), 7.20–7.5(m, 2H), 7.51(d, J=6.2 Hz, 2H), 7.84(d, J=6.2 Hz, 2H), 8.18(s, 1H) | DMSO-d6, 400 MHz |
| 10-8 | | | 1.5–1.85(m, 6H), 1.78(s, 6H), 2.0–2.1(m, 2H), 2.2–2.3(m, 2H), 2.75–2.95(m, 2H), 5.94(s, 1H), 7.10–7.2(m, 1H), 7.50(d, J=5.5 Hz, 2H), 7.83(d, J=5.5 Hz, 2H), 8.12(s, 1H) | DMSO-d6, 400 MHz |
| 10-9 | | | 1.50–1.85(m, 6H), 1.77(s, 6H), 2.0–2.1(m, 2H), 2.2–2.3(m, 2H), 2.65–2.85(m, 2H), 5.30(s, 1H), 7.10–7.20(m, 1H), 7.49(d, J=6.1 Hz, 2H), 7.81(d, J=6.1 Hz, 2H), 8.11(s, 1H) | DMSO-d6, 400 MHz |
| 10-10 | | | 1.05–1.20(m, 2H), 1.35–2.07(m, 15H), 2.15(d, J=6.9 Hz, 2H, major isomer only), 2.28(d, J=7.4 Hz, 2H, minor isomer only), 2.77–2.80(m, 2H), 5.97(br s, 2H), 7.03(d, J=7.9 Hz, 1H), 7.25–7.30(m, 2H), 7.97(s, 1H) | CDCl3, 400 MHz |

TABLE 10-continued

| New Ex. No. | MOLSTRUCTURE | m p | NMR(δ) | solvent |
|---|---|---|---|---|
| 10-11 | | | 1.05–1.17(m, 8H), 1.35–1.71(m, 17H), 2.02(d, J=6.9 Hz, 2H), 6.37(brs, 2H), 7.13–7.21(m, 2H), 7.31(s, 1H), 7.88(s, 1H) | CDCl3, 400 MHz |
| 10-12 | | | 0.72–0.76(m, 2H), 0.99–1.03(m, 2H), 1.40–1.82(m, 19H), 2.75(t, J=6.0 Hz), 7.15(brs, 2H), 7.36(s, 1H), 7.46(s, 2H), 7.99(s, 1H) | DMSO-d6, 400 MHz |
| 10-13 | | | 1.23(s, 6H), 1.21–1.45(m, 4H), 1.55–1.85(m, 7H), 1.81(s, 6H), 2.06(m, 2H), 2.96(m, 2H), 7.25(m, 1H), 7.51–7.54(m, 3H), 12.0(brs, 1H) | DMSO-d6, 400 MHz |
| 10-14 | | | 1.06(s, 6H), 1.15–1.26(m, 2H), 1.42–1.51(m, 2H), 1.60–1.66(m, 7H), 1.68–1.73(m, 2H), 1.82–1.89(m, 2H), 2.34(s, 3H), 2.50–2.53(m, 1H), 7.31(d, J=6.0 Hz, 2H), 7.55(brs, 2H), 7.66(d, J=6.0 Hz, 2H) | DMSO-d6, 400 MHz |

TABLE 10-continued

| New Ex. No. | MOLSTRUCTURE | m p | NMR(δ) | solvent |
|---|---|---|---|---|
| 10-15 | | | 1.06(d, J=5.6 Hz, 3H), 1.13–1.24(m, 2H), 1.42–1.53(m, 2H), 1.54–1.60(m, 7H), 1.71–1.92(m, 4H), 2.19(quin, J=5.6 Hz, 1H), 2.51–2.58(m, 1H), 7.32(d, J=6.6 Hz, 2H), 7.69(d, J=6.6 Hz, 2H), 12.06(brs, 1H) | DMSO-d6, 400 MHz |
| 10-16 | | | 1.23(s, 6H), 1.20–1.50(m, 3H), 1.55–1.85(m, 7H), 1.80(s, 6H), 2.06(m, 2H), 2.65(s, 3H), 2.96(m, 2H), 6.50(bs, 1H), 7.25(m, 1H), 7.51–7.54(m, 2H), 10.75(brs, 1H) | CDCl3, 400 MHz |
| 10-17 | | | 1.24(d, J=7.0 Hz, 3H), 1.20–1.50(m, 3H), 1.55–1.85(m, 7H), 1.75(s, 6H), 2.05(m, 2H), 2.48(m, 1H), 2.96(m, 2H), 5.76(brs, 1H), 7.15–7.25(m, 3H), 7.45–7.50(m, 1H) | CDCl3, 400 MHz |
| 10-18 | | | 1.12–1.22(m, 5H), 1.46–1.54(m, 2H), 1.60(s, 6H), 1.75–1.88(m, 5H), 2.16(d, J=7.2 Hz, 2H), 2.45–2.53(m, 1H), 3.42–3.48(m, 2H), 7.40(brs, 2H), 7.31(d, J=8.4 Hz, 2H), 7.63(d, J=8.4 Hz, 2H), 12.05(brs, 1H) | DMSO-d6, 400 MHz |

TABLE 10-continued

| New Ex. No. | MOLSTRUCTURE | m p | NMR(δ) | solvent |
|---|---|---|---|---|
| 10-19 | | | 0.84–0.89(m, 2H), 1.27–1.33(m, 2H), 1.44–1.53(m, 5H), 1.76(s, 6H), 1.84–1.90(m, 2H), 1.94–2.01(m, 2H), 2.55–2.62(m, 1H), 5.75(brs, 2H), 7.29(d, J=8.4 Hz, 2H), 7.58(d, J=8.4 Hz, 2H) | CDCl3, 400 MHz |
| 10-20 | | | 1.23(s, 6H), 1.25–1.55(m, 5H), 1.76(s, 6H), 1.83–1.89(m, 2H), 1.98–2.04(m, 2H), 2.52–2.60(m, 1H), 5.70(brs, 2H), 7.29(d, J=8.0 Hz, 2H), 7.58(d, J=8.0 Hz, 2H) | CDCl3, 400 MHz |
| 10-21 | | | 0.83–0.88(m, 2H), 1.27–1.31(m, 2H), 1.47–1.60(m, 5H), 1.72(s, 6H), 1.85–1.91(m, 2H), 1.93–2.00(m, 2H), 2.44(s, 3H), 2.55–2.62(m, 1H), 6.13(brs, 2H), 7.29(d, J=8.0 Hz, 2H), 7.56(d, J=8.0 Hz, 2H) | CDCl3, 400 MHz |
| 10-22 | | | 1.11–1.22(m, 2H), 1.43–1.51(m, 13H), 2.16(d, J=5.3 Hz, 2H), 2.34(s, 3H), 2.35(s, 3H), 2.62–2.74(m, 1H), 7.29(d, J=6.5 Hz, 1H), 7.46–7.52(m, 4H) | DMSO-d6, 400 MHz |
| 10-23 | | | 1.08–1.21(m, 11H), 1.42–1.53(m, 2H), 1.69–87(m, 5H), 2.15(d, J=7.2 Hz, 2H), 2.42–2.52(m, 3H), 4.07(s, 1H), 5.10(s, 1H), 6.14(s, 2H), 7.26(d, J=8.2 Hz, 2H), 7.37(d, J=8.2 Hz, 2H), 12.05(brs, 1H) | DMSO-d6, 400 MHz |

TABLE 10-continued

| New Ex. No. | MOLSTRUCTURE | m p | NMR(δ) | solvent |
|---|---|---|---|---|
| 10-24 | | | 0.88(m, 2H), 1.3(m, 2H), 1.50–1.99(m, 10H), 1.79(s, 6H), 2.1(m, 2H), 2.65(s, 3H), 2.96(m, 2H), 6.5(brs, 1H), 7.15–7.25(m, 1H), 7.45–7.50(m, 2H), 10.5(brs, 1H) | CDCl3, 400 MHz |
| 10-25 | | | 0.76(m, 2H), 1.02(m, 2H), 1.45–1.83(m, 10H), 1.7(s, 6H), 2.0(m, 2H), 2.95(m, 2H), 3.33(m, 1H), 7.15–7.25(m, 1H), 7.45–7.50(m, 2H), 12.0(brs, 1H) | CDCl3, 400 MHz |
| 10-26 | | | 1.0(m, 2H), 1.23(s, 6H), 1.20–1.50(m, 3H), 1.55–1.85(m, 6H), 1.76(s, 6H), 2.06(m, 2H), 2.95(m, 2H), 5.91(brs, 1H), 7.15–7.25(m, 2H), 7.45–7.50(m, 1H) | CDCl3, 400 MHz |
| 10-27 | | | 0.86(t, J=7.2 Hz, 3H), 1.05–1.12(m, 2H), 1.33–1.60(m, 10H), 1.70–2.04(m, 6H), 2.25(s, 3H), 2.45–2.52(m, 1H), 6.80(brs, 2H), 7.29(d, J=8.4 Hz, 2H), 7.62(d, J=8.4 Hz, 2H) | DMSO-d6, 400 MHz |

TABLE 10-continued

| New Ex. No. | MOLSTRUCTURE | m p | NMR(δ) | solvent |
|---|---|---|---|---|
| 10-28 | | | 0.99(t, J=7.2 Hz, 3H), 1.25–1.25(m, 18H), 2.50–2.60(m, 1H), 5.76(brs, 2H), 7.29(d, J=8.4 Hz, 2H), 7.58(d, J=8.4 Hz, 2H) | CDCl3, 400 MHz |
| 10-29 | | | 0.90–1.05(m, 1H), 1.10–1.28(m, 2H), 1.40–1.50(m, 2H), 1.57(s, 6H), 1.60–1.70(m, 2H), 1.80–1.90(m, 2H), 1.90(s, 2H), 2.24(s, 3H), 2.35–2.50(m, 1H), 6.81(brs, 2H), 7.21(d, J=8.2 Hz, 2H), 7.60(d, J=8.2 Hz, 2H), 11.9(brs, 1H) | DMSO-d6, 400 MHz |
| 10-30 | | | 1.05(d, J=6.9 Hz, 3H), 1.10–1.26(m, 2H), 1.41–1.51(m, 2H), 1.52–2.01(m, 7H), 1.71–1.87(m, 4H), 2.15–2.22(m, 1H), 2.39(s, 3H), 2.44–2.50(m, 1H), 6.65(s, 1H), 7.30(Abq, J=8.0 Hz 2H), 8.0(brs, 2H) | DMSO-d6, 400 MHz |
| 10-31 | | | 1.05(d, J=6.9 Hz, 3H), 1.10–1.25(m, 2H), 1.41–1.62(m, 9H), 1.71–1.88(m, 4H), 2.14–2.21(m, 1H), 2.42–2.50(m, 1H), 6.58(s, 1H), 7.03(brs, 2H), 7.27(Abq, J=7.9 Hz, 2H), 12.0(brs, 1H) | DMSO-d6, 400 MHz |

Example 10

This example describes assays that may be used to identify compounds having DGAT activity.

Numerous in vitro assay systems may be used to determine the modulation of DGAT activity. Examples of such assay systems utilize insect cell over-expression systems, tissue microsome preparations and cell culture. In the insect cell over-expression and tissue microsome preparation assay systems, the system itself provides the enzyme source for activity measurements. Such measurements are generally conducted using radiolabeled substrate, wherein the radiolabeled product that is generated is subsequently resolved by thin layer chromatography (TLC) (see, e.g., Cases, et al., Proc. Natl. Acad. Sci. (1998) 95:13018 and Cases, et al., J. Biol. Chem. (2001) 276:38870).

By comparison, cell culture-based assay systems measure intracellular synthesis of triglyceride by incubating living cells with radiolabeled fatty acid. The radiolabeled fatty acid is utilized in triglyceride biosynthesis. Triglycerides can then be extracted from the cells using organic solvent and resolved by thin layer chromatography to determine the level of radiolabel incorporation as a measure of enzyme activity (see e.g., Cases, et al., J. Biol. Chem. (2001) 276:38870).

Cell-Based Assays

In a preferred cellular assay, human colon tumor CaCO2, human hepatoma HepG2, or mouse adipocyte 3T3-L1 cells (undifferentiated or differentiated as described below) are cultured to confluency in 24 well plates. The medium is replaced with serum-free medium and the cells incubated for a further 24-48 h. Next, medium is replaced with serum-free medium containing 400 µM oleic acid (complexed with BSA, 2:1 mole:mole) and compound at varying doses in a final volume of 200 µL per well. Cells are incubated for 30 min. before adding 0.1 µCi of $^{14}C$ oleic acid directly to the cells and the incubation continued for 10-30 min. depending on the cell type. Cells are washed two times with 1 mL PBS and air dried at 37° C. for 10 min. Cell lipids are extracted with 0.5 mL hexane:isopropyl alcohol (3:2 v/v) for 5 min. twice. Lipid extracts are evaporated to dryness and used for TLC using hexane:ethyl ether:acetic acid (80:20:1 v/v) as solvent. The radioactive bands are visualized and quantified by exposure to X-ray film or phosphorimager screen.

3T3-L1 cell differentiation into adipocytes is induced by incubating confluent cells in medium containing 10% serum, insulin (10 µg/mL), dexamethasone (1 µM), isobutylmethyl xanthine (IBMX, 0.5 mM), and tri-iodothyronine (T3, 10 nM). After 2 days, cells are maintained in serum, insulin, T3, and BRL49653 (1 µM) containing medium for 4-10 days.

Biochemical Assays

A preferred assay that may be used for identifying DGAT inhibitors involves a high throughput screening Scintillation Proximity Assay (SPA). In such an assay human DGAT1 is cloned from a human liver cDNA library. PCR is used to add a restriction site and flag epitope at the most 5' end and a restriction site at the 3' end of the sequence. Thereafter, human flagtag (FT) DGAT1 baculovirus may be generated using a Bac-to-Bac Baculovirus Expression System® (Invitrogen). Insect cells (e.g., sf9, sf2 1, or High Five) are infected for 24 to 72 h and collected by centrifugation. Cell pellets are resuspended in homogenization buffer and lysed using a homogenization device, such as a Microfluidizer. Total cell membranes are collected by ultracentrifugation at 45,000 rpm for 1 h.

A small aliquot (0.2 µg/well) of membrane is incubated with 10 µM compound or mercuric chloride (as positive control for inhibition) in the presence of enzyme substrate, dioleoyl glycerol (200 µM) in 384 well plates, final volume 50 gL per well. The reaction is started by the addition of radioactive substrate, $^{14}C$ acyl coenzyme A (25 µM, such as decanoyl CoA, palmitoyl CoA, oleoyl CoA), and incubated at room temperature for 2 h. The reaction is stopped by adding Wheat Germ Agglutinin (WGA) SPA beads (0.2 mg) in mercuric chloride. Cell membranes are allowed to couple to the beads overnight. The signal can be measured using, for example, a Chemiluminescence Image Plate Reader (CLIPR) or TopCount device.

Compounds of the present invention assessed by the above-described assay were found to have DGAT-inhibiting activity. See Table 11 below.

TABLE 11

| Example | hDGAT1 IC$_{50}$* |
|---------|-------------------|
| 1       | +                 |
| 1-2     | +                 |
| 1-3     | +                 |
| 1-4     | +                 |
| 1-5     | +                 |
| 1-6     | +                 |
| 1-7     | +                 |
| 1-8     | +                 |
| 1-9     | +                 |
| 1-10    | +                 |
| 1-11    | +                 |
| 1-12    | +                 |
| 1-13    | +                 |
| 1-14    | +                 |
| 1-15    | +                 |
| 1-16    | +                 |
| 1-17    | +                 |
| 1-18    | +                 |
| 1-19    | +                 |
| 1-20    | +                 |
| 1-21    | +                 |
| 1-22    | +                 |
| 1-23    | +                 |
| 1-24    | +                 |
| 1-25    | +                 |
| 1-26    | +                 |
| 1-27    | +                 |
| 1-28    | +                 |
| 1-29    | +                 |
| 1-30    | +                 |
| 1-31    | +                 |
| 1-32    | +                 |
| 1-33    | +                 |
| 1-34    | +                 |
| 1-35    | +                 |
| 1-36    | +                 |
| 1-37    | +                 |
| 2       | +++               |
| 2-2     | ++                |
| 2-3     | ++                |
| 2-4     | +++               |
| 2-5     | ++                |
| 2-6     | ++                |
| 2-7     | ++                |
| 2-8     | +                 |
| 2-9     | +                 |
| 2-10    | +                 |
| 2-11    | +                 |
| 2-12    | +                 |
| 2-13    | +                 |
| 2-14    | +                 |
| 2-15    | +                 |
| 2-16    | +                 |
| 2-17    | +                 |
| 2-18    | ++                |
| 2-19    | +                 |
| 2-20    | +                 |
| 2-21    | +                 |
| 2-22    | +                 |
| 2-23    | +                 |
| 2-24    | +                 |
| 2-25    | +                 |
| 2-26    | ++                |
| 2-27    | +                 |
| 2-28    | +                 |
| 2-29    | +                 |
| 2-30    | +                 |
| 2-31    | +                 |
| 2-32    | +                 |
| 2-33    | ++                |
| 2-34    | ++                |
| 2-35    | +                 |
| 2-36    | ++                |
| 2-37    | +                 |
| 2-38    | +                 |
| 2-39    | +                 |
| 2-40    | +++               |
| 2-41    | +                 |
| 2-42    | ++                |
| 2-43    | ++                |
| 2-44    | ++                |
| 2-45    | ++                |
| 2-46    | ++                |
| 2-47    | ++                |
| 2-48    | ++                |
| 2-49    | ++                |
| 2-50    | ++                |
| 2-51    | ++                |

TABLE 11-continued

| Example | hDGAT1 IC$_{50}$* |
|---|---|
| 2-52 | ++ |
| 2-53 | ++ |
| 2-54 | ++ |
| 2-55 | ++ |
| 2-58 | ++ |
| 2-59 | ++ |
| 2-60 | ++ |
| 2-61 | ++ |
| 2-62 | ++ |
| 2-63 | ++ |
| 2-64 | ++ |
| 2-65 | +++ |
| 2-66 | + |
| 2-67 | ++ |
| 2-68 | + |
| 2-69 | +++ |
| 2-70 | ++ |
| 2-71 | + |
| 2-72 | ++ |
| 2-73 | ++ |
| 2-74 | +++ |
| 2-75 | + |
| 2-76 | ++ |
| 2-77 | ++ |
| 2-78 | ++ |
| 2-79 | ++ |
| 2-80 | ++ |
| 2-81 | + |
| 2-82 | + |
| 2-83 | + |
| 2-84 | + |
| 2-85 | + |
| 2-86 | + |
| 2-87 | + |
| 2-88 | + |
| 2-89 | + |
| 2-90 | + |
| 2-91 | ++ |
| 2-92 | ++ |
| 2-93 | ++ |
| 2-94 | ++ |
| 2-95 | ++ |
| 2-96 | ++ |
| 2-97 | ++ |
| 2-98 | ++ |
| 2-99 | ++ |
| 2-100 | ++ |
| 2-101 | ++ |
| 2-102 | ++ |
| 2-103 | ++ |
| 2-104 | ++ |
| 2-105 | ++ |
| 2-106 | ++ |
| 2-107 | +++ |
| 2-108 | ++ |
| 2-109 | ++ |
| 2-110 | ++ |
| 2-111 | ++ |
| 2-112 | ++ |
| 2-113 | ++ |
| 2-114 | ++ |
| 2-115 | + |
| 2-116 | ++ |
| 2-117 | ++ |
| 2-118 | ++ |
| 2-119 | ++ |
| 2-120 | ++ |
| 2-121 | ++ |
| 2-122 | ++ |
| 2-123 | ++ |
| 2-124 | ++ |
| 2-125 | +++ |
| 2-126 | ++ |
| 2-127 | ++ |
| 2-128 | ++ |
| 2-129 | ++ |
| 2-130 | ++ |
| 2-131 | ++ |
| 2-132 | ++ |
| 2-133 | ++ |
| 2-134 | +++ |
| 2-135 | ++ |
| 2-136 | ++ |
| 2-137 | +++ |
| 2-138 | ++ |
| 2-139 | ++ |
| 2-140 | ++ |
| 2-141 | ++ |
| 2-142 | ++ |
| 2-143 | +++ |
| 2-144 | ++ |
| 2-145 | ++ |
| 2-146 | ++ |
| 2-147 | ++ |
| 2-148 | +++ |
| 2-149 | ++ |
| 2-150 | ++ |
| 2-151 | +++ |
| 2-152 | ++ |
| 2-153 | +++ |
| 2-154 | ++ |
| 2-155 | ++ |
| 2-156 | ++ |
| 2-157 | +++ |
| 2-158 | ++ |
| 2-159 | ++ |
| 2-160 | ++ |
| 2-161 | ++ |
| 2-162 | ++ |
| 2-163 | ++ |
| 2-164 | ++ |
| 2-165 | ++ |
| 2-166 | ++ |
| 2-167 | ++ |
| 2-168 | ++ |
| 2-169 | ++ |
| 2-170 | ++ |
| 2-171 | + |
| 2-172 | ++ |
| 2-173 | ++ |
| 2-174 | ++ |
| 2-175 | ++ |
| 2-176 | ++ |
| 2-177 | ++ |
| 2-178 | ++ |
| 2-179 | ++ |
| 2-180 | ++ |
| 2-181 | ++ |
| 2-182 | ++ |
| 2-183 | ++ |
| 2-184 | ++ |
| 2-185 | ++ |
| 2-186 | ++ |
| 2-187 | +++ |
| 2-188 | ++ |
| 2-189 | ++ |
| 2-190 | ++ |
| 2-191 | +++ |
| 2-192 | +++ |
| 2-193 | ++ |
| 2-194 | ++ |
| 2-195 | ++ |
| 2-196 | ++ |
| 2-197 | ++ |
| 2-198 | ++ |
| 2-200 | +++ |
| 2-201 | +++ |
| 2-202 | ++ |
| 2-203 | ++ |
| 2-204 | ++ |
| 2-205 | ++ |
| 2-206 | ++ |
| 2-207 | ++ |
| 2-208 | ++ |

TABLE 11-continued

| Example | hDGAT1 IC$_{50}$* |
|---|---|
| 2-209 | ++ |
| 2-210 | ++ |
| 2-211 | ++ |
| 2-212 | +++ |
| 2-213 | ++ |
| 2-214 | +++ |
| 2-215 | ++ |
| 2-216 | ++ |
| 2-217 | ++ |
| 2-218 | ++ |
| 2-219 | ++ |
| 2-220 | ++ |
| 2-221 | + |
| 2-222 | + |
| 2-223 | + |
| 2-224 | + |
| 2-225 | + |
| 2-226 | + |
| 2-227 | + |
| 2-228 | + |
| 2-229 | + |
| 2-230 | ++ |
| 2-232 | ++ |
| 2-233 | + |
| 2-234 | ++ |
| 2-235 | ++ |
| 2-236 | ++ |
| 2-237 | ++ |
| 2-238 | + |
| 2-239 | + |
| 2-240 | ++ |
| 2-241 | ++ |
| 2-242 | + |
| 2-243 | ++ |
| 2-244 | ++ |
| 2-245 | ++ |
| 2-246 | ++ |
| 2-247 | ++ |
| 2-248 | ++ |
| 2-249 | ++ |
| 2-250 | ++ |
| 2-251 | ++ |
| 2-252 | ++ |
| 2-253 | +++ |
| 2-254 | ++ |
| 2-255 | ++ |
| 2-256 | ++ |
| 2-257 | ++ |
| 2-258 | ++ |
| 2-259 | ++ |
| 2-260 | ++ |
| 2-261 | ++ |
| 2-262 | ++ |
| 2-263 | +++ |
| 2-264 | ++ |
| 3 | ++ |
| 3-2 | + |
| 3-3 | + |
| 4 | + |
| 4-2 | + |
| 4-3 | + |
| 4-4 | ++ |
| 4-5 | + |
| 4-6 | + |
| 4-7 | + |
| 5 | + |
| 5-2 | + |
| 5-3 | + |
| 6 | +++ |
| 6-2 | ++ |
| 6-3 | ++ |
| 6-4 | + |
| 6-8 | ++ |
| 6-9 | +++ |
| 6-10 | ++ |
| 6-11 | ++ |
| 6-12 | +++ |
| 6-13 | +++ |
| 6-14 | ++ |
| 6-15 | ++ |
| 6-16 | + |
| 6-17 | + |
| 6-18 | ++ |
| 6-19 | ++ |
| 6-20 | +++ |
| 6-21 | ++ |
| 6-22 | ++ |
| 6-23 | ++ |
| 6-24 | ++ |
| 6-25 | ++ |
| 7 | ++ |
| 7-2 | ++ |
| 7-3 | + |
| 7-4 | ++ |
| 7-5 | ++ |
| 8 | +++ |
| 8-2 | ++ |
| 8-3 | ++ |
| 8-4 | ++ |
| 8-5 | ++ |
| 8-6 | ++ |
| 8-7 | +++ |
| 9 | ++ |
| 9-2 | ++ |
| 9-3 | +++ |
| 10 | +++ |
| 10-2 | ++ |
| 10-3 | +++ |
| 10-4 | ++ |
| 10-5 | ++ |
| 10-6 | ++ |
| 10-7 | ++ |
| 10-8 | ++ |
| 10-9 | ++ |
| 10-10 | +++ |
| 10-11 | ++ |
| 10-12 | ++ |
| 10-13 | +++ |
| 10-14 | ++ |
| 10-15 | +++ |
| 10-16 | ++ |
| 10-17 | +++ |
| 10-18 | ++ |
| 10-19 | ++ |
| 10-20 | ++ |
| 10-21 | ++ |
| 10-22 | ++ |
| 10-23 | ++ |
| 10-24 | ++ |
| 10-25 | ++ |
| 10-26 | ++ |
| 10-27 | ++ |
| 10-28 | +++ |
| 10-29 | ++ |
| 10-30 | ++ |
| 10-31 | ++ |

*Legend:
"+" represents: IC$_{50}$ value > 0.1 μM
"++" represents: 0.1 μM ≧ IC$_{50}$ value ≧ 0.01 μM
"+++" represents: IC$_{50}$ value < 0.01 μM All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of formula (I):

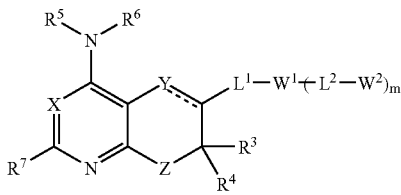

or a pharmaceutically acceptable salt or stereoisomer thereof, wherein

X is N;
Y is selected from the group consisting of N and $N(R^2)$;
Z is O;
$W^1$ is a substituted or unsubstituted member selected from the group consisting of cyclo($C_3$-$C_8$)alkyl, heterocyclo ($C_3$-$C_8$)alkyl, aryl and heteroaryl;
$W^2$ is a substituted or unsubstituted member selected from the group consisting of cyclo($C_3$-$C_8$)alkyl, heterocyclo ($C_3$-$C_8$)alkyl, aryl and heteroaryl;
$L^1$ is selected from the group consisting of a bond, ($C_1$-$C_4$)alkylene, ($C_2$-$C_4$)alkenylene, O and $N(R^a)C(O)$;
$L^2$ is selected from the group consisting of a bond, O, ($C_1$-$C_4$)alkylene, ($C_2$-$C_4$)alkenylene, ($C_1$-$C_4$)heteroalkylene and $N(R^a)C(O)$;
the subscript m is 0 or 1;
optionally, when m is 1 and $L^2$ is a bond, a substituent on $W^2$ may be combined with a substituent on $W^1$ to form a 5-, 6- or 7-membered ring fused to $W^1$ and spiro or fused to $W^2$, wherein said ring is saturated or unsaturated and has 0, 1 or 2 heteroatoms selected from the group consisting of N, O and S as ring members;
each $R^1$ is independently selected from the group consisting of H, ($C_1$-$C_8$)alkyl, ($C_2$-$C_8$)alkenyl, ($C_2$-$C_8$)alkynyl, fluoro($C_1$-$C_8$)alkyl, aryl, aryl($C_1$-$C_4$)alkyl, $C(O)R^a$, $CO_2R^a$ and $C(O)NR^aR^b$;
each $R^2$ is independently selected from the group consisting of H, ($C_1$-$C_8$)alkyl, ($C_2$-$C_8$)alkenyl, ($C_2$-$C_8$)alkynyl, fluoro($C_1$-$C_8$)alkyl, $C(O)R^a$, $CO_2R^a$, $C(O)NR^aR^b$, aryl and aryl($C_1$-$C_4$)alkyl;
$R^3$ and $R^4$ are independently selected from the group consisting of H, ($C_1$-$C_8$)alkyl, ($C_2$-$C_8$)alkenyl, ($C_2$-$C_8$)alkynyl, $C(O)R^a$, $CO_2R^a$, $C(O)NR^aR^b$ and ($C_1$-$C_4$)alkylene-$OR^a$;
optionally, $R^3$ and $R^4$ may be combined to form a 3-, 4-, 5- or 6-membered spiro ring;
optionally, $R^2$, $R^3$ or $R^4$ may be combined with $W^1$ to form a 5-, 6- or 7-membered fused ring having from 0 to 3 heteroatoms selected from the group consisting of N, O and S;
$R^5$ and $R^6$ are independently selected from the group consisting of H, ($C_1$-$C_8$)alkyl, ($C_2$-$C_8$)alkenyl, ($C_2$-$C_8$)alkynyl, $C(O)R^a$ and $CO_2R^a$;
optionally, $R^5$ and $R^6$ may be combined with the nitrogen atom to form a 5-, 6- or 7-membered ring;
optionally, when X is $C(R^1)$ or when Y includes an $R^1$ or $R^2$ group, $R^5$ or $R^6$ may be combined with $R^1$ or $R^2$ to form a 5-, 6- or 7-membered fused ring containing the nitrogen atom to which $R^5$ or $R^6$ is attached;
$R^7$ is selected from the group consisting of H, ($C_1$-$C_8$)alkyl, halo($C_1$-$C_4$)alkyl, ($C_2$-$C_8$)alkenyl, ($C_2$-$C_8$)alkynyl, and $C(O)R^a$,
optionally, when X is $C(R^1)$, $R^7$ may be combined with $R^1$ to form a 5-, 6- or 7-membered fused ring;
each $R^a$ and $R^b$ is independently selected from the group consisting of H, ($C_1$-$C_8$)alkyl, ($C_2$-$C_8$)alkenyl, ($C_2$-$C_8$) alkynyl, fluoro($C_1$-$C_8$)alkyl, aryl and aryl($C_1$-$C_4$)alkyl; and the dotted line indicates an optional bond.

2. A compound of claim 1 or a pharmaceutically acceptable salt or stereoisomer thereof, wherein $L^1$ is a bond and $W^1$ is a substituted or unsubstituted member selected from the group consisting of benzene, pyridine, thiophene, oxazole, thiazole, benzoxazole, benzthiazole, benzofuran, benzothiophene, ($C_4$-$C_7$)cycloalkane, ($C_5$-$C_7$)cycloalkene, 1,2,3,4-tetrahydronaphthalene and indane.

3. A compound of claim 2 or a pharmaceutically acceptable salt or stereoisomer thereof, wherein $W^1$ is a substituted or unsubstituted member selected from the group consisting of benzene, pyridine, thiophene, 1,2,3,4-tetrahydronaphthalene and indane.

4. A compound of claim 3 or a pharmaceutically acceptable salt or stereoisomer thereof, wherein the subscript m is 1.

5. A compound of claim 3 or a pharmaceutically acceptable salt or stereoisomer thereof, wherein the subscript m is 1 and $L^2$ is a bond.

6. A compound of claim 5 or a pharmaceutically acceptable salt or stereoisomer thereof, wherein $W^2$ is a substituted or unsubstituted member selected from the group consisting of benzene, pyridine, ($C_4$-$C_7$)cycloalkane, ($C_5$-$C_7$)cycloalkene, pyrrolidine, piperidine, piperazine and morpholine.

7. A compound of claim 2 or a pharmaceutically acceptable salt or stereoisomer thereof, wherein $R^5$ and $R^6$ are independently selected from the group consisting of H, ($C_1$-$C_8$)alkyl, $C(O)R^a$ and $CO_2R^a$.

8. A compound of claim 7, or a pharmaceutically acceptable salt or stereoisomer thereof, wherein $R^5$ and $R^6$ are independently selected from the group consisting of H and ($C_1$-$C_8$)alkyl.

9. A compound of claim 8 or a pharmaceutically acceptable salt or stereoisomer thereof, wherein $R^3$ and $R^4$ are independently selected from the group consisting of H and ($C_1$-$C_8$)alkyl.

10. A compound of claim 9, or a pharmaceutically acceptable salt or stereoisomer thereof, wherein $R^7$ is H, ($C_1$-$C_8$) alkyl or halo($C_1$-$C_4$)alkyl.

11. A pharmaceutical composition comprising a pharmaceutically acceptable excipient and a compound of formula (I):

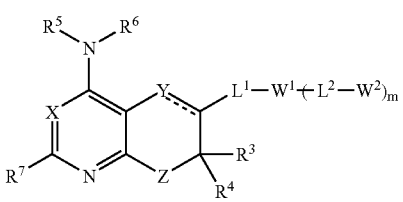

or a pharmaceutically acceptable salt or stereoisomer thereof, wherein

X is N;
Y is selected from the group consisting of N and N($R^2$);
Z is O;
$W^1$ is a substituted or unsubstituted member selected from the group consisting of cyclo($C_3$-$C_8$)alkyl, heterocyclo ($C_3$-$C_8$)alkyl, aryl and heteroaryl;
$W^2$ is a substituted or unsubstituted member selected from the group consisting of cyclo($C_3$-$C_8$)alkyl, heterocyclo ($C_3$-$C_8$)alkyl, aryl and heteroaryl;
$L^1$ is selected from the group consisting of a bond, ($C_1$-$C_4$)alkylene, ($C_2$-$C_4$)alkenylene, O and N($R^a$)C(O);
$L^2$ is selected from the group consisting of a bond, O, ($C_1$-$C_4$)alkylene, ($C_2$-$C_4$)alkenylene, ($C_1$-$C_4$)heteroalkylene and N($R^a$)C(O);
the subscript m is 0 or 1;
optionally, when m is 1 and $L^2$ is a bond, a substituent on $W^2$ may be combined with a substituent on $W^1$ to form a 5-, 6- or 7-membered ring fused to $W^1$ and spiro or fused to $W^2$, wherein said ring is saturated or unsaturated and has 0, 1 or 2 heteroatoms selected from the group consisting of N, O and S as ring members;
each $R^1$ is independently selected from the group consisting of H, ($C_1$-$C_8$)alkyl, ($C_2$-$C_8$)alkenyl, ($C_2$-$C_8$)alkynyl, fluoro($C_1$-$C_8$)alkyl, aryl, aryl($C_1$-$C_4$)alkyl, C(O)$R^a$, $CO_2R^a$ and C(O)N$R^aR^b$;
each $R^2$ is independently selected from the group consisting of H, ($C_1$-$C_8$)alkyl, ($C_2$-$C_8$)alkenyl, ($C_2$-$C_8$)alkynyl, fluoro($C_1$-$C_8$)alkyl, C(O)$R^a$, $CO_2R^a$, C(O)N$R^aR^b$, aryl and aryl($C_1$-$C_4$)alkyl;
$R^3$ and $R^4$ are independently selected from the group consisting of H, ($C_1$-$C_8$)alkyl, ($C_2$-$C_8$)alkenyl, ($C_2$-$C_8$)alkynyl, C(O)$R^a$, $CO_2R^a$, C(O)N$R^aR^b$ and ($C_1$-$C_4$)alkylene-O$R^a$;
optionally, $R^3$ and $R^4$ may be combined to form a 3-, 4-, 5- or 6-membered spiro ring;
optionally, $R^2$, $R^3$ or $R^4$ may be combined with $W^1$ to form a 5-, 6- or 7-membered fused ring having from 0 to 3 heteroatoms selected from the group consisting of N, O and S;
$R^5$ and $R^6$ are independently selected from the group consisting of H, ($C_1$-$C_8$)alkyl, ($C_2$-$C_8$)alkenyl, ($C_2$-$C_8$)alkynyl, C(O)$R^a$ and $CO_2R^a$;
optionally, $R^5$ and $R^6$ may be combined with the nitrogen atom to form a 5-, 6- or 7-membered ring;
optionally, when X is C($R^1$) or when Y includes an $R^1$ or $R^2$ group, $R^5$ or $R^6$ may be combined with $R^1$ or $R^2$ to form a 5-, 6- or 7-membered fused ring containing the nitrogen atom to which $R^5$ or $R^6$ is attached;
$R^7$ is selected from the group consisting of H, ($C_1$-$C_8$) alkyl, halo($C_1$-$C_4$)alkyl, ($C_2$-$C_8$)alkenyl, ($C_2$-$C_8$)alkynyl, and C(O)$R^a$,
optionally, when X is C($R^1$), $R^7$ may be combined with $R^1$ to form a 5-, 6- or 7-membered fused ring;
each $R^a$ and $R^b$ is independently selected from the group consisting of H, ($C_1$-$C_8$)alkyl, ($C_2$-$C_8$)alkenyl, ($C_2$-$C_8$) alkynyl, fluoro($C_1$-$C_8$)alkyl, aryl and aryl($C_1$-$C_4$)alkyl; and
the dotted line indicates an optional bond.

12. A pharmaceutical composition of claim 11, wherein in the compound, pharmaceutically acceptable salt thereof, or stereoisomer thereof, $L^1$ is a bond and $W^1$ is a substituted or unsubstituted member selected from the group consisting of benzene, pyridine, thiophene, oxazole, thiazole, benzoxazole, benzthiazole, benzofuran, benzothiophene, ($C_4$-$C_7$) cycloalkane, ($C_5$-$C_7$)cycloalkene, 1,2,3,4-tetrahydronaphthalene and indane.

13. A pharmaceutical composition of claim 12, wherein in the compound, pharmaceutically acceptable salt thereof, or stereoisomer thereof, $W^1$ is a substituted or unsubstituted member selected from the group consisting of benzene, pyridine, thiophene, 1,2,3,4-tetrahydronaphthalene and indane.

14. A pharmaceutical composition of claim 13, wherein in the compound, pharmaceutically acceptable salt thereof, or stereoisomer thereof, the subscript m is 1.

15. A pharmaceutical composition of claim 13, wherein in the compound, pharmaceutically acceptable salt thereof, or stereoisomer thereof, the subscript m is 1 and $L^2$ is a bond.

16. A pharmaceutical composition of claim 15, wherein in the compound, pharmaceutically acceptable salt thereof, or stereoisomer thereof, $W^2$ is a substituted or unsubstituted member selected from the group consisting of benzene, pyridine, ($C_4$-$C_7$)cycloalkane, ($C_5$-$C_7$)cycloalkene, pyrrolidine, piperidine, piperazine and morpholine.

17. A pharmaceutical composition of claim 12, wherein in the compound, pharmaceutically acceptable salt thereof, or stereoisomer thereof, $R^5$ and $R^6$ are independently selected from the group consisting of H, ($C_1$-$C_8$)alkyl, C(O)$R^a$ and $CO_2R^a$.

18. A pharmaceutical composition of claim 17, wherein in the compound, pharmaceutically acceptable salt thereof, or stereoisomer thereof, $R^5$ and $R^6$ are independently selected from the group consisting of H and ($C_1$-$C_8$)alkyl.

19. A pharmaceutical composition of claim 18, wherein in the compound, pharmaceutically acceptable salt thereof, or stereoisomer thereof, $R^3$ and $R^4$ are independently selected from the group consisting of H and ($C_1$-$C_8$)alkyl.

20. A pharmaceutical composition of claim 19, wherein in the compound, pharmaceutically acceptable salt thereof, or stereoisomer thereof, $R^7$ is H, ($C_1$-$C_8$)alkyl or halo($C_1$-$C_4$) alkyl.

21. A method of treating a disease or condition selected from the group consisting of obesity and insulin resistance, comprising administering to a subject in need thereof an effective amount of a compound of formula (I):

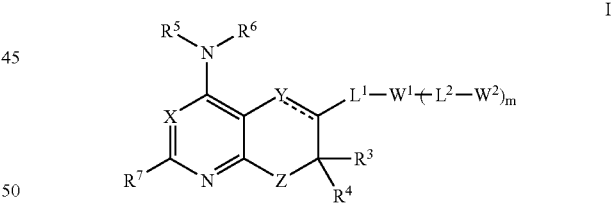

or a pharmaceutically acceptable salt or stereoisomer thereof, wherein
X is N;
Y is selected from the group consisting of N and N($R^2$);
Z is O;
$W^1$ is a substituted or unsubstituted member selected from the group consisting of cyclo($C_3$-$C_8$)alkyl, heterocyclo ($C_3$-$C_8$)alkyl, aryl and heteroaryl;
$W^2$ is a substituted or unsubstituted member selected from the group consisting of cyclo($C_3$-$C_8$)alkyl, heterocyclo ($C_3$-$C_8$)alkyl, aryl and heteroaryl;
$L^1$ is selected from the group consisting of a bond, ($C_1$-$C_4$)alkylene, ($C_2$-$C_4$)alkenylene, O and N($R^a$)C(O);

$L^2$ is selected from the group consisting of a bond, O, $(C_1-C_4)$alkylene, $(C_2-C_4)$alkenylene, $(C_1-C_4)$heteroalkylene and $N(R^a)C(O)$;

the subscript m is 0 or 1;

optionally, when m is 1 and $L^2$ is a bond, a substituent on $W^2$ may be combined with a substituent on $W^1$ to form a 5-, 6- or 7-membered ring fused to $W^1$ and spiro or fused to $W^2$, wherein said ring is saturated or unsaturated and has 0, 1 or 2 heteroatoms selected from the group consisting of N, O and S as ring members;

each $R^1$ is independently selected from the group consisting of H, $(C_1-C_8)$alkyl, $(C_2-C_8)$alkenyl, $(C_2-C_8)$alkynyl, fluoro$(C_1-C_8)$alkyl, aryl, aryl$(C_1-C_4)$alkyl, $C(O)R^a$, $CO_2R^a$ and $C(O)NR^aR^b$;

each $R^2$ is independently selected from the group consisting of H, $(C_1-C_8)$alkyl, $(C_2-C_8)$alkenyl, $(C_2-C_8)$alkynyl, fluoro$(C_1-C_8)$alkyl, $C(O)R^a$, $CO_2R^a$, $C(O)NR^aR^b$, aryl and aryl$(C_1-C_4)$alkyl;

$R^3$ and $R^4$ are independently selected from the group consisting of H, $(C_1-C_8)$alkyl, $(C_2-C_8)$alkenyl, $(C_2-C_8)$alkynyl, $C(O)R^a$, $CO_2R^a$, $C(O)NR^aR^b$ and $(C_1-C_4)$alkylene-$OR^a$;

optionally, $R^3$ and $R^4$ may be combined to form a 3-, 4-, 5- or 6-membered spiro ring;

optionally, $R^2$, $R^3$ or $R^4$ may be combined with $W^1$ to form a 5-, 6- or 7-membered fused ring having from 0 to 3 heteroatoms selected from the group consisting of N, O and S;

$R^5$ and $R^6$ are independently selected from the group consisting of H, $(C_1-C_8)$alkyl, $(C_2-C_8)$alkenyl, $(C_2-C_8)$alkynyl, $C(O)R^a$ and $CO_2R^a$;

optionally, $R^5$ and $R^6$ may be combined with the nitrogen atom to form a 5-, 6- or 7-membered ring;

optionally, when X is $C(R^1)$ or when Y includes an $R^1$ or $R^2$ group, $R^5$ or $R^6$ may be combined with $R^1$ or $R^2$ to form a 5-, 6- or 7-membered fused ring containing the nitrogen atom to which $R^5$ or $R^6$ is attached;

$R^7$ is selected from the group consisting of H, $(C_1-C_8)$alkyl, halo$(C_1-C_4)$alkyl, $(C_2-C_8)$alkenyl, $(C_2-C_8)$alkynyl, $C(O)R^a$, $OR^a$ and $NR^aR^b$;

optionally, when X is $C(R^1)$, $R^7$ may be combined with $R^1$ to form a 5-, 6- or 7-membered fused ring;

each $R^a$ and $R^b$ is independently selected from the group consisting of H, $(C_1-C_8)$alkyl, $(C_2-C_8)$alkenyl, $(C_2-C_8)$alkynyl, fluoro$(C_1-C_8)$alkyl, aryl and aryl$(C_1-C_4)$alkyl; and the dotted line indicates an optional bond.

22. A method in accordance with claim 21, wherein said compound, pharmaceutically acceptable salt thereof, or stereoisomer thereof is administered orally.

23. A method in accordance with claim 21, wherein said compound, pharmaceutically acceptable salt thereof, or stereoisomer thereof is administered in combination with an additional active agent.

24. A method in accordance with claim 23, wherein said additional active agent is selected from the group consisting of an antihyperlipidemic agent, a plasma HDL-raising agent, an antihypercholesterolemic agent, an HMG-CoA reductase inhibitor, an HMG-CoA synthase inhibitor, a pancreatic lipase inhibitor, SNRI, appetite suppressive agent, a PPAR modulator, a MTP inhibitor, a CETP inhibitor, a squalene epoxidase inhibitor, a squalene synthetase inhibitor, an acyl-coenzyme A cholesterol acyltransferase inhibitor, vitamin $B_3$, a cholesterol absorption inhibitor, a bile acid sequestrant anion exchange resin, a low density lipoprotein receptor inducer, a fibrate, probucol, vitamin $B_6$, vitamin $B_{12}$, an anti-oxidant vitamin, a β-blocker, an angiotensin II antagonist, an angiotensin converting enzyme inhibitor, a platelet aggregation inhibitor, a fibrinogen receptor antagonist, aspirin, phentiramines, $β_3$ adrenergic receptor agonists, sulfonylureas, biguanides, α-glucosidase inhibitors, insulin secretogogues, insulin and a hepatoprotective agent.

25. A method in accordance with claim 21, wherein said disease or condition is obesity.

26. A method in accordance with claim 21, wherein said disease is associated with DGAT.

27. A method in accordance with claim 21, wherein said disease is mediated by DGAT.

28. A method in accordance with claim 21, wherein said compound, pharmaceutically acceptable salt thereof, or stereoisomer thereof interferes with the interaction between DGAT and a ligand.

29. A method in accordance with claim 21, wherein said subject is selected from the group consisting of human, rat, dog, cow, horse and mouse.

30. A method in accordance with claim 21, wherein said subject is human.

31. A method in accordance with claim 21, wherein in the compound, pharmaceutically acceptable salt thereof, or stereoisomer thereof, $L^1$ is a bond and $W^1$ is a substituted or unsubstituted member selected from the group consisting of benzene, pyridine, thiophene, oxazole, thiazole, benzoxazole, benzthiazole, benzofuran, benzothiophene, $(C_4-C_7)$cycloalkane, $(C_5-C_7)$cycloalkene, 1,2,3,4-tetrahydronaphthalene and indane.

32. A method in accordance with claim 31, wherein the compound, pharmaceutically acceptable salt thereof, or stereoisomer thereof, $W^1$ is a substituted or unsubstituted member selected from the group consisting of benzene, pyridine, thiophene, 1,2,3,4-tetrahydronaphthalene and indane.

33. A method in accordance with claim 32, wherein in the compound, pharmaceutically acceptable salt thereof, or stereoisomer thereof, the subscript m is 1.

34. A method in accordance with claim 32, wherein in the compound, pharmaceutically acceptable salt thereof, or stereoisomer thereof, the subscript m is 1 and $L^2$ is a bond.

35. A method in accordance with claim 34, wherein in the compound, pharmaceutically acceptable salt thereof, or stereoisomer thereof, $W^2$ is a substituted or unsubstituted member selected from the group consisting of benzene, pyridine, $(C_4-C_7)$cycloalkane, $(C_5-C_7)$cycloalkene, pyrrolidine, piperidine, piperazine and morpholine.

36. A method in accordance with claim 31, wherein in the compound, pharmaceutically acceptable salt thereof, or stereoisomer thereof, $R^5$ and $R^6$ are independently selected from the group consisting of H, $(C_1-C_8)$alkyl, $C(O)R^a$ and $CO_2R^a$.

37. A method in accordance with claim 36, wherein in the compound, pharmaceutically acceptable salt thereof, or stereoisomer thereof, $R^5$ and $R^6$ are independently selected from the group consisting of H and $(C_1-C_8)$alkyl.

38. A method in accordance with claim 37, wherein in the compound, pharmaceutically acceptable salt thereof, or stereoisomer thereof, $R^3$ and $R^4$ are independently selected from the group consisting of H and $(C_1-C_8)$alkyl.

39. A method in accordance with claim 38, wherein in the compound, pharmaceutically acceptable salt thereof, or stereoisomer thereof, $R^7$ is selected from the group consisting of H, $(C_1-C_8)$alkyl, halo$(C_1-C_4)$alkyl, OH and $NR^aR^b$ wherein $R^a$ and $R^b$ are independently selected from the group consisting of H and $(C_1-C_8)$alkyl.

40. A method in accordance with claim 38, wherein in the compound, pharmaceutically acceptable salt thereof, or stereoisomer thereof, $R^7$ is H, $(C_1-C_8)$alkyl or halo$(C_1-C_4)$alkyl.

41. A compound of claim 1, selected from the group consisting of:
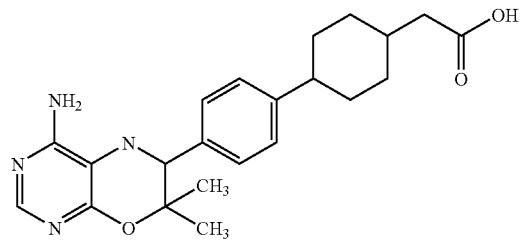
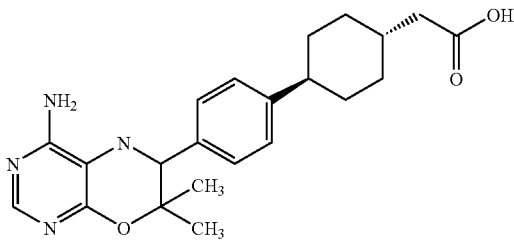
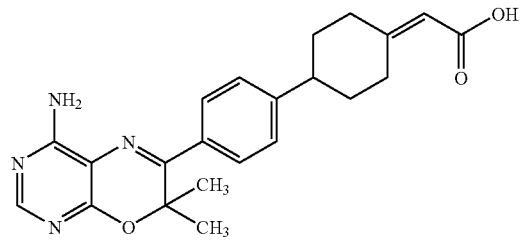
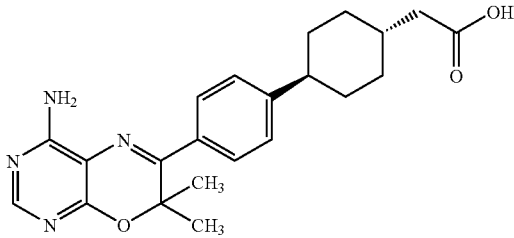
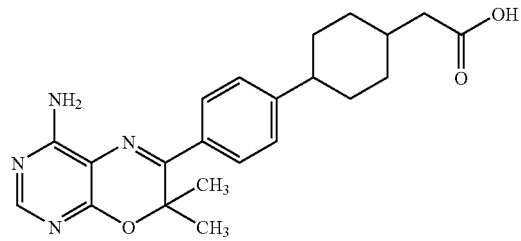
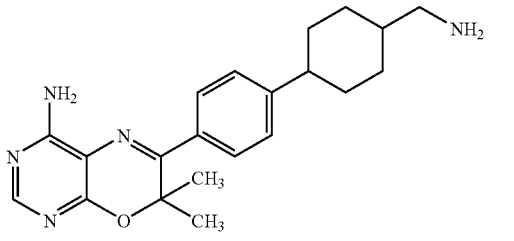
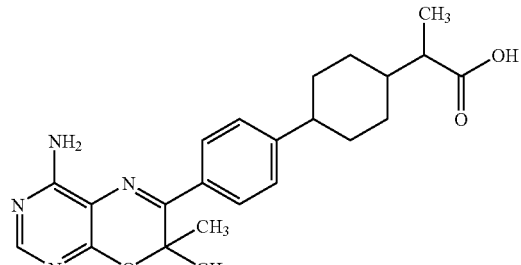
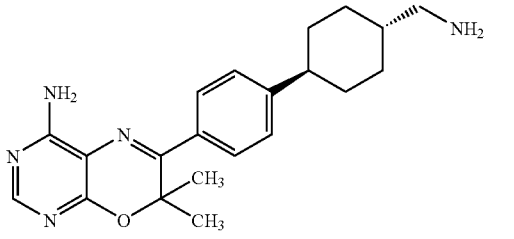
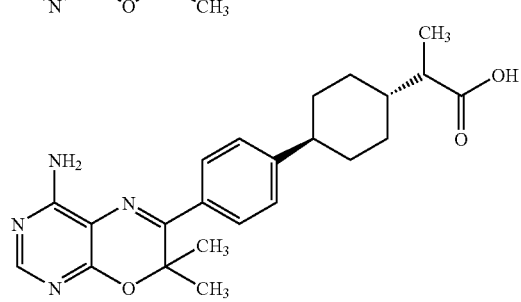
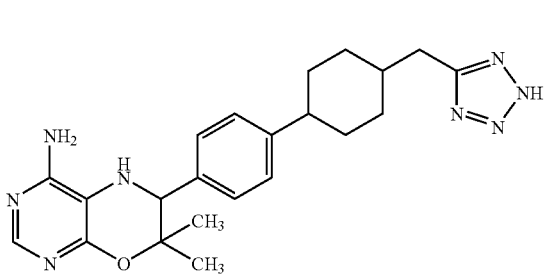
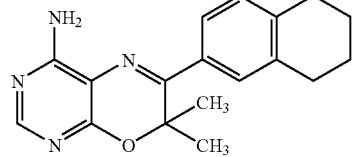
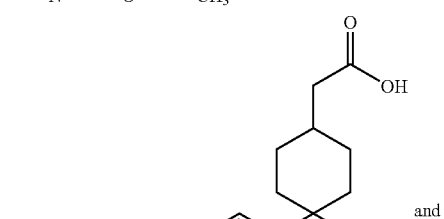
and
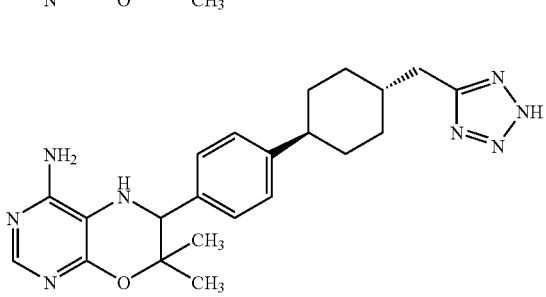

or a pharmaceutically acceptable salt or stereoisomer thereof.
42. A compound of claim 1, selected from the group consisting of
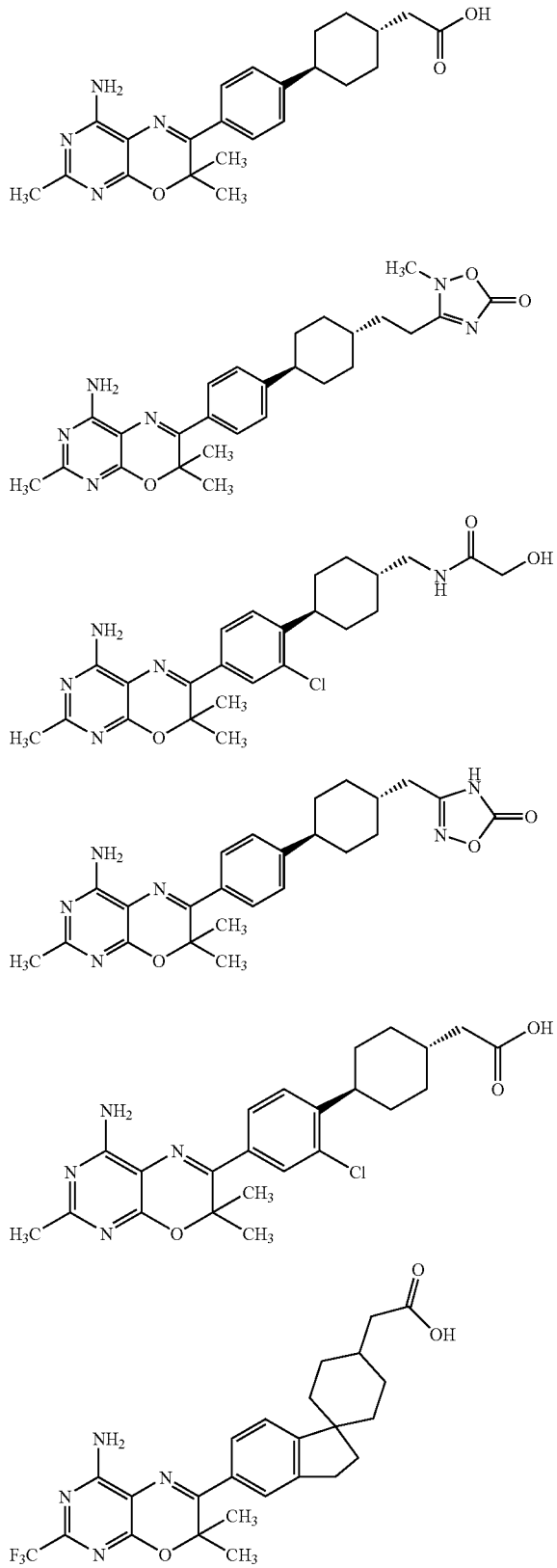
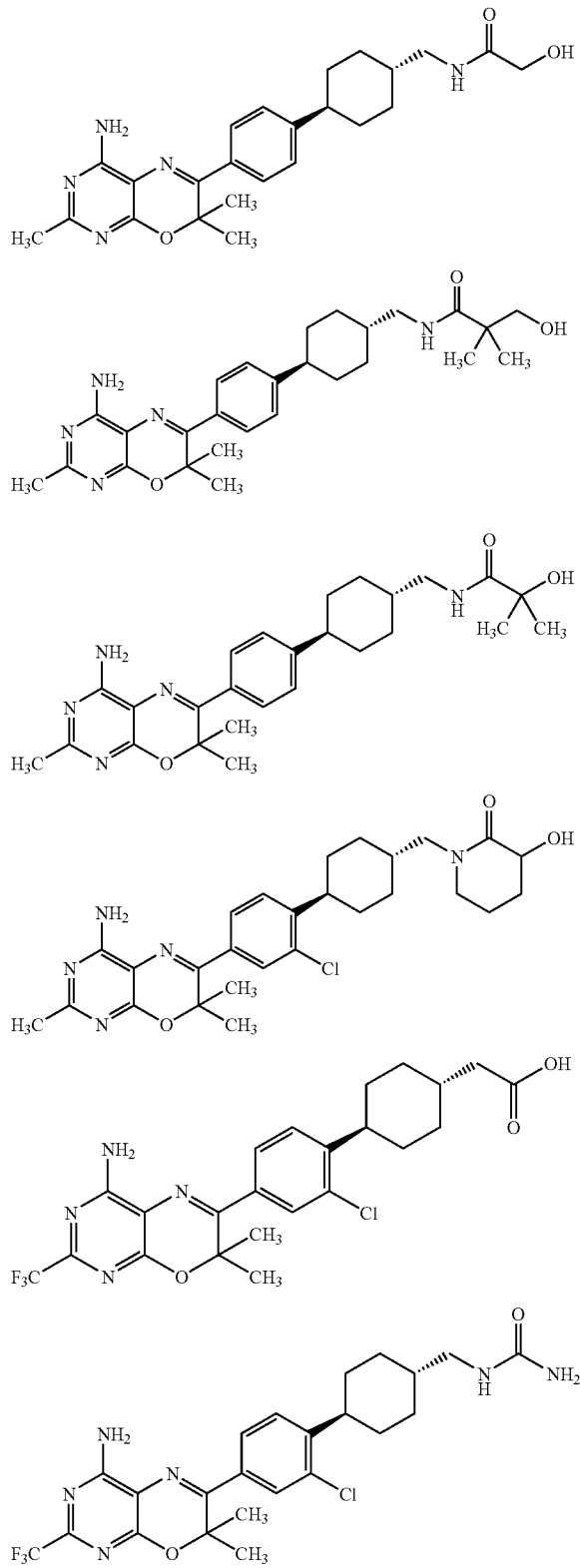

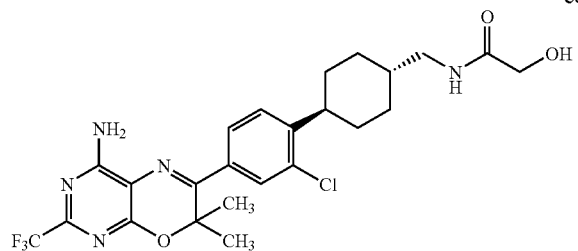
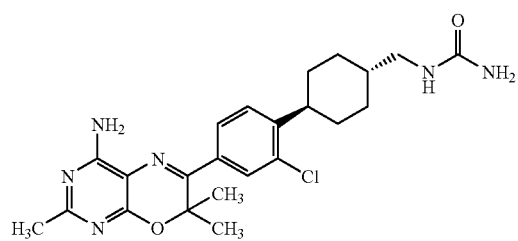
or a pharmaceutically acceptable salt or stereoisomer thereof.
43. A pharmaceutical composition of claim 11, wherein the compound of formula (I) is selected from the group consisting of:
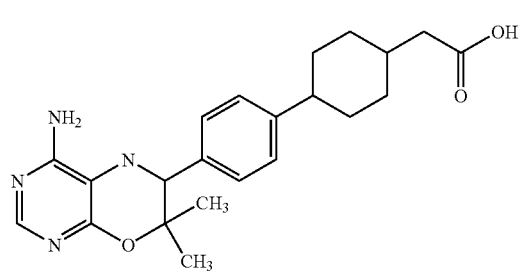
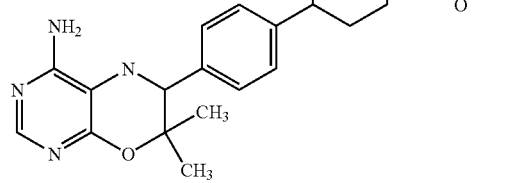
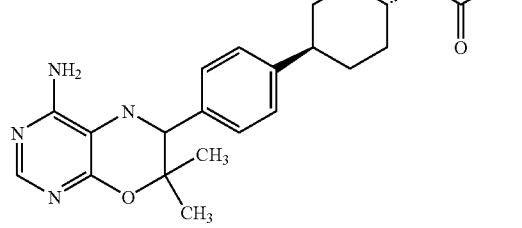
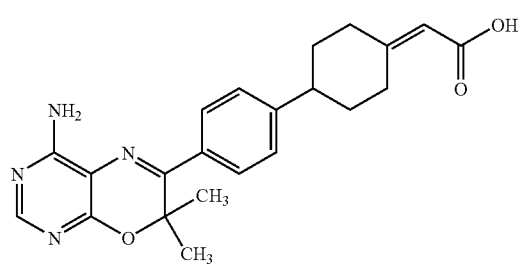
-continued
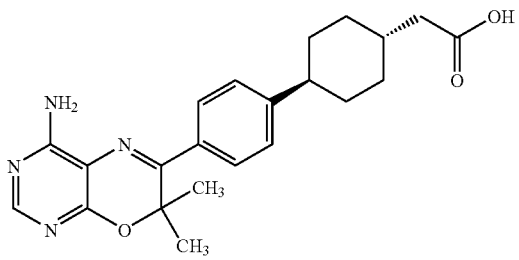
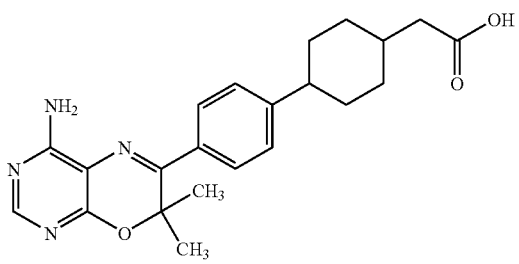
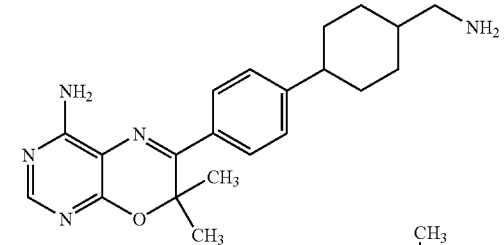
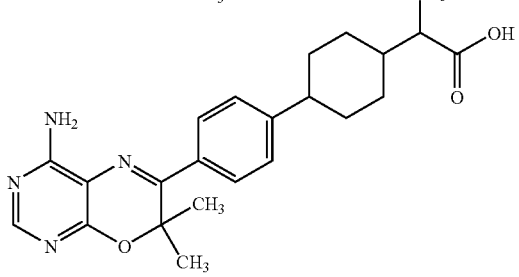

-continued
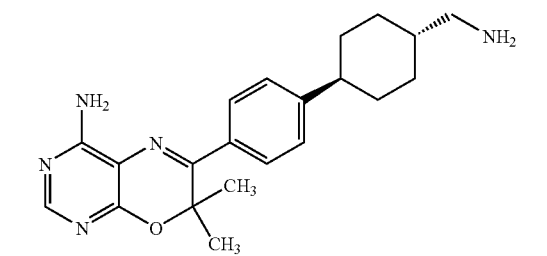
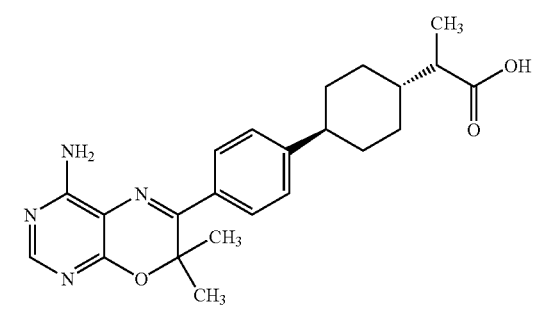
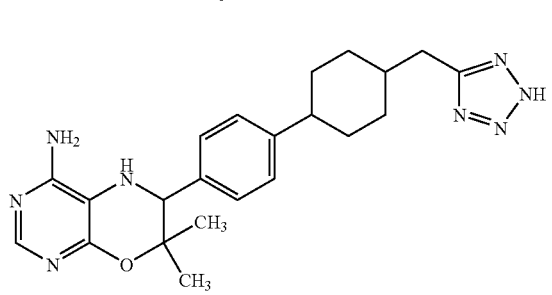
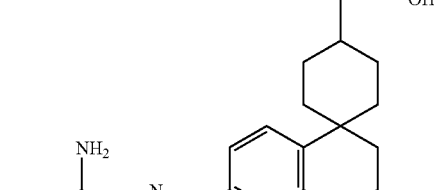
and
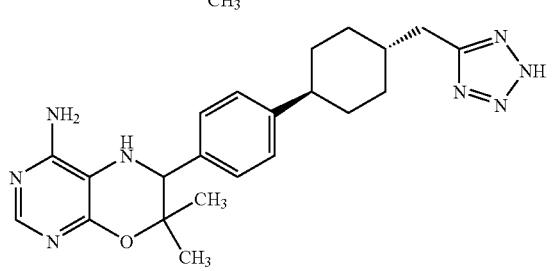
or a pharmaceutically acceptable salt or stereoisomer thereof.
44. A pharmaceutical composition of claim 11, wherein the compound of formula (I) is selected from the group consisting of:
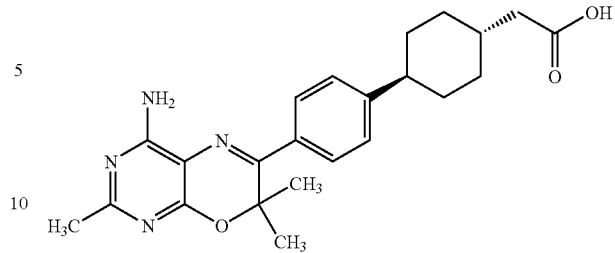
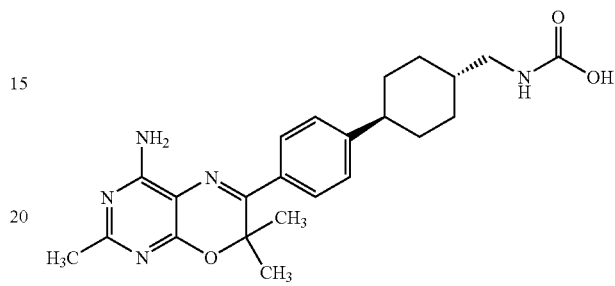
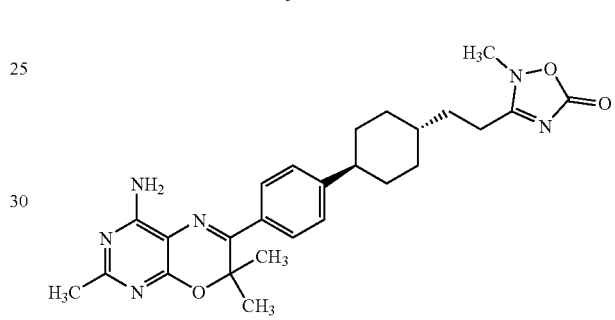
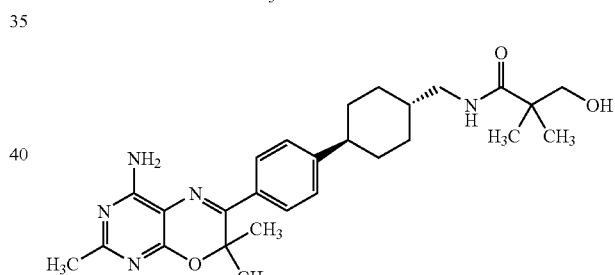
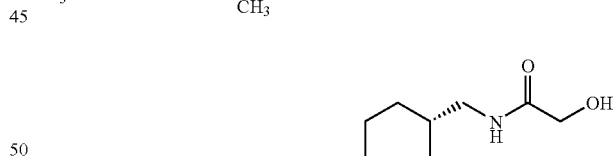
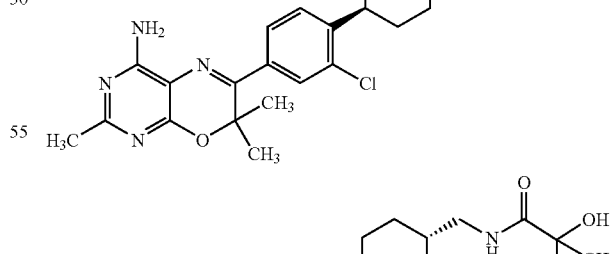
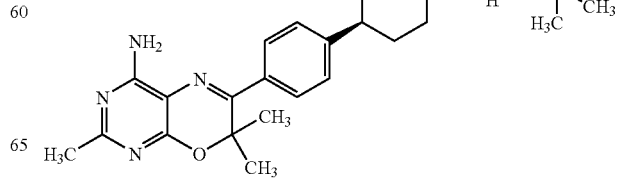

-continued
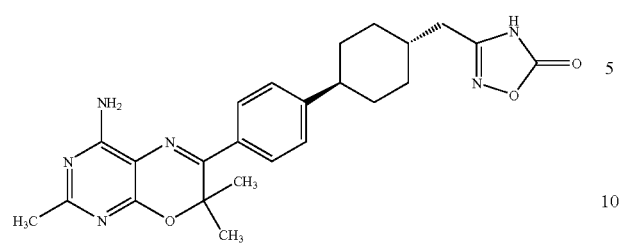
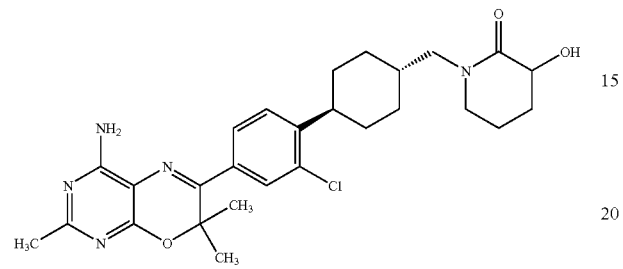
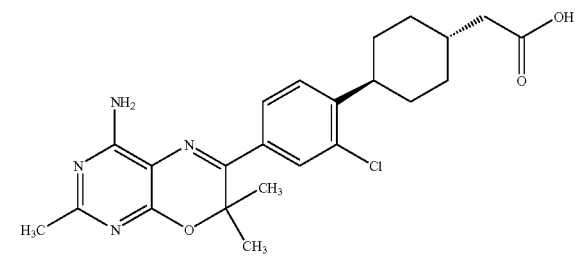
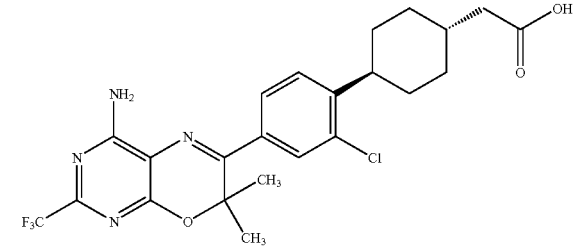
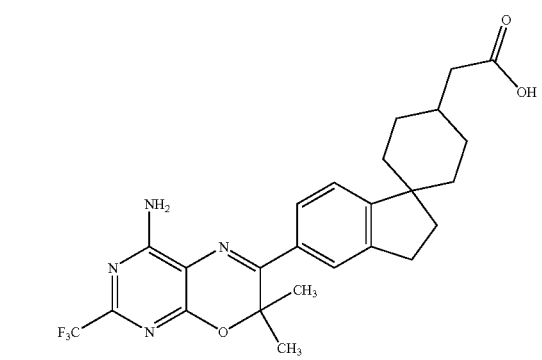
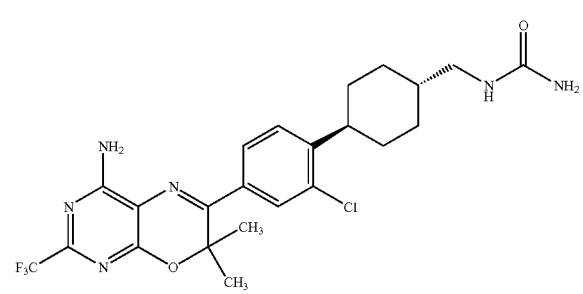
-continued
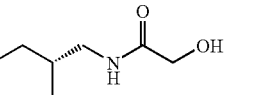
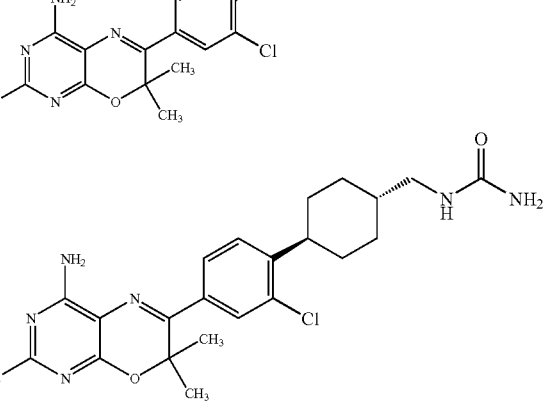
or a pharmaceutically acceptable salt or stereoisomer thereof.
45. A method in accordance with claim 21, wherein the compound of formula (I) is selected from the group consisting of:
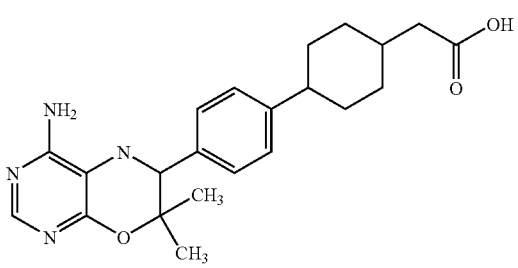
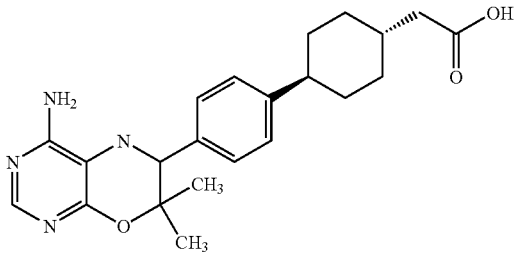
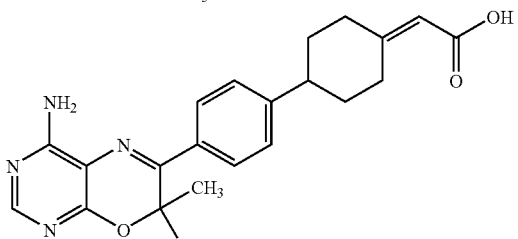
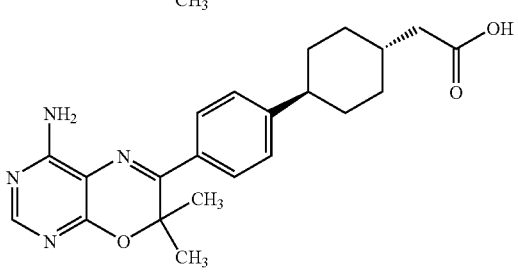

-continued
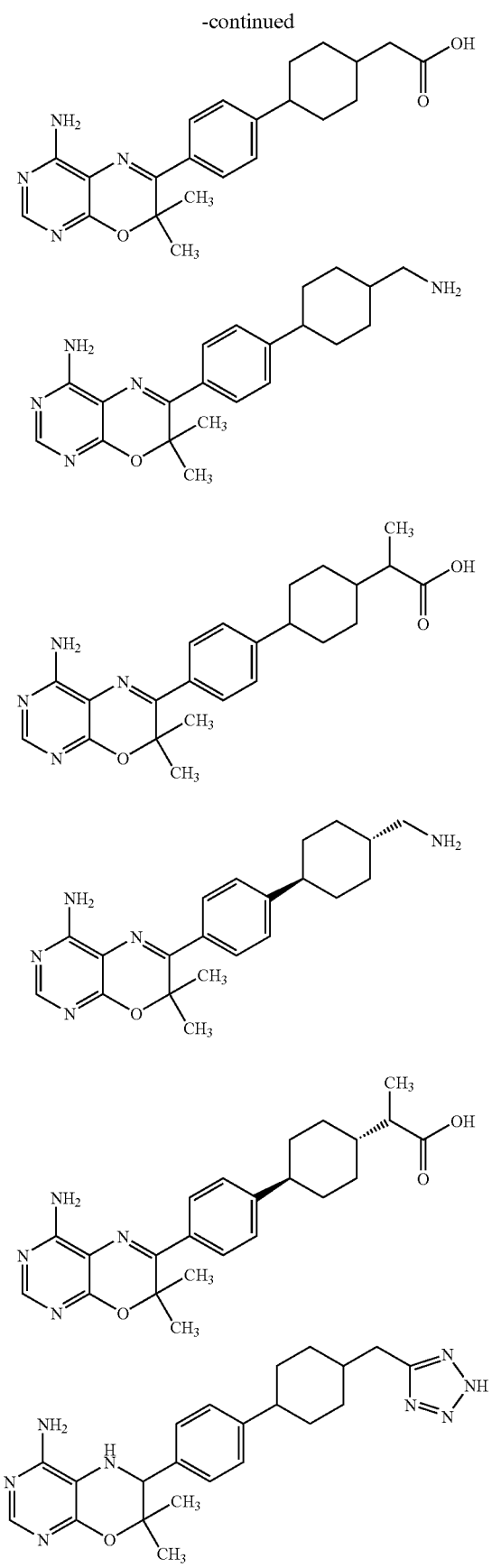
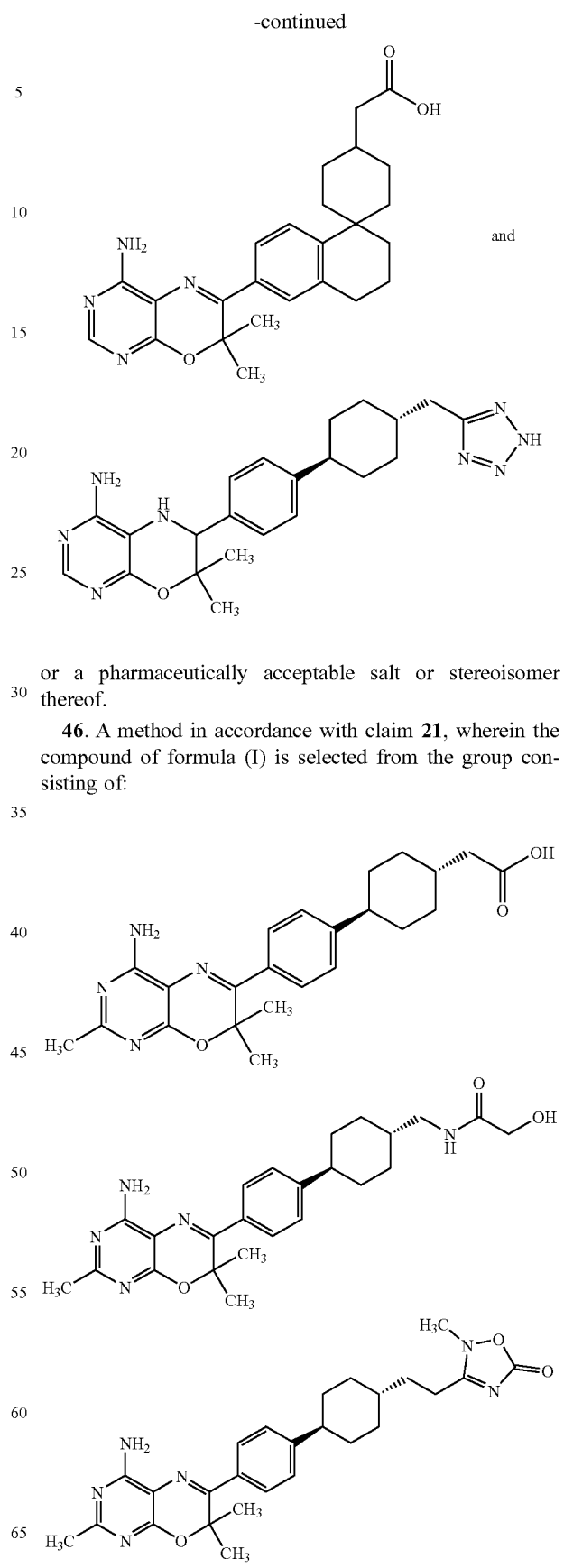
or a pharmaceutically acceptable salt or stereoisomer thereof.
46. A method in accordance with claim 21, wherein the compound of formula (I) is selected from the group consisting of:

-continued or a pharmaceutically acceptable salt or stereoisomer thereof.

47. A compound:

or a pharmaceutically acceptable salt or stereoisomer thereof.

48. A compound:

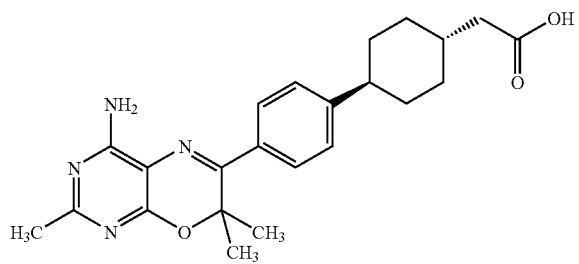

or a pharmaceutically acceptable salt or stereoisomer thereof.

49. A compound:

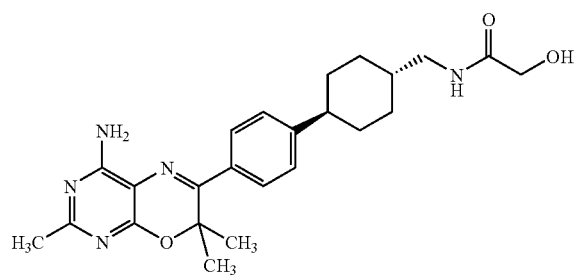

or a pharmaceutically acceptable salt or stereoisomer thereof.

50. A compound:

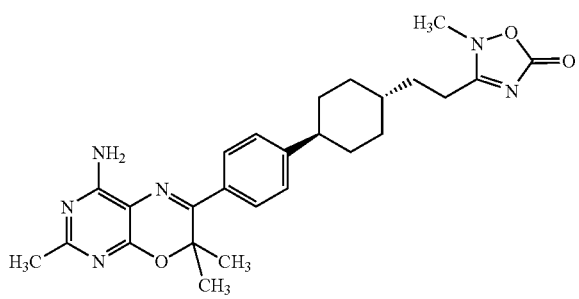

or a pharmaceutically acceptable salt or stereoisomer thereof.

51. A compound:
or a pharmaceutically acceptable salt or stereoisomer thereof.

52. A compound:

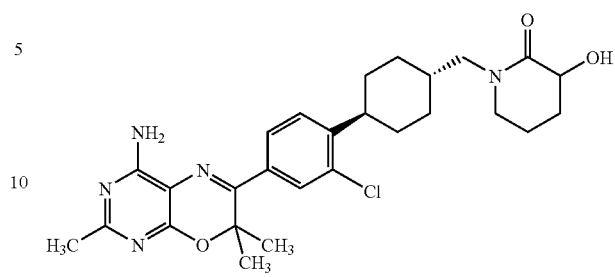

or a pharmaceutically acceptable salt or stereoisomer thereof.

53. A compound:

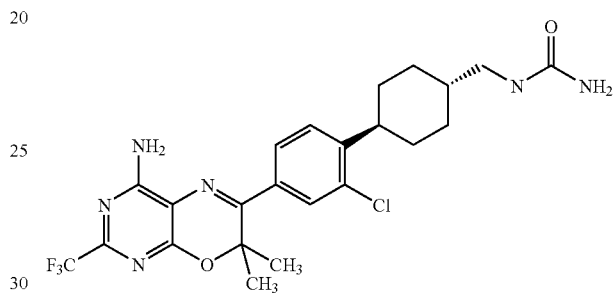

or a pharmaceutically acceptable salt or stereoisomer thereof.

54. A compound:

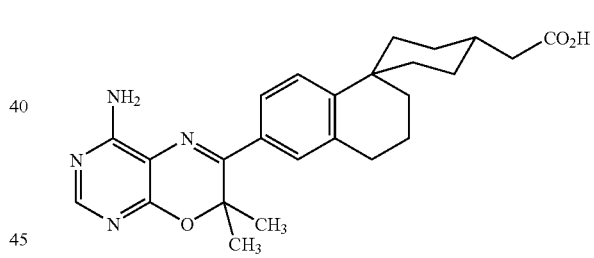

or a pharmaceutically acceptable salt or stereoisomer thereof.

55. A compound:

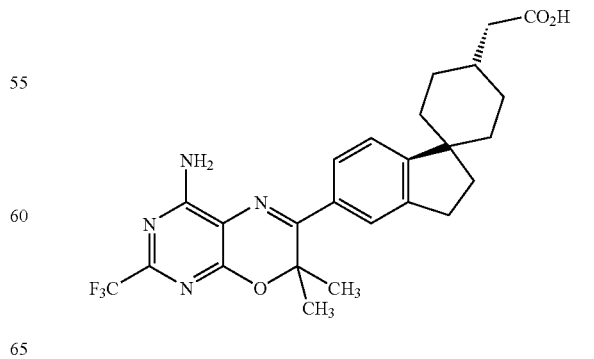

or a pharmaceutically acceptable salt or stereoisomer thereof.

56. A pharmaceutical composition comprising a pharmaceutically acceptable excipient and a compound, a pharmaceutically acceptable salt thereof, or a stereoisomer thereof of any one of claims 47-53, 54, and 55.

57. A method of treating a disease or condition selected from the group consisting of obesity and insulin resistance, comprising administering to a subject in need thereof an effective amount of a compound, a pharmaceutically acceptable salt thereof, or a stereoisomer thereof of any one of claims 47-53, 54, and 55.

* * * * *